(12) United States Patent
Mirkin et al.

(10) Patent No.: US 10,668,082 B2
(45) Date of Patent: *Jun. 2, 2020

(54) VAGINAL INSERTED ESTRADIOL PHARMACEUTICAL COMPOSITIONS AND METHODS

(71) Applicant: TherapeuticsMD, Inc., Boca Raton, FL (US)

(72) Inventors: Sebastian Mirkin, Boca Raton, FL (US); Julia M. Amadio, Boca Raton, FL (US); Brian A. Bernick, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,723

(22) Filed: May 9, 2018

(65) Prior Publication Data

US 2018/0256598 A1 Sep. 13, 2018

Related U.S. Application Data

(63) Continuation of application No. 15/372,385, filed on Dec. 7, 2016, which is a continuation-in-part of application No. 14/521,230, filed on Oct. 22, 2014.

(60) Provisional application No. 62/264,309, filed on Dec. 7, 2015, provisional application No. 62/296,552, filed on Feb. 17, 2016, provisional application No. 62/324,838, filed on Apr. 19, 2016, provisional application No. 62/329,940, filed on Apr. 29, 2016, provisional application No. 62/348,820, filed on Jun. 10, 2016.

(51) Int. Cl.
| | | |
|---|---|---|
| *A61K 31/565* | (2006.01) | |
| *A61K 9/00* | (2006.01) | |
| *A61K 9/02* | (2006.01) | |
| *A61K 9/48* | (2006.01) | |
| *A61K 47/14* | (2017.01) | |
| *A61K 31/57* | (2006.01) | |

(52) U.S. Cl.
CPC .......... *A61K 31/565* (2013.01); *A61K 9/0034* (2013.01); *A61K 9/0036* (2013.01); *A61K 9/02* (2013.01); *A61K 9/4825* (2013.01); *A61K 9/4858* (2013.01); *A61K 9/4866* (2013.01); *A61K 31/57* (2013.01); *A61K 47/14* (2013.01)

(58) Field of Classification Search
None
See application file for complete search history.

(56) References Cited

U.S. PATENT DOCUMENTS

| | | |
|---|---|---|
| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 6/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 8/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |

(Continued)

FOREIGN PATENT DOCUMENTS

| | | |
|---|---|---|
| BR | PI10001367-9 A2 | 7/2012 |
| CA | 2612380 | 12/2006 |

(Continued)

OTHER PUBLICATIONS

US 6,214,374 B1, 04/2001, Schmirler et al. (withdrawn)

(Continued)

*Primary Examiner* — Dennis J Parad
(74) *Attorney, Agent, or Firm* — Kilpatrick Townsend & Stockton LLP

(57) ABSTRACT

Disclosed herein is, among other things, a soft gel vaginal pharmaceutical composition and dosage form containing solubilized estradiol for the treatment of vulvovaginal atrophy (VVA) and female sexual dysfunction (FSD).

21 Claims, 22 Drawing Sheets

(56) References Cited

U.S. PATENT DOCUMENTS

| | | |
|---|---|---|
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,043,331 A | 8/1991 | Hirvonen et al. |
| 5,059,426 A | 10/1991 | Chiang |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,164,416 A | 11/1992 | Nagai et al. |
| 5,208,225 A | 5/1993 | Boissonneault et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 8/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth et al. |
| 5,543,150 A | 8/1996 | Bologna et al. |
| 5,547,948 A | 8/1996 | Barcomb |
| 5,556,635 A | 9/1996 | Grognet et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Iiorzou et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Math et al. |
| 5,607,691 A | 3/1997 | Solas et al. |
| 5,607,693 A | 3/1997 | Bonte et al. |
| 5,609,617 A | 3/1997 | Cady et al. |
| 5,620,705 A | 4/1997 | Dong et al. |
| 5,626,866 A | 5/1997 | Heiber et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 6/1997 | Lacy et al. |
| 5,653,983 A | 8/1997 | Bonte et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Dumas et al. |
| 5,676,968 A | 10/1997 | Lipp et al. |
| 5,677,292 A | 10/1997 | Li et al. |
| 5,686,097 A | 11/1997 | Crisologo et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Mantelle et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Tipton et al. |
| 5,780,050 A | 7/1998 | Jain et al. |
| 5,788,980 A | 8/1998 | Nabahi |
| 5,788,984 A | 8/1998 | Schmidt et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Shinmura et al. |
| 5,827,200 A | 10/1998 | Caillouette |
| 5,840,327 A | 11/1998 | Gale et al. |
| 5,843,468 A | 12/1998 | Yum et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Yum et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Gunther et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Fikstad et al. |
| 5,958,446 A | 9/1999 | Miranda et al. |
| 5,962,445 A | 10/1999 | Stewart |
| 5,968,919 A | 10/1999 | Gyurik et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon Lapillonne et al. |
| 6,010,715 A | 1/2000 | Pollock et al. |
| 6,013,276 A | 1/2000 | Teillaud et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann et al. |
| 6,039,968 A | 3/2000 | Nabahi |
| 6,040,340 A | 3/2000 | Garfield et al. |
| 6,056,972 A | 5/2000 | Hermsmeyer |
| 6,060,077 A | 5/2000 | Meignant |
| 6,068,853 A | 5/2000 | Berner et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 7/2000 | Lacy et al. |
| 6,106,848 A | 8/2000 | Willcox et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |

(56) References Cited

U.S. PATENT DOCUMENTS

| | | |
|---|---|---|
| 6,139,868 A | 10/2000 | Hoffmann |
| 6,139,873 A | 10/2000 | Hughes, Jr. et al. |
| 6,149,935 A | 11/2000 | Tenzel et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Rubinstein et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Macqueen et al. |
| 6,245,811 B1 | 6/2001 | Horrobin et al. |
| 6,262,115 B1 | 7/2001 | Guittard et al. |
| 6,267,984 B1 | 7/2001 | Hamlin et al. |
| 6,274,165 B1 | 8/2001 | Meconi et al. |
| 6,277,418 B1 | 8/2001 | Marakverich et al. |
| 6,283,927 B1 | 9/2001 | Caillouette |
| 6,284,263 B1 | 9/2001 | Place |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer et al. |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Vo et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Leyba et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Houze et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Seibertz et al. |
| 6,526,980 B1 | 3/2003 | Tracy et al. |
| 6,528,094 B1 | 3/2003 | Savoir et al. |
| 6,531,149 B1 | 3/2003 | Meconi et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Murray et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo et al. |
| 6,610,652 B2 | 8/2003 | Adams et al. |
| 6,610,670 B2 | 8/2003 | Bickensfeld et al. |
| 6,610,674 B1 | 8/2003 | Schreiber |
| 6,635,274 B1 | 10/2003 | Carter et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Tamarkin et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Pike et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Boyd et al. |
| 6,977,250 B2 | 12/2005 | Rodriguez |
| 6,978,945 B2 | 12/2005 | Wong et al. |
| 6,987,129 B2 | 1/2006 | Mak et al. |
| 6,995,149 B1 | 2/2006 | Reilhac et al. |
| 7,004,321 B2 | 2/2006 | Hackbarth et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Paris et al. |
| 7,030,157 B2 | 4/2006 | Ke et al. |
| RE39,104 E | 5/2006 | Duclos et al. |
| 7,074,779 B2 | 7/2006 | Sui et al. |

(56) References Cited

U.S. PATENT DOCUMENTS

| | | |
|---|---|---|
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Keister et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villaneuva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Ring et al. |
| 7,550,142 B2 | 6/2009 | Giles-Komar et al. |
| 7,563,565 B1 | 7/2009 | Matsuo et al. |
| 7,569,274 B2 | 8/2009 | Alphonse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Frye et al. |
| RE42,012 E | 12/2010 | Deaver et al. |
| 7,850,992 B2 | 12/2010 | Hwang et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Rao et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Visser et al. |
| 8,071,729 B2 | 12/2011 | Giles-Komar et al. |
| 8,075,916 B2 | 12/2011 | Park et al. |
| 8,075,917 B2 | 12/2011 | Park et al. |
| 8,076,317 B2 | 12/2011 | Kulmann |
| 8,076,319 B2 | 12/2011 | Leonard |
| 8,080,553 B2 | 12/2011 | Auspitz et al. |
| 8,088,605 B2 | 1/2012 | Beudet et al. |
| 8,096,940 B2 | 1/2012 | Iverson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Baasner et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Watkinson et al. |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Wood, Jr. et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Narkunan et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Karan et al. |
| 8,268,806 B2 | 9/2012 | Labrie |
| 8,268,878 B2 | 9/2012 | Johnson et al. |
| 8,273,730 B2 | 9/2012 | Fernandez et al. |
| 8,287,888 B2 | 10/2012 | Song et al. |
| 8,288,366 B2 | 10/2012 | Gonzalez et al. |
| 8,318,898 B2 | 11/2012 | Fasel et al. |
| 8,324,193 B2 | 12/2012 | Lee et al. |
| 8,329,680 B2 | 12/2012 | Evans et al. |
| 8,337,814 B2 | 12/2012 | Osbakken et al. |
| 8,344,007 B2 | 1/2013 | Chui et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Besonov et al. |
| 8,372,424 B2 | 2/2013 | Berry et al. |
| 8,372,806 B2 | 2/2013 | Bragagna et al. |
| 8,377,482 B2 | 2/2013 | Laurie et al. |
| 8,377,994 B2 | 2/2013 | Drechsler et al. |
| 8,394,759 B2 | 3/2013 | Barathur et al. |
| 8,415,332 B2 | 4/2013 | Reape et al. |
| 8,420,111 B2 | 4/2013 | Hermsmeyer |
| 8,435,561 B2 | 5/2013 | Besins et al. |
| 8,435,972 B2 | 5/2013 | Sayeed et al. |
| 8,449,879 B2 | 5/2013 | Laurent et al. |
| 8,450,108 B2 | 5/2013 | Boyce |
| 8,454,945 B2 | 6/2013 | Narain et al. |
| 8,455,468 B2 | 6/2013 | Kellermann et al. |

(56) References Cited

U.S. PATENT DOCUMENTS

| | | |
|---|---|---|
| 8,461,138 B2 | 6/2013 | Boissonneault |
| 8,476,252 B2 | 7/2013 | Pickersgill et al. |
| 8,481,488 B2 | 7/2013 | Carter |
| 8,486,374 B2 | 7/2013 | Zlatkis et al. |
| 8,486,442 B2 | 7/2013 | Yamaji et al. |
| 8,492,368 B2 | 7/2013 | Lewandowski et al. |
| 8,507,467 B2 | 8/2013 | Ueda et al. |
| 8,512,693 B2 | 8/2013 | Azevedo et al. |
| 8,512,754 B2 | 8/2013 | Needham |
| 8,518,376 B2 | 8/2013 | Schuz et al. |
| 8,536,159 B2 | 9/2013 | Zeng et al. |
| 8,540,967 B2 | 9/2013 | Trivedi et al. |
| 8,541,400 B2 | 9/2013 | Joabsson et al. |
| 8,551,462 B2 | 10/2013 | Marenus et al. |
| 8,551,508 B2 | 10/2013 | Lee et al. |
| 8,557,281 B2 | 10/2013 | Tuominen et al. |
| 8,568,374 B2 | 10/2013 | de Graaff et al. |
| 8,591,951 B2 | 11/2013 | Kohn et al. |
| 8,613,951 B2 | 12/2013 | Troiano et al. |
| 8,633,178 B2 | 1/2014 | Cacace et al. |
| 8,633,180 B2 | 1/2014 | Zeng et al. |
| 8,636,787 B2 | 1/2014 | Sabaria |
| 8,636,982 B2 | 1/2014 | Schuz et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Moldavski et al. |
| 8,664,207 B2 | 3/2014 | Zheng et al. |
| 8,669,293 B2 | 3/2014 | Sharoni et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Zeng et al. |
| 8,703,105 B2 | 4/2014 | Besonov et al. |
| 8,709,385 B2 | 4/2014 | Schuz et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Eini et al. |
| 8,734,846 B2 | 5/2014 | Hrkach et al. |
| 8,735,381 B2 | 5/2014 | Podolski |
| 8,741,336 B2 | 6/2014 | Dipierro et al. |
| 8,741,373 B2 | 6/2014 | Rao et al. |
| 8,753,661 B2 | 6/2014 | Gassner et al. |
| 8,784,882 B2 | 7/2014 | Mattern |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,006,222 B2 | 4/2015 | Bernick et al. |
| 9,012,434 B2 | 4/2015 | Bernick et al. |
| 9,114,145 B2 | 8/2015 | Bernick et al. |
| 9,114,146 B2 | 8/2015 | Bernick et al. |
| 9,180,091 B2 | 11/2015 | Bernick et al. |
| 9,248,136 B2 | 2/2016 | Bernick et al. |
| 9,289,382 B2 | 3/2016 | Bernick et al. |
| 9,301,920 B2 | 4/2016 | Bernick et al. |
| 9,931,349 B2 | 4/2018 | Shadiack et al. |
| 10,052,386 B2 | 8/2018 | Bernick et al. |
| 2001/0005728 A1 | 2/2001 | Guittard et al. |
| 2001/0009673 A1 | 7/2001 | Gunther et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2012/0269878 A2 | 10/2001 | Cantor et al. |
| 2001/0053383 A1 | 12/2001 | Sablotsky et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Garfield et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Gunther et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0091620 A1 | 2/2003 | Venkateshwaran et al. |
| 2003/0044453 A1 | 3/2003 | Volkel et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Beckmann et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Yoon et al. |
| 2003/0175329 A1 | 9/2003 | Mak et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Friedman et al. |
| 2003/0225048 A1 | 12/2003 | Friedman et al. |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |

(56) References Cited

U.S. PATENT DOCUMENTS

| | | |
|---|---|---|
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Sciano et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Latif et al. |
| 2005/0020552 A1 | 1/2005 | Aschkenasay et al. |
| 2005/0021009 A1 | 1/2005 | Massara |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Paterson et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobild et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Wuttke et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Le et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 11/2005 | Jorda et al. |
| 2005/0266088 A1 | 12/2005 | Frijlink et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Seibertz et al. |
| 2006/0089337 A1 | 4/2006 | Casper et al. |
| 2006/0093678 A1 | 5/2006 | Chickering, III et al. |
| 2006/0100180 A1 | 5/2006 | Bohlmann et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Anyarambhatla et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Pushpala et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh et al. |
| 2006/0251581 A1 | 11/2006 | Madenjian et al. |
| 2006/0252049 A1 | 11/2006 | Shuler et al. |
| 2006/0257472 A1 | 11/2006 | Neilsen |
| 2006/0275218 A1 | 12/2006 | Besonov et al. |
| 2006/0275360 A1 | 12/2006 | Ahmed et al. |
| 2006/0276414 A1 | 12/2006 | Coelingh et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Mc Ilroy et al. |
| 2007/0004693 A1 | 1/2007 | Woolfson et al. |
| 2007/0004694 A1 | 1/2007 | Woolfson et al. |
| 2007/0009559 A1 | 1/2007 | Alosio et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Goldstein et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0036843 A1 | 2/2007 | Hirsh et al. |
| 2007/0037780 A1 | 2/2007 | Anigbogu et al. |
| 2007/0037782 A1 | 2/2007 | Suzuki et al. |
| 2007/0042038 A1 | 2/2007 | Besse |
| 2007/0060589 A1 | 3/2007 | Purandare et al. |

(56) References Cited

U.S. PATENT DOCUMENTS

| | | |
|---|---|---|
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0071777 A1 | 3/2007 | Bromer et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Wall et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Chiao et al. |
| 2007/0191319 A1 | 8/2007 | Ke et al. |
| 2007/0191321 A1 | 8/2007 | Ahmed |
| 2007/0196415 A1 | 8/2007 | Houston et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Bernard et al. |
| 2007/0238713 A1 | 10/2007 | Gast et al. |
| 2007/0243229 A1 | 10/2007 | Smith et al. |
| 2007/0248658 A1 | 10/2007 | Bracht et al. |
| 2007/0254858 A1 | 11/2007 | Cronk |
| 2007/0255197 A1 | 11/2007 | Wilkins et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0270394 A1 | 11/2007 | El-Alfy et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Schuz et al. |
| 2007/0292387 A1 | 12/2007 | Jon et al. |
| 2007/0292461 A1 | 12/2007 | Danziger et al. |
| 2007/0292493 A1 | 12/2007 | Brierre |
| 2007/0298089 A1 | 12/2007 | Yoshinaga et al. |
| 2008/0026035 A1 | 1/2008 | Chollet et al. |
| 2008/0026040 A1 | 1/2008 | Rivera et al. |
| 2008/0026062 A1 | 1/2008 | Farr et al. |
| 2008/0038219 A1 | 2/2008 | Carlson et al. |
| 2008/0038350 A1 | 2/2008 | Gerecke et al. |
| 2008/0039405 A1 | 2/2008 | Joseph et al. |
| 2008/0050317 A1 | 2/2008 | Besonov et al. |
| 2008/0051351 A1 | 2/2008 | Ghisalberti |
| 2008/0063607 A1 | 3/2008 | Berman et al. |
| 2008/0069779 A1 | 3/2008 | Schuz et al. |
| 2008/0069791 A1 | 3/2008 | Beissert |
| 2008/0085877 A1 | 4/2008 | Bortz |
| 2008/0095831 A1 | 4/2008 | Mc Graw |
| 2008/0095838 A1 | 4/2008 | Abou Chacra-Vernet |
| 2008/0113953 A1 | 5/2008 | De Vries et al. |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Gricenko et al. |
| 2008/0139392 A1 | 6/2008 | Yuan et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Biksh et al. |
| 2008/0175908 A1 | 7/2008 | Biksh et al. |
| 2008/0188829 A1 | 8/2008 | Creasy |
| 2008/0206156 A1 | 8/2008 | Cronk |
| 2008/0206159 A1 | 8/2008 | Schuz et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Beste et al. |
| 2008/0227763 A1 | 9/2008 | Paris et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Stenlof et al. |
| 2008/0114050 A1 | 12/2008 | Fensome et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Peyrot et al. |
| 2009/0011041 A1 | 1/2009 | Musaeva et al. |
| 2009/0017120 A1 | 1/2009 | Brisco et al. |
| 2009/0022683 A1 | 1/2009 | Park et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Kresevic |
| 2009/0130029 A1 | 5/2009 | Tamarkin et al. |
| 2009/0131385 A1 | 5/2009 | Voskuhl |
| 2009/0136574 A1 | 5/2009 | Diaz-Astruc et al. |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Slot et al. |
| 2009/0197843 A1 | 8/2009 | Notelovitz et al. |
| 2009/0203658 A1 | 8/2009 | Rose et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Kresevic et al. |
| 2009/0325916 A1 | 12/2009 | Zhang et al. |
| 2010/0008985 A1 | 1/2010 | Vermeulen et al. |
| 2010/0028360 A1 | 2/2010 | Atwood |
| 2010/0034838 A1 | 2/2010 | Staniforth et al. |
| 2010/0034880 A1 | 2/2010 | Sintov |
| 2010/0040671 A1 | 2/2010 | Ahmed et al. |
| 2010/0048523 A1 | 2/2010 | Bachman et al. |
| 2010/0055138 A1 | 3/2010 | Jacobs et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Lee et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |

(56) References Cited

U.S. PATENT DOCUMENTS

| | | |
|---|---|---|
| 2010/0221195 A1 | 9/2010 | Ziv et al. |
| 2010/0227797 A1 | 9/2010 | Danielsson et al. |
| 2010/0240626 A1 | 9/2010 | Kulkarni et al. |
| 2010/0247482 A1 | 9/2010 | Chen et al. |
| 2010/0247632 A1 | 9/2010 | Dong et al. |
| 2010/0247635 A1 | 9/2010 | Schmidt et al. |
| 2010/0255085 A1 | 10/2010 | Liu et al. |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Lapitsky et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Wilkins et al. |
| 2010/0330168 A1 | 12/2010 | Gicquel et al. |
| 2011/0028439 A1 | 2/2011 | Witt-Enderby et al. |
| 2011/0039814 A1 | 2/2011 | Ross et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Canet et al. |
| 2011/0098631 A1 | 4/2011 | McIntyre et al. |
| 2011/0104268 A1 | 5/2011 | Segot et al. |
| 2011/0104289 A1 | 5/2011 | Savoir Vilboeuf et al. |
| 2011/0130372 A1 | 6/2011 | Marliani et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Fisher et al. |
| 2011/0171140 A1 | 7/2011 | Illum et al. |
| 2011/0182997 A1 | 7/2011 | Lewis et al. |
| 2011/0190201 A1 | 8/2011 | Wood, Jr. et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Karabelas et al. |
| 2011/0244043 A1 | 10/2011 | Wang et al. |
| 2011/0250256 A1 | 10/2011 | Hyun et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert |
| 2011/0262494 A1 | 10/2011 | Achleitner et al. |
| 2011/0268665 A1 | 11/2011 | Tamarkin et al. |
| 2011/0275584 A1 | 11/2011 | Volkmann et al. |
| 2011/0281832 A1 | 11/2011 | Wennogle et al. |
| 2011/0287094 A1 | 11/2011 | Penhasi et al. |
| 2011/0293720 A1 | 12/2011 | General et al. |
| 2011/0294738 A1 | 12/2011 | Kuliopulos et al. |
| 2011/0300167 A1 | 12/2011 | Covic et al. |
| 2011/0301087 A1 | 12/2011 | Mcbride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Takruri et al. |
| 2012/0028936 A1 | 2/2012 | Popova et al. |
| 2012/0045532 A1 | 2/2012 | Cohen |
| 2012/0046264 A1 | 2/2012 | Lieb et al. |
| 2012/0046518 A1 | 2/2012 | Yoakum et al. |
| 2012/0052077 A1 | 3/2012 | Truitt, III et al. |
| 2012/0058171 A1 | 3/2012 | Zeeman et al. |
| 2012/0058962 A1 | 3/2012 | Sparrow et al. |
| 2012/0058979 A1 | 3/2012 | Auspitz et al. |
| 2012/0064135 A1 | 3/2012 | Harms et al. |
| 2012/0065179 A1 | 3/2012 | Andersson |
| 2012/0065221 A1 | 3/2012 | Babul |
| 2012/0087872 A1 | 4/2012 | Schuz et al. |
| 2012/0101073 A1 | 4/2012 | Mannion |
| 2012/0121517 A1 | 5/2012 | Kim et al. |
| 2012/0121692 A1 | 5/2012 | Fang et al. |
| 2012/0122829 A1 | 5/2012 | Masini et al. |
| 2012/0128625 A1 | 5/2012 | Shalwitz et al. |
| 2012/0128654 A1 | 5/2012 | Teipstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Wennogle et al. |
| 2012/0142645 A1 | 6/2012 | Marx |
| 2012/0148670 A1 | 6/2012 | Lee et al. |
| 2012/0149748 A1 | 6/2012 | Shanler et al. |
| 2012/0172343 A1 | 7/2012 | Schuermann et al. |
| 2012/0184515 A1 | 7/2012 | Schwede et al. |
| 2012/0231052 A1 | 9/2012 | Brinton et al. |
| 2012/0232011 A1 | 9/2012 | Kneissel et al. |
| 2012/0232042 A1 | 9/2012 | Krenz et al. |
| 2012/0263679 A1 | 10/2012 | Wallace et al. |
| 2012/0269721 A1 | 10/2012 | Weng et al. |
| 2012/0277249 A1 | 11/2012 | Tarrand et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Warner et al. |
| 2012/0301538 A1 | 11/2012 | Latere et al. |
| 2012/0302535 A1 | 11/2012 | Caufriez et al. |
| 2012/0316130 A1 | 12/2012 | Hendrix |
| 2012/0316496 A1 | 12/2012 | Horres et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Goh et al. |
| 2013/0011342 A1 | 1/2013 | Hazot et al. |
| 2013/0017239 A1 | 1/2013 | Fernandez et al. |
| 2013/0022674 A1 | 1/2013 | Dudley et al. |
| 2013/0023505 A1 | 1/2013 | Garfield et al. |
| 2013/0023823 A1 | 1/2013 | Volland et al. |
| 2013/0028850 A1 | 1/2013 | Hazot et al. |
| 2013/0029947 A1 | 1/2013 | Nachaegari et al. |
| 2013/0029957 A1 | 1/2013 | Venkateshwaran et al. |
| 2013/0045266 A1 | 2/2013 | Kang et al. |
| 2013/0045953 A1 | 2/2013 | Grenier et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Zhao et al. |
| 2013/0089574 A1 | 4/2013 | Stock et al. |
| 2013/0090318 A1 | 4/2013 | Gainer et al. |
| 2013/0102781 A1 | 4/2013 | Ely et al. |
| 2013/0108551 A1 | 5/2013 | Gruell et al. |
| 2013/0116215 A1 | 5/2013 | Lleo et al. |
| 2013/0116222 A1 | 5/2013 | Altomari et al. |
| 2013/0122051 A1 | 5/2013 | Gullapalli et al. |
| 2013/0123175 A1 | 5/2013 | Mckee et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Schmitz et al. |
| 2013/0131028 A1 | 5/2013 | Snyder et al. |
| 2013/0131029 A1 | 5/2013 | Baltussen et al. |
| 2013/0149314 A1 | 6/2013 | Bullerdiek et al. |
| 2013/0164225 A1 | 6/2013 | Besonov et al. |
| 2013/0164346 A1 | 6/2013 | Son et al. |
| 2013/0165744 A1 | 6/2013 | Carson et al. |
| 2013/0178452 A1 | 7/2013 | King |
| 2013/0183254 A1 | 7/2013 | Cochran et al. |
| 2013/0183325 A1 | 7/2013 | Sforzini et al. |
| 2013/0189193 A1 | 7/2013 | Besonov et al. |

(56) References Cited

U.S. PATENT DOCUMENTS

| | | |
|---|---|---|
| 2013/0189196 A1 | 7/2013 | Tamarkin et al. |
| 2013/0189230 A1 | 7/2013 | Kooy et al. |
| 2013/0189368 A1 | 7/2013 | Mosqueira et al. |
| 2013/0210709 A1 | 8/2013 | Covic et al. |
| 2013/0216550 A1 | 8/2013 | Penninger et al. |
| 2013/0216596 A1 | 8/2013 | Fernandez et al. |
| 2013/0224177 A1 | 8/2013 | Kim et al. |
| 2013/0224257 A1 | 8/2013 | Sah et al. |
| 2013/0224268 A1 | 8/2013 | Jaikaria et al. |
| 2013/0224300 A1 | 8/2013 | Maggio |
| 2013/0225412 A1 | 8/2013 | Sardari et al. |
| 2013/0225542 A1 | 8/2013 | Frick et al. |
| 2013/0226113 A1 | 8/2013 | Langguth et al. |
| 2013/0243696 A1 | 9/2013 | Wang et al. |
| 2013/0245253 A1 | 9/2013 | Mook et al. |
| 2013/0245570 A1 | 9/2013 | Jackson |
| 2013/0261096 A1 | 10/2013 | Merian et al. |
| 2013/0266645 A1 | 10/2013 | Schoenecker et al. |
| 2013/0267485 A1 | 10/2013 | Da Silva |
| 2013/0273167 A1 | 10/2013 | Kim et al. |
| 2013/0274211 A1 | 10/2013 | Prusthy et al. |
| 2013/0280213 A1 | 10/2013 | Voskuhl |
| 2013/0316374 A1 | 11/2013 | Menon et al. |
| 2013/0317065 A1 | 11/2013 | Seto et al. |
| 2013/0317315 A1 | 11/2013 | Tsang et al. |
| 2013/0324565 A1 | 12/2013 | Zhao et al. |
| 2013/0331363 A1 | 12/2013 | Zhao et al. |
| 2013/0338122 A1 | 12/2013 | Bernick et al. |
| 2013/0338123 A1 | 12/2013 | Bernick et al. |
| 2013/0338124 A1 | 12/2013 | Zhao et al. |
| 2013/0345187 A1 | 12/2013 | Rodriguez |
| 2014/0018335 A1 | 1/2014 | Seto et al. |
| 2014/0024590 A1 | 1/2014 | Taylor et al. |
| 2014/0031289 A1 | 1/2014 | Kim et al. |
| 2014/0031323 A1 | 1/2014 | Perez |
| 2014/0066416 A1 | 3/2014 | Leunis et al. |
| 2014/0072531 A1 | 3/2014 | Oh et al. |
| 2014/0079686 A1 | 3/2014 | Prouty et al. |
| 2014/0088051 A1 | 3/2014 | Bernick et al. |
| 2014/0088058 A1 | 3/2014 | Maurizio |
| 2014/0088059 A1 | 3/2014 | Santha et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Cacace et al. |
| 2014/0113889 A1 | 4/2014 | Haine et al. |
| 2014/0127185 A1 | 5/2014 | Sayeed et al. |
| 2014/0127280 A1 | 5/2014 | Jukarainen et al. |
| 2014/0127308 A1 | 5/2014 | Opara et al. |
| 2014/0128798 A1 | 5/2014 | Malanchin et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Wennogle et al. |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0148323 A1 | 5/2015 | Bernick et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2018/0161343 A1 | 6/2018 | Mirkin et al. |
| 2018/0161344 A1 | 6/2018 | Bernick et al. |
| 2018/0161345 A1 | 6/2018 | Bernick et al. |
| 2018/0221389 A1 | 8/2018 | Amadio et al. |

FOREIGN PATENT DOCUMENTS

| | | |
|---|---|---|
| CN | 102258455 A | 11/2011 |
| EP | 0275716 A1 | 7/1988 |
| EP | 0279977 A2 | 8/1988 |
| EP | 0622075 A1 | 11/1994 |
| EP | 0785211 A1 | 7/1997 |
| EP | 0785212 A1 | 7/1997 |
| EP | 0811381 A1 | 12/1997 |
| EP | 0904064 A1 | 3/1999 |
| EP | 0750495 B1 | 12/2002 |
| EP | 1300152 A1 | 4/2003 |
| EP | 1094781 B1 | 7/2008 |
| EP | 2191833 A1 | 6/2010 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 2005KOL00053 | 8/2005 |
| IN | 216026 | 3/2008 |
| IN | 244217 | 11/2010 |
| JP | H4-503810 | 9/1990 |
| JP | H2-264725 A | 10/1990 |
| JP | 2002 510336 A | 4/2002 |
| JP | 2006 513182 A | 4/2006 |
| RU | 2155582 C2 | 9/2000 |
| WO | 199010425 A1 | 9/1990 |
| WO | 1990011064 | 10/1990 |
| WO | 1993017686 | 9/1993 |
| WO | 1994022426 | 10/1994 |
| WO | 1995030409 | 11/1995 |
| WO | 1996009826 | 4/1996 |
| WO | 1996019975 | 7/1996 |
| WO | 1996030000 | 10/1996 |
| WO | 1997005491 | 2/1997 |
| WO | 1997043989 | 11/1997 |
| WO | 1998010293 | 3/1998 |
| WO | 1998032465 | 7/1998 |
| WO | 1998051280 | 11/1998 |
| WO | 1999022680 A1 | 5/1999 |
| WO | 1999032072 | 7/1999 |
| WO | 1999039700 | 8/1999 |
| WO | 1999042109 | 8/1999 |
| WO | 1999043304 | 9/1999 |
| WO | 1999048477 | 9/1999 |
| WO | 1999052528 A1 | 10/1999 |
| WO | 1999053910 | 10/1999 |
| WO | 1999062497 A1 | 12/1999 |
| WO | 1999063974 | 12/1999 |
| WO | 2000001351 | 1/2000 |
| WO | 2000006175 | 2/2000 |
| WO | 2000038659 | 6/2000 |
| WO | 2000045795 | 8/2000 |
| WO | 2000050007 | 8/2000 |
| WO | 2000059577 | 10/2000 |
| WO | 2000076522 | 12/2000 |
| WO | 2001037808 | 5/2001 |
| WO | 2001054699 | 8/2001 |
| WO | 2001060325 | 8/2001 |
| WO | 2001087276 | 11/2001 |
| WO | 2001091757 | 12/2001 |
| WO | 2002007700 | 1/2002 |

(56) References Cited

FOREIGN PATENT DOCUMENTS

| | | |
|---|---|---|
| WO | 2002011768 | 2/2002 |
| WO | 2002022132 | 3/2002 |
| WO | 2002040008 | 5/2002 |
| WO | 2002041878 | 5/2002 |
| WO | 2002053131 | 7/2002 |
| WO | 2002078602 | 10/2002 |
| WO | 2002078604 | 10/2002 |
| WO | 2003028667 | 4/2003 |
| WO | 2003041718 | 5/2003 |
| WO | 2003041741 | 5/2003 |
| WO | 2003068186 | 8/2003 |
| WO | 2003077923 | 9/2003 |
| WO | 2003082254 | 10/2003 |
| WO | 2003092588 | 11/2003 |
| WO | 2004014397 A1 | 2/2004 |
| WO | 2004014432 | 2/2004 |
| WO | 2004017983 | 3/2004 |
| WO | 2004032897 | 4/2004 |
| WO | 2004052336 | 6/2004 |
| WO | 2004054540 | 7/2004 |
| WO | 2004054576 A1 | 7/2004 |
| WO | 2004080413 | 9/2004 |
| WO | 2004105694 A2 | 12/2004 |
| WO | 2004110408 A2 | 12/2004 |
| WO | 2005027911 | 3/2005 |
| WO | 2005030175 | 4/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | 2007076144 A2 | 7/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013078422 A2 | 5/2013 |
| WO | 2013088254 | 6/2013 |
| WO | 2013102665 A1 | 7/2013 |
| WO | 2013106437 A1 | 7/2013 |
| WO | 2013112947 A1 | 8/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |
| WO | 2015179782 A1 | 11/2015 |
| WO | 2016018993 A1 | 2/2016 |

OTHER PUBLICATIONS

Martelli, "Vaginal Medicine Administration," The Gale Encyclopedia of Nursing and Allied Health, Gale Group, pp. 2542-2543 (Year: 2002).*
Abbas et al., Regression of endometrial implants treated with vitamin $D_3$ in a rat model of endometriosis, European J of Pharma, 715 (2013) 72-75, Elsevier.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Safety Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Abitec, Excipients for the Pharmaceutical Industry—Regulatory and Product Information, 2013, 2 pages.
Acarturk, Fusun, Mucoadhesive Vaginal Drug Delivery System, Recent Patents on Drug Delivery & Formulation, 2009, vol. 3, pp. 193-195.

(56) References Cited

OTHER PUBLICATIONS

Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
Alvarez et al., Ectopic uterine tissue as a chronic pain generator, Neuroscience, Dec. 6, 2012, 225: 269-272.
Application Note FT-IR: JI-Ap-FT0508-008, CD spectra of pharmaceuticals substances—Steroids (2), JASCO International Co., Ltd., 2 pages.
Araya-Sibaja et al., Crystallization of progesterone polymorphs using polymer-induced heteronucleation (PIHn) method, Drug Development and Industrial Pharmacy, Early Online, pp. 1-8, 2014, Informa Healthcare.
Araya-Sibaja, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Sibaja, Andrea Manela, et al., Chemical Properties of Progesterone Selected Refer., SciFinder, 2014, American Chemical Society & US Natl. Lib. of Med.
Araya-Sibaja, Andrea Manela, et al., Polymorphism in Progesterone Selected References, SciFinder, Feb. 24, 2014, pp. 1-12, American Chem. Society & Natl. Lib. of Med.
Araya-Sibaja, Andrea Manela, et al., Polymorphism in Progesterone, SciFinder, pp. 1-46, Feb. 24, 2014, American Chem. Society & Natl. Lib. of Med.
Archer et al., Effects of ospemifene on the female reproductive and urinary tracts: translation from preclinical models into clinical evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.
Azure Pharma, Inc., ELESTRIN™—Estradiol Gel, Drug Info, http://dailymed.nlm.nih.gov/dailymed/archives/fdaDrugInfo.cfm?archiveid=11885, 26 pages, Aug. 2009.
Bakhmutova-Albert, Ekaterina, et al., Enhancing Aqueous Dissolution Rates of Progesterone via Cocrystallization, SSCI, Division of Aptuit, Poster No. R6247, West Lafayette.
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bartosova, Transdermal Drug Delivery in Vitro Using Diffusion Cells, Current Medicinal Chemistry, 2012, 19, 4671-4677, Bentham Science Publishers.
Benbow et al., Distribution and Metabolism of Maternal Progesterone in the Uterus, Placenta, and Fetus during Rat Pregnancy, Biology of Reproduction 52, 1327-1333 (1995).
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani Bhagu R. et al., "Misconception and Concerns about Bioidentical Hormones Used for Custom-Compounded Hormone Therapy," J Clin Endocrinol Metab, Mar. 2012, 97(3):756-759.
Bhavnani et al., Structure Activity Relationships and Differential Interactions and Functional Activity of Various Equine Estrogens Mediated via Estrogen Receptors (ERs) ERα and ER⊕ , Endocrinology, Oct. 2008, 149(10):4857-4870.

Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
British Pharmacocopoeia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Moleculaire de la Progesterone C21H3002, Acta Cryst., B28 pp. 3032-3042, 1972.
Castelo-Branco Camil et al., "Treatment of atrophic vaaginitis," Therapy, 2007, vol. 4, No. 3, pp. 349-353.
Cendejas-Santana, G, et al., Growth and characterization of progesterone crystallites, Revista Mexicana de Fisica, 50, Suplemento 1 pp. 1-3, 2004.
Chambin et al., Interest of Multifunctional Lipid Excipients: Case of Gelucire® 44/14, Drug Development and Industrial Pharmacy, vol. 31, No. 6, pp. 527-534 (Year: 2005).
ChemPro, Top-Notch Technology in Production of Oils and Fats, Chempro-Edible-Oil-Refining-ISO-TUV-Austria.
Cho, Y.A. et al., Transdermal Delivery of Ketorolac Tromethamine: Effects of Vehicles and Penetration Enhancers, Drug Development and Industrial Pharmacy, 30(6):557-564, Jun. 2004.
Christen et al., Phase I/Pharmacokinetic Study of High-Dose Progesterone and Doxorubicin, J Clin Oncol 11:2417-2426, 1993.
Christensson et al., Limonene hydroperoxide analogues differ in allergenic activity, Contact Dermatitis 2008: 59: 344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance , Contact Dermatitis, 71, 264-272, 2014.
Chun et al., Transdermal Delivery of Estradiol and Norethrindrone Acetate: Effect of Vehicles . . . , J. Kor. Pharm. Sci., vol. 35, No. 3, pp. 173-177 (2005).
Cicinelli et al., Direct Transport of Progesterone From Vagina to Uterus, Obstetrics & Gynecology, vol. 95, No. 3, Mar. 2000, pp. 403-406.
Cicinelli et al., "First uterine pass effect" is observed when estradiol is placed in the upper but not lower third of the vagina, Fertility and Sterility, vol. 81, No. 5, May 2004, pp. 1414-1416.
Cicinelli, Intravaginal oestrogen and progestin administration: advantages and disadvantages, Best Practices & Research Clinical Obstretrics and Gynaecology vol. 22, No. 2, 2008, pp. 391-405.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Committee Opinion, Incidentally Detected Short Cervical Length, Committee of Obstetric Practice, Obstetrics & Gynecology, ACOG, vol. 119, No. 4, Apr. 2012, pp. 879-882.

(56) References Cited

OTHER PUBLICATIONS

Commodari, Fernando, Comparison of 17β-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-56, Research Letters, Apr. 25, 1998.
Corbett et al., "Trends in Pharmacy Compounding for Women's Health in North Carolina: Focus on Vulvodynia," Southern Medical Journal, vol. 107, No. 7, Jul. 2014, pp. 433-436.
Corn Refiners Association, Corn Oil, 5th Edition, Washington, D.C., 2006.
Crandall, Carolyn, "Vaginal Estrogen Preparations: A Review of Safety and Efficacy for Vaginal Atrophy," Journal of Women's Health, 2002, vol. 11, No. 10, pp. 857-877.
Cremer Care, ""MIGLYOL® 810, 812 INCI: Caprylic/Capric Triglyceride,"" CREMER OLEO GmbH & Co. KG, pp. 1-7, available at http://s3.amazonaws.com/petercremema/products/spec_sheets/159/339/301 /originai/MIGL YOL_81 0_812_ TDS.pdf? 1389204445 (Mar. 2013) accessed on Dec. 30, 2016.
Critchley et al., Estrogen Receptor β, but Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.
Dauqan, Eqbal M. A., et al., Fatty Acids Composition of Four Different Vegetable Oils (Red Palm Olein, Palm Olem, Corn Oil, IPCBEE, vol. 14, 2011, IACSIT Press, Singapore.
Dideberg, O, et al., Crystal data on progesterone (C21H3002), desoxycorticosterone (C21H3003), corticosterone (C21H3004) and aldosterone . . . , J. Appl. Cryst. vol. 4 pp. 80, 1971.
Diramio, Jackie A., Polyethylene Glycol Methacrylate/ Dimetacrylate Hydrogels for Controlled Release of Hydrophobic Drugs, Masters of Science Thesis, University of Georgia, Athens, Georgia, 2002, 131 pages.
Drakulic, Branko J, Role of complexes formation between drugs and penetration enhancers in transdermal . . . , Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of the North American Menopause Society, 2013, vol. 20, No. 11, pp. 1-7.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Engelhardt et al., Conceptus Influences the Distribution of Uterine Leukocytes During Early Porcine Pregnancy, Biology of Reproduction 66, 1875-1880 (2002).
Estradiol, The Merck Index Online, Royal Society of Chemistry, https://www.rsc.org/Merck-Index/monograph/mono 1500003758/ estradiol?q=unauthorize.
Ettinger et al., Comparison of endometrial growth produced by unopposed conjugated estrogens or by micronized estradiol in postmenopausal women, Am J Obstet Gynecol 1997; 176:112-117.
Excipients for Pharmaceuticals, Sasol Olefins & Surfactants GMBH, 2010, 28 pages.
Faassen, Fried, Physicochemical Properties and Transport of Steroids across Caco-2 Cells, Pharmaceutical Research, vol. 20(2), 2003, Plenum Pub. Corp.

FDA, Draft Guidance on Progesterone, Recommended Apr. 2010, Revised Feb. 2011 http://www.fda.gov/downloads/Drugs/ GuidanceComplianceRegulatoryInformation/Guidances/UCM209294.pdf.
Ferrari, Roseli AP., et al., Oxidative Stability of Biodiesel From Soybean Oil Fatty Acid Ethyl Esters, Sci. Agric., vol. 62(3), pp. 291-295, 2005, Piracicaba, Braz.
Filipsson et al., Concise International Chemical Assessment Document 5: Limonene, first draft, World Health Organization, Geneva, 1998, 36 pages.
Final Report on the Safety Assessment of BHT, International Journal of Toxicology, 21(Suppl. 2):19-94, 2002/.
Flyvholm, Sensitizing risk of butylated hydroxytoluene Based on exposure and effect data, Contact Dermatitis 1990: 23: 341-345.
Fotherby, K., Bioavailability of Orally Administered Sex Steroids Used in Oral Contraception and Hormone Replacement Therapy, Contraception, 1996; 54:59-69.
Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Freedman, R.R., Menopausal hot flashes: Mechanisms, endocrinology, treatment, J. Steroid Biochem. Mol. Biol.(2013), Elsevier.
Fuchs et al., the Effects of an Estrogen and Glycolic Acid Cream on the Facial Skin of Postmenopausal Women: A Randomized Histologic Study, Cutis. Jun. 2003;71(6):481-8.
Fugh-Berman, Adriane, Bioidentical Hormones for Menopausal Hormone Therapy: Variation on a Theme, Journal of General Internal Medicine, vol. 22, pp. 1030-1034, 2007.
Furness et al., Hormone therapy in postmenopausal women and risk of endometrial hyperplasia (Review), 2012, pp. 1-204, The Cochrane Collaboration. Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Garad S. et al., "Preclinical Development for Suspensions," A.K. Kulshreshtha et al. (eds.), *Pharmaceutical Suspensions: From Formulation Development to Manufacturing*, Springer, New York 2010, pp. 127-176.
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-NonInvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.
Gillet et al., Induction of amenorrhea during hormone replacement therapy: optimal micronized progesterone dose. A multicenter study, Maturitas 19 (1994) 103-115.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Giron-Forest, D, Thermal analysis and calorimetric methods in the characterisation of polymorphs and solvates, Thermochimica Acta, vol. 248 pp. 1-59, 1995, Elsevier.
Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.

(56) References Cited

OTHER PUBLICATIONS

Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Gunstone, Frank D, et al., Vegetable Oils in Food Technology: Composition, Properties and Uses, Blackwell Publishing, CRC Press, 2002.
Gurney, E.P. et al., The Women's Health Initiative trial and related studies: 10 years later: A clinician's view, J. Steroid Biochem. Mol. Biol. (2013), Elsevier.
Hamid et al., The effects of common solubilizing agents on the intestinal membrane Barrier functions and membrane toxicity in rats, International Journal of Pharmaceutics 379 (2009) 100-108, Elsevier.
Haner, Barbara, Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Hargrove et al., Menopausal Hormone Replacement Therapy with Continuous Daily Oral Micronize Estradiol and Progesterone, Obstet Gynecol, vol. 73, No. 4, Apr. 1989, pp. 606-612.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helbling, Ignacio M, et al., The Optimization of an Intravaginal Ring Releasing Progesterone Using a Mathematical Model, Pharm Res, vol. 31 pp. 795-808, 2014, Springer Science.
Helmy et al., Estrogenic Effect of Soy Phytoestrogens on the Uterus of Ovariectomized Female Rats, Clinic Pharmacol Biopharmaceut, 2014, S2, 7 pages.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hodis, H.N., Mack, W.J., Hormone replacement therapy and the association with heart disease and overall mortality: Clinical . . . , J. Steroid Biochem. Mol. Biol. (2013), Elsevier.
Holm et al., "Examination of oral absorption and lymphatic transport of halofantrine in a triple-cannulated canine model after administration in self-microemulsifying drug delivery systems (SMEDDS) containing structured triglycerides," European Journal of Pharmaceutical Sciences 20 (2003) 91-97.
Hospital, Michel, et al., X-ray Crystallography of Estrogens and Their Binding to Receptor Sites, Mol. Pharmacology, vol. 8 pp. 438-445, Acedemic Press, Inc., 1972.
Hostynek, JJ, Predictinga bsorptiono f fragrancec hemicalst hrough human skin, j. Soc.C osmeCt. hem.,4 6, 221-229 (Jul./Aug. 1995).
Hulsmann, Stefan, Stability of Extruded 17B-Estradiol Solid Dispersions, Pharmaceutical Development and Tech., vol. 6(2) pp. 223-229, 2001, Marcel Dekker, Inc.
Humberstone, Andrew et al., "Lipid-based vehicles for the oral delivery of poorly water soluble drugs," Advanced Drug Delivery Reviews, 25 (1997) 103-128.
Hurn et al., Estrogen as a Neuroprotectant in Stroke, Journal of Cerebral Blood Flow and Metabolism 20:631-652, 2000, Lippincott Williams & Wilkins, Inc., Philadelphia.
Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.
Idder, Salima, et al., Physicochemical properties of Progesterone, SciFinder, pp. 1-26, Feb. 24, 2014, American Chem. Society & US Natl. Lib. of Med.
Johanson, Gunnar, Toxicity Review of Ethylene Glycol Monomethyl Ether and its Acetate Ester, Critical Reviews in Toxicology, 2000, vol. 30, No. 3 , pp. 307-345 (abstract only). http://informahealthcare.com/doi/abs/10.1080/10408440091159220.
Johnson, William S, et al., Racemic Progesterone, Tetrahedron Letters No. 4, pp. 193-196, 1963, Pergamon Press Ltd., Great Britain.
Joshi et al., Detection and synthesis of a progestagen-dependent protein in human endometrium, J Reprod Fert (1980) 59, 273-285.
Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.
Karande, et al. Enhancement of transdermal drug delivery via synergistic action of chemicals, Biochimica et Biophysica Acta, 1788:2362-2373, Sep. 2009.
Karlberg et al., Air oxidation of d-limonene (the citrus solvent) creates potent allergens, Contact Dermatitis, 1992: 26: 332-340.
Karlberg et al., Influence of an anti-oxidant on the formation of allergenic compounds during auto-oxication of d-limonene, Ann. Occup. Hyg., vol. 38, No. 2, pp. 199-207, 1994.
Kaunitz, Andrew M., Extended duration use of menopausal hormone therapy, Menopause: The Journal of the North American Menopause Society, 2014, vol. 21, No. 6, pp. 1-3.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Kharode et al., The Pairing of a Selective Estrogen Receptor Modulator, Bazedoxifene, with Conjugated Estrogens as a New Paradigm for the Treatment of Menopausal Symptoms and Osteoporosis Prevention, Endocrinology 149(12):6084-6091, 2008.
Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.
Kincl et al., Increasing Oral Bioavailability of Progesterone by Formulation, Journal of Steroid Biochemistry, 1978, vol. 9, pp. 83-84.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167.
Koga et al., Enhancing mechanism of Labrasol on intestinal membrane permeability of the hydrophilic drug gentamicin sulfate, European Journal of Pharmaceutics and Biopharmaceutics 64 (2006) 82-91.
Komm et al., Bazedoxifene Acetate: A Selective Estrogen Receptor Modulator with Improved Selectivity, Endocrinology 146(9):3999-4008, 2005.
Korkmaz, Filiz, Byophysical Studies of Progesterone-Model Membrane Interactions, Thesis, Grad. School of Nat. and App. Sci. of the Middle East Tech. University, Sep. 2003.
Kotiyan, P.N., Stability indicating HPTLC method for the estimation of estradiol, Journal of Pharmaceutical and Biomedical Analysis, vol. 22 pp. 667-671, 2000, Elsevier.
Krzyminiewski, R, et al., EPR Study of the Stable Radical in a y-Irradiated Single Crystal of Progesterone, Jour. of Mag. Resonance, vol. 46 pp. 300-305, 1982, Academic Press.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier (abstract only).

(56) References Cited

OTHER PUBLICATIONS

Kuhnert-Brandstaetter and Grimm. Zur Unterscheidung von losungsmittelhaltigen pseudopolymorphen Kristallformen and polymorphen Modifikationen bei Steroidhormonen.II, Mikrochimica Acta, vol. 1, pp. 127-139, 1968.

Kuhnert-Brandstaetter and Junger and Kofler. Thermo-microscopic and spectrophotometric: Determination of steroid hormones, Microchemical Journal 9, pp. 105-133, 1965.

Kuhnert-Brandstaetter and Kofler. Zur mikroskopischen Identitatsprufung and zur Polymorphie der Sexualhormone, Mikrochimica Acta, vol. 6, pp. 847-853, 1959.

Kuhnert-Brandstaetter and Linder. Zur Hydratbildung bei Steroidhormonen, Sci. Pharm, vol. 41(2), pp. 109-116, 1973.

Kumasaka et al., Effects of Various Forms of Progestin on the Estrogen-Primed, Ovariectomized Rat, Endocrine Journal 1994, 41(2), 161-169.

Kuon et al., A Novel Optical Method to Assess Cervical Changes during Pregnancy and Use to Evaluate the Effects of Progestins on Term and Preterm Labor, Am J Obstet Gynecol. Jul. 2011 ; 205(1): 82.e15-82.e20.

Kuon et al., Actions of progestins for the inhibition of cervical ripening and uterine contractions to prevent preterm birth, FVV in OBGYN, 2012, 4 (2): 110-119.

Kuon et al., Pharmacological actions of progestins to inhibit cervical ripening and prevent delivery depend upon their properties, the route of administration and the vehicle, Am J Obstet Gynecol. May 2010 ; 202(5): 455.e1-455.e9.

Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.

Lacey, J.V. Jr., The WHI ten year's later: An epidemiologist's view, J. Steroid Biochem. Mol. Biol. (2013), Elsevier.

Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.

Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.

Land, Laura M, The influence of water content of triglyceride oils on the solubility of steriods, Pharmaceutical Research, vol. 22(5) May 2005, Springer Science+Business Media.

Lane, Majella E., "Skin penetration enhancers," International Journal of Pharmaceutics 447 (2013) 12-21.

Lauer et al., "Evaluation of the hairless rat as a model for in vivo percutaneous absorption," Journal of Pharmaceutical Sciences, vol. 86, No. 1, Jan. 1997, pp. 13-18.

Leonetti et al., Transdermal progesterone cream as an alternative progestin in hormone therapy, Alternative Therapies, Nov./Dec. 2005, vol. 11, No. 6, pp. 36-38.

Leonetti, Helene B, et al., Topical progesterone cream has an antiproliferative effect on estrogen-stimulated endometrium, Fertility and Sterility, vol. 79(1), Jan. 2003.

Lewis, John G. et al., Caution on the use of saliva measurements to monitor absorption of progesterone from transdermal creams in postmenopausal women, Maturitas, The European Menopause Journal, vol. 41, pp. 1-6, 2002.

Li, Guo-Chian, Solid-state NMR analysis of steroidal conformation of 17a- and 17B-estradiol in the absence and presence of lipi . . . , Steroids, Elsevier, vol. 77, pp. 185-192, 2012.

Lindmark, Tuulikki et al., "Absorption Enhancement through Intracellular Regulation of Tight Junction Permeability by Medium Chain Fatty Acids in Caco-2 Cells," JPET 284(1):362-369, 1998.

Lindmark, Tuulikki et al., "Mechanisms of Absorption Enhancement by Medium Chain Fatty Acids in Intestinal Epithelial Caco-2 Cell Monolayers," JPET 275(2):958-964, 1995.

Lobo, R.A., Foreword, J. Steroid Biochem. Mol. Biol. (2014), Elsevier.

Lopes, Luciana B. et al., Enhancement of transdermal delivery of progesterone using medium-chain mono and diglycerides as skin penetration enhancers, Pharmaceutical Development and Technology, 14:5, 524-529, Mar. 2009.

López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.

Lucy et al., Gonadotropin-releasing hormone at estrus: lutenizing hormone, estradiol, and progesterone during . . . Biol Reprod Sep. 1986;35(2):300-311 (abstract only).

Lvova, M. SH., et al., Thermal Analysis in the Quality Control and Standardization of Some Drugs, J Thermal Anal., vol. 40 pp. 405-411, 1993, Wiley.

Mac Bride, Maire B. et al., "Vulvovaginal Atrophy," Mayo Clin Proc, Jan. 2010, 85(1):87-94.

Madishetti et al., Development of domperidone bilayered matrix type transdermal patches: physicochemical, in vitro and ex vivo characterization, DARU vol. 18, No. 3, 2010, pp. 221-229.

Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.

Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.

McGuffy, Irena, Softgel Technology as a Lipid-Based Delivery Tool for Bioavailability Enhancement, Catalent Pharma Solutions, Somerset, NJ, Mar. 2011.

Mesley, R.J., Clathrate Formation from Steroids, Chemistry and Industry, vol. 37 pp. 1594-1595, Sep. 1965.

Miao, Wenbin, et al., Chemical Properties of Progesterone, SciFinder, 2014, American Chemical Society & US Natl. Lib. of Med.

Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.

Miller et al., Safety and Feasibility of Topical Application of Limonene as a Massage Oil to the Breast, Journal of Cancer Therapy, 2012, 3, 749-754.

Monti, D. et al., Effect of different terpene-containing essential oils on permeation of estradiol through hairless mouse skin, International Journal of Pharmaceutics, 237:209-24, 2002.

Mueck, A.O. et al., Genomic and non-genomic actions of progestogens in the breast, J. Steroid Biochem. Mol.Biol. (2013), Elsevier.

Muramatsu, Mitsuo, Thermodynamic Relationship between a- and B-Forms of Crystalline Progesterone, J. Pharmaceutical Sciences, vol. 68(2) pp. 175-178, 1979, Amer. Pharm. Assoc.

Ng, Jo-Han et al., Advances in biodiesel fuel for application in compression ignition engines, Clean Techn Environ Policy, vol. 12, pp. 459-493, 2010, Springer-Verlag.

Nicklas, Martina, Preparation and characterization of marine sponge collagen nanoparticles and employment for the trans . . . , Drug Devel. & Indust. Pharmacy,35(9) pp. 1035, 2009.

Nilsson et al., Analysis of Contact Allergenic Compounds in Oxidized d-Limonene, Chromatographia vol. 42, No. 3/4, Feb. 1996, pp. 199-205.

Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.

NuGen, What is NuGen HP Hair Growth System.

NuGest900, NuGest 900™.

O'Leary, Peter, Salivary, but not serum or urinary levels of progesterone are elevated after topical application of progersterone cream to pre-and post-menopausal women, Clinical Endocrinology, vol. 53 pp. 615-620, Blackwell Science 2000.

Opinion on the Diethylene Glycol Momoethyl Ether (DEGEE), Scientific Committee on Consumer Products, Dec. 19, 2006, 27 pages.

Outterson, K., The Drug Quality and Security Act—Mind the Gaps, n engl j med 370;2 nejm.org Jan. 9, 2014, pp. 97-99.

(56) References Cited

OTHER PUBLICATIONS

Pachman et al., "Management of menopause-associated vasomotor symptoms: current treatment options, challenges and future directions," International Journal of Women's Health, May 7, 2010.
Palamakula et al., Preparation and in Vitro Characterization of Self-Nanoemulsified Drug Delivery Systems of Coenzyme Q10 Using Chiral Essential Oil Components, Pharmaceutical Technology Oct. 2004, pp. 74-88.
Panay et al., The 2013 British Menopause Society & Women's Health Concern recommendations on hormone replacement therapy, Menopause International: The Integrated Journal of Postreproductive Health, published online May 23, 2013, Sage Publications. http://min.sagepub.com/content/early/2013/05/23/1754045313489645. 1.
Panchangnula et al., Development and evaluation of an intracutaneous depot formulation of corticosteroids using Transcutol . . . , J Pharm Pharmacol. Sep. 1991;43(9):609-614 (abstract only).
Parasuraman et al., Blood sample collection in small laboratory animals, Journal of Pharmacology & Pharmacotherapeutics | Jul.-Dec. 2010 | vol. 1 | Issue 2, pp. 87-93.
Park, Jeong-Sook, Solvent effects on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Patel et al., Transdermal Drug Delivery System: A Review, www.thepharmajournal.com, vol. 1, No. 4, 2012, pp. 78-87.
Payne, R.S., et al., Examples of successful crystal structure prediction: polymorphs of primidone and progesterone, Intl. Jour. of Pharma., vol. 177 pp. 231-245, 1999, Elsevier.
PCCA, Apothogram, PCCA, May 2014, Houston, TX.
Persson, Linda C, et al., Physicochemical Properties of Progesterone Selecte, SciFinder, pp. 1-5, Feb. 24, 2014, American Chem. Society & US Natl. Lib. of Med.
Pfaus et al., Selective facilitation of sexual solicitation in the female rat by a melanocortin receptor agonist, PNAS, Jul. 6, 2004, vol. 101, No. 27, pp. 10201-10204.
Pheasant, Richard, Polymorphism of 17-Ethinylestradiol, Schering Corporation, Bloomfield, NJ, May 1950.
Pickles, VR, Cutaneous reactions to injection of progesterone solutions into the skin, Br Med Journal, Aug. 16, 1952, pp. 373-374.
Pinkerton et al., What are the concerns about custom-compounded "bioidentical" hormone therapy? Menopause: The Journal of the North American Menopause Society, vol. 21, No. 12, 2014,pp. 1-3.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Portman, David et al., One-year treatment persistence with local estrogen therapy in postmenopausal women diagnosed as having vaginal atrophy, Menopause, vol. 22, No. 11, 2015, pp. 000/000 (8 pages).
Position Statement, Management of symptomatic vulvovaginal atrophy: 2013 position statement of the North American Menopause Society (NAMS), Menopause, vol. 20, No. 9, pp. 888-902.
Potluri, Praveen and Gum V. Betageri, "Mixed-micellar proliposomal systems for enhanced oral delivery of progesterone," Drug Delivery, 2006, vol. 13, No. 3, pp. 227-232.
Practice Bulletin No. 141, Management of Menopausal Symptoms, Obstetrics & Gynecology, ACOG, vol. 123, No. 1, Jan. 2014, pp. 202-216.
Prajapati Hetal N. et al., "A Comparative Evaluation of Mono-, Di- and Triglyceride of Medium Chain Fatty Acids by Lipid/Surfactant/ Water Phase Diagram, Solubility Determination and Dispersion Testing for Application in Pharmaceutical Dosage Form Development," Pharm Res. Jan. 2012; 29(1): 285-305. Published online Aug. 23, 2011. doi: 10.1007/s11095-011-0541-3.

Prajapati Hetal N. et al., "Effect of Difference in Fatty Acid Chain Lengths of Medium-Chain Lipids on Lipid/Surfactant/Water Phase Diagrams and Drug Solubility," J. Excipients and Food Chem. 2 (3) 2011:73-88.
Prajapati, Hetal N, et al., A comparative Evaluation of Mono-, Di- and Triglyceride of Medium Chain Fatty Acids by Lipid/Surfactant/ Water, Springerlink.com, pp. 1-21, Apr. 2011.
Prausnitz et al., Transdermal drug delivery, Nat Biotechnol. Nov. 2008 ; 26(11): 1261-1268.
Price, Sarah L, The computational prediction of pharmaceutical crystal structures and polymorphism, Adv. Drug Delivery Reviews, vol. 56 pp. 301-319, 2004, Elsevier.
Product Information Sheet, Body Ballance Cream, Tahitian Noni International, 2013, 1 page.
Product Safety Assessment: Diethylene Glycol Monoethyl Ether, Created: Sep. 24, 2007 The Dow Chemical Company Page, 5 pages.
Progesterone, The Merck Index Online, Royal Society of Chemistry, 2013, search Feb. 17, 2017.https ://www.rsc.org/Merck-Index/ monograph/print/mono1500007889/progesterone?q=authorize.
Progynova TS 100, available online at file:///C:/Users/Call%20Family/ Desktop/Progynova%20TS%20100%2012%20Patches_Pack%20% 28Estradiol%20Hemihydrate%29.html, 2010.
Provider Data Sheet, About Dried Blood Spot Testing, ZRT Laboratory, 2014, 3 pages.
Rahn et al., Vaginal Estrogen for Genitourinary Syndrome of Menopause a Systematic Review, Obstet Gynecol 2014;124(6): 1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.
Rao, R. et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability, 7(2):095-107, 2015.
Reisman et al., Topical Application of the Synthetic Triterpenoid RTA 408 Protects Mice from Radiation-Induced Dermatitis, Radiation Research 181, 512-520 (2014).
Rosilio, V, et al., Physical Aging of Progesterone-Loaded Poly(D,L,- lactide-co-glycolide) Microspheres, Pharmaceutical Research, vol. 15(5) pp. 794-799,1998, Plenum Pub. Corp.
Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Sallee, Verney L. et al., "Determinants of intestinal mucosal uptake of short- and medium-chain fatty acids and alcohols," Journal of Lipid Research, 1973, vol. 14, 475-484.
Salole, Eugene G., Estradiol, Analytical Profiles of Drug Substances, vol. 15, pp. 283-318, 1986.
Salole, Eugene G., The physicochemical properties of oestradiol, Journal of Pharmaceutical & Biomedical Analysis, vol. 5, No. 7, pp. 635-648, 1987.
Santen, R.J., Menopausal hormone therapy and breast cancer, J. Steroid Biochem. Mol. Biol. (2013), Elsevier.
Santen, RJ, Vaginal administration of estradiol: effects of dose, preparation and timing on plasma estradiol levels, CLIMACTERIC 2014;17:1-14.
Sarkar, Basu, et al., Chemical Stability of Progesterone in Compounded Topical Preparations using PLO Transdermal Cream™ and HRT Cream™ Base . . . , J Steroids Horm Sci, 4:2, 2013.
Sarpal, K. et al., "Self emulsifying drug delivery systems: a strategy to improve oral bioavailability," Current Research & Information on Pharmaceuticals Sciences (CRIPS), 2010, vol. 11, No. 3, pp. 42-49.
Sarrel, et al., The Mortality Toll of Estrogen Avoidance: An Analysis of Excess Deaths Among Hysterectomized Women Aged 50 to 59 Years, American Journal of Public Health, Research and Practice, e1-e6. Published online ahead of print Jul. 18, 2013.

(56) References Cited

OTHER PUBLICATIONS

Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague—Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Search Report, Extended European Search Report for EP13741053.6, dated Jul. 1, 2015.
Search Report, Extended European Search Report for EP13807188.1, dated Nov. 23, 2015.
Search Report, International Search Report and Written Opinion for PCT/US12/66406, dated Jan. 24, 2013.
Search Report, International Search Report and Written Opinion for PCT/US13/23309, dated Apr. 9, 2013.
Search Report, International Search Report and Written Opinion for PCT/US13/46442, dated Nov. 1, 2013.
Search Report, International Search Report and Written Opinion for PCT/US13/46443, dated Oct. 31, 2013.
Search Report, International Search Report and Written Opinion for PCT/US13/46444, dated Oct. 31, 2013.
Search Report, International Search Report and Written Opinion for PCT/US13/46445, dated Nov. 1, 2013.
Search Report, International Search Report and Written Opinion for PCT/US14/61811, dated Jan. 21, 2015.
Search Report, International Search Report and Written Opinion for PCT/US15/23041, dated Jun. 30, 2015.
Search Report, International Search Report and Written Opinion for PCT/US15/42621, dated Oct. 29, 2015.
Serantoni, Foresti, et al., 4-Pregnen-3,20-dione (progesterone, form II), Crystal Structure Comm., vol. 4(1) pp. 189-192, 1975, CAPLUS Database.
Shao et al., Review Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Sharma, H.C., et al., Physical Properties of Progesterone Selected Refer, SciFinder, pp. 1-5, Feb. 24, 2014, American Chem. Society & US Natl. Lib. of Med.
Shrier et al., "Mucosal Immunity of the Adolescent Female Genital Tract," Journal of Adolescent Health, 2003; 32:183-186.
Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.
Siew, Adeline, moderator, Bioavailability Enhancement with Lipid-Based Drug-Delivery Systems, Pharmaceutical Technology, Aug. 2014, pp. 28, 30-31.
Sigma-Aldrich, Progesterone-Water Soluble: powder, BioReagent, suitable for cell culture), MSDS available online: http://www.sigmaaldrich.com/catalog/product/sigma/p7556.
Simon et al., Effective Treatment of Vaginal atrophy with an Ultra-low-dose estradiol vaginal tablet, Obstetrics & Gynocology, vol. 112, No. 5, Nov. 2008, pp. 1053-1060.
Simon, James A., What if the Women's Health Initiative had used transdermal estradiol and oral progesterone instead? Menopause: The Journal of the North American Menopause Society, 2014, vol. 21, No. 7, pp. 1-15.
Sitruk-Ware et al., Progestogens in hormonal replacement therapy: new molecules, risks, and benefits, Menopause: The Journal of the North American Menopause Society. vol. 9, No. 1, pp. 6-15, 2002.
Sitruk-Ware, Regine, "Pharmacological profile of progestins," Maturitas 47 (2004) 277-283.
Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.
Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.
Smyth et al., Summary of Toxicological Data, a 2-Yr Study of Diethylene Glycol Monoethyl Ether in Rats, Fd Cosmet. Toxicol. vol. 2, pp. 641-642, 1964.
Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of the North American Menopause Society, 2005, vol. 12, No. 2, pp. 232-237.
Stanczyk, F.Z. et al., Ethinyl estradiol and 17⊕-estradiol in combined oral contraceptives: pharmacokinetics, pharmacodynamics and risk assessment, Contraception 87 (Jun. 2013) vol. 87, No. 6, pp. 706-727.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014;17 (Suppl 2):8-11.
Stanczyk, F.Z., Bhavnani, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stephenson et al., "Transdermal progesterone: Effects on Menopausal symptoms and on thrombotic, anticoagulant, and inflanunatory factors in postmenopausal women," Int J Pharmaceutical Compounding, vol. 12, No. 4, Jul./Aug. 2008, pp. 295-304.
Strickley, Robert T., Solubilizing excipients in oral and injectable formulations, Pharmaceutical Research Feb. 2004, vol. 21, Issue 2, pp. 201-230 (abstract only).
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M. et al., The light sensitivity of corticosteroids in crystalline form, Pharmaceutica acta Helvetiae, vol. 66 (5-6) pp. 137-140, 1991, Hardin Library.
Tan, Melvin S. et al., A Sensitive Method for the Determination of Progesterone in Human Plasma by LC-MS-MS, M1025, Cedra Corporation, Austin, Texas.

(56) References Cited

OTHER PUBLICATIONS

Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.
Tripathi, R, et al., Study of Polymorphs of Progesterone by Novel Melt Sonocrystallization Technique: A Technical Note, AAPS PhamSciTech, vol. 11, No. 3, Sep. 2010.
Trommer et al., Overcoming the stratum Corneum: The modulation of Skin Penetration, Skin Pharmacol Physiol 2006;19:106-121.
Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
USP, 401 Fats and Fixed Oils, Chemical Tests, Second Suplement to USP36-NF 31, pp. 6141-6151, 2013.
USP, Certificate-Corn Oil, Lot G0L404, Jul. 2013.
USP, Lauroyl Polyoxylglycerides, Safety Data Sheet, US, 5611 Version #02, pp. 1-9, 2013.
USP, Monographs: Progesterone, USP29, www.pharmacopeia.cn/v29240/usp29nf24s0_m69870.html, search done: Feb. 25, 2014.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
USPTO US12561515 Dec. 12, 2011 Non-Final Office Action.
USPTO US12561515 Oct. 26, 2012 Final Office Action.
USPTO US12561515 Sep. 11, 2013 Notice of Allowance.
USPTO US13684002 Mar. 20, 2013 Non-Final Office Action.
USPTO US13684002 Jul. 16, 2013 Final Office Action.
USPTO US13684002 Dec. 6, 2013 Notice of Allowance.
USPTO US13843362 Mar. 16, 2015 Restriction Requirement.
USPTO US13843428 Apr. 14, 2015 Restriction Requirement.
USPTO US13843428 Jul. 2, 2015 Non-Final Office Action.
USPTO_US14099545_Feb. 18, 2014_Non_Final_Office_Action.
USPTO_US14099545_Jul. 14, 2014_Notice_of_Allowance.
USPTO_US14099562_Feb. 20, 2014_Restriction_Requirement.
USPTO_US14099562_Mar. 27, 2014_Non-Final_Office_Action.
USPTO_US14099562_Jul. 2, 2014_Final_Office_Action.
USPTO_US14099562_Dec. 10, 2014_Notice_of_Allowance.
USPTO_US14099571_Mar. 28, 2014_Restriction_Requirement.
USPTO_US14099571_Jul. 15, 2014_Notice_of_Allowance.
USPTO_US14099582_Apr. 29, 2014_Restriction_Requirement.
USPTO_US14099582_Jun. 17, 2014_Non-Final_Office_Action.
USPTO_US14099582_Nov. 7, 2014_Notice_of_Allowance.
USPTO_US14099582_Jan. 22, 2015_Notice_of_Allowance.
USPTO_US14099598_May 13, 2014_Restriction_Requirement.
USPTO_US14099598_Jul. 3, 2014_Non-Final_Office_Action.
USPTO_US14099598_Dec. 10, 2014_Notice_of_Allowance.
USPTO_US14099612_Mar. 20, 2014_Restriction_Requirement.
USPTO_US14099612_Oct. 30, 2014_Non-Final_Office_Action.
USPTO_US14099612_Nov. 26, 2014_Notice_of_Allowance.
USPTO_US14099623_Mar. 5, 2014_Restriction_Requirement.
USPTO_US14099623_Jul. 18, 2014_Non-Final_Office_Action.
USPTO_US14099623_Dec. 15, 2014_Notice_of_Allowance.
USPTO_US14106655_Jul. 3, 2014_Restriction_Requirement.
USPTO_US14106655_Dec. 8, 2014_Non-Final_Office_Action.
USPTO US14106655 Jun. 19, 2015 Final Office Action.
USPTO_US14125554_Dec. 5, 2014_Restriction_Requirement.
USPTO_US14125554_Apr. 14, 2015_Non-Final_Office_Action.
USPTO_US14136048_Nov. 4, 2014_Restriction_Requirement.
USPTO_US14136048_Mar. 12, 2015_Non-Final_Office_Action.
USPTO_US14475814_Oct. 1, 2014_Non-Final_Office_Action.
USPTO_US14475814_Feb. 13, 2015_Notice_of_Allowance.
USPTO_US14475864_Oct. 2, 2014_Non-Final_Office_Action.
USPTO_US14475864_Feb. 11, 2015_Notice_of_Allowance.
USPTO_US14521230_Dec. 5, 2014_Restriction_Requirement.
USPTO_US14521230_Feb. 18, 2015_Non-Final_Office_Action.
USPTO_US14624051_Apr. 7, 2015_Non-Final_Office_Action.
USPTO_US14690955_Feb. 1, 2016_Non-Final_Office_Action.
Utian, Wulf H, et al., Relief of vasomotor symptoms and vaginal atrophy with lower doses of conjugated equine estrogens, Fertility and Sterility, vol. 75(6) pp. 1065, Jun. 2001.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone in the Pregnant Rat: Absence of a Physiological Role for the Lung, Biology of Reproduction 40, 1188-1193 (1989).
Walter et al., The role of progesterone in endometrial angiogenesis in pregnant and ovariectomised mice, Reproduction (2005) 129 765-777.
Weber, E.J., Corn Lipids, Cereal Chem., vol. 55(5), pp. 572-584, The American Assoc of Cereal Chem, Sep.-Oct. 1978.
Weber, M.T., et al., Cognition and mood in perimenopause: A systematic review and meta-analysis, J. Steroid Biochem. Mol. Biol. (2013), Elsevier.
Weintraub, Arlene, "Women fooled by untested hormones from compounding pharmacies,"Forbes, Feb. 20, 2015; retrieved online at http://onforb.es/IL1Um1V_on Feb. 23, 2015, 3 pages.
Whitehead et al., Absorption and metabolism of oral progesterone, The British Medical Journal, vol. 280, No. 6217 (Mar. 22, 1980), pp. 825-827, BMJ Publishing Group.
Wiranidchapong, Chutima, Method of preparation does not affect the miscibility between steroid hormone and polymethacrylate, Thermochimica Acta 485, Elsevier, pp. 57, 2009.
Wood et al., Effects of estradiol with micronized progesterone or medroxyprogesterone acetate on risk markers for breast cancer in postmenopausal monkeys, Breast Cancer Res Treat (2007) 101:125-134.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, 2003, pp. 1110-1111, CRC Press, Boca Raton, London, New York, Wash. D.C.
Yue, W., Genotoxic metabolites of estradiol in breast: potential mechanism of estradiol induced carcinogenesis, Journal of Steroid Biochem & Mol Biology, vol. 86 pp. 477-486, 2003.
Zava, David T. et al., Percutaneous absorption of progesterone, Maturitas 77 (2014) 91-92, Elsevier.

(56) References Cited

OTHER PUBLICATIONS

Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.
U.S. Appl. No. 13/843,362, filed Mar. 15, 2013.
U.S. Appl. No. 14/106,655, filed Dec. 13, 2013.
U.S. Appl. No. 14/512,046, filed Oct. 10, 2014.
U.S. Appl. No. 14/521,002, filed Oct. 22, 2014.
U.S. Appl. No. 14/521,230, filed Oct. 22, 2014.
U.S. Appl. No. 14/649,818, filed Jun. 18, 2013.
U.S. Appl. No. 14/690,913, filed Apr. 20, 2015.
U.S. Appl. No. 14/690,955, filed Apr. 20, 2015.
U.S. Appl. No. 14/719,933, filed May 22, 2015.
U.S. Appl. No. 14/812,179, filed Jul. 29, 2015.
U.S. Appl. No. 14/830,398, filed Aug. 19, 2015.
U.S. Appl. No. 15/090,493, filed Apr. 4, 2016.
U.S. Appl. No. 15/372,385, filed Dec. 7, 2016.
U.S. Appl. No. 15/420,019, filed Jan. 30, 2017.
U.S. Appl. No. 15/475,052, filed Mar. 30, 2017.
U.S. Appl. No. 15/475,068, filed Mar. 30, 2017.
U.S. Appl. No. 15/832,750, filed Dec. 5, 2017.
U.S. Appl. No. 15/832,757, filed Dec. 5, 2017.
U.S. Appl. No. 15/893,542, filed Feb. 9, 2018.
U.S. Appl. No. 15/893,546, filed Feb. 9, 2018.
U.S. Appl. No. 15/893,550, filed Feb. 9, 2018.
Ettinger et al., "Measuring symptom relief in studies of vaginal and vulvar atrophy: the most bothersome symptom approach," Menopause, vol. 15, No. 5, 2008, pp. 885-889.
Eugster-Hausmann et al., "Minimized estradiol absorption with ultra-low-dose 10 µg 17β-estradiol vaginal tablets," Climacteric 2010;13:219-227.
Regidor, P., "Progesterone in Pen- and Postmenopause: A Review," Geburtshilfe Frauenheilkd, Nov. 2014 74(11):995-1002.
Simon, James A. et al., "A vaginal estradiol softgel capsule, TX-004HR, has negligible to verylow systemic absorption of estradiol: Efficacy and pharmacokineticdata review," Maturitas 99 (2017) 51-58.
Stefanick, "Estrogens and progestins: background and history, trends in use, and guidelines and regimens approved by the US Food and Drug Administration," The American Journal of Medicine (2005) vol. 118 (12B), 64S-73S.

\* cited by examiner

*P<0.05; †P=0.0019 vs placebo.

*P<0.0013; †P=0.0003 vs placebo.

P=0.0085 vs placebo.

*P=0.0073 vs placebo.

VAGINAL INSERTED ESTRADIOL PHARMACEUTICAL COMPOSITIONS AND METHODS

CROSS-REFERENCES TO RELATED APPLICATIONS

The present application is a continuation of U.S. patent application Ser. No. 15/372,385, filed Dec. 7, 2016, which is a continuation-in-part of U.S. patent application Ser. No. 14/521,230, filed Oct. 22, 2014, and which claims priority to U.S. Provisional Pat. Appl. No. 62/264,309, filed Dec. 7, 2015; U.S. Provisional Pat. Appl. No. 62/296,552, filed Feb. 17, 2016; U.S. Provisional Pat. Appl. No. 62/324,838, filed Apr. 19, 2016; U.S. Provisional Pat. Appl. No. 62/329,940, filed Apr. 29, 2016; and U.S. Provisional Pat. Appl. No. 62/348,820, filed Jun. 10, 2016; which applications are incorporated herein by reference in their entirety.

FIELD OF THE INVENTION

This application is directed to pharmaceutical compositions, methods, and devices related to hormone replacement therapy.

BACKGROUND OF THE INVENTION

Postmenopausal women frequently suffer from atrophic vaginitis or vulvar and vaginal atrophy (hereinafter "vulvovaginal atrophy" or "VVA") with symptoms including, for example, vaginal dryness, vaginal odor, vaginal or vulvar irritation or itching, dysuria (pain, burning, or stinging when urinating), dyspareunia (vaginal pain associated with sexual activity), or vaginal bleeding associated with sexual activity. Other symptoms include soreness; with urinary frequency and urgency; urinary discomfort and incontinence also occurring ("estrogen-deficient urinary state(s)"). One symptom of vaginal atrophy is an increased vaginal pH, which creates an environment more susceptible to infections. The mucosal epithelium of the VVA patients also reported to show signs of severe atrophy and upon cytological examination accompanied by an increased number of the parabasal cells and a reduced number of superficial cells.

Each of these VVA-related states manifest symptoms associated with decreased estrogenization of the vulvovaginal tissue, and can even occur in women treated with oral administration of an estrogen-based pharmaceutical drug product. Although VVA is most common with menopausal women, it can occur at any time in a woman's life cycle. VVA symptoms also interfere with sexual activity and satisfaction. Women with female sexual dysfunction (FSD) are almost 4 times more likely to have VVA than those without FSD.

Estrogen treatment has proven to be very successful in controlling menopausal symptoms, including VVA and FSD. Several studies have shown that the symptoms connected with vaginal atrophy are often relieved by estrogen treatment given either systemically or topically. The existing treatments have numerous problems, for example compliance issues with patients not completing or continuing treatment due to the problems associated with the form of treatment.

Accordingly, there remains a need in the art for treatments for VVA and FSD that overcome these limitations.

BRIEF SUMMARY OF THE INVENTION

Disclosed herein is, among other things, a new soft gel vaginal pharmaceutical composition and dosage form containing solubilized estradiol for the treatment of VVA. The soft gel vaginal pharmaceutical composition has been designed to mitigate common limitations found with other vaginal forms of estradiol. The soft gel vaginal pharmaceutical composition eases vaginal administration, provides improved safety of insertion, minimizes vaginal discharge following administration, and provides a more effective dosage form having improved efficacy, safety and patient compliance.

According to various aspects and embodiments of this disclosure, a soft gel vaginal pharmaceutical composition as a treatment for post-menopausal women suffering with moderate to severe symptoms of VVA is provided.

Provided herein is a suppository comprising: a) a therapeutically effective amount of estradiol; and b) a solubilizing agent comprising a medium chain oil.

In some embodiments, the suppository includes about 1 µg to about 25 µg of estradiol. For example, the suppository can include about 1 µg to about 10 µg of estradiol; and about 10 µg to about 25 µg of estradiol.

In some embodiments, the estradiol is solubilized.

In some embodiments, the medium chain oil includes at least one C6-C12 fatty acid or a glycol, monoglyceride, diglyceride, or triglyceride ester thereof.

In some embodiments, the solubilizing agent includes at least one ester selected from the group consisting of: an ester of caproic fatty acid, an ester of caprylic fatty acid, an ester of capric fatty acid, and combinations thereof. For example, the solubilizing agent can include a caprylic/capric triglyceride.

In some embodiments, the suppository further includes a capsule. For example, the capsule can be a soft gelatin capsule.

Also provided herein is a suppository comprising: a) a therapeutically effective amount of estradiol; b) a caprylic/capric triglyceride; c) a non-ionic surfactant comprising PEG-6 palmitostearate and ethylene glycol palmitostearate; and d) a soft gelatin capsule.

In some embodiments, a suppository provided herein includes about 25 µg of estradiol, wherein administration of the suppository to a patient provides, in a plasma sample from the patient: 1) a corrected geometric mean peak plasma concentration ($C_{max}$) of estradiol of about 19 pg*hr/mL to about 29 pg*hr/mL; and 2) a corrected geometric mean area under the curve ($AUC$)$_{0-24}$ of estradiol of about 75 pg*hr/mL to about 112 pg*hr/mL.

In some embodiments, a suppository provided herein includes about 25 µg of estradiol, wherein administration of the suppository to a patient provides, in a plasma sample from the patient: 1) a corrected geometric mean peak plasma concentration ($C_{max}$) of estrone of about 9 pg*hr/mL to about 14 pg*hr/mL; and 2) a corrected geometric mean area under the curve ($AUC$)$_{0-24}$ of estrone of about 43 pg*hr/mL to about 65 pg*hr/mL.

In some embodiments, a suppository provided herein includes about 25 µg of estradiol, wherein administration of the suppository to a patient provides, in a plasma sample from the patient: 1) a corrected geometric mean peak plasma concentration ($C_{max}$) of estrone sulfate of about 416 pg*hr/mL to about 613 pg*hr/mL; and 2) a corrected geometric mean area under the curve ($AUC$)$_{0-24}$ of estrone sulfate of about 3598 pg*hr/mL to about 5291 pg*hr/mL.

In some embodiments, a suppository provided herein includes about 10 µg of estradiol, wherein administration of the suppository to a patient provides, in a plasma sample from the patient: 1) a corrected geometric mean peak plasma concentration ($C_{max}$) of estradiol of about 12 pg*hr/mL to about 18 pg*hr/mL; and 2) a corrected geometric mean area under the curve $(AUC)_{0-24}$ of estradiol of about 42 pg*hr/mL to about 63 pg*hr/mL. In some embodiments, the suppository further provides a corrected geometric mean time to peak plasma concentration $(T_{max})$ of estradiol of about 1 hrs to about 3 hrs.

In some embodiments, a suppository provided herein includes about 10 µg of estradiol, wherein administration of the suppository to a patient provides, in a plasma sample from the patient: 1) a corrected geometric mean peak plasma concentration $(C_{max})$ of estrone of about 4 pg*hr/mL to about 7 pg*hr/mL; and 2) a corrected geometric mean area under the curve $(AUC)_{0-24}$ of estrone of about 20 pg*hr/mL to about 31 pg*hr/mL. In some embodiments, the suppository further provides a corrected geometric mean time to peak plasma concentration $(T_{max})$ of estrone of about 4 hrs to about 8 hrs.

In some embodiments, a suppository provided herein includes about 10 µg of estradiol, wherein administration of the suppository to a patient provides, in a plasma sample from the patient: 1) a corrected geometric mean peak plasma concentration $(C_{max})$ of estrone sulfate of about 10 pg*hr/mL to about 16 pg*hr/mL; and 2) a corrected geometric mean area under the curve $(AUC)_{0-24}$ of estrone sulfate of about 56 pg*hr/mL to about 84 pg*hr/mL. In some embodiments, the suppository further provides a corrected geometric mean time to peak plasma concentration $(T_{max})$ of estrone sulfate of about 4 hrs to about 7 hrs.

In some embodiments, a suppository provided herein includes about 4 µg of estradiol, wherein administration of the suppository to a patient provides, in a plasma sample from the patient: 1) a corrected geometric mean peak plasma concentration $(C_{max})$ of estradiol of about 4 pg*hr/mL to about 8 pg*hr/mL; and 2) a corrected geometric mean area under the curve $(AUC)_{0-24}$ of estradiol of about 16 pg*hr/mL to about 26 pg*hr/mL. In some embodiments, the suppository further provides a corrected geometric mean time to peak plasma concentration $(T_{max})$ of estradiol of about 0.25 hrs to about 2 hrs.

In some embodiments, a suppository provided herein includes about 4 µg of estradiol, wherein administration of the suppository to a patient provides, in a plasma sample from the patient: 1) a corrected geometric mean peak plasma concentration $(C_{max})$ of estrone of about 1 pg*hr/mL to about 3 pg*hr/mL; and 2) a corrected geometric mean area under the curve $(AUC)_{0-24}$ of estrone of about 8 pg*hr/mL to about 13 pg*hr/mL. In some embodiments, the suppository further provides a corrected geometric mean time to peak plasma concentration $(T_{max})$ of estrone of about 1 hrs to about 4 hrs.

In some embodiments, a suppository provided herein includes about 4 µg of estradiol, wherein administration of the suppository to a patient provides, in a plasma sample from the patient: 1) a corrected geometric mean peak plasma concentration $(C_{max})$ of estrone sulfate of about 4 pg*hr/mL to about 7 pg*hr/mL; and 2) a corrected geometric mean area under the curve $(AUC)_{0-24}$ of estrone sulfate of about 22 pg*hr/mL to about 34 pg*hr/mL. In some embodiments, the suppository further provides a corrected geometric mean time to peak plasma concentration $(T_{max})$ of estrone sulfate of about 1 hrs to about 3 hrs.

Also provided herein is a suppository comprising about 1 µg to about 25 µg of estradiol, wherein administration of the suppository to a patient provides a corrected geometric mean peak plasma concentration $(C_{max})$ of estradiol that is less than about 30 pg*hr/mL. For example, administration of the suppository to a patient provides a corrected geometric mean peak plasma concentration $(C_{max})$ of estradiol that is less than about 18 pg*hr/mL.

In some embodiments, a suppository comprising about 1 µg to about 25 µg of estradiol is provided, wherein administration of the suppository to a patient provides a corrected geometric mean area under the curve $(AUC)_{0-24}$ of estradiol that is less than about 112 pg*hr/mL. For example, administration of the suppository to a patient provides a corrected geometric mean area under the curve $(AUC)_{0-24}$ of estradiol that is less than about 63 pg*hr/mL.

In some embodiments, a suppository comprising about 1 µg to about 25 µg of estradiol is provided, wherein administration of the suppository to a patient provides a corrected geometric mean peak plasma concentration $(C_{max})$ of estrone that is less than about 14 pg*hr/mL. For example, administration of the suppository to a patient provides a corrected geometric mean peak plasma concentration $(C_{max})$ of estrone that is less than about 7 pg*hr/mL.

In some embodiments, a suppository comprising about 1 µg to about 25 µg of estradiol is provided, wherein administration of the suppository to a patient provides a corrected geometric mean area under the curve $(AUC)_{0-24}$ of estrone that is less than about 65 pg*hr/mL. For example, administration of the suppository to a patient provides a corrected geometric mean area under the curve $(AUC)_{0-24}$ of estrone that is less than about 31 pg*hr/mL.

In some embodiments, a suppository comprising about 1 µg to about 25 µg of estradiol is provided, wherein administration of the suppository to a patient provides a corrected geometric mean peak plasma concentration $(C_{max})$ of estrone sulfate that is less than about 613 pg*hr/mL. For example, administration of the suppository to a patient provides a corrected geometric mean peak plasma concentration $(C_{max})$ of estrone sulfate that is less than about 16 pg*hr/mL.

In some embodiments, a suppository comprising about 1 µg to about 25 µg of estradiol is provided, wherein administration of the suppository to a patient provides a corrected geometric mean area under the curve $(AUC)_{0-24}$ of estrone sulfate that is less than about 5291 pg*hr/mL. For example, administration of the suppository to a patient provides a corrected geometric mean area under the curve $(AUC)_{0-24}$ of estrone sulfate that is less than about 84 pg*hr/mL.

Further provided herein is a suppository comprising about 1 µg to about 25 µg of estradiol, wherein administration of the suppository to the proximal region of the vagina of a patient provides a therapeutically effective concentration of estradiol over 24 hours in the proximal region of the vagina.

This disclosure also provides a method of treating an estrogen-deficient state, the method comprising administering to a patient in need thereof, a suppository as provided herein. In some embodiments, a method of treating vulvovaginal atrophy is provided, the method comprising administering to a patient in need thereof, a suppository as provided herein.

In some embodiments of the methods provided herein, treatment includes reducing the severity of one or more symptoms selected from the group consisting of: vaginal dryness, dyspareunia, vaginal or vulvar irritation, vaginal or vulvar burning, vaginal or vulvar itching, dysuria, and vaginal bleeding associated with sexual activity.

In some embodiments of the methods provided herein treatment includes reducing the vaginal pH of the patient. For example, treatment includes reducing the vaginal pH of the patient to a pH of less than about 5.0.

In some embodiments of the methods provided herein treatment includes a change in cell composition of the patient. For example, the change in cell composition includes reducing the number of parabasal vaginal cells or increasing the number of superficial vaginal cells. In some embodiments, the number of parabasal vaginal cells in the patient are reduced by at least about 35% (e.g., at least about 50%). In some embodiments, the number of superficial vaginal cells are increased by at least about 5% (e.g., at least about 35%).

Further provided herein is a method for reducing vaginal discharge following administration of a suppository, the method comprising administering to a patient in need thereof, a suppository provided herein, wherein the vaginal discharge following administration of the suppository is compared to the vaginal discharge following administration of a reference drug.

Also provided herein is a method for treating female sexual dysfunction in a female subject in need thereof. The method includes administering to the subject a vaginal suppository as described herein. In some embodiments, the method includes administering to the subject a vaginal suppository comprising: (a) a pharmaceutical composition comprising: a therapeutically effective amount of estradiol; a caprylic/capric triglyceride; a non-ionic surfactant comprising PEG-6 palmitostearate and ethylene glycol palmitostearate; and (b) a soft gelatin capsule; wherein the vaginal suppository includes from about 1 microgram to about 25 micrograms of estradiol; wherein estradiol is the only active hormone in the vaginal suppository. In some embodiments, the vaginal suppository does not include a hydrophilic gel-forming bioadhesive agent in the solubilizing agent. In some embodiments, treating female sexual dysfunction includes increasing the subject's desire, arousal, lubrication, satisfaction, and or/orgasms.

BRIEF DESCRIPTION OF THE DRAWINGS

The above-mentioned features and objects of the this disclosure will become more apparent with reference to the following description taken in conjunction with the accompanying drawings wherein like reference numerals denote like elements and in which.

DETAILED DESCRIPTION OF THE INVENTION

Figure 1:
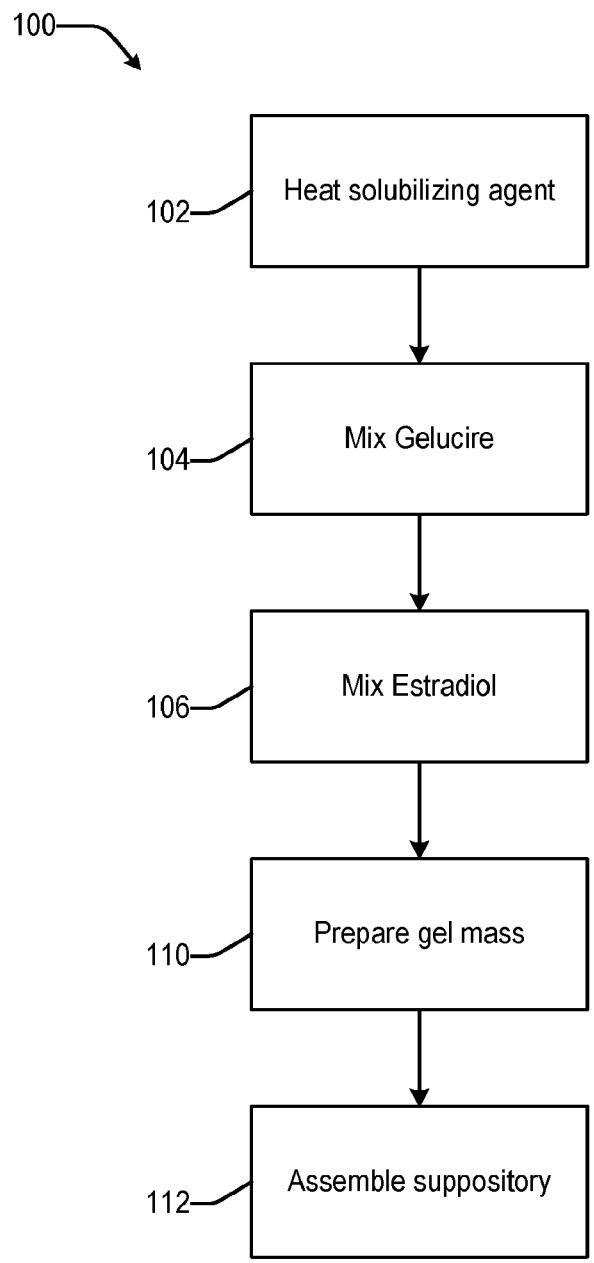
FIG. 1 is a flow diagram illustrating a process in accordance with various embodiments of the invention.

In the following detailed description of embodiments of this disclosure, reference is made to the accompanying drawings in which like references indicate similar elements, and in which is shown by way of illustration specific embodiments in which this disclosure may be practiced. These embodiments are described in sufficient detail to enable those skilled in the art to practice this disclosure, and it is to be understood that other embodiments may be utilized and that other changes may be made without departing from the scope of the this disclosure. The following detailed description is, therefore, not to be taken in a limiting sense, and the scope of this disclosure is defined only by the appended claims. As used in this disclosure, the term "or" shall be understood to be defined as a logical disjunction (i.e., and/or) and shall not indicate an exclusive disjunction unless expressly indicated as such with the terms "either," "unless," "alternatively," and words of similar effect.

I. Definitions

The term "active pharmaceutical ingredient" ("API") as used herein, means the active compound(s) used in formulating a drug product.

The term "co-administered" as used herein, means that two or more drug products are administered simultaneously or sequentially on the same or different days.

The term "drug product" as used herein means at least one active pharmaceutical ingredient in combination with at least one excipient and provided in unit dosage form.

The term "area under the curve" ("AUC") refers to the area under the curve defined by changes in the blood concentration of an active pharmaceutical ingredient (e.g., estradiol or progesterone), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with a measurable concentration.

The term "$C_{max}$" refers to the maximum value of blood concentration shown on the curve that represents changes in blood concentrations of an active pharmaceutical ingredient (e.g., progesterone or estradiol), or a metabolite of the active pharmaceutical ingredient, over time.

The term "$T_{max}$" refers to the time that it takes for the blood concentration an active pharmaceutical ingredient (e.g., estradiol or progesterone), or a metabolite of the active pharmaceutical ingredient, to reach the maximum value.

The term "bioavailability," which has the meaning defined in 21 C.F.R. § 320.1(a), refers to the rate and extent to which an API or active ingredient or active moiety is absorbed from a drug product and becomes available at the site of action. For example, bioavailability can be measured as the amount of API in the blood (serum or plasma) as a function of time. Pharmacokinetic (PK) parameters such as AUC, $C_{max}$, or $T_{max}$ may be used to measure and assess bioavailability. For drug products that are not intended to be absorbed into the bloodstream, bioavailability may be assessed by measurements intended to reflect the rate and extent to which the API or active ingredient or active moiety becomes available at the site of action.

The term "bioequivalent," which has the meaning defined in 21 C.F.R. § 320.1(e), refers to the absence of a significant difference in the rate and extent to which the API or active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC, $C_{max}$, or optionally $T_{max}$ is within 80.00% to 125.00%.

The term "bio-identical," "body-identical," or "natural" used in conjunction with the hormones disclosed herein, means hormones that match the chemical structure and effect of those that occur naturally or endogenously in the human body. An exemplary natural estrogen is estradiol.

The term "bio-identical hormone" or "body-identical hormone" refers to an active pharmaceutical ingredient that is structurally identical to a hormone naturally or endogenously found in the human body (e.g., estradiol and progesterone).

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

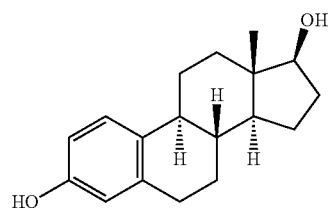

Estradiol is supplied in an anhydrous or hemi-hydrate form. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agent(s) or the formulations disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body having the structure:

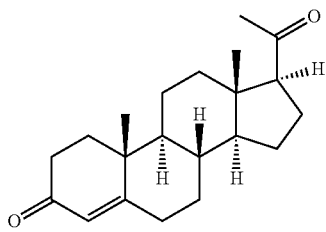

The term "solubilized progesterone" means that the progesterone or a portion thereof is solubilized or dissolved in the solubilizing agent(s) or the formulations disclosed herein. In some embodiments, the progesterone is "partially solubilized" with a portion of the progesterone being solubilized or dissolved in the solubilizing agent and a portion of the progesterone being suspended in the solubilizing agent. Partially solubilized progesterone may include progesterone that is about 1% solubilized, about 5% solubilized, about 10% solubilized, about 15% solubilized, about 20% solubilized, about 30% solubilized, about 40% solubilized, about 50% solubilized, about 60% solubilized, about 70% solubilized, about 80% solubilized, about 85% solubilized, about 90% solubilized or about 95% solubilized. In other embodiments, the progesterone is "fully solubilized" with all or substantially all of the progesterone being solubilized or dissolved in the solubilizing agent. Fully solubilized progesterone may include progesterone that is about 97% solubilized, about 98% solubilized, about 99% solubilized or about 100% solubilized. Solubility can be expressed as a mass fraction (% w/w, which is also referred to as wt %).

The terms "micronized progesterone" and "micronized estradiol," as used herein, include micronized progesterone and micronized estradiol having an X50 particle size value below about 15 microns or having an X90 particle size value below about 25 microns. The term "X50" means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "glyceride" is an ester of glycerol (1,2,3-propanetriol) with acyl radicals of fatty acids and is also known as an acylglycerol. If only one position of the glycerol molecule is esterified with a fatty acid, a "monoglyceride" or "monoacylglycerol" is produced; if two positions are esterified, a "diglyceride" or "diacylglycerol" is produced; and if all three positions of the glycerol are esterified with fatty acids, a "triglyceride" or "triacylglycerol" is produced. A glyceride is "simple" if all esterified positions contain the same fatty acid; whereas a glyceride is "mixed" if the esterified positions contained different fatty acids. The carbons of the glycerol backbone are designated sn-1, sn-2 and sn-3, with sn-2 being in the middle carbon and sn-1 and sn-3 being the end carbons of the glycerol backbone.

The term "solubilizing agent" refers to an agent or combination of agents that solubilize an active pharmaceutical ingredient (e.g., estradiol or progesterone). For example and without limitation, suitable solubilizing agents include medium chain oils and other solvents and co-solvents that solubilize or dissolve an active pharmaceutical ingredient to a desirable extent. Solubilizing agents suitable for use in the formulations disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc. In some embodiments, the solubilizing agent is a medium chain oil and, in some other embodiments, the medium chain oil is combined with a co-solvent(s) or other excipient(s).

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain 6 (C6) to 14 (C14) carbon atoms, 8 (C8) to 12 (C12) carbon atoms, or 8 (C8) to 10 (C10) carbon atoms.

The terms "medium chain fatty acid" and "medium chain fatty acid derivative" are used to describe fatty acids or fatty acid derivatives with aliphatic tails (i.e., carbon chains) having 6 to 14 carbon atoms. Fatty acids consist of an unbranched or branched aliphatic tail attached to a carboxylic acid functional group. Fatty acid derivatives include, for example, fatty acid esters and fatty acid containing molecules, including, without limitation, mono-, di- and triglycerides that include components derived from fatty acids. Fatty acid derivatives also include fatty acid esters of ethylene or propylene glycol. The aliphatic tails can be saturated or unsaturated (i.e., having one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. Examples of medium chain fatty acids include, without limitation, caproic acid, caprylic acid, capric acid, lauric acid, myristic acid, and derivatives thereof.

The term "oil," as used herein, refers to any pharmaceutically acceptable oil, especially medium chain oils, and specifically excluding peanut oil, that can suspend or solubilize bioidentical progesterone or estradiol, including starting materials or precursors thereof, including micronized progesterone or micronized estradiol as described herein.

The term "medium chain oil" refers to an oil wherein the composition of the fatty acid fraction of the oil is substantially medium chain (i.e., C6 to C14) fatty acids, i.e., the composition profile of fatty acids in the oil is substantially medium chain. As used herein, "substantially" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. As used herein, "predominantly" means that greater than or equal to 50% of the fatty acid fraction of the oil is made up of medium-chain fatty acids, i.e., fatty acids with aliphatic carbon chains having 6 to 14 carbon atoms. Those of skill in the art that will readily appreciate that the terms "alkyl content" or "alkyl distribution" of an oil can be used in place of the term "fatty acid fraction" of an oil in characterizing a given oil or solubilizing agent, and these terms are used interchangeable herein. As such, medium chain oils suitable for use in the formulations disclosed herein include medium chain oils wherein the fatty acid fraction of the oil is substantially medium chain fatty acids, or medium chain oils wherein the alkyl content or alkyl distribution of the oil is substantially medium chain alkyls (C6-C12 alkyls). It will be understood by those of skill in the art that the medium chain oils suitable for use in the formulations disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16 and 16; 10, 14 and 16; 8, 14 and 18; etc. Naturally occurring oils are frequently "mixed" with respect to specific fatty acids, but tend not to contain both long chain fatty acids and medium chain fatty acids in the same glycerol backbone. Thus, triglycerides with ECN's of 21-42 typically contain predominantly medium chain fatty acids; while triglycerides with ECN's of greater than 43 typically contain predominantly long chain fatty acids. For example, the ECN of corn oil triglyceride in the USP would be in the range of 51-54. Medium chain diglycerides with ECN's of 12-28 will often contain predominanty medium chain fatty chains, while diglycerides with ECN's of 32 or greater will typically contain predominanty long chain fatty acid tails. Monoglycerides will have an ECN that matches the chain length of the sole fatty acid chain. Thus, monoglyceride ECN's in the range of 6-14 contain mainly medium chain fatty acids, and monoglycerides with ECN's 16 or greater will contain mainly long chain fatty acids.

The average ECN of a medium chain triglyceride oil is typically 21-42. For example, as listed in the US Pharmacopeia (USP), medium chain triglycerides have the following composition as the exemplary oil set forth in the table below:

| Fatty-acid Tail Length | % of oil | Exemplary Oil |
|---|---|---|
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | and would have an average ECN of 3*[(6*0.02)+(8*0.70)+(10*0.25)+(12*0.02)+(14*0.01)]=25.8. The ECN of the exemplary medium chain triglycerides oil can also be expressed as a range (per the ranges set forth in the USP) of 24.9-27.0. For oils that have mixed mono-, di-, and triglycerides, or single and double fatty acid glycols, the ECN of the entire oil can be determined by calculating the ECN of each individual component (e.g., C8 monoglycerides, C8 diglycerides, C10 monoglycerides, and C10 monoglycerides) and taking the sum of the relative percentage of the component multiplied by the ECN normalized to a monoglyceride for each component. For example, the oil having C8 and C10 mono- and diglycerides shown in the table below has an ECN of 8.3, and is thus a medium chain oil.

| Fatty-acid Chain Length | % of oil | ECN as % of oil (chain length) × (% in oil) | ECN as % of oil normalized to monoglyceride |
|---|---|---|---|
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: (8*0.85)+(10*0.15)=8.3.

The term "excipients," as used herein, refers to non-API ingredients such as solubilizing agents, anti-oxidants, oils, lubricants, and others used in formulating pharmaceutical products.

The term "patient" or "subject" refers to an individual to whom the pharmaceutical composition is administered.

The term "pharmaceutical composition" refers to a pharmaceutical composition comprising at least a solubilizing agent and estradiol. As used herein, pharmaceutical compositions are delivered, for example via suppository (i.e., vaginal suppository), or absorbed vaginally.

The term "progestin" means any natural or man-made substance that has pharmacological properties similar to progesterone.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

The terms "atrophic vaginitis," "vulvovaginal atrophy," "vaginal atrophy," and "VVA" are used herein interchangeably. The molecular morphology of VVA is well known in the medical field.

As used herein, "sexual dysfunction" refers to a condition having one or more symptoms of difficulty during any one or more stages. The dysfunction can prevent an individual from enjoying sexual activity. Non-limiting examples of symptoms of sexual dysfunction include: reduced sexual desire, reduced sexual pleasure, reduced sexual arousal and excitement, aversion to and avoidance of genital sexual contact, inability to attain or maintain arousal, and persistent or recurrent delay of, or absence of orgasm. Sexual dysfunction may be lifelong (no effective performance ever) or acquired (after a period of normal function); generalized or limited to certain situations or certain partners; and total or partial.

As used herein, "sexual desire" refers to the frequency of wanting to engage in sexual activity and/or the frequency of engaging in sexual activity as perceived by the individual. Sexual desire can be expressed, for example, in one or more cognitive activities, including the frequency of sexual thoughts, the extent of enjoyment of movies, books, music, etc. having sexual content and/or the extent of enjoyment or pleasure of thinking and fantasizing about sex as perceived by the individual.

As used herein, "sexual arousal" refers to the frequency of becoming sexually aroused, how readily sexual arousal occurs and/or if arousal is maintained, as perceived by the individual. Psychologically, arousal can include factors such as increased desire for sexual activity and excitement related to sexual activity. Physiologically, arousal can include increased blood flow to the genitals, causing clitoral engorgement, as well as vaginal lubrication.

As used herein, "lubrication" refers to wetness in and around the vagina before, during, or after sexual activity. Increasing lubrication can include increasing the frequency of lubrication; decreasing the difficulty of becoming lubricated; and/or decreasing the difficulty in maintaining lubrication.

As used herein, "satisfaction" refers to one or more positive emotions (e.g., contentment, fulfillment, gratification, and the like) related to a sexual activity or sexual relationship. Satisfaction can include, for example, satisfaction with occurrence of sexual arousal or orgasm, satisfaction with the amount of closeness with a partner, and satisfaction with overall sex life.

As used herein, "orgasm" refers to the highest point of sexual excitement characterized by a subjective experience of intense pleasure marked normally by vaginal contractions in females. Increasing orgasm can include increasing the frequency, duration, and/or intensity of orgasms in a subject. Increasing orgasm can also include decreasing the difficulty of reaching orgasm.

II. Introduction

Provided herein are pharmaceutical compositions comprising solubilized estradiol designed to be absorbed vaginally. The pharmaceutical compositions disclosed herein are designed to be absorbed and have their therapeutic effect locally, e.g., in vaginal or surrounding tissue. Further disclosed herein are data demonstrating efficacy of the pharmaceutical compositions disclosed, as well as methods relating to the pharmaceutical compositions. Generally, the pharmaceutical compositions disclosed herein are useful in VVA, dyspareunia, and other indications caused by decrease or lack of estrogen.

Additional aspects and embodiments of this disclosure include: providing increased patient ease of use while potentially minimizing certain side effects from inappropriate insertion, minimizing incidence of vulvovaginal mycotic infection compared to incidence of vulvovaginal mycotic infection due to usage of other vaginally applied estradiol products; and, improved side effect profile (e.g., pruritus) compared to, for example, VAGIFEM® (estradiol vaginal tablets, Novo Nordisk; Princeton, N.J.).

III. Pharmaceutical Compositions

Functionality

According to embodiments, the pharmaceutical compositions disclosed herein are alcohol-free or substantially alcohol-free. The pharmaceutical compositions offer provide for improved patient compliance because of improvements over the prior offering. According to embodiments, the pharmaceutical compositions disclosed herein are encapsulated in soft gelatin capsules, which improve comfort during use. According to embodiments, the pharmaceutical compositions are substantially liquid, which are more readily absorbed in the vaginal tissue, and also are dispersed over a larger surface area of the vaginal tissue.

Estradiol

According to embodiments, the pharmaceutical compositions disclosed herein are for vaginal insertion in a single or multiple unit dosage form. According to embodiments, the estradiol in the pharmaceutical compositions is at least about: 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% solubilized. According to embodiments and where the estradiol is not 100% solubilized, the remaining estradiol is present in a micronized (crystalline) form that is absorbable by the body and retains biological functionality, either in its micronized form or in another form which the micronized form is converted to after administration.

According to embodiments, all or some of the estradiol is solubilized in a solubilizing agent during manufacturing process. According to embodiments, all or some of the estradiol is solubilized following administration (e.g., the micronized portion where the estradiol is not 100% solubilized is solubilized in a body fluid after administration). According to embodiments, because the estradiol is solubilized, the solubilizing agents taught herein, with or without additional excipients other than the solubilizing agents, are liquid or semi-solid. To the extent the estradiol is not fully solubilized at the time of administration/insertion, the estradiol should be substantially solubilized at a body temperature (average of 37° C.) and, generally, at the pH of the vagina (ranges from 3.8 to 4.5 in healthy patients; or 4.6 to 6.5 in VVA patients).

According to embodiments, the estradiol can be added to the pharmaceutical compositions disclosed herein as estradiol, estradiol hemihydrate, or other grade estradiol forms used in pharmaceutical compositions or formulations.

According to embodiments, estradiol dosage strengths vary. Estradiol (or estradiol hemihydrate, for example, to the extent the water content of the estradiol hemihydrate is accounted for) dosage strength of is from at least about 1 microgram (μg or μg) to at least about 50 μg. Specific dosage embodiments contain at least about: 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, or 50 μg estradiol. According to embodiments, the pharmaceutical compositions contain at least about 2.5 μg, 4 μg, 6.25 μg, 7.5 μg, 12.5 μg, or 18.75 μg of estradiol. According to embodiments, the pharmaceutical compositions contain from about 1 μg to about 10 μg, from 3 μg to 7 μg, from about 7.5 μg to 12.5 μg, from about 10 μg to about 25 μg, about 1 μg, about 2.5 μg, from about 23.5 μg to 27.5 μg, from about 7.5 μg to 22.5 μg, from 10 μg to 25 μg of estradiol. The lowest clinically effective dose of estradiol is used for treatment of VVA and other indications set forth herein. In some embodiments, the estradiol dosage is about 4 μg. In one embodiment, the estradiol dosage is about 10 μg. In another embodiment, the estradiol dosage is about 25 μg.

Solvent System

According to embodiments, the solvent system that solubilizes the estradiol are medium chain fatty acid based solvents, together with other excipients. According to embodiments, the solvent system includes non-toxic, pharmaceutically acceptable solvents, co-solvents, surfactants, and other excipients suitable for vaginal delivery or absorption.

According to embodiments, oils having medium chain fatty acids as a majority component are used as solubilizing agents to solubilize estradiol. According to embodiments, the solubilizing agents comprise medium chain fatty acid esters (e.g., esters of glycerol, ethylene glycol, or propylene glycol) or mixtures thereof. According to embodiments, the medium chain fatty acids comprise chain lengths from C6 to C14. According to embodiments the medium chain fatty acids comprise chain lengths from C6 to C12. According to embodiments the medium chain fatty acids substantially comprise chain lengths from C8-C10. ECN's for medium chain oils will be in the range of 21-42 for triglycerides, 12-28 for diglycerides, and 6-14 for monoglycerides.

According to embodiments, the medium chain fatty acids are saturated. According to embodiments, the medium chain fatty acids are predominantly saturated, i.e., greater than about 60% or greater than about 75% saturated.

According to embodiments, estradiol is soluble in the solubilizing agent at room temperature, although it may be desirable to warm certain solubilizing agents during manufacture to improve viscosity. According to embodiments, the solubilizing agent is liquid at between room temperature and about 50° C., at or below 50° C., at or below 40° C., or at or below 30° C.

According to embodiments, the solubility of estradiol in the medium chain oil, medium chain fatty acid, or solubilizing agent (or oil/surfactant) is at least about 0.01 wt %, 0.02 wt %, 0.05 wt %, 0.06 wt %, 0.08 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, or higher.

According to embodiments, medium chain solubilizing agents include, for example and without limitation saturated medium chain fatty acids: caproic acid (C6), enanthic acid (C7), caprylic acid (C8), pelargonic acid (C9), capric acid (C10), undecylic acid (C11), lauric acid (C12), tridecylic acid (C13), or myristic acid (C14). According to embodiments, the solubilizing agent includes oils made of these free medium chain fatty acids, oils of medium chain fatty acid esters of glycerin, propylene glycol, or ethylene glycol, or combinations thereof. These examples comprise predominantly saturated medium chain fatty acids (i.e., greater than 50% of the fatty acids are medium chain saturated fatty acids). According to embodiments, predominantly C6 to C12 saturated fatty acids are contemplated. According to embodiments, the solubilizing agent is selected from at least one of a solvent or co-solvent.

According to embodiments, glycerin based solubilizing agents include: mono-, di-, or triglycerides and combinations and derivatives thereof. Exemplary glycerin based solubilizing agents include MIGLYOLs®, which are caprylic/capric triglycerides (SASOL Germany GMBH, Hamburg). MIGLYOLs includes MIGLYOL 810 (caprylic/capric triglyceride), MIGLYOL 812 (caprylic/capric triglyceride), MIGLYOL 816 (caprylic/capric triglyceride), and MIGLYOL 829 (caprylic/capric/succinic triglyceride). Other caprylic/capric triglyceride solubilizing agents are likewise contemplated, including, for example: caproic/caprylic/capric/lauric triglycerides; caprylic/capric/linoleic triglycerides; caprylic/capric/succinic triglycerides. According to embodiments, CAPMUL MCM, medium chain mono- and di-glycerides, is the solubilizing agent. Other and triglycerides of fractionated vegetable fatty acids, and combinations or derivatives thereof can be the solubilizing agent, according to embodiments. For example, the solubilizing agent can be 1,2,3-propanetriol (glycerol, glycerin, glycerine) esters of saturated coconut and palm kernel oil and derivatives thereof.

Ethylene and propylene glycols (which include polyethylene and polypropylene glycols) solubilizing agents include: glyceryl mono- and di-caprylates; propylene glycol monocaprylate (e.g., CAPMUL® PG-8 (the CAPMUL brands are owned by ABITEC, Columbus, Ohio)); propylene glycol monocaprate (e.g., CAPMUL PG-10); propylene glycol mono- and dicaprylates; propylene glycol mono- and dicaprate; diethylene glycol mono ester (e.g., TRANSCUTOL®, 2-(2-ethoxyethoxy)ethanol, GATTEFOSSÉ SAS); and diethylene glycol monoethyl ether. Other combinations of mono- and di-esters of propylene glycol or ethylene glycol are expressly contemplated are the solubilizing agent.

According to embodiments, the solubilizing agent includes combinations of mono- and di-propylene and ethylene glycols and mono-, di-, and triglyceride combinations. According to embodiments, polyethylene glycol glyceride (GELUCIRE®, GATTEFOSSÉ SAS, Saint-Priest, France) can be used herein as the solubilizing agent or as a surfactant. For example, GELUCIRE 44/14 (PEG-32 glyceryl laurate EP), a medium chain fatty acid esters of polyethylene glycol, is a polyethylene glycol glyceride composed of mono-, di- and triglycerides and mono- and diesters of polyethylene glycol.

According to embodiments, commercially available fatty acid glycerol and glycol ester solubilizing agents are often prepared from natural oils and therefore may comprise components in addition to the fatty acid esters that predominantly comprise and characterize the solubilizing agent. Such other components may be, e.g., other fatty acid mono-, di-, and triglycerides; fatty acid mono- and diester ethylene or propylene glycols, free glycerols or glycols, or free fatty acids, for example. In some embodiments, when an oil/solubilizing agent is described herein as a saturated $C_8$ fatty acid mono- or diester of glycerol, the predominant component of the oil, i.e., >50 wt % (e.g., >75 wt %, >85 wt % or >90 wt %) is caprylic monoglycerides and caprylic diglycerides. For example, the Technical Data Sheet by ABITEC for CAPMUL MCM C8 describes CAPMUL MCM C8 as being composed of mono and diglycerides of medium chain fatty acids (mainly caprylic) and describes the alkyl content as ≤1% C6, ≥95% C8, ≤5% C10, and ≤1.5% C12 and higher.

For example, MIGLYOL 812 is a solubilizing agent that is generally described as a C8-C10 triglyceride because the fatty acid composition is at least about 80% triglyceride esters of caprylic acid (C8) and capric acid (C10). However, it also includes small amounts of other fatty acids, e.g., less than about 5% of caproic acid (C6), lauric acid (C12), and myristic acid (C14). The product information sheet for various MIGLYOLs illustrate the various fatty acid components as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |

-continued

| Tests | 810 | 812 | 818 | 829 | 840 |
|---|---|---|---|---|---|
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |
| ECN | 25.5-26.4 | 26.1-27 | 26.52-28.56 | 26-27.6 | 25.5-26.4 |

According to embodiments, anionic or non-ionic surfactants may be used in pharmaceutical compositions containing solubilized estradiol. Ratios of solubilizing agent(s) to surfactant(s) vary depending upon the respective solubilizing agent(s) and the respective surfactant(s) and the desired physical characteristics of the resultant pharmaceutical composition. For example and without limitation, CAPMUL MCM and a non-ionic surfactant may be used at ratios including 65:35, 70:30, 75:25, 80:20, 85:15 and 90:10. Other non-limiting examples include: CAPMUL MCM and GELUCIRE 39/01 used in ratios including, for example and without limitation, 6:4, 7:3, and 8:2; CAPMUL MCM and GELUCIRE 43/01 used in ratios including, for example and without limitation, 7:3, and 8:2; CAPMUL MCM and GELUCIRE 50/13 used in ratios including, for example and without limitation, 7:3, and 8:2, and 9:1.

Other Excipients

According to embodiments, the pharmaceutical composition further includes a surfactant. The surfactant can be a nonionic surfactant, cationic surfactant, anionic surfactant, or mixtures thereof. Suitable surfactants include, for example, water-insoluble surfactants having a hydrophilic-lipophilic balance (HLB) value less than 12 and water-soluble surfactants having a HLB value greater than 12. Surfactants that have a high HLB and hydrophilicity, aid the formation of oil-water droplets. The surfactants are amphiphilic in nature and are capable of dissolving or solubilizing relatively high amounts of hydrophobic drug compounds.

Non-limiting examples, include, Tween, Dimethylacetamide (DMA), Dimethyl sulfoxide (DMSO), Ethanol, Glycerin, N-methyl-2-pyrrolidone (NMP), PEG 300, PEG 400, Poloxamer 407, Propylene glycol, Phospholipids, Hydrogenated soy phosphatidylcholine (HSPC), Di stearoylphosphatidylglycerol (DSPG), L-α-dimyristoylphosphatidylcholine (DMPC), L-α-dimyristoylphosphatidylglycerol (DMPG), Polyoxyl 35 castor oil (CREMOPHOR EL, CREMOPHOR ELP), Polyoxyl 40 hydrogenated castor oil (Cremophor RH 40), Polyoxyl 60 hydrogenated castor oil (CREMOPHOR RH 60), Polysorbate 20 (TWEEN 20), Polysorbate 80 (TWEEN 80), d-α-tocopheryl polyethylene glycol 1000 succinate (TPGS), Solutol HS-15, Sorbitan monooleate (SPAN 20), PEG 300 caprylic/capric glycerides (SOFTIGEN 767), PEG 400 caprylic/capric glycerides (LABRASOL), PEG 300 oleic glycerides (LABRAFIL M-1944CS), Polyoxyl 35 Castor oil (ETOCAS 35), Glyceryl Caprylate (Mono- and Diglycerides) (IMWITOR), PEG 300 linoleic glycerides (LABRAFIL M-2125CS), Polyoxyl 8 stearate (PEG 400 monosterate), Polyoxyl 40 stearate (PEG 1750 monosterate), and combinations thereof. Additionally, suitable surfactants include, for example, polyoxyethylene derivative of sorbitan monolaurate such as polysorbate, caprylcaproyl macrogol glycerides, polyglycolyzed glycerides, and the like.

According to embodiments, the non-ionic surfactant is selected from one or more of glycerol and polyethylene glycol esters of long chain fatty acids, for example, lauroyl macrogol-32 glycerides or lauroyl polyoxyl-32 glycerides, commercially available as GELUCIRE, including, for example, GELUCIRE 39/01 (glycerol esters of saturated C12-C18 fatty acids), GELUCIRE 43/01 (hard fat NF/JPE) and GELUCIRE 50/13 (stearoyl macrogol-32 glycerides EP, stearoyl polyoxyl-32 glycerides NF, stearoyl polyoxylglycerides (USA FDA IIG)). These surfactants may be used at concentrations greater than about 0.01%, and typically in various amounts of about 0.01%-10.0%, 10.1%-20%, and 20.1%-30%. In some embodiments, surfactants may be used at concentrations of about 1% to about 10% (e.g., about 1% to about 5%, about 2% to about 4%, about 3% to about 8%).

According to embodiments, non-ionic surfactants include, for example and without limitation: one or more of oleic acid, linoleic acid, palmitic acid, and stearic acid. According to embodiments, non-ionic surfactants comprise polyethylene sorbitol esters, including polysorbate 80, which is commercially available under the trademark TWEEN® 80 (polysorbate 80) (Sigma Aldrich, St. Louis, Mo.). Polysorbate 80 includes approximately 60%-70% oleic acid with the remainder comprising primarily linoleic acids, palmitic acids, and stearic acids. Polysorbate 80 may be used in amounts ranging from about 5 to 50%, and according to embodiments, about 30% of the pharmaceutical composition total mass.

According to embodiments, the non-ionic surfactant includes PEG-6 palmitostearate and ethylene glycol palmitostearate, which are available commercially as TEFOSE® 63 (GATTEFOSSÉ SAS, Saint-Priest, France), which can be used with, for example, CAPMUL MCM having ratios of MCM to TEFOSE 63 of, for example, 8:2 or 9:1. According to embodiments, other solubilizing agents/non-ionic surfactants combinations include, for example, MIGLYOL 812: GELUCIRE 50/13 or MIGLYOL 812:TEFOSE 63.

According to embodiments, the surfactant can be an anionic surfactant, for example: ammonium lauryl sulfate, dioctyl sodium sulfosuccinate, perfluoro-octane sulfonic acid, potassium lauryl sulfate, or sodium stearate. Cationic surfactants are also contemplated.

According to embodiments, non-ionic or anionic surfactants can be used alone with at least one solubilizing agent or can be used in combination with other surfactants. Accordingly, such surfactants, or any other excipient as set forth herein, may be used to solubilize estradiol. The combination of solubilizing agent, surfactant, and other excipients should be designed whereby the estradiol is absorbed into the vaginal tissue. According to embodiments, the pharmaceutical composition will result in minimal vaginal discharge.

According to embodiments, the pharmaceutical composition further includes at least one thickening agent. Generally, a thickening agent is added when the viscosity of the pharmaceutical composition results less than desirable absorption. According to embodiments, the surfactant(s) disclosed herein may also provide thickening of the pharmaceutical composition that, upon release, will aid the estradiol in being absorbed by the vaginal mucosa while minimizing vaginal discharge. Examples of thickening agents include: hard fats; propylene glycol; a mixture of hard fat EP/NF/JPE, glyceryl ricinoleate, ethoxylated fatty alcohols (ceteth-20, steareth-20) EP/NF (available as OVUCIRE® 3460, GATTEFOSSÉ, Saint-Priest, France); a mixture of hard fat EP/NF/JPE, glycerol monooleate (type 40) EP/NF (OVUCIRE WL 3264; a mixture of hard fat EP/NF/

JPE, glyceryl monooleate (type 40) EP/NF (OVUCIRE WL 2944); a non-ionic surfactant comprising PEG-6 stearate, ethylene glycol palmitostearate, and PEG-32 stearate; TEFOSE 63 or a similar product; and a mixture of various hard fats (WITEPSOL®, Sasol Germany GmbH, Hamburg, Germany). Other thickening agents such as the alginates, certain gums such as xanthan gums, agar-agar, iota carrageenans, kappa carrageenans, etc. Several other compounds can act as thickening agents like gelatin, and polymers like HPMC, PVC, and CMC. According to embodiments, the viscosity of pharmaceutical compositions in accordance with various embodiments may comprise from about 50 cps to about 1000 cps at 25° C. A person of ordinary skill in the art will readily understand and select from suitable thickening agents.

According to embodiments, the thickening agent is a non-ionic surfactant. For example, polyethylene glycol saturated or unsaturated fatty acid ester or diester is the non-ionic surfactant thickening agent. In embodiments, the non-ionic surfactant includes a polyethylene glycol long chain (C16-C20) fatty acid ester and further includes an ethylene glycol long chain fatty acid ester, such as PEG-fatty acid esters or diesters of saturated or unsaturated C16-C18 fatty acids, e.g., oleic, lauric, palmitic, and stearic acids. In embodiments, the non-ionic surfactant includes a polyethylene glycol long chain saturated fatty acid ester and further includes an ethylene glycol long chain saturated fatty acid ester, such as PEG- and ethylene glycol-fatty acid esters of saturated C16-C18 fatty acids, e.g., palmitic and stearic acids. Such non-ionic surfactant can comprise PEG-6 stearate, ethylene glycol palmitostearate, and PEG-32 stearate, such as but not limited to TEFOSE 63.

According to embodiments, TEFOSE 63 is used to provide additional viscosity and/or spreadability in the vagina so as to retard flow of the composition out of the vagina. While the pharmaceutical composition remains liquid, the viscosity of such a pharmaceutical composition causes the liquid to remain in the API absorption area whereby the pharmaceutical composition is substantially absorbed by the tissue. Surprisingly, the addition of an excipient to increase the viscosity and/or spreadability of the pharmaceutical compositions herein allows the administration of a pharmaceutical composition that is liquid at body temperature but does not excessively discharge from the vagina when the patient is standing, which allows the patients to be ambulatory after administration of the pharmaceutical compositions.

According to embodiments, the non-ionic surfactant used as a thickening agent is not hydrophilic and has good emulsion properties. An illustrative example of such surfactant is TEFOSE 63, which has a hydrophilic-lipophilic balance (HLB) value of about 9-10.

According to embodiments, the pharmaceutical composition further includes one or more mucoadherent agents to improve vaginal absorption of the estradiol by, for example, increasing the viscosity of the pharmaceutical composition whereby flow out of the vagina is retarded. According to other embodiments, alone or in addition to changes in viscosity, the mucoadhesive agent causes the pharmaceutical composition to adhere to the vaginal tissue chemically or mechanically. For example, a mucoadherent agent can be present to aid the pharmaceutical composition with adherence to the mucosa upon activation with water. According to embodiments, polycarbophil is the mucoadherent agent. According to embodiments, other mucoadherent agents include, for example and without limitation: poly (ethylene oxide) polymers having a molecular weight of from about 100,000 to about 900,000; chitosans; carbopols including polymers of acrylic acid crosslinked with allyl sucrose or allyl pentaerythritol; polymers of acrylic acid and C10-C30 alkyl acrylate crosslinked with allyl pentaerythritol; carbomer homopolymer or copolymer that contains a block copolymer of polyethylene glycol and a long chain alkyl acid ester; and the like. According to embodiments, various hydrophilic polymers and hydrogels may be used as the mucoadherent agent. According to certain embodiments, the polymers or hydrogels can swell in response to contact with vaginal tissue or secretions, enhancing moisturizing and mucoadherent effects. The selection and amount of hydrophilic polymer may be based on the selection and amount of solubilizing agent. In some embodiments, the pharmaceutical composition includes a hydrophilic polymer but optionally excludes a gelling agent. In embodiments having a hydrogel, from about 5% to about 10% of the total mass may comprise the hydrophilic polymer. In further embodiments, hydrogels may be employed. A hydrogel may comprise chitosan, which swell in response to contact with water. In various embodiments, a cream pharmaceutical composition may comprise PEG-90M. In some embodiments, a mucoadherent agent is present in the pharmaceutical formulation, in the soft gel capsule, or both.

According to embodiments, the pharmaceutical compositions include one or more thermoreversible gels, typically of the hydrophilic nature including for example and without limitation, hydrophilic sucrose and other saccharide-based monomers (U.S. Pat. No. 6,018,033, which is incorporated by reference).

According to embodiments, the pharmaceutical composition further includes a lubricant. In some embodiments, a lubricant can be present to aid in formulation of a dosage form. For example, a lubricant may be added to ensure that capsules or tablets do not stick to one another during processing or upon storage. Any suitable lubricant may be used. For example, lecithin, which is a mixture of phospholipids, is the lubricant.

According to embodiments, the pharmaceutical composition further includes an antioxidant. Any suitable antioxidant may be used. For example, butylated hydroxytoluene, butylated hydroxyanisole, and Vitamin E TPGS.

According to embodiments, the pharmaceutical composition includes about 20% to about 80% solubilizing agent by weight, about 0.1% to about 5% lubricant by weight, and about 0.01% to about 0.1% antioxidant by weight.

The choice of excipient will depend on factors such as, for example, the effect of the excipient on solubility and stability. Additional excipients used in various embodiments may include colorants and preservatives. Examples of colorants include FD&C colors (e.g., blue No. 1 and Red No. 40), D&C colors (e.g., Yellow No. 10), and opacifiers (e.g., Titanium dioxide). According to embodiments, colorants, comprise about 0.1% to about 2% of the pharmaceutical composition by weight. According to embodiments, preservatives in the pharmaceutical composition comprise methyl and propyl paraben, in a ratio of about 10:1, and at a proportion of about 0.005% and 0.05% by weight.

Generally, the solubilizing agents, excipients, other additives used in the pharmaceutical compositions described herein, are non-toxic, pharmaceutically acceptable, compatible with each other, and maintain stability of the pharmaceutical composition and the various components with respect to each other. Additionally, the combination of various components that comprise the pharmaceutical compositions will maintain will result in the desired therapeutic effect when administered to a subject.

Solubility of Estradiol

According to embodiments, solubilizing agents comprising mixtures of medium chain fatty acid glycerides, e.g., $C_6$-C12, $C_8$-C12, or $C_8$-C10 fatty acid mono- and diglycerides or mono-, di-, and triglycerides dissolve estradiol. As illustrated in the Examples, good results were obtained with solubilizing agents that are predominantly a mixture of C8-C10 saturated fatty acid mono- and diglycerides, or medium chain triglycerides (e.g., MIGLYOL 810 or 812). Longer chain glycerides appear to be not as well suited for dissolution of estradiol.

A solubilizing agent comprising propylene glycol monocaprylate (e.g., CAPRYOL) and 2-(2-Ethoxyethoxy)ethanol (e.g., TRANSCUTOL) solubilized estradiol well.

IV. Manufacture of the Pharmaceutical Composition

According to embodiments, the pharmaceutical composition is prepared via blending estradiol with a pharmaceutically acceptable solubilizing agent, including for example and without limitation, at least one medium chain fatty acid such as medium chain fatty acids consisting of at least one mono-, di-, or triglyceride, or derivatives thereof, or combinations thereof. According to embodiments, the pharmaceutical composition also includes at least one glycol or derivatives thereof or combinations thereof or combinations of at least one glyceride and glycol. The glycol(s) may be used as solubilizing agents or to adjust viscosity and, thus, may be considered thickening agents, as discussed further herein. Optionally added are other excipients including, for example and without limitation, anti-oxidants, lubricants, and the like. According to embodiments, the pharmaceutical composition includes sufficient solubilizing agent to fully solubilize the estradiol. It is expressly understood, however, the other volumes of solubilizing agent can be used depending on the level of estradiol solubilization desired. Persons of ordinary skill in the art will know and understand how to determine the volume of solubilizing agent and other excipients depending on the desired percent of estradiol to be solubilized in the pharmaceutical composition.

In illustrative embodiments, GELUCIRE 44/14 (lauroyl macrogol-32 glycerides EP, lauroyl polyoxyl-32 glycerides NF, lauroyl polyoxylglycerides (USA FDA IIG)) is heated to about 65° C. and CAPMUL MCM is heated to about 40° C. to facilitate mixing of the oil and non-ionic surfactant, although such heating is not necessary to dissolve the estradiol.

Specific Examples disclosed herein provide additional principles and embodiments illustrating the manufactures of the pharmaceutical compositions disclosed herein.

V. Delivery Vehicle

Generally, the pharmaceutical compositions described herein delivered intravaginally inside of a delivery vehicle, for example a capsule. According to embodiments, the capsules are soft capsules made of materials well known in the pharmaceutical arts, for example, gelatin. However, according to embodiments, the delivery vehicle is integral with the pharmaceutical composition (i.e., the pharmaceutical composition is the delivery vehicle). In such embodiments the pharmaceutical compositions is a gel, cream, ointment, tablet, or other preparation that is directly applied and absorbed vaginally.

According to embodiments, the capsules do not contain one or more of the following: a hydrophilic gel-forming bioadhesive agent, a lipophilic agent, a gelling agent for the lipophilic agent, and/or a hydrodispersible agent. According to embodiments, the capsules do not contain a hydrophilic gel-forming bioadhesive agent selected from: carboxyvinylic acid, hydroxypropylcellulose, carboxymethylcellulose, gelatin, xanthan gum, guar gum, aluminum silicate, and mixtures thereof. According to embodiments, the capsules do not contain a lipophilic agent selected from: a liquid triglyceride, a solid triglyceride (with a melting point of about 35° C.), carnauba wax, cocoa butter, and mixtures thereof. According to embodiments, the capsules do not contain a hydrophobic colloidal silica gelling agent. According to embodiments, the capsules do not contain a hydrodispersible agent selected from: polyoxyethylene glycol, polyoxyethylene glycol 7-glyceryl-cocoate, and mixtures thereof. In some embodiments, the estradiol is formulated as a liquid composition consisting of a therapeutically effective amount of estradiol; a caprylic/capric triglyceride; and a non-ionic surfactant comprising PEG-6 palmitostearate and ethylene glycol palmitostearate. In such embodiments, a hydrophilic gel-forming bioadhesive agent in the liquid composition. In some such embodiments, the liquid composition is contained with a gelatin capsule as described herein. In some such embodiments, the capsule comprises gelatin and optionally one or more further components selected from the group consisting of gelatin, hydrolyzed gelatin, sorbitol-sorbitan solution, water, glycerin, titanium dioxide, FD&C Red #40, ethanol, ethyl acetate, propylene glycol, polyvinyl acetate phthalate, isopropyl alcohol, polyethylene glycol, and ammonium hydroxide.

According to embodiments, the delivery vehicle is designed for ease of insertion. According to embodiments, the delivery vehicle is sized whereby it can be comfortably inserted into the vagina. According to embodiments, the delivery vehicle is prepared in a variety of geometries. For example, the delivery vehicle is shaped as a tear drop, a cone with frustoconical end, a cylinder, a cylinder with larger "cap" portion, or other shapes suitable for and that ease insertion into the vagina. According to embodiments, the delivery vehicle is used in connection with an applicator. According to other embodiments, the delivery vehicle is inserted digitally.

According to embodiments, a method for the treatment of VVA, including dyspareunia, vaginal dryness, and estrogen-deficient urinary states (including urinary tract infections), is provided wherein a composition for the treatment of VVA is digitally insert approximately two inches into the vagina or in the third of the vagina closest to the opening of the vagina and results in at least one of: improved compliance compared to other products for the treatment of VVA; improved user experience compared to other products for the treatment of VVA; and statistically significantly improved symptoms of VVA, compared to placebo or baseline within one of two, four, six, eight, ten, or twelve or more weeks after initiation of administration. According to embodiments, a method for the treatment of VVA, including dyspareunia, vaginal dryness, and estrogen-deficient urinary states (including urinary tract infections), is provided wherein a delivery vehicle containing a composition for the treatment of VVA and a tear drop shape as disclosed herein is insert approximately two inches into the vagina or in the third of the vagina closest to the opening of the vagina and results in at least one of: improved compliance compared to other products for the treatment of VVA; improved user experience compared to other products for the treatment of VVA; and statistically significantly improved symptoms of VVA, compared to placebo or baseline within one of two, four, six, eight, ten, or twelve or more weeks after initiation of administration.

Figure 2:
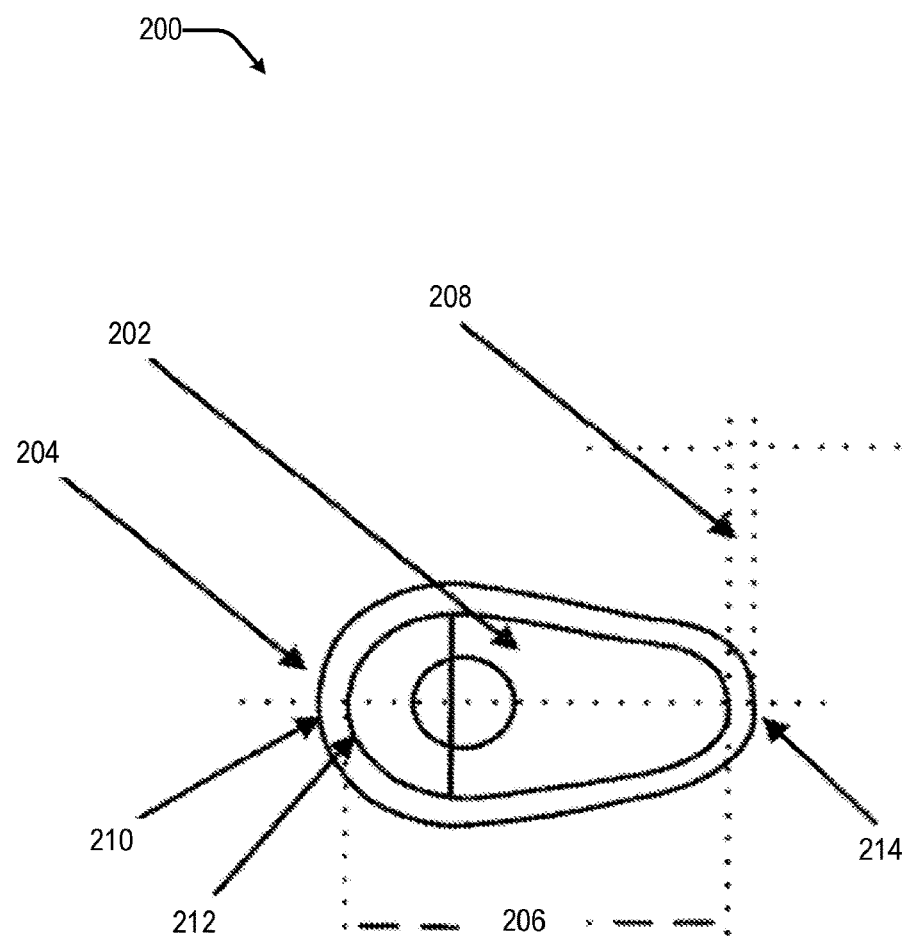
FIG. 2 illustrates a suppository in accordance with various embodiments of the invention.
Figure 3:
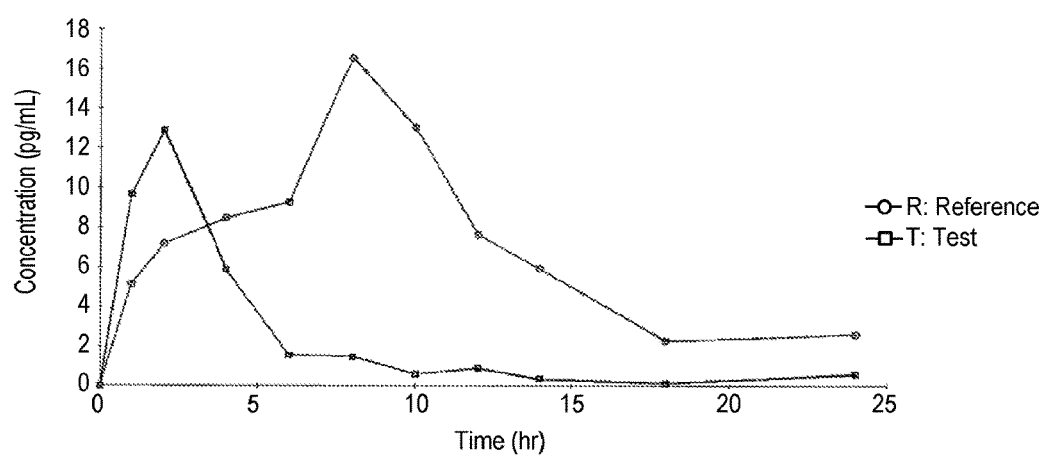
FIG. 3 is a linear plot of mean plasma estradiol-baseline adjusted concentrations versus time (N=34)
Figure 4:
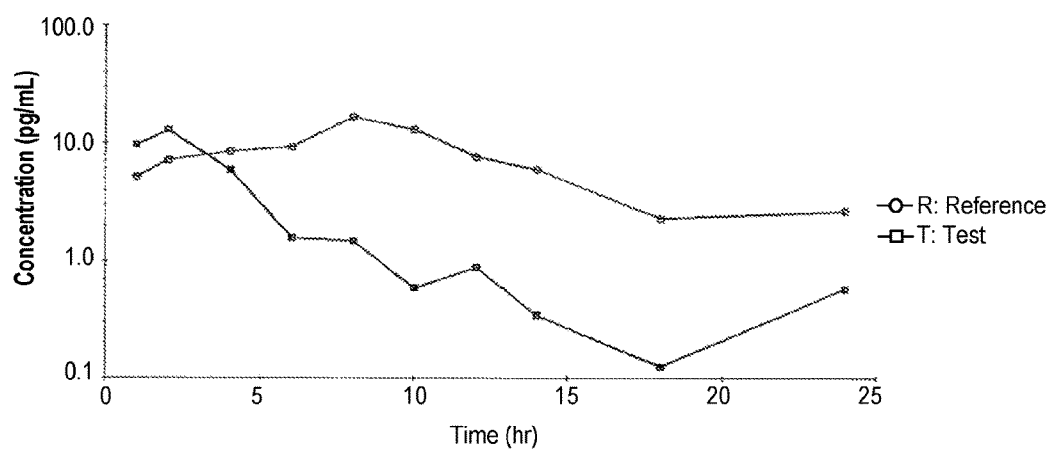
FIG. 4 is a semi-logarithmic plot of mean plasma estradiol-baseline adjusted concentrations versus time (N=34)
Figure 5:
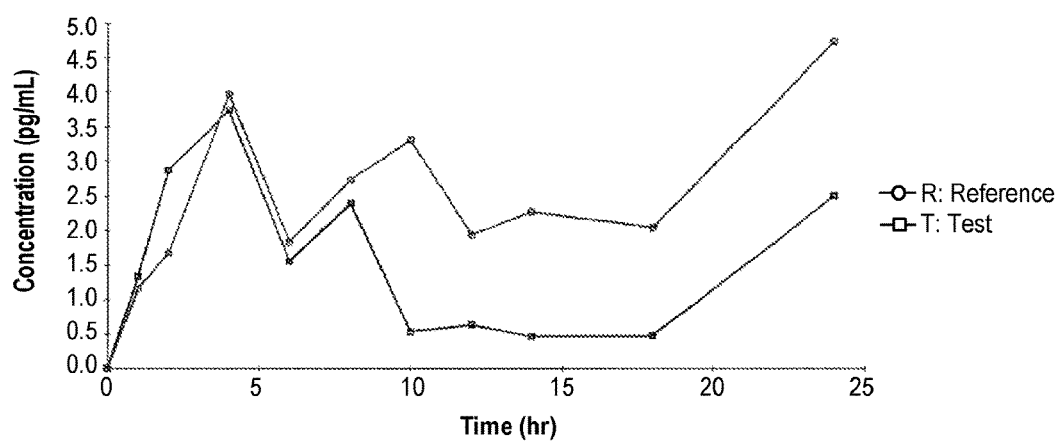
FIG. 5 is a linear plot of mean plasma estrone-baseline adjusted concentrations versus time (N=33)
Figure 6:
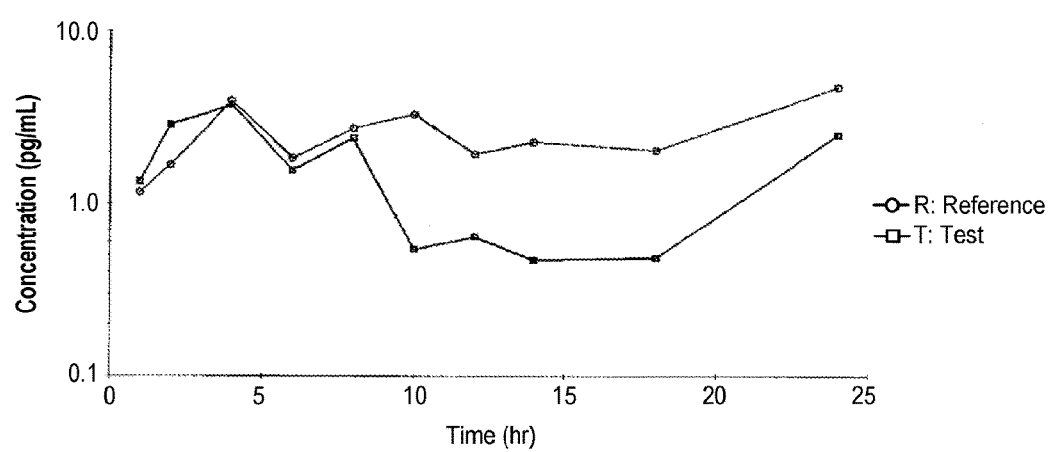
FIG. 6 is a semi-logarithmic plot of mean plasma estrone-baseline adjusted concentrations versus time (N=33)
Figure 7:
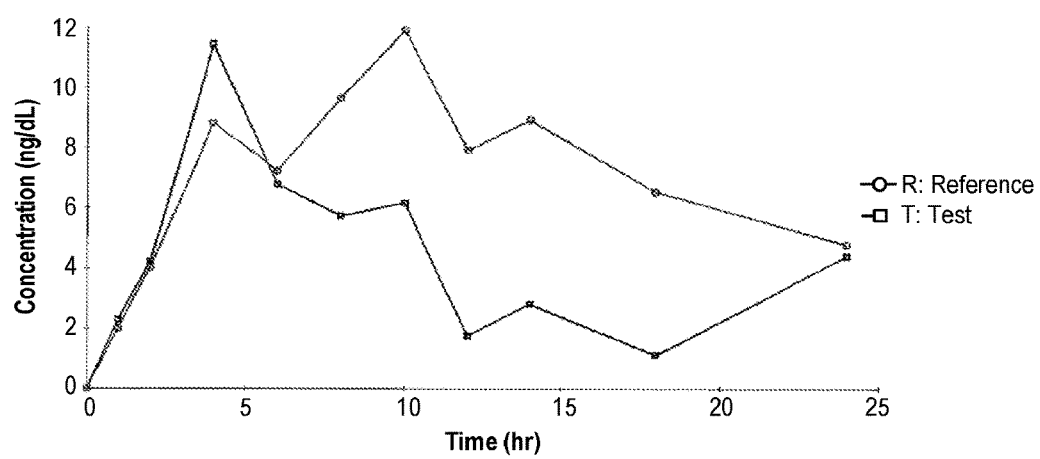
FIG. 7 is a linear plot of mean plasma estrone sulfate-baseline adjusted concentrations versus time (N=24)
Figure 8:
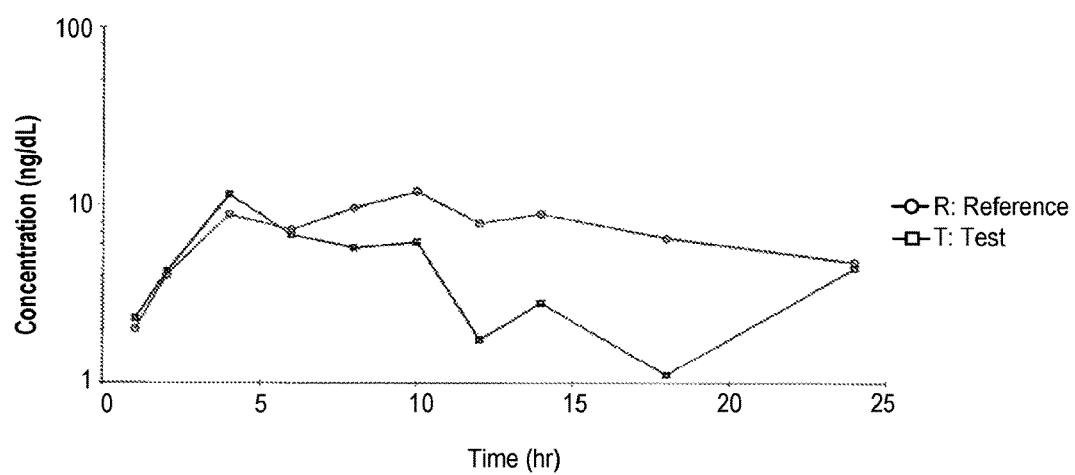
FIG. 8 is a semi-logarithmic plot of mean plasma estrone sulfate-baseline adjusted concentrations versus time (N=24).

With reference to FIG. 2, delivery vehicle 200 includes pharmaceutical composition 202 and capsule 204. Width 208 represents the thickness of capsule 204, for example about 0.108 inches. The distance from one end of delivery vehicle 200 to another is represented by distance 206, for example about 0.690 inches. The size of delivery vehicle 200 may also be described by the arc swept by a radius of a given length. For example, arc 210, which is defined by the exterior of gelatin 204, is an arc swept by a radius of about 0.189 inches. Arc 212, which is defined by the interior of capsule 204, is an arc swept by a radius of about 0.0938 inches. Arc 214, which is defined by the exterior of gelatin 204 opposite arc 210, is an arc swept by a radius of about 0.108 inches. Suitable capsules of other dimensions may be provided. According to embodiments, capsule 204 has dimensions the same as or similar to the ratios as provided above relative to each other. In some embodiment, the gelatin capsule further comprises one or more components selected from the group consisting of hydrolyzed gelatin, sorbitol-sorbitan solution, water, glycerin, titanium dioxide, FD&C Red #40, ethanol, ethyl acetate, propylene glycol, polyvinyl acetate phthalate, isopropyl alcohol, polyethylene glycol, and ammonium hydroxide.

According to embodiments, the delivery vehicle is designed to remaining in the vagina until the pharmaceutical compositions are released. According to embodiments, delivery vehicle dissolves intravaginally and is absorbed into the vaginal tissue with the pharmaceutical composition, which minimizes vaginal discharge. In such embodiments, delivery mechanism is made from constituents that are non-toxic, for example, gelatin.

Design Factors for Vaginally Inserted Pharmaceutical Compositions

According to embodiments, the pharmaceutical composition is designed to maximize favorable characteristics that lead to patient compliance (patients that discontinue treatment prior to completion of the prescribed course of therapy), without sacrificing efficacy. Favorable characteristics include, for example, lack of or reduction of irritation relative to other hormone replacement pessaries, lack of or reduction in vaginal discharge of the pharmaceutical composition and delivery vehicle relative to other hormone replacement pessaries, lack of or reduction of pharmaceutical composition or delivery vehicle residue inside the vagina, ease of administration compared to other hormone replacement pessaries, or improved efficacy of drug product relative to otherwise similar pharmaceutical compositions.

According to embodiments, the pharmaceutical composition is non-irritating or minimizes irritation. Patient irritation includes pain, pruritus (itching), soreness, excessive discharge, swelling, or other similar conditions. Patient irritation results in poor compliance. Non-irritating or reduced irritation pharmaceutical compositions are measured relative to competing hormone pessaries, including tablets, creams, or other intravaginal estrogen delivery forms.

According to embodiments, the pharmaceutical compositions does not result in systemic exposure (e.g., blood circulation of estradiol), which improves safety. According to other embodiments, the pharmaceutical compositions disclosed herein result in significantly reduced systemic exposure (e.g., blood circulation of estradiol) when compared to other vaginally administered drugs on the market for the treatment of VVA.

In certain embodiments, the administration of the pharmaceutical composition provides a mean concentration ($C_{ave}$) value below 20.6 pg/mL on Day 1 of the treatment, and/or a $C_{ave}$ value below 19.4 pg/mL on Day 14 of the treatment, and/or a $C_{ave}$ value below 11.5 pg/mL on Day 83 of the treatment. In certain embodiments, the administration of the pharmaceutical composition provides a mean concentration ($C_{ave}$) value below 10 pg/mL on Day 1 of the treatment, and/or a $C_{ave}$ value below 7.3 pg/mL on Day 14 of the treatment, and/or a $C_{ave}$ value below 5.5 pg/mL on Day 83 of the treatment.

According to embodiments, the pharmaceutical composition does not leave residue inside the vagina. Rather, the pharmaceutical composition and delivery vehicle are substantially absorbed or dispersed without resulting in unabsorbed residue or unpleasant sensations of non-absorbed or non-dispersed drug product. Measurement of lack of residue is relative to other vaginally inserted products or can be measured objectively with inspection of the vaginal tissues. For example, certain other vaginally inserted products contain starch which can result in greater discharge from the vagina following administration than. In some embodiments, the pharmaceutical compositions provided herein provide a lower amount, duration, or frequency of discharge following administration compared to other vaginally inserted products (e.g., compressed tablets).

According to embodiments, the pharmaceutical composition improves vaginal discharge compared to other pessaries, including pessaries that deliver hormones. Ideally, vaginal discharge is eliminated, minimized, or improved compared to competing products.

According to embodiments, the pharmaceutical compositions disclosed herein are inserted digitally. According to embodiments, the pharmaceutical compositions are digitally inserted approximately two inches into the vagina without a need for an applicator. According to embodiments, the pharmaceutical compositions are designed to be also inserted with an applicator, if desired. According to some embodiments, because the site of VVA is in the proximal region of the vagina (towards the vaginal opening), the pharmaceutical compositions disclosed herein are designed to be inserted in the proximal portion of the vagina.

Through extensive experimentation, various medium chain fatty acid esters of glycerol and propylene glycol demonstrated one or more favorable characteristics for development as a human drug product. According to embodiments, the solubilizing agent was selected from at least one of a solvent or co-solvent. Suitable solvents and co-solvents include any mono-, di- or triglyceride and glycols, and combinations thereof.

According to embodiments, the pharmaceutical composition is delivered via a gelatin capsule delivery vehicle. According to these embodiments, the pharmaceutical composition is a liquid pharmaceutical composition. According to embodiments, the delivery vehicle is a soft capsule, for example a soft gelatin capsule. Thus, the pharmaceutical composition of such embodiments is encapsulated in the soft gelatin capsule or other soft capsule.

According to embodiments, the pharmaceutical composition includes estradiol that is at least about 80% solubilized in a solubilizing agent comprising one or more C6 to C14 medium chain fatty acid mono-, di-, or triglycerides and, optionally, a thickening agent. According to embodiments, the pharmaceutical composition includes estradiol that is at least about 80% solubilized one or more C6 to C12 medium chain fatty acid mono-, di-, or triglycerides, e.g., one or more C6 to C14 triglycerides, e.g., one or more C6 to C12 triglycerides, such as one or more C8-C10 triglycerides. These embodiments specifically contemplate the estradiol being at least 80% solubilized. These embodiments specifically contemplate the estradiol being at least 90% solubilized. These embodiments specifically contemplate the estradiol being at least 95% solubilized. These embodiments specifically contemplate the estradiol being fully solubilized.

As noted above, liquid pharmaceutical compositions are liquid at room temperature or at body temperature. For example, in some embodiments, a pharmaceutical composition provided herein is a liquid formulation contained within a soft gel capsule. Gels, hard fats, or other solid forms that are not liquid at room or body temperature are less desirable in embodiments of the pharmaceutical composition that are liquid.

The thickening agent serves to increase viscosity, e.g., up to about 10,000 cP (10,000 mPa-s), typically to no more than about 5000 cP, and more typically to between about 50 and 1000 cP. In embodiments, the non-ionic surfactant, e.g., GELUCIRE or TEFOSE, may be solid at room temperature and require melting to effectively mix with the solubilizing agent. However, in these embodiments, the resultant pharmaceutical composition remains liquid, albeit with greater viscosity, not solid.

According to embodiments, the pharmaceutical composition includes estradiol, the medium chain solubilizing agent, and the thickening agent as the ingredients delivered via a soft capsule delivery vehicle. Other ingredients, e.g., colorants, antioxidants, preservatives, or other ingredients may be included as well. However, the addition of other ingredients should be in amounts that do not materially change the solubility of the estradiol, the pharmacokinetics of the pharmaceutical composition, or efficacy of the pharmaceutical composition. Other factors that should be considered when adjusting the ingredients of the pharmaceutical composition include the irritation, vaginal discharge, intravaginal residue, and other relevant factors, for example those that would lead to reduced patient compliance. Other contemplated ingredients include: oils or fatty acid esters, lecithin, mucoadherent agents, gelling agents, dispersing agents, or the like.

VI. Methods

According to embodiments, the pharmaceutical compositions disclosed herein can be used for the treatment of VVA, including the treatment of at least one VVA symptom including: vaginal dryness, vaginal or vulvar irritation or itching, dysuria, dyspareunia, and vaginal bleeding associated with sexual activity, among others. According to embodiments the methods of treatment are generally applicable to females.

According to embodiments, the pharmaceutical compositions disclosed herein can be used for the treatment of estrogen-deficient urinary states. According to embodiments, the pharmaceutical compositions disclosed herein can be used for the treatment of dyspareunia, or vaginal bleeding associated with sexual activity.

Figure 26A:
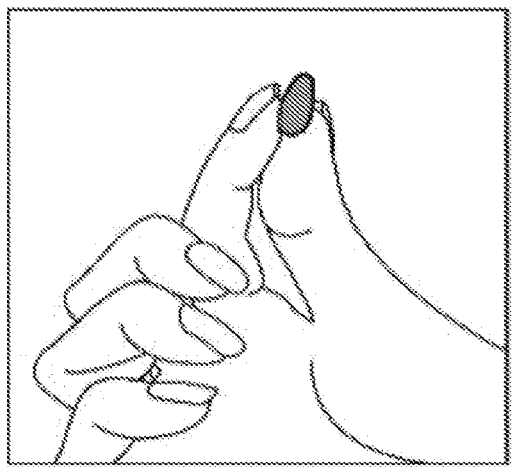
FIG. 26A shows an estradiol softgel capsule held with the larger end between the fingers.

According to embodiments, treatment of the VVA, estrogen-deficient urinary states, and dyspareunia and vaginal bleeding associated with sexual activity occurs by administering the pharmaceutical compositions intravaginally. According to embodiments where the delivery vehicle is a capsule, the patient obtains the capsule and inserts the capsule into the vagina, where the capsule dissolves and the pharmaceutical composition is released into the vagina where it is absorbed into the vaginal tissue. In some embodiments, the pharmaceutical composition is completely absorbed into the vaginal tissue. In some embodiments, the pharmaceutical composition is substantially absorbed into the vaginal tissue (e.g., at least about 80% by weight, at least about 85% by weight, at least about 90% by weight, at least about 95% by weight, at least about 97% by weight, at least about 98% by weight, or at least about 99% by weight of the composition is absorbed). According to embodiments, the capsule is inserted about two inches into the vagina, however the depth of insertion is generally any depth that allows for adsorption of substantially all of the pharmaceutical composition. According to embodiments, the capsule can also be applied using an applicator that deposits the capsule at an appropriate vaginal depth as disclosed herein. According to embodiments, the capsule is insert into the lower third of the vagina (i.e., the third closest to the vaginal opening). According to embodiments, the softgel capsule can be held with the larger end between the fingers as shown in FIG. 26A.

Figure 26B:
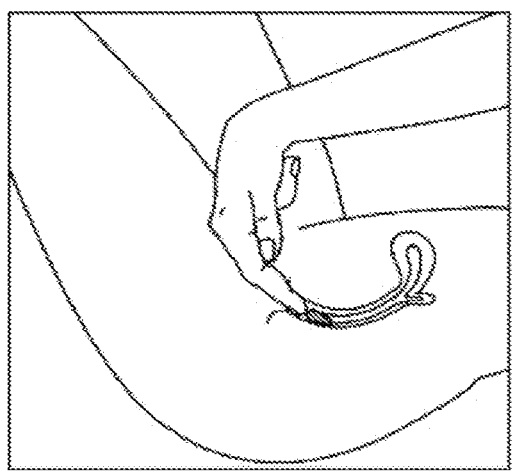
FIG. 26B shows insertion of an estradiol softgel capsule in a reclining position. The softgel is inserted into the lower third of the vagina with the smaller end up.
Figure 26C:
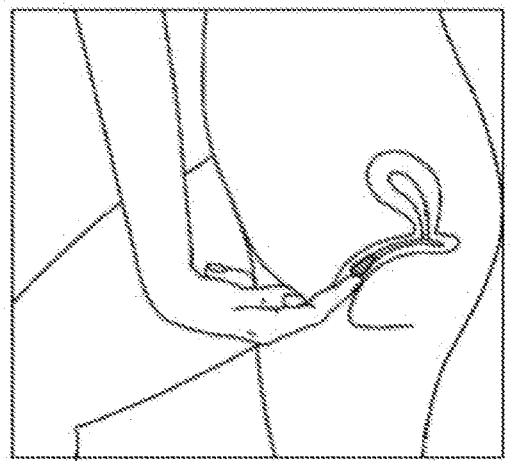
FIG. 26C shows insertion of an estradiol softgel capsule in a standing position. The softgel is inserted into the lower third of the vagina with the smaller end up.

The subject will select a position that is most comfortable (e.g., a reclining position as shown in FIG. 26B or a standing position as shown in FIG. 26C), and the subject will insert the softgel into the lower third of the vagina with the smaller end up. The softgel capsule will dissolve rapidly. The softgel can be inserted at any time of day and normal activities can be immediately resumed. According to embodiments, the same time of day for all insertions of the softgel is used.

According to embodiments where the pharmaceutical composition is a cream, gel, ointment, or other similar preparation, the pharmaceutical composition is applied digitally, as is well known and understood in the art.

Upon release of the pharmaceutical composition in the vagina, estradiol is locally absorbed. For example, following administration of the suppository to the proximal region of the vagina of a patient provides a therapeutically effective concentration of estradiol over 24 hours in the proximal region of the vagina.

According to embodiments, the timing of administration of the pharmaceutical composition of this disclosure may be conducted by any safe means as prescribed by an attending physician. According to embodiments, a patient will administer the pharmaceutical composition (e.g., a capsule) intravaginally each day for 14 days, then twice weekly thereafter. In some such embodiments, the doses administered during the twice weekly dosing period are administered approximately 3-4 days apart. Typically, doses administered during the twice weekly dosing period do not exceed more than twice in a seven day period.

According to embodiments, the pharmaceutical compositions are vaginally administered with co-administration of an orally administered estrogen-based (or progestin-based or progestin- and estrogen-based) pharmaceutical drug product, or patch, cream, gel, spray, transdermal delivery system or other parenterally-administered estrogen-based pharmaceutical drug product, each of which can include natural, bio-similar, or synthetic or other derived estrogens or progestins. According to embodiments, modulation of circulating estrogen levels provided via the administration of the pharmaceutical compositions disclosed herein, if any, are not intended to be additive to any co-administered estrogen product and its associated circulating blood levels. According to other embodiments, co-administrated estrogen products are intended to have an additive effect as would be determined by the patient physician.

According to embodiments, a method for estrogenizing vaginal tissue is provided. The method includes administration of a (i.e., a suppository) or dosage as described herein. Estrogenized vaginal tissue is typically characterized by one or more of the following properties: the presence clear secretions on vaginal walls; rogation and elasticity of the vaginal walls; intact vaginal epithelium; and pink tissue color. In contrast, de-estrogenized vaginal is characterized by decreased or absent secretions; smooth tissue with fewer or no rugae; bleeding of the vaginal surface; development of petechiae (i.e., pinpoint, round spots on the skin due to bleeding, appearing red, brown, or purple); and pale or transparent tissues. Accordingly, estrogenizing vaginal tissue according to the method disclosed herein can include, increasing the level of vaginal secretions in a subject; increasing the number of vaginal rugae in the subject; and/or decreasing bleeding or petechiae in the subject. According to embodiments, a method for estrogenizing vaginal tissue is provided, the method including administering a suppository so as to provide an estradiol $C_{max}$ or AUC as described herein. According to embodiments, a method for estrogenizing vaginal tissue is provided, the method including administering a suppository so as to provide an estrone $C_{max}$ or AUC as described herein.

According to embodiments, a method for estrogenizing the labia majora and labia minora (collectively "labia") is provided as described herein. Generally, the pharmaceutical composition is inserted digitally into the vagina approximately two inches or inserted into the third of the vagina closest to the vaginal opening as shown in FIGS. 26A, 26B, and 26C. The gelatin capsule containing the pharmaceutical composition dissolves, ruptures, or otherwise releases the pharmaceutical composition into the vagina, whereby the lower third of the vagina and labia are both reestrogenized. According to some embodiments, the pharmaceutical composition is a liquid that partially flows to the labia and directly reestrogenizes the labia.

According to embodiments, a method for estrogenizing the vulva is provided as described herein. Generally, the pharmaceutical composition is inserted digitally into the vagina approximately two inches or inserted into the third of the vagina closest to the vaginal opening as shown in FIGS. 26A, 26B, and 26C. The gelatin capsule containing the pharmaceutical composition dissolves, ruptures, or otherwise releases the pharmaceutical composition into the vagina, whereby the lower third of the vagina and vulva are both reestrogenized. According to some embodiments, the pharmaceutical composition is a liquid that partially flows to the vulval tissue and directly reestrogenizes the vulva.

According to embodiments, a method for treating vaginal dryness is provided. The method includes administration of a soft gel vaginal estradiol formulation (i.e., a suppository) or dosage as described herein. Treating vaginal dryness according to the method disclosed herein can include, decreasing the severity of vaginal dryness by 1%, 5%, 10%, 15%, 20%, 25%, 30%, 45%, 50%, 55%, 60%, 65%, 70%, 75%, 80%, 85%, 90%, 95%, or 99%. The decrease in severity can be obtained following 2 weeks of treatment, or 6 weeks of treatment, or 8 weeks of treatment, or 12 weeks of treatment. In some embodiments, vaginal dryness is assessed using a severity scale, ranging from 0 to 4 points wherein 0 indicates no dryness, 1 indicates mild dryness, 2 indicates moderate dryness, and 3 indicates severe dryness.

In some embodiments, the method for treating vaginal dryness includes reducing the dryness severity score from 3, prior to treatment of a subject, to 2, after 2 weeks of treatment of the subject. In some embodiments, the method for treating vaginal dryness includes reducing the dryness severity score from 2, prior to treatment of a subject, to 1, after 2 weeks of treatment of the subject. In some embodiments, the method for treating vaginal dryness includes reducing the dryness severity score from 1, prior to treatment of subject, to 0, after 2 weeks of treatment of the subject.

In some embodiments, the method for treating vaginal dryness includes reducing the dryness severity score from 3, prior to treatment of a subject, to 2, after 6 weeks of treatment of the subject. In some embodiments, the method for treating vaginal dryness includes reducing the dryness severity score from 2, prior to treatment of a subject, to 1, after 6 weeks of treatment of the subject. In some embodiments, the method for treating vaginal dryness includes reducing the dryness severity score from 1, prior to treatment of subject, to 0, after 6 weeks of treatment of the subject.

In some embodiments, the method for treating vaginal dryness includes reducing the dryness severity score from 3, prior to treatment of a subject, to 2, after 8 weeks of treatment of the subject. In some embodiments, the method for treating vaginal dryness includes reducing the dryness severity score from 2, prior to treatment of a subject, to 1, after 8 weeks of treatment of the subject. In some embodiments, the method for treating vaginal dryness includes reducing the dryness severity score from 1, prior to treatment of subject, to 0, after 8 weeks of treatment of the subject.

In some embodiments, the method for treating vaginal dryness includes reducing the dryness severity score from 3, prior to treatment of a subject, to 2, after 12 weeks of treatment of the subject. In some embodiments, the method for treating vaginal dryness includes reducing the dryness severity score from 2, prior to treatment of a subject, to 1, after 12 weeks of treatment of the subject. In some embodiments, the method for treating vaginal dryness includes reducing the dryness severity score from 1, prior to treatment of subject, to 0, after 12 weeks of treatment of the subject.

In some embodiments, the method for treating vaginal dryness includes decreasing the severity of dryness after two weeks of treatment, wherein the severity is assessed on a scale of 0-3 points, and the average decrease ranges from a 0.5-point decrease to a 1.25-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating vaginal dryness includes decreasing the severity of dryness after six weeks of treatment, wherein the severity is assessed on a scale of 0-3 points, and the average decrease ranges from a 0.75-point decrease to a 1.5-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 μg of estradiol. In some embodiments, the vaginal estradiol formulation contains 25 μg of estradiol.

In some embodiments, the method for treating vaginal dryness includes decreasing the severity of dryness after eight weeks of treatment, wherein the severity is assessed on a scale of 0-3 points, and the average decrease ranges from a 0.9-point decrease to a 1.5-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 μg of estradiol. In some embodiments, the vaginal estradiol formulation contains 10 μg of estradiol. In some embodiments, the vaginal estradiol formulation contains 25 μg of estradiol.

In some embodiments, the method for treating vaginal dryness includes decreasing the severity of dryness after twelve weeks of treatment, wherein the severity is assessed on a scale of 0-3 points, and the average decrease ranges from a 0.9-point decrease to a 1.5-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 μg of estradiol. In some embodiments, the vaginal estradiol formulation contains 10 μg of estradiol. In some embodiments, the vaginal estradiol formulation contains 25 μg of estradiol.

In some embodiments, the method for treating vaginal dryness includes administering a suppository so as to provide an estradiol $C_{max}$ or AUC as described herein. According to embodiments, a method for treating vaginal dryness is provided, the method including administering a suppository so as to provide an estrone $C_{max}$ or AUC as described herein.

According to embodiments, a method for treating vulvar and/or vaginal itching or irritation is provided. The method includes administration of a soft gel vaginal estradiol formulation (i.e., a suppository) or dosage as described herein. Treating vulvar and/or vaginal itching or irritation according to the method disclosed herein can include, decreasing the severity of vulvar and/or vaginal itching or irritation by 1%, 5%, 10%, 15%, 20%, 25%, 30%, 45%, 50%, 55%, 60%, 65%, 70%, 75%, 80%, 85%, 90%, 95%, or 99%. The decrease in severity can be obtained following 2 weeks of treatment, or 6 weeks of treatment, or 8 weeks of treatment, or 12 weeks of treatment. In some embodiments, vulvar and/or vaginal itching or irritation is assessed using a severity scale, ranging from 0 to 4 points wherein 0 indicates no itching or irritation, 1 indicates mild itching or irritation, 2 indicates moderate itching or irritation, and 3 indicates severe itching or irritation.

In some embodiments, the method for treating vulvar and/or vaginal itching or irritation includes reducing the itching/irritation severity score from 3, prior to treatment of a subject, to 2, after 2 weeks of treatment of the subject. In some embodiments, the method for treating vulvar and/or vaginal itching or irritation includes reducing the itching/irritation severity score from 2, prior to treatment of a subject, to 1, after 2 weeks of treatment of the subject. In some embodiments, the method for treating vulvar and/or vaginal itching or irritation includes reducing the itching/irritation severity score from 1, prior to treatment of subject, to 0, after 2 weeks of treatment of the subject.

In some embodiments, the method for treating vulvar and/or vaginal itching or irritation includes reducing the itching/irritation severity score from 3, prior to treatment of a subject, to 2, after 6 weeks of treatment of the subject. In some embodiments, the method for treating vulvar and/or vaginal itching or irritation includes reducing the itching/irritation severity score from 2, prior to treatment of a subject, to 1, after 6 weeks of treatment of the subject. In some embodiments, the method for treating vulvar and/or vaginal itching or irritation includes reducing the itching/irritation severity score from 1, prior to treatment of subject, to 0, after 6 weeks of treatment of the subject.

In some embodiments, the method for treating vulvar and/or vaginal itching or irritation includes reducing the itching/irritation severity score from 3, prior to treatment of a subject, to 2, after 8 weeks of treatment of the subject. In some embodiments, the method for treating vulvar and/or vaginal itching or irritation includes reducing the itching/irritation severity score from 2, prior to treatment of a subject, to 1, after 8 weeks of treatment of the subject. In some embodiments, the method for treating vulvar and/or vaginal itching or irritation includes reducing the itching/irritation severity score from 1, prior to treatment of subject, to 0, after 8 weeks of treatment of the subject.

In some embodiments, the method for treating vulvar and/or vaginal itching or irritation includes reducing the itching/irritation severity score from 3, prior to treatment of a subject, to 2, after 12 weeks of treatment of the subject. In some embodiments, the method for treating vulvar and/or vaginal itching or irritation includes reducing the itching/irritation severity score from 2, prior to treatment of a subject, to 1, after 12 weeks of treatment of the subject. In some embodiments, the method for treating vulvar and/or vaginal itching or irritation includes reducing the itching/irritation severity score from 1, prior to treatment of subject, to 0, after 12 weeks of treatment of the subject.

In some embodiments, the method for treating vulvar and/or vaginal itching or irritation includes decreasing the severity of itching/irritation after two weeks of treatment, wherein the severity is assessed on a scale of 0-3 points, and the average decrease ranges from a 0.3-point decrease to a 0.6-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 μg of estradiol. In some embodiments, the vaginal estradiol formulation contains 10 μg of estradiol. In some embodiments, the vaginal estradiol formulation contains 25 μg of estradiol.

In some embodiments, the method for treating vulvar and/or vaginal itching or irritation includes decreasing the severity of itching/irritation after six weeks of treatment, wherein the severity is assessed on a scale of 0-3 points, and the average decrease ranges from a 0.5-point decrease to a 0.7-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating vulvar and/or vaginal itching or irritation includes decreasing the severity of itching/irritation after eight weeks of treatment, wherein the severity is assessed on a scale of 0-3 points, and the average decrease ranges from a 0.5-point decrease to a 0.8-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating vulvar and/or vaginal itching or irritation includes decreasing the severity of itching/irritation after twelve weeks of treatment, wherein the severity is assessed on a scale of 0-3 points, and the average decrease ranges from a 0.5-point decrease to a 1.0-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating vulvar and/or vaginal itching or irritation includes administering a suppository so as to provide an estradiol $C_{max}$ or AUC as described herein. According to embodiments, a method for treating vulvar and/or vaginal itching or irritation is provided, the method including administering a suppository so as to provide an estrone $C_{max}$ or AUC as described herein.

According to embodiments, a method for treating dyspareunia is provided. The method includes administration of a suppository or dosage as described herein. Treating dyspareunia according to the method disclosed herein can include, decreasing the severity of dyspareunia by 1%, 5%, 10%, 15%, 20%, 25%, 30%, 45%, 50%, 55%, 60%, 65%, 70%, 75%, 80%, 85%, 90%, 95%, or 99%. The decrease in severity can be obtained following 2 weeks of treatment, or 6 weeks of treatment, or 8 weeks of treatment, or 12 weeks of treatment. In some embodiments, dyspareunia is assessed using a severity scale, ranging from 0 to 4 points wherein 0 indicates no pain associated with sexual activity (with vaginal penetration), 1 indicates mild pain associated with sexual activity (with vaginal penetration), 2 indicates moderate pain associated with sexual activity (with vaginal penetration), and 3 indicates severe pain associated with sexual activity (with vaginal penetration).

In some embodiments, the method for treating dyspareunia includes reducing the dyspareunia severity score from 3, prior to treatment of a subject, to 2, after 2 weeks of treatment of the subject. In some embodiments, the method for treating dyspareunia includes reducing the dyspareunia severity score from 2, prior to treatment of a subject, to 1, after 2 weeks of treatment of the subject. In some embodiments, the method for treating dyspareunia includes reducing the dyspareunia severity score from 1, prior to treatment of subject, to 0, after 2 weeks of treatment of the subject.

In some embodiments, the method for treating dyspareunia includes reducing the dyspareunia severity score from 3, prior to treatment of a subject, to 2, after 6 weeks of treatment of the subject. In some embodiments, the method for treating dyspareunia includes reducing the dyspareunia severity score from 2, prior to treatment of a subject, to 1, after 6 weeks of treatment of the subject. In some embodiments, the method for treating dyspareunia includes reducing the dyspareunia severity score from 1, prior to treatment of subject, to 0, after 6 weeks of treatment of the subject.

In some embodiments, the method for treating dyspareunia includes reducing the dyspareunia severity score from 3, prior to treatment of a subject, to 2, after 8 weeks of treatment of the subject. In some embodiments, the method for treating dyspareunia includes reducing the dyspareunia severity score from 2, prior to treatment of a subject, to 1, after 8 weeks of treatment of the subject. In some embodiments, the method for treating dyspareunia includes reducing the dyspareunia severity score from 1, prior to treatment of subject, to 0, after 8 weeks of treatment of the subject.

In some embodiments, the method for treating dyspareunia includes reducing the dyspareunia severity score from 3, prior to treatment of a subject, to 2, after 12 weeks of treatment of the subject. In some embodiments, the method for treating dyspareunia includes reducing the dyspareunia severity score from 2, prior to treatment of a subject, to 1, after 12 weeks of treatment of the subject. In some embodiments, the method for treating dyspareunia includes reducing the dyspareunia severity score from 1, prior to treatment of subject, to 0, after 12 weeks of treatment of the subject.

In some embodiments, the method for treating dyspareunia includes decreasing the severity of dyspareunia after two weeks of treatment, wherein the severity is assessed on a scale of 0-3 points, and the average decrease ranges from a 0.9-point decrease to a 1.1-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating dyspareunia includes decreasing the severity of dyspareunia after six weeks of treatment, wherein the severity is assessed on a scale of 0-3 points, and the average decrease ranges from a 1.3-point decrease to a 1.5-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating dyspareunia includes decreasing the severity of dyspareunia after eight weeks of treatment, wherein the severity is assessed on a scale of 0-3 points, and the average decrease ranges from a 1.5-point decrease to a 1.8-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating dyspareunia includes decreasing the severity of dyspareunia after twelve weeks of treatment, wherein the severity is assessed on a scale of 0-3 points, and the average decrease ranges from a 1.5-point decrease to a 1.8-point decrease. The average decrease can be determined by observing any suitable number of subjects. In some embodiments, the number of subjects is at least 100. In some embodiments, the number of subjects is at least 500. In some embodiments, the number of subjects ranges from 700 to 800. In some embodiments, the number of subjects ranges from 740 to 750. In some embodiments, the vaginal estradiol formulation contains 4 µg of estradiol. In some embodiments, the vaginal estradiol formulation contains 10 µg of estradiol. In some embodiments, the vaginal estradiol formulation contains 25 µg of estradiol.

In some embodiments, the method for treating dyspareunia includes administering a suppository so as to provide an estradiol $C_{max}$ or AUC as described herein. According to embodiments, a method for treating dyspareunia is provided, the method including administering a suppository so as to provide an estrone $C_{max}$ or AUC as described herein.

According to embodiments, a method for treating urinary tract infections is provided. As used herein the term "urinary tract infection" refers to an infection of the kidneys, ureters, bladder and urethra by a microorganism such as *Escherichia coli*, *Staphylococcus saprophyticus*, *Klebsiella* sp., *Enterobacter* sp., or *Proteus* sp. The method for treating urinary tract infections generally includes administering a soft gel vaginal estradiol formulation (i.e., a suppository) as described herein. According to certain embodiments, the method further includes decreasing urethral discomfort, frequency or urination, hematuria, dysuria, and/or stress incontinence. According to certain embodiments, a method for treating urinary tract infections is provided, the method including administering a suppository as described herein and decreasing vaginal pH from above 4.5 to between 3.5 and 4.5 (inclusive). The method can be particularly effective for treating urinary tract infections in elderly subjects (e.g., subjects older than 65 years, or older than 75 years, or older than 85 years). According to embodiments, a method for treating urinary tract infections is provided, the method including administering a suppository so as to provide an estradiol $C_{max}$ or AUC as described herein. According to embodiments, a method for treating urinary tract infections is provided, the method including administering a suppository so as to provide an estrone $C_{max}$ or AUC as described herein. According to embodiments, a method for treating sexual dysfunction is provided. As used herein with respect to female subjects, the term "sexual dysfunction" generally refers to pain or discomfort during sexual intercourse, diminished vaginal lubrication, delayed vaginal engorgement, increased time for arousal, diminished ability to reach orgasm, diminished clitoral sensation, diminished sexual desire, and/or diminished arousal. According to embodiments, a method for treating sexual dysfunction is provided, the method including administering a suppository so as to provide an estradiol $C_{max}$ or AUC as described herein. According to embodiments, a method for treating sexual dysfunction is provided, the method including administering a suppository so as to provide an estrone $C_{max}$ or AUC as described herein.

Sexual function and dysfunction can be assessed using the Female Sexual Function Index (FSFI) (see, Rosen R, Brown C, Heiman J, et al. "The Female Sexual Function Index (FSFI): A Multidimensional Self-Report Instrument for the Assessment of Female Sexual Function." *Journal of Sex & Marital Therapy* 2000. 26: p. 191-208). The FSFI is useful for assessing various domains of sexual functioning (e.g. sexual desire, arousal, orgasm, satisfaction and pain). Accordingly, the method for treating sexual dysfunction as provided herein can include administering a vaginal soft gel formulation to a subject and increasing a subject's full-scale FSFI score, FSFI-desire score, FSFI-arousal score, FSFI-lubrication score and/or FSFI-orgasm score.

Female Sexual Function Index (FSFI)

| Question | Answer Options |
|---|---|
| Q1: Over the past 4 weeks, how often did you feel sexual desire or interest? | 5 = Almost always or always<br>4 = Most times (more than half the time)<br>3 = Sometimes (about half the time)<br>2 = A few times (less than half the time)<br>1 = Almost never or never |
| Q2: Over the past 4 weeks, how would you rate your level (degree) of sexual desire or interest? | 5 = Very high<br>4 = High<br>3 = Moderate<br>2 = Low<br>1 = Very low or none at all |
| Q3. Over the past 4 weeks, how often did you feel sexually aroused ("turned on") during sexual activityo r intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| Q4. Over the past 4 weeks, how would you rate your level of sexual arousal ("turn on") during sexual activity or intercourse? | 0 = No sexual activity<br>5 = Very high<br>4 = High<br>3 = Moderate<br>2 = Low<br>1 = Very low or none at all |

| Question | Answer Options |
|---|---|
| Q5. Over the past 4 weeks, how confident were you about becoming sexually aroused during sexual activity or intercourse? | 0 = No sexual activity<br>5 = Very high confidence<br>4 = High confidence<br>3 = Moderate confidence<br>2 = Low confidence<br>1 = Very low or no confidence |
| Q6. Over the past 4 weeks, how often have you been satisfied with your arousal (excitement) during sexual activity or intercourse? Response Options | 0 = No sexual activity<br>5 = Almost always or always<br>4 = Most times (more than half the time)<br>3 = Sometimes (about half the time)<br>2 = A few times (less than half the time)<br>1 = Almost never or never |
| Q7: Over the past 4 weeks, how often did you become lubricated ("wet") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| Q8. Over the past 4 weeks, how difficult was it to become lubricated ("wet") during sexual activity or intercourse? | 0 = No sexual activity<br>1 = Extremely difficult or impossible<br>2 = Very difficult<br>3 = Difficult<br>4 = Slightly difficult<br>5 = Not difficult |
| Q9: Over the past 4 weeks, how often did you maintain your lubrication ("wetness") until completion of sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| Q10: Over the past 4 weeks, how difficult was it to maintain your lubrication ("wetness") until completion of sexual activity or intercourse? | 0 = No sexual activity<br>1 = Extremely difficult or impossible<br>2 = Very difficult<br>3 = Difficult<br>4 = Slightly difficult<br>5 = Not difficult |
| Q11. Over the past 4 weeks, when you had sexual stimulation or intercourse, how often did you reach orgasm (climax)? | 0 = No sexual activity<br>5 = Almost always or always<br>4 = Most times (more than half the time)<br>3 = Sometimes (about half the time)<br>2 = A few times (less than half the time)<br>1 = Almost never or never |
| Q12: Over the past 4 weeks, when you had sexual stimulation or intercourse, how difficult was it for you to reach orgasm (climax)? | 0 = No sexual activity<br>1 = Extremely difficult or impossible<br>2 = Very difficult<br>3 = Difficult<br>4 = Slightly difficult<br>5 = Not difficult |
| Q13: Over the past 4 weeks, how satisfied were you with your ability to reach orgasm (climax) during sexual activity or intercourse? | 0 = No sexual activity<br>5 = Very satisfied 4<br>4 = Moderately satisfied<br>3 = About equally satisfied and dissatisfied<br>2 = Moderately dissatisfied<br>1 = Very dissatisfied |
| Q14: Over the past 4 weeks, how satisfied have you been with the amount of emotional closeness during sexual activity between you and your partner? | 0 = No sexual activity<br>5 = Very satisfied<br>4 = Moderately satisfied<br>3 = About equally satisfied and dissatisfied<br>2 = Moderately dissatisfied<br>1 = Very dissatisfied |
| Q15: Over the past 4 weeks, how satisfied have you been with your sexual relationship with your partner? | 5 = Very satisfied<br>4 = Moderately satisfied<br>3 = About equally satisfied and dissatisfied<br>2 = Moderately dissatisfied<br>1 = Very dissatisfied |
| Q16: Over the past 4 weeks, how satisfied have you been with your overall sexual life? | 5 = Very satisfied<br>4 = Moderately satisfied<br>3 = About equally satisfied and dissatisfied<br>2 = Moderately dissatisfied<br>1 = Very dissatisfied |
| Q17: Over the past 4 weeks, how often did you experience discomfort or pain during vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |

-continued

| Question | Answer Options |
|---|---|
| Q18: Over the past 4 weeks, how often did you experience discomfort or pain following vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |
| Q19. Over the past 4 weeks, how would you rate your level (degree) of discomfort or pain during or following vaginal penetration? | 0 = Did not attempt intercourse<br>1= Very high<br>2 = High<br>3 = Moderate<br>4 = Low<br>5 = Very low or none at all |

FSFI Scoring System

| Domain | Questions | Score Range | Factor | Minimum | Maximum |
|---|---|---|---|---|---|
| Desire | 1, 2 | 1-5 | 0.6 | 1.2 | 6.0 |
| Arousal | 3, 4, 5, 6 | 0-5 | 0.3 | 0 | 6.0 |
| Lubrication | 7, 8, 9, 10 | 0-5 | 0.3 | 0 | 6.0 |
| Orgasm | 11, 12, 13 | 0-5 | 0.4 | 0 | 6.0 |
| Satisfaction | 14, 15, 16 | 0 (or 1)-5 | 0.4 | 0.8 | 6.0 |
| Pain | 17, 18, 19 | 0-5 | 0.4 | 0 | 6.0 |
| Full Scale Score Range: | | | | 2.0 | 36.0 |

In some embodiments, the method for treating sexual dysfunction includes administering estradiol to the subject and increasing the FSFI-desire score by at least about 20%, or at least about 25%, or at least about 30% as compared to baseline.

In some embodiments, the method for treating sexual dysfunction includes administering estradiol to the subject and increasing the FSFI-arousal score by at least about 30%, or at least about 40%, or at least about 50% as compared to baseline.

In some embodiments, the method for treating sexual dysfunction includes administering estradiol to the subject and increasing the FSFI-lubrication score by at least about 85%, or at least about 95%, or at least about 115% as compared to baseline.

In some embodiments, the method for treating sexual dysfunction includes administering estradiol to the subject and increasing the FSFI-orgasm score by at least about 40%, or at least about 60% as compared to baseline.

In some embodiments, the method for treating sexual dysfunction includes administering estradiol to the subject and increasing the total FSFI score by at least about 50%, or at least about 55%, or at least about 70% as compared to baseline.

Examples of other metrics for assessment of sexual function include, but are not limited to, Changes in Sexual Function Questionnaire ("CSFQ"; Clayton et al., *Psychopharmacol Bull.* 33(4):731-45 (1997) and Clayton et al., *Psychopharmacol. Bull.* 33(4):747-53 (1997)); the Derogatis Interview for Sexual Functioning—Self-Report ("DISF-SR"; Derogatis, *J Sex Marital Ther.* 23:291-304 (1997)); the Golombok-Rust Inventory of Sexual Satisfaction ("GRISS"; Rust et al., *Arch. Sex Behav.* 15:157-165 (1986)); the Sexual Function Questionnaire ("SFQ"; Quirk et al., *J Womens Health Gend Based Med.* 11:277-289 (2002)); and the Arizona Sexual Experience Scale ("ASEX"; McGahuey et al., *J Sex Marital Ther.* 26:25-40 (2000)), the entire disclosures of which are incorporated herein by reference. For assessment using a questionnaire, a measure of sexual dysfunction function is increased when the score in the appropriate domain, subscale or subtest is indicative of sexual dysfunction, as established for that questionnaire. For instance, a female's sexual interest is considered reduced, when assessed using the CSFQ, if the subscale for sexual interest score is less than or equal to 9. Conversely, sexual dysfunction is considered improved when the score in the appropriate domain, subscale or subtest is indicative of higher (e.g., normal or desired) sexual function. For a clinician's assessment, sexual dysfunction may be assessed in comparison to a previous point in time for the patient and/or in comparison to a patient's peers with respect to age, gender, sexual experience, and health, or may also be determined via a validated questionnaire administered by the clinician.

According to embodiments, the efficacy and safety of the pharmaceutical compositions described herein in the treatment of the symptoms of VVA may be determined. According to embodiments, the size, effect, cytology, histology, and variability of the VVA may be determined using various endpoints to determine efficacy and safety of the pharmaceutical compositions described herein or as otherwise accepted in the art, at present or as further developed. One source of endpoints is with the US Food and Drug Administration's (FDA) published guidelines for treatment of VVA with estradiol.

According to embodiments, a method of treating VVA, including dyspareunia, vaginal dryness, and estrogen-deficient urinary states (including urinary tract infections), is provided that allows a subject to be ambulatory immediately or within minutes after a gelatin capsule containing the pharmaceutical compositions disclosed herein are administered. According to embodiments, a gelatin capsule containing a pharmaceutical composition as disclosed herein is administered by digitally inserting the gelatin capsule containing the pharmaceutical composition into the vagina approximately two inches or inserting into the third of the vagina closest to the vaginal opening as shown in FIGS. 26A, 26B, and 26C. According to embodiments, the gelatin capsule adheres to the vaginal tissue and dissolves, ruptures, or otherwise disintegrates soon after being inserted into the vagina thereby releasing the pharmaceutical composition. The pharmaceutical composition spreads onto the vaginal tissue and is rapidly absorbed. According to embodiments, the gelatin capsule is also fully absorbed by the vaginal tissue. According to some embodiments, a viscosity enhancer such as TEFOSE 63 provides increased viscosity to ensure the pharmaceutical composition stays within the desired absorption area, thereby estrogenizing the vagina, labia, and/or vulva. The combination of high viscosity, bioadhesion, and rapid absorption prevents the need for subjects to remain supine after administration to allow the tissue to absorb the estradiol, thereby allowing subjects to be ambulatory immediately or almost immediately after administration.

According to embodiments, a method for treating VVA, including dyspareunia, vaginal dryness, and estrogen-deficient urinary states (including urinary tract infections), without causing non-natural discharge (e.g., discharge of a pharmaceutical composition or a component thereof) is provided. According to the method, a soft gelatin capsule is administered containing a liquid pharmaceutical composition that is able to be fully absorbed by the vaginal tissue. According to embodiments, the pharmaceutical composition itself is fully absorbed by the vaginal tissue. According to embodiments, the pharmaceutical composition and gelatin capsule are administered in a volume and size, respectively, that allows a subject's vaginal tissue to fully absorb the pharmaceutical composition. According to embodiments, such absorption will occur contemporaneously with the subject being ambulatory. According to the method, the gelatin capsule and liquid pharmaceutical composition are fully absorbed by the vaginal tissue, wherein the only discharge that occurs after estrogenizing the vagina is natural discharge that a woman would have experienced prior to menopause. "Natural" vaginal discharge refers to a small amount of fluid that flows out of the vagina each day, carrying out old cells that have lined the vagina. Natural discharge is usually clear or milky. Non-natural discharge can refer to discharge that is higher in volume than natural discharge, different in color than natural discharge, or different in consistency than natural discharge. Non-natural discharge can also refer to the discharge (e.g., leaking) of a pharmaceutical composition from the vagina.

According to embodiments, a method of treating VVA, including dyspareunia, vaginal dryness, and estrogen-deficient urinary states (including urinary tract infections), using a liquid pharmaceutical composition is provided. According to the method, a soft gelatin capsule containing a liquid composition for treating VVA is provided to a subject. The subject inserts the soft gelatin capsule containing the liquid composition for treating VVA into their vagina either digitally or with an applicator, wherein the soft gelatin capsule dissolves, ruptures, or disintegrates and the liquid composition is released into the vagina. According to embodiments, the liquid composition for treating VVA is a pharmaceutical composition disclosed herein. According to embodiments, the subject inserts the gelatin capsule about two inches into the vagina, or in the third of the vagina closest to the vaginal opening. According to embodiments, the subject is ambulatory immediately after or soon after administration.

According to embodiments, a method is disclosed herein for treating VVA, including dyspareunia, vaginal dryness, and estrogen-deficient urinary states (including urinary tract infections), comprising improving the symptoms of VVA, compared to placebo or baseline, within two weeks by vaginally administering a composition for the treatment of VVA. One of skill in the art will understand that the improvements can be assessed statistically as described herein, and that any improvement can be a statistically significant improvement. According to embodiments, the composition for the treatment of VVA is a liquid pharmaceutical composition as disclosed herein. According to embodiments, the composition for the treatment of VVA is a liquid containing from 1 µg to 25 µg of estradiol. According to embodiments, the method of administration is a method disclosed herein, including the insertion method shown in FIGS. 26A, 26B, and 26C. According to embodiments, at the two week point of measurement, the estradiol is not detected systemically when measured using standard pharmaceutical pharmacokinetic parameters, such as AUC and $C_{max}$.

According to embodiments, a method is disclosed herein for treating VVA, including dyspareunia, vaginal dryness, and estrogen-deficient urinary states (including urinary tract infections), comprising improving the symptoms of VVA, compared to placebo or baseline, within four weeks by vaginally administering a composition for the treatment of VVA. One of skill in the art will understand that the improvements can be assessed statistically as described herein, and that any improvement can be a statistically significant improvement. According to embodiments, the composition for the treatment of VVA is a liquid pharmaceutical composition as disclosed herein. According to embodiments, the composition for the treatment of VVA is a liquid containing from 1 µg to 25 µg of estradiol. According to embodiments, the method of administration is a method disclosed herein, including the insertion method shown in FIGS. 26A, 26B, and 26C. According to embodiments, at the two week point of measurement and/or the four week point of measurement, the estradiol is not detected systemically when measured using standard pharmaceutical pharmacokinetic parameters, such as AUC and $C_{max}$.

According to embodiments, a method is disclosed herein for treating VVA, including dyspareunia, vaginal dryness, and estrogen-deficient urinary states (including urinary tract infections), comprising improving the symptoms of VVA, compared to placebo or baseline, within eight weeks by vaginally administering a composition for the treatment of VVA. One of skill in the art will understand that the improvements can be assessed statistically as described herein, and that any improvement can be a statistically significant improvement. According to embodiments, the composition for the treatment of VVA is a liquid pharmaceutical composition as disclosed herein. According to embodiments, the composition for the treatment of VVA is a liquid containing from 1 µg to 25 µg of estradiol. According to embodiments, the method of administration is a method disclosed herein, including the insertion method shown in FIGS. 26A, 26B, and 26C. According to embodiments, at the two week point of measurement and/or the eight week point of measurement, the estradiol is not detected systemically when measured using standard pharmaceutical pharmacokinetic parameters, such as AUC and $C_{max}$.

According to embodiments, a method is disclosed herein for treating VVA, including dyspareunia, vaginal dryness, and estrogen-deficient urinary states (including urinary tract infections), comprising improving the symptoms of VVA, compared to placebo or baseline, within ten weeks by vaginally administering a composition for the treatment of VVA. One of skill in the art will understand that the improvements can be assessed statistically as described herein, and that any improvement can be a statistically significant improvement. According to embodiments, the composition for the treatment of VVA is a liquid pharmaceutical composition as disclosed herein. According to embodiments, the composition for the treatment of VVA is a liquid containing from 1 µg to 25 µg of estradiol. According to embodiments, the method of administration is a method disclosed herein, including the insertion method shown in FIGS. 26A, 26B, and 26C. According to embodiments, at the two week point of measurement and/or the ten week point of measurement, the estradiol is not detected systemically when measured using standard pharmaceutical pharmacokinetic parameters, such as AUC and $C_{max}$.

According to embodiments, a method for treating VVA, including dyspareunia, vaginal dryness, and estrogen-deficient urinary states (including urinary tract infections), comprising administering a composition containing estradiol for the treatment of VVA is provided, wherein the method improves the symptoms of VVA, compared with baseline or placebo, in at least one of two weeks, four weeks, six weeks, eight weeks, or twelve weeks, wherein the estradiol is not detected systemically using standard pharmaceutical pharmacokinetic parameters, such as AUC and $C_{max}$. One of skill in the art will understand that the improvements can be assessed statistically as described herein, and that any improvement can be a statistically significant improvement. According to embodiments, the composition containing estradiol is a liquid composition as disclosed herein. According to embodiments, the copomosition contains 1 μg to 25 μg of estradiol.

According to embodiments, a method for reestrogenizing the vagina, labia, or vulva is provided, wherein the method comprises administering a composition containing estradiol for the treatment of VVA, wherein the composition is a liquid containing estradiol or a synthetic estrogen, and wherein the liquid spreads over a surface area of the vagina, labia, or vulva which is larger than the area covered by a solid composition. For example, the liquid can spread over a surface area ranging from about 50 cm² to about 120 cm² (e.g., from about 50 cm² to about 60 cm²; or from about 60 cm² to about 70 cm²; or from about 70 cm² to about 80 cm²; or from about 80 cm² to about 90 cm²; or from about 90 cm² to about 100 cm²; or from about 100 cm² to about 110 cm²; or from about 110 cm² to about 120 cm²; or from about 65 cm² to about 110 cm²). According to embodiments, the subject inserts a liquid composition into her vagina in a capsule, such as a hard or soft gelatin capsule, that then dissolves, ruptures, disintegrates, or otherwise releases the liquid in the vagina. According to embodiments, the liquid contains at least one of a bio-adhesive or viscosity enhancer to prevent the liquid from discharging from the vagina before the estradiol or synthetic estrogen can be absorbed into the vaginal tissue in a dose sufficient to effect reestrongenization of the vagina. According to embodiments, the vagina will be statistically significantly reestrogenized within two weeks of administration compared to baseline or placebo levels. According to embodiments, the vagina will be statistically significantly reestrogenized within four weeks of administration compared to baseline or placebo levels.

According to embodiments, the vagina will be statistically significantly reestrogenized within six weeks of administration compared to baseline or placebo levels. According to embodiments, the vagina will be statistically significantly reestrogenized within eight weeks of administration compared to baseline or placebo levels. According to embodiments, the vagina will be statistically significantly reestrogenized within ten weeks of administration compared to baseline or placebo levels. According to embodiments, the vagina will be statistically significantly reestrogenized within twelve or more weeks of administration compared to baseline or placebo levels.

VII. Measurement of Efficacy

According to embodiments, administration of the pharmaceutical compositions described herein resulted in treatment of the VVA, as well as improvement of one or more of the associated symptoms. Patients with VVA experience shrinking of the vaginal canal in both length and diameter and the vaginal canal has fewer glycogen-rich vaginal cells to maintain moisture and suppleness. In addition, the vaginal wall can become thin, pale, dry, or sometimes inflamed (atrophic vaginitis). These changes can manifest as a variety of symptoms collectively referred to as VVA. Such symptoms include, without limitations, an increase in vaginal pH; reduction of vaginal epithelial integrity, vaginal secretions, or epithelial surface thickness; pruritus; vaginal dryness; dyspareunia (pain or bleeding during sexual intercourse); urinary tract infections; or a change in vaginal color. According to embodiments, efficacy is measured as a reduction of vulvar and vaginal atrophy in a patient back to premenopausal conditions. According to embodiments, the change is measured as a reduction in the severity of one or more atrophic effects measured at baseline (screening, Day 1) and compared to a measurement taken at Day 15 (end of treatment). Severity of the atrophic effect may be measured using a scale of 0 to 3 where, for example, none=0, mild=1, moderate=2, or severe=3. Such scoring is implemented to evaluate the pre-treatment condition of patients; to determine the appropriate course of a treatment regime; such as dosage, dosing frequency, and duration, among others; and post-treatment outcomes.

One of the symptoms of VVA is increased vaginal pH. In further aspects of this disclosure, treatment with the pharmaceutical compositions described herein resulted in a decrease in vaginal pH. A decrease in vaginal pH is measured as a decrease from the vaginal pH at baseline (screening) to the vaginal pH at Day 15, according to embodiments. In some embodiments, a pH of 5 or greater may be associated with VVA. In some embodiments, pH is measured using a pH indicator strip placed against the vaginal wall. In some embodiments, a change in vaginal pH is a change in a patient's vaginal pH to a pH of less than about pH 5.0. In some embodiments, a subject's vaginal pH may be less than about pH 4.9, pH 4.8, pH 4.7, pH 4.6, pH 4.5, pH 4.4, pH 4.3, pH 4.2, pH 4.1, pH 4.0, pH 3.9, pH 3.8, pH 3.7, pH 3.6, or pH 3.5.

According to embodiments, treatment with the pharmaceutical compositions described herein resulted in improvements in the vaginal Maturation Index. The Maturation Index is measured as a change in cell composition. According to embodiments and as related to VVA, a change in cell composition is measured as the change in percent of composition or amount of parabasal vaginal cells, intermediate cells, and superficial vaginal cells, such as a change in the composition or amount of parabasal vaginal cells compared with or, relative to, a change in superficial vaginal cells. A subject having VVA symptoms often has an increased number of parabasal cells and a reduced number of superficial cells (e.g., less than about 5%) compared with women who do not suffer from VVA. Conversely, a subject having decreasing VVA symptoms, or as otherwise responding to treatment, may demonstrate an improvement in the Maturation Index, specifically a decrease in the amount of parabasal cells or an increase in the amount of superficial cells compared to baseline (screening). In embodiments, a decrease in parabasal cells is measured as a reduction in the percent of parabasal cells; the percent reduction may be at least about an 85%, 80%, 75%, 70%, 65%, 60%, 55%, 50%, 45%, 40%, 35%, 30%, 25%, 20%, 15% or 10% reduction in the number of parabasal cells. In embodiments, a percent reduction may be at least about a 54% reduction in the number of parabasal cells. In embodiments, an increase in superficial cells is measured as an increase in the percent of superficial cells; the percent increase in superficial cells may be at least about 5%, 10%, 15%, 20%, 25%, 30%, 35%, 40%, 45%, or 50% increase in the number of superficial cells. In further embodiments, a percent increase may be at least about a 35% increase in the number of superficial cells.

In some embodiments, an improvement in the Maturation Index is assessed as a change over time. For example, as a change in cell composition measured at a baseline (screening) at Day 1 compared to the cell composition measured at Day 15. The change in cell composition may also be assessed as a change in the amount of parabasal cells over time, optionally in addition to measuring changes in parabasal cells and superficial cells as described above. Such cells may be obtained from the vaginal mucosal epithelium through routine gynecological examination and examined by means of a vaginal smear.

In various further aspects of this disclosure, treatment with the pharmaceutical compositions described herein resulted in any of: an increase in superficial cells; a decrease in parabasal cells; and an increase in intermediate cells.

In further aspects of this disclosure, samples may be collected to determine hormone levels, in particular, estradiol levels. In some embodiments, blood samples may be taken from a subject and the level of estradiol measured (pg/mL). In some embodiments, estradiol levels may be measured at 0 hours (for example, at time of first treatment), at 1 hour (for example, post first treatment), at 3 hours, and at 6 hours. In some embodiments, samples may be taken at day 8 (for example, post first treatment) and at day 15 (for example, one day post the last treatment on day 14). In some embodiments, descriptive statistics of plasma estradiol concentrations at each sampling time and observed $C_{max}$ and $T_{max}$ values may be measured and the AUC calculated.

In some embodiments, a suppository can comprise about 25 µg of estradiol. In such cases, administration of the suppository to a patient can provide, in a plasma sample from the patient, parameters including one or more parameters selected from: 1) a corrected geometric mean peak plasma concentration ($C_{max}$) of estradiol of about 19 pg*hr/mL to about 29 pg*hr/mL (e.g., 19.55 pg*hr/mL to about 28.75 pg*hr/mL); or 2) a corrected geometric mean area under the curve $(AUC)_{0-24}$ of estradiol of about 75 pg*hr/mL to about 112 pg*hr/mL (e.g., 75.82 pg*hr/mL to about 111.50). In some embodiments, administration of the suppository to a patient provides, in a plasma sample from the patient, one or more parameters selected from: 1) a corrected geometric mean peak plasma concentration ($C_{max}$) of estrone of about 9 pg*hr/mL to about 14 pg*hr/mL (e.g., 9.17 pg*hr/mL to about 13.49 pg*hr/mL); and 2) a corrected geometric mean area under the curve $(AUC)_{0-24}$ of estrone of about 43 pg*hr/mL to about 65 pg*hr/mL (e.g., 43.56 pg*hr/mL to about 64.06 pg*hr/mL). In some embodiments, administration of the suppository to a patient provides, in a plasma sample from the patient, provides one or more parameters selected from: 1) a corrected geometric mean peak plasma concentration ($C_{max}$) of estrone sulfate of about 416 pg*hr/mL to about 613 pg*hr/mL (e.g., 416.53 pg*hr/mL to about 612.55 pg*hr/mL); and 2) a corrected geometric mean area under the curve $(AUC)_{0-24}$ of estrone sulfate of about 3598 pg*hr/mL to about 5291 pg*hr/mL (e.g., 3598.04 pg*hr/mL to about 5291.24 pg*hr/mL).

In some embodiments, a suppository includes about 25 µg of estradiol. In some such embodiments, administration of the suppository to a patient can provide, in a plasma sample from the patient, parameters including one or more parameters selected from: 1) a corrected geometric mean peak plasma concentration ($C_{max}$) of estradiol ranging from about 20.9 pg/mL to about 32.8 pg/mL (e.g., 20.96 pg/mL to about 32.75 pg/mL); 2) a corrected geometric mean area under the curve $(AUC)_{0-24}$ of estradiol ranging from about 104.3 pg*hr/mL to about 163.1 pg*hr/mL (e.g., 104.32 pg*hr/mL to about 163.0 pg*hr/mL); and 3) an average concentration ($C_{avg}$) of estradiol ranging from about 4.3 pg/mL to about 6.8 pg/mL (e.g., 4.32 pg/mL to about 6.75 pg/mL), as assessed at day 1.

In some embodiments, administration of a suppository comprising about 25 µg of estradiol to a patient can provide, in a plasma sample from the patient, parameters including one or more parameters selected from: 1) a corrected geometric mean peak plasma concentration ($C_{max}$) of estradiol of about 26.2 pg/mL; 2) a corrected geometric mean area under the curve $(AUC)_{0-24}$ of estradiol of about 130 pg*hr/mL; and 3) an average concentration ($C_{avg}$) of estradiol of about 5.4 pg/mL, as assessed at day 1.

In some embodiments, administration of a suppository comprising about 25 µg of estradiol to a patient can provide, in a plasma sample from the patient, parameters including one or more parameters selected from: 1) a corrected geometric mean peak plasma concentration ($C_{max}$) of estradiol ranging from about 9.5 pg/mL to about 15.1 pg/mL (e.g., 9.60 pg*hr/mL to about 15.00 pg/mL); 2) a corrected geometric mean area under the curve $(AUC)_{0-24}$ of estradiol ranging from about 67.6 pg*hr/mL to about 105.8 pg*hr/mL (e.g., 67.68 pg*hr/mL to about 105.75 pg*hr/mL); and 3) an average concentration ($C_{avg}$) of estradiol ranging from about 2.7 pg/mL to about 4.4 pg/mL (e.g., 2.80 pg/mL to about 4.38 pg/mL) of estradiol as assessed at day 14.

In some embodiments, administration of a suppository comprising about 25 µg of estradiol to a patient can provide, in a plasma sample from the patient, parameters including one or more parameters selected from: 1) a corrected geometric mean peak plasma concentration ($C_{max}$) of estradiol of about 12.0 pg/mL; 2) a corrected geometric mean area under the curve $(AUC)_{0-24}$ of estradiol of about 84.6 pg*hr/mL; and 3) an average concentration ($C_{avg}$) of estradiol of about 3.5 pg/mL, as assessed at day 14.

In some embodiments, administration of a suppository comprising about 25 µg of estradiol to a patient provides, in a plasma sample from the patient, one or more parameters selected from: 1) a corrected geometric mean peak plasma concentration ($C_{max}$) of estrone conjugates ranging from about 158.8 pg/mL to about 248.3 pg/mL (e.g., 158.88 hr/mL to about 248.25 pg*hr/mL); and 2) a corrected geometric mean area under the curve $(AUC)_{0-24}$ of estrone conjugates ranging from about 1963.1 pg*hr/mL to about 3067.6 pg*hr/mL (e.g., 1963.20 pg*hr/mL to about 3067.50 pg*hr/mL) as assessed at day 1.

In some embodiments, administration of a suppository comprising about 25 µg of estradiol to a patient provides, in a plasma sample from the patient, one or more parameters selected from: 1) a corrected geometric mean peak plasma concentration ($C_{max}$) of estrone conjugates of about 198.6 pg/mL; and 2) a corrected geometric mean area under the curve $(AUC)_{0-24}$ of estrone conjugates of about 2454 pg*hr/mL as assessed at day 1.

In some embodiments, administration of a suppository comprising about 25 µg of estradiol to a patient provides, in a plasma sample from the patient, one or more parameters selected from: 1) an unadjusted arithmetic mean area under the curve $(AUC)_{0-24}$ of estradiol ranging from about 173.5 pg*hr/mL to about 271.3 pg*hr/mL (e.g., from 173.60 pg*hr/mL to about 271.25 pg*hr/mL; or about 217 pg*hr/mL), as assessed at day 1; 2) a corrected arithmetic mean peak plasma concentration ($C_{avg[0-24]}$) of estradiol ranging from about 7.2 pg/mL to about 11.4 pg/mL (e.g., from 7.25 pg/mL to about 11.33 pg/mL; or about 9.06 pg/mL), as assessed at day 1; 3) an unadjusted arithmetic mean area under the curve $(AUC)_{0-24}$ of estradiol ranging from about 137.5 pg*hr/mL to about 215.1 pg*hr/mL (e.g., from 137.60 pg*hr/mL to about 215.00 pg*hr/mL; or about 172 pg*hr/mL), as assessed at day 14; and 4) a corrected arithmetic mean peak plasma concentration $(C_{avg[0-24]})$ of estradiol ranging from about 5.7 pg/mL to about 9.0 pg/mL (e.g., from 5.72 pg/mL to about 8.94 pg/mL; or about 7.15 pg/mL), as assessed at day 14.

In some embodiments, administration of a suppository comprising about 25 µg of estradiol to a patient provides, in a plasma sample from the patient, one or more parameters selected from: 1) an unadjusted arithmetic mean area under the curve $(AUC)_{0-24}$ of estrone ranging from about 335.1 pg*hr/mL to about 523.8 pg*hr/mL (e.g., from 335.20 pg*hr/mL to about 523.75 pg*hr/mL; or about 419 pg*hr/mL), as assessed at day 1; 2) a corrected arithmetic mean peak plasma concentration $(C_{avg[0-24]})$ of estrone ranging from about 13.9 pg/mL to about 21.9 pg/mL (e.g., from 14.00 pg/mL to about 21.88 pg/mL; or about 17.5 pg/mL), as assessed at day 1; 3) an unadjusted arithmetic mean area under the curve $(AUC)_{0-24}$ of estrone ranging from about 343.1 pg*hr/mL to about 536.2 pg*hr/mL (e.g., from 343.20 pg*hr/mL to about 536.25 pg*hr/mL; or about 429 pg*hr/mL), as assessed at day 14; and 4) a corrected arithmetic mean peak plasma concentration $(C_{avg[0-24]})$ of estrone ranging from about 14.3 pg/mL to about 22.4 pg/mL (e.g., from 14.32 pg/mL to about 22.38 pg/mL; or about 17.9 pg/mL), as assessed at day 14.

In some embodiments, administration of a suppository comprising about 25 µg of estradiol to a patient provides, in a plasma sample from the patient, one or more parameters selected from: 1) an unadjusted arithmetic mean area under the curve $(AUC)_{0-24}$ of estrone conjugates ranging from about 7,300.7 pg*hr/mL to about 11,407.6 pg*hr/mL (e.g., from 7,300.80 pg*hr/mL to about 11,407.50 pg*hr/mL; or about 9,126 pg*hr/mL), as assessed at day 1; 2) a corrected arithmetic mean peak plasma concentration $(C_{avg[0-24]})$ of estrone conjugates ranging from about 303.9 pg/mL to about 475.1 pg/mL (e.g., from 304.00 pg/mL to about 475.00 pg/mL; or about 380 pg/mL), as assessed at day 1; 3) an unadjusted arithmetic mean area under the curve $(AUC)_{0-24}$ of estrone conjugates ranging from about 7,943.9 pg*hr/mL to about 12,412.6 pg*hr/mL (e.g., from 7,944.00 pg*hr/mL to about 12,412.50 pg*hr/mL; or about 9,930 pg*hr/mL), as assessed at day 14; and 4) a corrected arithmetic mean peak plasma concentration $(C_{avg[0-24]})$ of estrone conjugates ranging from about 331.1 pg/mL to about 517.4 pg/mL (e.g., from 331.20 pg/mL to about 517.50 pg/mL; or about 414 pg/mL), as assessed at day 14.

In some embodiments, a suppository can comprise about 10 µg of estradiol. In such cases, administration of the suppository to a patient can provide, in a plasma sample from the patient, one or more parameters selected from: 1) a corrected geometric mean peak plasma concentration $(C_{max})$ of estradiol of about 12 pg*hr/mL to about 18 pg*hr/mL (e.g., 12.22 pg*hr/mL to about 17.98 pg*hr/mL); 2) a corrected geometric mean area under the curve $(AUC)_{0-24}$ of estradiol of about 42 pg*hr/mL to about 63 pg*hr/mL (e.g., 42.18 pg*hr/mL to about 62.02 pg*hr/mL); and 3) a corrected geometric mean time to peak plasma concentration $(T_{max})$ of estradiol of about 1 hrs to about 3 hrs (e.g., 1.49 hrs to about 2.19 hrs). In some embodiments, administration of the suppository to a patient provides, in a plasma sample from the patient, one or more parameters selected from: 1) a corrected geometric mean peak plasma concentration $(C_{max})$ of estrone of about 4 pg*hr/mL to about 7 pg*hr/mL (e.g., 4.38 pg*hr/mL to about 6.44 pg*hr/mL); 2) a corrected geometric mean area under the curve $(AUC)_{0-24}$ of estrone of about 20 pg*hr/mL to about 31 pg*hr/mL (e.g., 20.60 pg*hr/mL to about 30.30 pg*hr/mL); and 3) a corrected geometric mean time to peak plasma concentration $(T_{max})$ of estrone of about 4 hrs to about 8 hrs (e.g., 4.99 hrs to about 7.34 hrs). In some embodiments, administration of the suppository to a patient provides, in a plasma sample from the patient, one or more parameters selected from: 1) a corrected geometric mean peak plasma concentration $(C_{max})$ of estrone sulfate of about 10 pg*hr/mL to about 16 pg*hr/mL (e.g., 10.34 pg*hr/mL to about 15.20 pg*hr/mL); 2) a corrected geometric mean area under the curve $(AUC)_{0-24}$ of estrone sulfate of about 56 pg*hr/mL to about 84 pg*hr/mL (e.g., 56.61 pg*hr/mL to about 83.25 pg*hr/mL); and 3) a corrected geometric mean time to peak plasma concentration $(T_{max})$ of estrone sulfate of about 4 hrs to about 7 hrs (e.g., 4.67 hrs to about 6.86 hrs).

In some embodiments, a suppository includes about 10 µg of estradiol. In some such embodiments, administration of the suppository to a patient can provide, in a plasma sample from the patient, a corrected geometric mean peak plasma concentration $(C_{max})$ of estradiol ranging from about 4.7 pg/mL to about 7.6 pg/mL (e.g., 4.80 pg*hr/mL to about 7.50 pg*hr/mL), as assessed at day 1. In some embodiments, administration of a suppository comprising about 10 µg of estradiol to a patient can provide, in a plasma sample from the patient, a corrected geometric mean peak plasma concentration $(C_{max})$ of estradiol ranging from about 2.3 pg*hr/mL to about 3.8 pg*hr/mL (e.g., 2.40 pg*hr/mL to about 3.75 pg*hr/mL) of estradiol as assessed at day 14.

In some embodiments, administration of a suppository comprising about 10 µg of estradiol to a patient provides, in a plasma sample from the patient, a corrected geometric mean peak plasma concentration $(C_{max})$ of estradiol of about 6.0 pg/mL, as assessed at day 1. In some embodiments, administration of a suppository comprising about 10 µg of estradiol to a patient can provide, in a plasma sample from the patient, a corrected geometric mean peak plasma concentration $(C_{max})$ of estradiol of about 3.0 pg/mL, as assessed at day 14.

In some embodiments, administration of a suppository comprising about 10 µg of estradiol to a patient provides, in a plasma sample from the patient, a corrected geometric mean area under the curve $(AUC)_{0-24}$ of estradiol ranging from about 17.5 pg/mL to about 27.4 pg/mL (e.g., 17.52 pg*hr/mL to about 27.37 pg*hr/mL), as assessed at day 1. In some embodiments, administration of a suppository comprising about 10 µg of estradiol to a patient can provide, in a plasma sample from the patient, a corrected geometric mean area under the curve $(AUC)_{0-24}$ of estradiol ranging from about 10.9 pg*hr/mL to about 17.2 pg*hr/mL (e.g., 10.96 pg*hr/mL to about 17.13 pg*hr/mL) of estradiol as assessed at day 14.

In some embodiments, administration of a suppository comprising about 10 µg of estradiol to a patient provides, in a plasma sample from the patient, a corrected geometric mean area under the curve $(AUC)_{0-24}$ of estradiol of about 21.9 pg*hr/mL, as assessed at day 1. In some embodiments, administration of a suppository comprising about 10 µg of estradiol to a patient can provide, in a plasma sample from the patient, a corrected geometric mean area under the curve $(AUC)_{0-24}$ of estradiol of about 13.7 pg*hr/mL, as assessed at day 14.

In some embodiments, administration of a suppository comprising about 10 μg of estradiol to a patient provides, in a plasma sample from the patient, an average concentration ($C_{avg}$) of estradiol ranging from about 0.6 pg/mL to about 1.1 pg/mL (e.g., 0.64 pg/mL to about 1.0 pg/mL), as assessed at day 1. In some embodiments, administration of a suppository comprising about 10 μg of estradiol to a patient can provide, in a plasma sample from the patient, an average concentration ($C_{avg}$) of estradiol ranging from about 0.1 pg/mL to about 0.3 pg/mL (e.g., 0.16 pg/mL to about 0.25 pg/mL) of estradiol as assessed at day 14.

In some embodiments, administration of a suppository comprising about 10 μg of estradiol to a patient provides, in a plasma sample from the patient, an average concentration ($C_{avg}$) of estradiol of about 0.8 pg/mL, as assessed at day 1. In some embodiments, administration of a suppository comprising about 10 μg of estradiol to a patient can provide, in a plasma sample from the patient, an average concentration ($C_{avg}$) of estradiol of about 0.2 pg/mL, as assessed at day 14.

In some embodiments, administration of a suppository comprising about 10 μg of estradiol to a patient provides, in a plasma sample from the patient, one or more parameters selected from: 1) a corrected geometric mean peak plasma concentration ($C_{max}$) of estrone conjugates ranging from about 72.1 pg/mL to about 112.8 pg/mL (e.g., 72.16 pg/mL to about 112.75 pg/mL); and 2) an average concentration ($C_{avg}$) of estrone conjugates ranging from about 6.3 pg/mL to about 10.1 pg/mL (e.g., 6.40 pg/mL to about 10.00 pg/mL) as assessed at day 1.

In some embodiments, administration of a suppository comprising about 10 μg of estradiol to a patient provides, in a plasma sample from the patient, one or more parameters selected from: 1) a corrected geometric mean peak plasma concentration ($C_{max}$) of estrone conjugates of about 90.2 pg/mL; and 2) an average concentration ($C_{avg}$) of estrone conjugates of about 8.0 pg/mL, as assessed at day 1.

In some embodiments, administration of a suppository comprising about 10 μg of estradiol to a patient provides, in a plasma sample from the patient, one or more parameters selected from: 1) an unadjusted arithmetic mean area under the curve $(AUC)_{0-24}$ of estradiol ranging from about 110.3 pg*hr/mL to about 172.6 pg*hr/mL (e.g., from 110.40 pg*hr/mL to about 172.50 pg*hr/mL; or about 138 pg*hr/mL), as assessed at day 1; 2) a corrected arithmetic mean peak plasma concentration ($C_{avg[0-24]}$) of estradiol ranging from about 4.6 pg/mL to about 7.8 pg/mL (e.g., from 4.61 pg/mL to about 7.20 pg/mL; or about 5.76 pg/mL), as assessed at day 1; 3) an unadjusted arithmetic mean area under the curve $(AUC)_{0-24}$ of estradiol ranging from about 87.9 pg*hr/mL to about 137.4 pg*hr/mL (e.g., from 88.00 pg*hr/mL to about 137.50 pg*hr/mL; or about 110 pg*hr/mL), as assessed at day 14; and 4) a corrected arithmetic mean peak plasma concentration ($C_{avg[0-24]}$) of estradiol ranging from about 3.6 pg/mL to about 5.8 pg/mL (e.g., from 3.67 pg/mL to about 5.74 pg/mL; or about 4.59 pg/mL), as assessed at day 14.

In some embodiments, administration of a suppository comprising about 10 μg of estradiol to a patient provides, in a plasma sample from the patient, one or more parameters selected from: 1) an unadjusted arithmetic mean area under the curve $(AUC)_{0-24}$ of estrone ranging from about 370.3 pg*hr/mL to about 578.8 pg*hr/mL (e.g., from 370.40 pg*hr/mL to about 578.75 pg*hr/mL; or about 463 pg*hr/mL), as assessed at day 1; 2) a corrected arithmetic mean peak plasma concentration ($C_{avg[0-24]}$) of estrone ranging from about 15.4 pg/mL to about 24.2 pg/mL (e.g., from 15.44 pg/mL to about 24.13 pg/mL; or about 19.3 pg/mL), as assessed at day 1; 3) an unadjusted arithmetic mean area under the curve $(AUC)_{0-24}$ of estrone ranging from about 371.1 pg*hr/mL to about 580.1 pg*hr/mL (e.g., from 371.20 pg*hr/mL to about 580.00 pg*hr/mL; or about 464 pg*hr/mL), as assessed at day 14; and 4) a corrected arithmetic mean peak plasma concentration ($C_{avg[0-24]}$) of estrone ranging from about 15.4 pg/mL to about 24.2 pg/mL (e.g., from 15.44 pg/mL to about 24.13 pg/mL; or about 19.3 pg/mL), as assessed at day 14.

In some embodiments, administration of a suppository comprising about 10 μg of estradiol to a patient provides, in a plasma sample from the patient, one or more parameters selected from: 1) an unadjusted arithmetic mean area under the curve $(AUC)_{0-24}$ of estrone conjugates ranging from about 4,745.5 pg*hr/mL to about 7,414.9 pg*hr/mL (e.g., from 4,745.60 pg*hr/mL to about 7,415.00 pg*hr/mL; or about 5,932 pg*hr/mL), as assessed at day 1; 2) a corrected arithmetic mean peak plasma concentration ($C_{avg[0-24]}$) of estrone conjugates ranging from about 197.5 pg/mL to about 308.8 pg/mL (e.g., from 197.60 pg/mL to about 308.75 pg/mL; or about 247 pg/mL), as assessed at day 1; 3) an unadjusted arithmetic mean area under the curve $(AUC)_{0-24}$ of estrone conjugates ranging from about 7,182.3 pg*hr/mL to about 11,222.6 pg*hr/mL (e.g., from 7,182.40 pg*hr/mL to about 11,222.50 pg*hr/mL; or about 8,978 pg*hr/mL), as assessed at day 14; and 4) a corrected arithmetic mean peak plasma concentration ($C_{avg[0-24]}$) of estrone conjugates ranging from about 299.1 pg/mL to about 467.6 pg/mL (e.g., from 299.20 pg/mL to about 467.50 pg/mL; or about 374 pg/mL), as assessed at day 14.

In some embodiments, a suppository can comprise about 4 μg of estradiol. In such cases, administration of the suppository to a patient can provide, in a plasma sample from the patient, one or more parameters selected from: 1) a corrected geometric mean peak plasma concentration ($C_{max}$) of estradiol of about 4 pg*hr/mL to about 8 pg*hr/mL; 2) a corrected geometric mean area under the curve $(AUC)_{0-24}$ of estradiol of about 16 pg*hr/mL to about 26 pg*hr/mL; and 3) a corrected geometric mean time to peak plasma concentration ($T_{max}$) of estradiol of about 0.25 hrs to about 2 hrs. In some embodiments, administration of the suppository to a patient provides, in a plasma sample from the patient, one or more parameters selected from: 1) a corrected geometric mean peak plasma concentration ($C_{max}$) of estrone of about 1 pg*hr/mL to about 3 pg*hr/mL; 2) a corrected geometric mean area under the curve $(AUC)_{0-24}$ of estrone of about 8 pg*hr/mL to about 13 pg*hr/mL; and 3) a corrected geometric mean time to peak plasma concentration ($T_{max}$) of estrone of about 1 hrs to about 4 hrs. In some embodiments, administration of the suppository to a patient provides, in a plasma sample from the patient, one or more parameters selected from: 1) a corrected geometric mean peak plasma concentration ($C_{max}$) of estrone sulfate of about 4 pg*hr/mL to about 7 pg*hr/mL; 2) a corrected geometric mean area under the curve $(AUC)_{0-24}$ of estrone sulfate of about 22 pg*hr/mL to about 34 pg*hr/mL; and 3) a corrected geometric mean time to peak plasma concentration ($T_{max}$) of estrone sulfate of about 1 hrs to about 3 hrs.

In some embodiments, a suppository includes about 4 μg of estradiol. In some such embodiments, administration of the suppository to a patient can provide, in a plasma sample from the patient, one or more parameters selected from: 1) a corrected geometric mean peak plasma concentration ($C_{max}$) of estradiol ranging from about 2.0 pg/mL to about 3.3 pg/mL (e.g., 2.08 pg/mL to about 3.25 pg/mL); and 2) a corrected geometric mean area under the curve $(AUC)_{0-24}$ of estradiol ranging from about 9.5 pg*hr/mL to about 15.1 pg*hr/mL (e.g., 9.60 pg*hr/mL to about 15.0 pg*hr/mL), as assessed at day 1. In some embodiments, administration of a suppository comprising about 4 µg of estradiol to a patient can provide, in a plasma sample from the patient, one or more parameters selected from: 1) a corrected geometric mean peak plasma concentration ($C_{max}$) of estradiol ranging from about 1.0 pg*hr/mL to about 1.7 pg*hr/mL (e.g., 1.04 pg*hr/mL to about 1.63 pg*hr/mL) of estradiol, and 2) a corrected geometric mean area under the curve $(AUC)_{0-24}$ of estradiol ranging from about 5.7 pg*hr/mL to about 9.1 pg*hr/mL (e.g., 5.76 pg*hr/mL to about 9.0 pg*hr/mL).

In some embodiments, administration of a suppository comprising about 4 µg of estradiol to a patient provides, in a plasma sample from the patient, one or more parameters selected from: 1) a corrected geometric mean peak plasma concentration ($C_{max}$) of estradiol of about 2.6 pg/mL; and 2) a corrected geometric mean area under the curve $(AUC)_{0-24}$ of estradiol of about 12 pg*hr/mL, as assessed at day 1. In some embodiments, administration of a suppository comprising about 10 µg of estradiol to a patient can provide, in a plasma sample from the patient, one or more parameters selected from: 1) a corrected geometric mean peak plasma concentration ($C_{max}$) of estradiol of about 1.3 pg/mL; 2) a corrected geometric mean area under the curve $(AUC)_{0-24}$ of estradiol of about 7.2 pg*hr/mL, as assessed at day 14.

In some embodiments, administration of a suppository comprising about 4 µg of estradiol to a patient provides, in a plasma sample from the patient, a corrected geometric mean peak plasma concentration ($C_{max}$) of estrone conjugates ranging from about 0.3 pg/mL to about 0.5 pg/mL (e.g., 0.32 pg/mL to about 0.5 pg/mL) as assessed at day 1.

In some embodiments, administration of a suppository comprising about 4 µg of estradiol to a patient provides, in a plasma sample from the patient, a corrected geometric mean peak plasma concentration ($C_{max}$) of estrone conjugates of about 0.4 pg/mL as assessed at day 1.

In some embodiments, administration of a suppository comprising about 4 µg of estradiol to a patient provides, in a plasma sample from the patient, one or more parameters selected from: 1) an unadjusted arithmetic mean area under the curve $(AUC)_{0-24}$ of estradiol ranging from about 73.3 pg*hr/mL to about 114.7 pg*hr/mL (e.g., from 73.36 pg*hr/mL to about 114.63 pg*hr/mL; or about 91.7 pg*hr/mL), as assessed at day 1; 2) a corrected arithmetic mean peak plasma concentration ($C_{avg[0-24]}$) of estradiol ranging from about 3.1 pg/mL to about 4.8 pg/mL (e.g., from 3.14 pg/mL to about 4.90 pg/mL; or about 3.92 pg/mL), as assessed at day 1; 3) an unadjusted arithmetic mean area under the curve $(AUC)_{0-24}$ of estradiol ranging from about 69.7 pg*hr/mL to about 108.9 pg*hr/mL (e.g., from 69.76 pg*hr/mL to about 109.00 pg*hr/mL; or about 87.2 pg*hr/mL), as assessed at day 14; and 4) a corrected arithmetic mean peak plasma concentration ($C_{avg[0-24]}$) of estradiol ranging from about 2.8 pg/mL to about 4.6 pg/mL (e.g., from 2.90 pg/mL to about 4.54 pg/mL; or about 3.63 pg/mL), as assessed at day 14.

In some embodiments, administration of a suppository comprising about 4 µg of estradiol to a patient provides, in a plasma sample from the patient, one or more parameters selected from: 1) an unadjusted arithmetic mean area under the curve $(AUC)_{0-24}$ of estrone ranging from about 231.9 pg*hr/mL to about 362.4 pg*hr/mL (e.g., from 232.00 pg*hr/mL to about 362.50 pg*hr/mL; or about 290 pg*hr/mL), as assessed at day 1; 2) a corrected arithmetic mean peak plasma concentration ($C_{avg[0-24]}$) of estrone ranging from about 10.3 pg/mL to about 16.3 pg/mL (e.g., from 10.40 pg/mL to about 16.25 pg/mL; or about 13 pg/mL), as assessed at day 1; 3) an unadjusted arithmetic mean area under the curve $(AUC)_{0-24}$ of estrone ranging from about 261.5 pg*hr/mL to about 408.8 pg*hr/mL (e.g., from 261.60 pg*hr/mL to about 408.75 pg*hr/mL; or about 327 pg*hr/mL), as assessed at day 14; and 4) a corrected arithmetic mean peak plasma concentration ($C_{avg[0-24]}$) of estrone ranging from about 10.8 pg/mL to about 17.1 pg/mL (e.g., from 10.88 pg/mL to about 17.00 pg/mL; or about 13.6 pg/mL), as assessed at day 14.

In some embodiments, administration of a suppository comprising about 4 µg of estradiol to a patient provides, in a plasma sample from the patient, one or more parameters selected from: 1) an unadjusted arithmetic mean area under the curve $(AUC)_{0-24}$ of estrone conjugates ranging from about 4,062.3 pg*hr/mL to about 6,347.6 pg*hr/mL (e.g., from 4,062.40 pg*hr/mL to about 6,347.50 pg*hr/mL; or about 5,078 pg*hr/mL), as assessed at day 1; 2) a corrected arithmetic mean peak plasma concentration ($C_{avg[0-24]}$) of estrone conjugates ranging from about 172.7 pg/mL to about 270.1 pg/mL (e.g., from 172.80 pg/mL to about 270.00 pg/mL; or about 216 pg/mL), as assessed at day 1; 3) an unadjusted arithmetic mean area under the curve $(AUC)_{0-24}$ of estrone conjugates ranging from about 4,138.3 pg*hr/mL to about 6,466.3 pg*hr/mL (e.g., from 4,138.40 pg*hr/mL to about 6,466.25 pg*hr/mL; or about 5173 pg*hr/mL), as assessed at day 14; and 4) a corrected arithmetic mean peak plasma concentration ($C_{avg[0-24]}$) of estrone conjugates ranging from about 172.7 pg/mL to about 270.1 pg/mL (e.g., from 172.80 pg/mL to about 270.00 pg/mL; or about 216 pg/mL), as assessed at day 14.

A pharmaceutical composition provided herein can result in substantially local delivery of estradiol. For example, plasma concentrations of estradiol, estrone, and estrone sulfate measured in the plasma of a patient following administration of a pharmaceutical composition as provided herein be statistically similar to those measured following administration of a placebo formulation (i.e., a similar formulation lacking the estradiol). Accordingly, in some embodiments, the plasma concentrations of estradiol, estrone, or estrone sulfate measured following administration of a pharmaceutical composition provided herein may be low compared to RLD formulations.

In some embodiments, a suppository can include about 1 µg to about 25 µg of estradiol. Upon administration the suppository to a patient, a plasma sample from the patient can provide a corrected geometric mean peak plasma concentration ($C_{max}$) of estradiol that is less than about 30 pg*hr/mL. For example, administration of the suppository to a patient provides a corrected geometric mean peak plasma concentration ($C_{max}$) of estradiol that is less than about 18 pg*hr/mL. In some embodiments, administration of the suppository to a patient provides a corrected geometric mean area under the curve $(AUC)_{0-24}$ of estradiol that is less than about 112 pg*hr/mL. For example, administration of the suppository to a patient provides a corrected geometric mean area under the curve $(AUC)_{0-24}$ of estradiol that is less than about 63 pg*hr/mL.

In some embodiments, administration of the suppository to a patient provides a corrected geometric mean peak plasma concentration ($C_{max}$) of estrone that is less than about 14 pg*hr/mL. For example, administration of the suppository to a patient provides a corrected geometric mean peak plasma concentration ($C_{max}$) of estrone that is less than about 7 pg*hr/mL. In some embodiments, administration of the suppository to a patient provides a corrected geometric mean area under the curve $(AUC)_{0-24}$ of estrone that is less than about 65 pg*hr/mL. For example, administration of the suppository to a patient provides a corrected geometric mean area under the curve $(AUC)_{0-24}$ of estrone that is less than about 31 pg*hr/mL.

In some embodiments, administration of the suppository to a patient provides a corrected geometric mean peak plasma concentration $(C_{max})$ of estrone sulfate that is less than about 613 pg*hr/mL. For example, administration of the suppository to a patient provides a corrected geometric mean peak plasma concentration $(C_{max})$ of estrone sulfate that is less than about 16 pg*hr/mL. In some embodiments, administration of the suppository to a patient provides a corrected geometric mean area under the curve $(AUC)_{0-24}$ of estrone sulfate that is less than about 5291 pg*hr/mL. For example, administration of the suppository to a patient provides a corrected geometric mean area under the curve $(AUC)_{0-24}$ of estrone sulfate that is less than about 84 pg*hr/mL.

In further aspects of this disclosure, capsule disintegration may be determined. In some embodiments, delivery vehicle disintegration or absorption (presence or absence of the delivery vehicle after administration) at day 1 of treatment (for example, at 6 hours post first treatment) and at day 15 (for example, one day post the last treatment on day 14).

The pharmaceutical compositions can be formulated as described herein to provide desirable pharmacokinetic parameters in a subject (e.g., a female subject) to whom the composition is administered. In some embodiments, a pharmaceutical composition as described herein produces desirable pharmacokinetic parameters for estradiol in the subject. In some embodiments, a pharmaceutical composition as described herein produces desirable pharmacokinetic parameters for one or more metabolites of estradiol in the subject, for example, estrone or total estrone.

Following the administration of a composition comprising estradiol to a subject, the concentration and metabolism of estradiol can be measured in a sample (e.g., a blood, serum, or plasma sample) from the subject. Estradiol is typically converted reversibly to estrone, and both estradiol and estrone can be converted to the metabolite estriol. In postmenopausal women, a significant proportion of circulating estrogens exist as sulfate conjugates, especially estrone sulfate. Thus, estrone can be measured with respect to "estrone" amounts (excluding conjugates such as estrone sulfate) and "total estrone" amounts (including both free, or unconjugated, estrone and conjugated estrone such as estrone sulfate).

The pharmaceutical compositions of this disclosure can be characterized for one or more pharmacokinetic parameters of estradiol or a metabolite thereof following administration of the composition to a subject or to a population of subjects. These pharmacokinetic parameters include AUC, $C_{max}$, $C_{avg}$, and $T_{max}$. AUC is a determination of the area under the curve (AUC) plotting the blood, serum, or plasma concentration of drug along the ordinate (Y-axis) against time along the abscissa (X-axis). AUCs are well understood, frequently used tools in the pharmaceutical arts and have been extensively described. $C_{max}$ is well understood in the art as an abbreviation for the maximum drug concentration in blood, serum, or plasma of a subject. $T_{max}$ is well understood in the art as an abbreviation for the time to maximum drug concentration in blood, serum, or plasma of a subject.

In some embodiments, one or more pharmacokinetic parameters, e.g., AUC, $C_{max}$, $C_{avg}$, or $T_{max}$, is measured for estradiol. In some embodiments, one or more pharmacokinetic parameters, e.g., AUC, $C_{max}$, $C_{avg}$, or $T_{max}$, is measured for estrone. In some embodiments, one or more pharmacokinetic parameters, e.g., AUC, $C_{max}$, $C_{avg}$, or $T_{max}$, is measured for total estrone. Any pharmacokinetic parameter can be a "corrected" parameter, wherein the parameter is determined as a change over a baseline level.

Any of a variety of methods can be used for measuring the levels of estradiol, estrone, or total estrone in a sample, including immunoassays, mass spectrometry (MS), high performance liquid chromatography (HPLC) with ultraviolet fluorescent detection, liquid chromatography in conjunction with mass spectrometry (LC-MS), tandem mass spectrometry (MS/MS), and liquid chromatography-tandem mass spectrometry (LC-MS/MS). In some embodiments, the levels of estradiol, estrone, or total estrone are measured using a validated LC-MS/MS method. Methods of measuring hormone levels are well described in the literature.

Statistical Measurements

According to embodiments, pharmacokinetics of the pharmaceutical composition disclosed herein are measured using statistical analysis. According to embodiments, Analysis of Variance ("ANOVA") or Analysis of CoVariance ("ANCOVA") are used to evaluate differences between a patient receiving treatment with a pharmaceutical composition comprising an active pharmaceutical composition (for example, a pharmaceutical composition comprising estradiol) and a patient receiving treatment with a placebo (for example, the same pharmaceutical composition but without estradiol) or a reference drug. A person of ordinary skill in the art will understand how to perform statistical analysis of the data collected.

VIII. Examples

The following examples are of pharmaceutical compositions, delivery vehicles, and combinations thereof. Methods of making are also disclosed. Data generated using the pharmaceutical compositions disclosed herein are also disclosed.

Example 1: Pharmaceutical Composition

In embodiments, estradiol is procured and combined with one or more pharmaceutically acceptable solubilizing agents. The estradiol is purchased as a pharmaceutical grade ingredient, often as micronized estradiol, although other forms can also be used. In embodiments, the pharmaceutical composition includes estradiol in a dosage strength of from about 1 μg to about 50 μg. In embodiments, the pharmaceutical composition includes 10 μg of estradiol. In embodiments, the pharmaceutical composition includes 25 μg of estradiol.

In embodiments, the estradiol is combined with pharmaceutically acceptable solubilizing agents, and, optionally, other excipients, to form a pharmaceutical composition. In embodiments, the solubilizing agent is one or more of CAPMUL MCM, MIGLYOL 812, GELUCIRE 39/01, GELUCIRE 43/01, GELUCIRE 50/13, and TEFOSE 63.

GELUCIRE 39/01 and GELUCIRE 43/01 each have an HLB value of 1. GELUCIRE 50/13 has an HLB value of 13. TEFOSE 63 has an HLB value of between 9 and 10.

Various combinations of pharmaceutically acceptable solubilizing agents were combined with estradiol and examined as shown in Table 1.

TABLE 1

Capmul MCM ("MCM"), Gelucire 39/01 ("39/01"), Gelucire 43/01("43/01"), Gelucire 50/13("50/13"), and Tefose ("Tefose 63")

| # | Vehicle system | Ratio | Physical state @ Room Temperature | Physical state @ 37° C. after ~30 minutes | Viscosity (cps) | Melting Time @ 37° C. | Dispersion in water 37° C. |
|---|---|---|---|---|---|---|---|
| 1 | MCM: 39/01 | 8:2 | Solid | Clear liquid | 50 @ 37° C. | Start: 6 min Finish: 12 min | Small oil drops on top |
| 2 | MCM: 39/01 | 7:3 | Solid | Clear liquid | | Start: 9 min Finish: 19 min | |
| 3 | MCM: 39/01 | 6:4 | Solid | Clear liquid | | Start: 20 min Finish: 32 min | |
| 4 | MCM: 43/01 | 8:2 | Solid | Liquid with solid particles | | | |
| 5 | MCM: 43/01 | 7:3 | Solid | Liquid with solid particles | | | |
| 6 | MCM: 50/13 | 9:1 | Liquid/cloudy | Liquid/cloudy | 140@ 25° C. | Clear after 20 min | Uniformly cloudy dispersion |
| 7 | MCM: 50/13 | 8:2 | Liquid/cloudy | Liquid/cloudy | 190@ 25° C. | | Uniformly cloudy dispersion |
| 8 | MCM: 50/13 | 7:3 | Semisolid | Semisolid | | | |
| 9 | MCM: TEFOSE 63 | 9:1 | Semisolid | Liquid/cloudy | 150@ 25° C. | Start: 1 min Finish: 5 min | Uniformly cloudy dispersion |
| 10 | MCM: TEFOSE 63 | 8:2 | Semisolid | Semisolid | 240@ 25° C. | | Uniformly cloudy dispersion |
| 11 | MCM: TEFOSE 63 | 7:3 | Semisolid | Semisolid | 380@ 25° C. | Semisolid after 30 min at 37° C., doesn't melt at 41° C. | Uniformly cloudy dispersion |
| 12 | MIGLYOL 812: 50/13 | 9:1 | Semisolid | Semisolid | 140@ 25° C. | | 2 phases, oil on top |
| 13 | MIGLYOL 812: TEFOSE 63 | 9:1 | Liquid/cloudy | Liquid/cloudy | 90@ 25° C. | Start: 1 min Finish: 5 min | 2 phases, oil on top |

Pharmaceutical compositions in Table 1 that were liquid or semisolid at room temperature were tested using a Brookfield viscometer (Brookfield Engineering Laboratories, Middleboro, Mass.) at room temperature. Pharmaceutical compositions appearing in Table 1 that were solid at ambient temperature were tested using a Brookfield viscometer at 37° C.

Pharmaceutical compositions appearing in Table 1 that were solid at room temperature were assessed at 37° C. to determine their melting characteristics. The viscosity of the gels can be important during encapsulation of the formulation. For example, in some cases, it is necessary to warm the formulation prior to filing of the gelatin capsules. In addition, the melting characteristics of the composition can have important implications following administration of the formulation into the body. For example, in some embodiments, the formulation will melt at temperatures below about 37° C. Pharmaceutical Composition 11 (Capmul MCM/Tefose 63), for example, did not melt at 37° C. or 41° C.

A dispersion assessment of the pharmaceutical compositions appearing in Table 1 was performed. The dispersion assessment was performed by transferring 300 mg of each vehicle system in 100 mL of 37° C. water, without agitation, and observing for mixing characteristics. Results varied from formation of oil drops on the top to separation of phases to uniform, but cloudy dispersions. Generally speaking, it is believed that formulations able to readily disperse in aqueous solution will have better dispersion characteristics upon administration. It was surprisingly found, however, as shown below in Examples 7-9, that formulations that did not readily disperse in aqueous solution (e.g., Formulation 13) and instead formed two phases upon introduction to the aqueous solution were found to be the most effective when administered to the human body.

Example 2: Delivery Vehicle

In embodiments, the pharmaceutical composition is delivered in a gelatin capsule delivery vehicle. The gelatin capsule delivery vehicle includes, for example, gelatin (e.g., Gelatin, NF (150 Bloom, Type B)), hydrolyzed collagen (e.g., GELITA®, GELITA AG, Eberbach, Germany), glycerin, sorbitol special, or other excipients in proportions that are well known and understood by persons of ordinary skill in the art. Sorbitol special may be obtained commercially and may tend to act as a plasticizer and humectant.

A variety of delivery vehicles were developed, as show in Table 2, Gels A through F. In Table 2, each delivery vehicle A through F differs in the proportion of one or more components.

TABLE 2

| Ingredient | A % w/w | B % w/w | C % w/w | D % w/w | E % w/w | F % w/w |
|---|---|---|---|---|---|---|
| Gelatin, NF (150 Bloom, Type B) | 41.0 | 41.0 | 41.0 | 41.0 | 43.0 | 43.0 |
| Glycerin 99.7%, USP | 6.0 | 6.0 | 6.0 | 6.0 | 18.0 | 18.0 |
| Sorbitol Special, USP | 15.0 | 15.0 | 15.0 | 15.0 | | |
| GELITA ® (hydrolyzed collagen) | 3 | | | | 3.0 | |
| Citric acid | | 0.1 | 0.5 | 1 | | 0.1 |
| Purified Water | 35.0 | 37.9 | 37.5 | 37.0 | 36.0 | 38.9 |
| Total | 100.0 | 100.0 | 100.0 | 100.0 | 100.0 | 100.0 |
| Dissolution gel strips, Avg of 3 (500 mL DH2O, 50 rpm @ 37° C.) | 48 min (42, 45, 58) | 50 min (50, 51, 50) | 75 min (76, 75, 74) | 70 min (70, 71, 70) | | |
| Dissolution gel strips, Avg of 3 (500 mL pH 4 buffer, 50 rpm @ 37° C.) | 70 min | | | | 78 min | 82 min |

Each delivery vehicle A through F was prepared at a temperature range from about 45° C. to about 85° C. Each molten delivery vehicle A through F was cast into a film, dried, and cut into strips. The strips were cut into uniform pieces weighing about 0.5 g, with about 0.5 mm thickness. Strips were placed into a USP Type 2 dissolution vessel in either water or pH 4 buffer solution and the time for them to completely dissolve was recorded (see Table 2). Delivery vehicle A had the fastest dissolution in both water and pH 4 buffer solution.

Example 3: Pharmaceutical Compositions and Delivery Vehicle

Various combinations of the pharmaceutical compositions from Table 1 and from Table 2 were prepared. The combinations are shown in Table 3.

TABLE 3

| Trial | Pharmaceutical Composition | Ratio | Batch Size g | Delivery Vehicle |
|---|---|---|---|---|
| 1 | MCM: 39/01 | 8:2 | 750 | A |
| 2 | MCM: 50/13 | 8:2 | 750 | A |
| 3 | MCM: TEFOSE 63 | 8:2 | 750 | A |
| 4 | MCM: TEFOSE 63 | 8:2 | 750 | B |
| 5 | MIGLYOL 812: TEFOSE 63 | 9:1 | 750 | A |

Each aliquot of the pharmaceutical compositions of Table 3 about 300 mg to about 310 mg. Batch size was as listed in Table 3. To encapsulate the vehicle system, each 300 mg to about 310 mg pharmaceutical composition aliquot was encapsulated in about 200 mg of the gelatin capsule delivery vehicle. Thus, for example, in Trial 1, the pharmaceutical composition denoted by MCM:39/01 was encapsulated in gelatin capsule delivery vehicle A for a total encapsulated weight of about 500 mg to about 510 mg. The aliquot size is arbitrary depending on the concentration of the estradiol and the desired gelatin capsule delivery vehicle size. Artisans will readily understand how to adjust the amount of estradiol in the pharmaceutical composition to accommodate a given size of delivery vehicle, when the delivery vehicle encapsulates the pharmaceutical composition.

Example 4: Estradiol Solubility

In various experiments, solubilizing agents were tested to determine whether they were able to solubilize 2 mg of estradiol for a total pharmaceutical composition weight of 100 mg. The solubilizing agents were considered suitable if estradiol solubility in the solubilizing agent was greater than or equal to about 20 mg/g. Initial solubility was measured by dissolving micronized estradiol into various solubilizing agents until the estradiol was saturated (the estradiol/solubilizing agent equilibrated for three days), filtering the undissolved estradiol, and analyzing the resulting pharmaceutical composition for estradiol concentration by HPLC.

TABLE 4

| Solubility of Solubilizing Agents | |
|---|---|
| Ingredient | Solubility (mg/g) |
| PEG 400 | 105* |
| Propylene Glycol | 75* |
| Polysorbate 80 | 36* |
| TRANSCUTOL HP | 141 |
| CAPMUL PG8 | 31.2 |

*denotes literature reference

Example 5: Pharmaceutical Compositions

The following pharmaceutical compositions are contemplated.

Gel Mass

| Ingredient | % w/w | Qty/Batch (kg) |
|---|---|---|
| Gelatin 150 Bloom Limed Bone, NF | 41.00 | 82.00 |
| Hydrolyzed Gelatin | 3.00 | 6.00 |
| Glycerin 99.7% | 6.00 | 12.00 |
| Sorbitol Special, NF | 15.00 | 30.00 |
| Opatint White G-18006 | 1.20 | 2.40 |
| Opatine Red DG-15001 | 0.06 | 0.12 |
| Purified Water, USP | 33.74 | 67.48 |
| Total | 100.00 | 200.00 Kg |

Pharmaceutical Composition 1: 10 μg Estradiol

| Ingredients | Qty/Capsule (mg) | % w/w | Qty/Batch |
|---|---|---|---|
| Estradiol hemihydrate micronized, USP | 0.010 | 0.003 | 0.10 g |
| CAPMUL ® MCM, NF (Glyceryl Caprylate/Caprate or Medium Chain Mono- and Diglycerides) | 240.0 | 79.997 | 2.40 kg |
| GELUCIRE ® 50/13 (stearoyl polyoxyl-32 glycerides NF) | 60.0 | 20.0 | 600.0 g |
| Total | 300.0 | 100.0 | 3.0 kg |

Pharmaceutical Composition 2: 10 μg Estradiol

| Ingredients | Qty/Capsule (mg) | % w/w | Qty/Batch |
|---|---|---|---|
| Estradiol hemihydrate micronized, USP | 0.010 | 0.003 | 0.10 g |
| MIGLOYL ® 812 (medium chain triglyceride) | 270.0 | 89.997 | 2.70 kg |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 300.0 g |
| Total | 300.0 | 100.0 | 3.00 kg |

Pharmaceutical Composition 3: 25 μg Estradiol

| Ingredients | Qty/Capsule (mg) | % w/w | Qty/Batch |
|---|---|---|---|
| Estradiol hemihydrate micronized, USP | 0.026* | 0.009 | 0.26 g |
| MIGLOYL ® 812 (medium chain triglyceride) | 270.0 | 89.991 | 2.70 kg |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.02 | 10.0 | 300.0 g |
| Total | 300.0 | 100.0 | 3.00 kg |

*1.0 mg estradiol is equivalent to 1.03 mg estradiol hemihydrate

Pharmaceutical Composition 4: 4 μg Estradiol

| Ingredients | Qty/Capsule (mg) | % w/w | Qty/Batch (alternate batch size) |
|---|---|---|---|
| Estradiol hemihydrate micronized, USP | 0.0041* | 0.001 | 0.041 g (0.615 g) |
| MIGLOYL ® 812 (medium chain triglyceride) | 269.99 | 89.999 | 2700.0 g (40.50 kg) |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 300.0 g (4.50 kg) |
| Total | 300.0 | 100.0 | 3000.0 g 45.0 kg |

*1.0 mg estradiol is equivalent to 1.03 mg estradiol hemihydrate

Pharmaceutical Composition 5: 10 μg Estradiol

| Ingredients | Qty/Capsule (mg) | % w/w | Qty/Batch |
|---|---|---|---|
| Estradiol hemihydrate micronized, USP | 0.0103* | 0.003 | 1.545 g |
| MIGLOYL ® 812 (medium chain triglyceride) | 269.99 | 89.997 | 40.5 kg |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 4.50 kg |
| Total | 300.0 | 100.0 | 45.00 kg |

*1.0 mg estradiol is equivalent to 1.03 mg estradiol hemihydrate

Pharmaceutical Composition 6: 25 μg Estradiol

| Ingredients | Qty/Capsule (mg) | % w/w | Qty/Batch |
|---|---|---|---|
| Estradiol hemihydrate micronized, USP | 0.026* | 0.009 | 3.90 g |
| MIGLOYL ® 812 (medium chain triglyceride) | 269.97 | 89.991 | 40.50 kg |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 4.50 kg |
| Total | 300.0 | 100.0 | 45.00 kg |

*1.0 mg estradiol is equivalent to 1.03 mg estradiol hemihydrate

Pharmaceutical Composition 7: Placebo

| Ingredients | Qty/Capsule (mg) | % w/w | Qty/Batch |
|---|---|---|---|
| Estradiol hemihydrate micronized, USP | 0.00 | 0.00 | 0.00 g |
| MIGLOYL ® 812 (medium chain triglyceride) | 270.0 | 90.0 | 40.5 kg |

-continued

| Ingredients | Qty/ Capsule (mg) | % w/w | Qty/ Batch |
|---|---|---|---|
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 4.5 kg |
| Total | 300.0 | 100.0 | 3000.0 g |

In the Examples below, TX-004HR is Pharmaceutical Compositions 4, 5, and 6 (TX-004HR 4 µg, TX-004HR 10 µg, and TX-004HR 25 µg) compared to Pharmaceutical Composition 7.

Example 6: Process

FIG. 1 illustrates an embodiment of a method making pharmaceutical composition comprising estradiol solubilized in CapmulMCM/Gelucire solubilizing agent encapsulated in a soft gelatin delivery vehicle 100. In operation 102, the CapmulMCM is heated to 40° C.±5° C. Heating may be accomplished through any suitable means. The heating may be performed in any suitable vessel, such as a stainless steel vessel. Other pharmaceutical compositions can be made using the same general method by substituting various excipients, including the solubilizing agent.

In operation 104, GELUCIRE is mixed with the CapmulMCM to form the finished solubilizing agent. As used herein, any form of GELUCIRE may be used in operation 104. For example, one or more of GELUCIRE 39/01, GELUCIRE 43/01, GELUCIRE 50/13 may be used in operation 104. Mixing is performed as would be known to persons of ordinary skill in the art, for example by impeller, agitator, stirrer, or other like devices used to mix pharmaceutical compositions. Operation 104 may be performed under an inert or relatively inert gas atmosphere, such as nitrogen gas. Mixing may be performed in any vessels that are known to persons of ordinary skill in the art, such as a stainless steel vessel or a steel tank.

In operation 106 estradiol is mixed into the solubilizing agent. In embodiments, the estradiol in micronized when mixed into the solubilizing agent. In other embodiments, the estradiol added is in a non-micronized form. Mixing may be facilitated by an impeller, agitator, stirrer, or other like devices used to mix pharmaceutical compositions. Operation 106 may be performed under an inert or relatively inert gas atmosphere, such as nitrogen gas.

In embodiments, however, the addition of estradiol may be performed prior to operation 104. In that regard, operations 104 and 106 are interchangeable with respect to timing or can be performed contemporaneously with each other.

In operation 110, the gelatin delivery vehicle is prepared. Any of the gelatin delivery vehicles described herein may be used in operation 110. In embodiments, gelatin, hydrolyzed collagen, glycerin, and other excipients are combined at a temperature range from about 45° C. to about 85° C. and prepared as a film. Mixing may occur in a steel tank or other container used for preparing gelatin delivery vehicles. Mixing may be facilitated by an impellor, agitator, stirrer, or other devices used to combine the contents of gelatin delivery vehicles. Operation 110 may be performed under an inert or relatively inert gas atmosphere, such as nitrogen gas.

In embodiments, the gelatin delivery vehicle mixture is degassed prior to being used to encapsulate the pharmaceutical composition.

In operation 112, the gelatin delivery vehicle encapsulates the pharmaceutical composition, according to protocols well known to persons of ordinary skill in the art. In operation 112, a soft gelatin capsule delivery vehicle is prepared by combining the pharmaceutical composition made in operation 106 with the gelatin delivery vehicle made in operation 110. The gelatin may be wrapped around the material, partially or fully encapsulating it or the gelatin can also be injected or otherwise filled with the pharmaceutical composition made in operation 106.

In embodiments, operation 112 is completed in a suitable die to provide a desired shape. Vaginal soft gel capsules may be prepared in a variety of geometries. For example, vaginal soft gel capsules may be shaped as a tear drop, a cone with frustoconical end, a cylinder, a cylinder with larger "cap" portion as illustrated in FIG. 2, or other shapes suitable for insertion into the vagina. The resulting pharmaceutical composition encapsulated in the soft gelatin delivery vehicle may be inserted digitally or with an applicator.

Example 7: Study of Estradiol Pharmaceutical Composition on the Improvement of Vulvovaginal Atrophy (VVA)

The objective of this study was designed to evaluate the efficacy and safety of a pharmaceutical composition comprising 10 µg estradiol (i.e., Pharmaceutical Composition 2) in treating moderate to severe symptoms of VVA associated with menopause after 14 days of treatment, and to estimate the effect size and variability of vulvovaginal atrophy endpoints. In addition, the systemic exposure to estradiol from single and multiple doses of the pharmaceutical composition was investigated.

This study was a phase 1, randomized, double-blind, placebo-controlled trial to evaluate safety and efficacy of the pharmaceutical composition in reducing moderate to severe symptoms of vaginal atrophy associated with menopause and to investigate the systemic exposure to estradiol following once daily intravaginal administrations of a pharmaceutical composition for 14 days.

Postmenopausal subjects who met the study entry criteria were randomized to one of two treatment groups (pharmaceutical composition or placebo). During the screening period subjects were asked to self-assess the symptoms of VVA, including vaginal dryness, vaginal or vulvar irritation or itching, dysuria, vaginal pain associated with sexual activity, and vaginal bleeding associated with sexual activity. Subjects with at least one self-assessed moderate to severe symptom of VVA identified by the subject as being most bothersome to her were eligible to participate in the study.

Clinical evaluations were performed at the following time points:
Screening Period (up to 28 days);
Visit 1—Randomization/Baseline (day 1);
Visit 2—Interim (day 8); and
Visit 3—End of the treatment (day 15).

Eligible subjects were randomized in a 1:1 ratio to receive either pharmaceutical composition comprising estradiol 10 µg or a matching placebo vaginal softgel capsule, and self-administered their first dose of study medication at the clinical facility under the supervision of the study personnel. Serial blood samples for monitoring of estradiol level were collected at 0.0, 1.0, 3.0, and 6.0 hours relative to first dose administration on day 1. Subjects remained at the clinical site until completion of the 6-hour blood draw and returned to clinical facility for additional single blood draws for measurement of estradiol concentration on day 8 (before the morning dose) and day 15. Subjects were provided with enough study medication until the next scheduled visit and were instructed to self-administer their assigned study treatment once a day intravaginally at approximately the same time (±1 hour) every morning. Each subject was provided with a diary in which she was required to daily record investigational drug dosing dates and times. Subjects returned to clinical facility on day 8 for interim visit and on day 15 for end of treatment assessments and post study examinations. Capsule disintegration state was assessed by the investigator at day 1 (6 hours post-dose) and day 15.

The study involved a screening period of up to 28 days before randomization and treatment period of 14 days. Selection of dosage strength (estradiol 10 μg) and treatment regimen (once daily for two weeks) was based on the FDA findings on safety and efficacy of the RLD.

Number of Subjects (Planned and Analyzed)

Up to 50 (25 per treatment group) postmenopausal female subjects 40 to 75 years old with symptoms of moderate to severe VVA were randomized. 50 subjects were enrolled, 48 subjects completed the study, and 48 subjects were analyzed.

Diagnosis and Main Criteria for Inclusion

Fifty female subjects were enrolled in the study. Postmenopausal female subjects 40 to 75 years of age, with a mean age of 62.3 years were enrolled. Subjects' mean weight (kg) was 71.2 kg with a range of 44.5-100 kg. Subjects' mean height (cm) was 162.6 cm with a range of 149.9-175.2 cm, and the mean BMI (kg/m²) was 26.8 kg/m² with a range of 19-33 kg/m². Criteria of inclusion in the study included: self-identification of at least one moderate to severe symptom of VVA, for example, vaginal dryness, dyspareunia, vaginal or vulvar irritation, burning, or itching, dysuria, vaginal bleeding associated with sexual activity, that was identified by the subject as being most bothersome to her; ≤5% superficial cells on vaginal smear cytology; vaginal pH>5.0; and estradiol level ≤50 pg/mL. Subject who were judged as being in otherwise generally good health on the basis of a pre-study physical examination, clinical laboratory tests, pelvic examination, and mammography were enrolled.

Estradiol 10 μg or Placebo, Dose, and Mode of Administration

Subjects were randomly assigned (in 1:1 allocation) to self-administer one of the following treatments intravaginally once daily for 14 days:
Treatment A: The pharmaceutical composition of Example 5 (Pharmaceutical Composition 2: 10 μg estradiol); or
Treatment B: Placebo vaginal softgel capsule, containing the same formulation as Treatment A, except for the 10 μg of estradiol.

The estradiol formulation was a tear drop shaped light pink soft gel capsule. Treatment B had the same composition, appearance, and route of administration as the Treatment A, but contained no estradiol.

Duration of Treatment

The study involved a screening period of up to 28 days before randomization and a treatment period of 14 days.

Criteria for Evaluation

Efficacy Endpoints:
Change from baseline (screening) to day 15 in the Maturation Index (percent of parabasal vaginal cells, superficial vaginal cells, and intermediate vaginal cells) of the vaginal smear. Data for this endpoint are shown in Tables 6-8.
Change from baseline (screening) to day 15 in vaginal pH. Data for this endpoint are shown in Table 9.
Change from baseline (randomization) to day 15 in severity of the most bothersome symptoms: (1) vaginal dryness; (2) vaginal or vulvar irritation, burning, or itching; (3) dysuria; (4) dyspareunia; (5) vaginal bleeding associated with sexual activity. Data for this endpoint are shown in Tables 13 and 15.
Change from baseline (randomization) to day 15 in investigator's assessment of the vaginal mucosa. Data for this endpoint are shown in Tables 18-21.
Unless otherwise noted, the efficacy endpoints were measured as a change-from Visit 1—Randomization/Baseline (day 1) to Visit 3—End of the treatment (day 15), except for vaginal bleeding which was expressed as either treatment success or failure.

Other endpoints include:
Vital signs, weight, changes in physical exam, pelvic and breast exam, and adverse events were evaluated as part of the safety endpoints.
Concentration of estradiol at each sampling time.
Peak concentration of estradiol on day 1 and sampling time at which peak occurred.
Delivery vehicle disintegration to measure the amount of residual delivery vehicle remains in the vagina post treatment.

Results from the assessment of plasma concentrations of estradiol are presented in Table 5.

TABLE 5

Safety Results: The descriptive statistics for Day 1 plasma estradiol $C_{max}$ and $T_{max}$ are provided below.

| | Estradiol 10 μg | | Placebo | |
|---|---|---|---|---|
| | $C_{max}$ | $T_{max}$ | $C_{max}$ | $T_{max}$ |
| N | 24 | 24 | 26 | 26 |
| Mean ± SD | 30.7 ± 7.47 | 2.12 ± 1.73 | 27.5 ± 17.26 | 4.00 ± 2.68 |
| Geometric Mean | 29.9 | — | 24.7 | — |
| Median | 29.8 | 1.00 | 22.1 | 6.00 |
| Min, Max | 19.7, 52.3 | 1.00, 6.00 | 15.1, 90.0 | 0.00, 6.00 |
| CV % | 24.3% | 81.3% | 62.9% | 67.1% |

Maturation Index Results

Vaginal cytology data was collected as vaginal smears from the lateral vaginal walls according to standard procedures to evaluate vaginal cytology at screening and Visit 3—End of treatment (day 15). The change in the Maturation Index was assessed as a change in cell composition measured at Visit 1—Baseline (day 1) compared to the cell composition measured at Visit 3—End of treatment (day 15). The change in percentage of superficial, parabasal, and intermediate cells obtained from the vaginal mucosal epithelium from a vaginal smear was recorded. Results from these assessments are presented in Tables 6, 7, and 8.

TABLE 6

Primary Efficacy Analysis Results of Change from Baseline (Screening) to Day 15 in the Maturation Index of the Vaginal Smear (Percent Parabasal Cells)

| Population | Statistics | Estradiol 10 µg | Placebo | Difference Between Treatment Means | 90% CI for Difference | Estradiol 10 µg vs. Placebo P-value |
|---|---|---|---|---|---|---|
| Intent-to-Treat | N | 24 | 24 | — | — | — |
| | Least-Squares Mean | −54.4 | −4.80 | −49.6 | (−60.4, −38.8) | <0.0001 |
| | Mean ± SD | −53.8 ± 39.7 | −5.4 ± 22.3 | — | — | — |
| | Median | −60.0 | −5.0 | — | — | — |
| | Min, Max | −100.0, 0.0 | −60.0, 60.0 | — | — | — |

[1] Confidence interval for the estradiol 10 µg-Placebo from ANCOVA with treatment as a fixed effect and baseline as a covariate.
[2] P-value for treatment comparison from ANCOVA with treatment as a fixed effect and baseline as a covariate.

TABLE 7

Primary Efficacy Analysis Results of Change from Baseline (Screening) to Day 15 in the Maturation Index of the Vaginal Smear (Superficial Cells)

| Population | Statistics | Estradiol 10 µg | Placebo | Difference Between Treatment Means | 90% CI for Difference | Estradiol 10 µg vs. Placebo P-value |
|---|---|---|---|---|---|---|
| Intent-to-Treat | N | 24 | 24 | — | — | — |
| | Least-Squares Mean | 35.2 | 8.75 | 26.5 | (15.4, 37.6) | 0.0002 |
| | Mean ± SD | 35.2 ± 26.4 | 8.8 ± 18.7 | — | — | — |
| | Median | 40.0 | 0.0 | — | — | — |
| | Min, Max | 0.0, 80.0 | 0.0, 90.0 | — | — | — |

[1] Confidence interval for the estradiol 10 µg-Placebo from ANOVA with treatment as a fixed effect.
[2] P-value for treatment comparison from ANOVA with treatment as a fixed effect.

TABLE 8

Primary Efficacy Analysis Results of Change from Baseline (Screening) to Day 15 in the Maturation Index of the Vaginal Smear (Intermediate Cells)

| Population | Statistics | Estradiol 10 µg | Placebo | Difference Between Treatment Means | 90% CI for Difference | Estradiol 10 µg vs. Placebo P-value[2] |
|---|---|---|---|---|---|---|
| Intent-to-Treat | N | 24 | 24 | — | — | — |
| | Least-Squares Mean | 18.7 | −3.54 | 22.3 | (11.1, 33.5) | 0.0017 |
| | Mean ± SD | 18.5 ± 42.7 | −3.3 ± 21.6 | — | — | — |
| | Median | 22.5 | −5.0 | — | — | — |
| | Min, Max | −60.0, 100.0 | −60.0, 20.0 | — | — | — |

[1] Confidence interval for the estradiol 10 µg-Placebo from ANCOVA with treatment as a fixed effect and baseline as a covariate.
[2] P-value for treatment comparison from ANCOVA with treatment as a fixed effect and baseline as a covariate.

Change in pH Results

Vaginal pH was measured at Screening and Visit 3—End of treatment (day 15). The pH measurement was obtained by pressing a pH indicator strip against the vaginal wall. The subjects entering the study were required to have a vaginal pH value greater than 5.0 at screening. pH values were recorded on the subject's case report form. The subjects were advised not to have sexual activity and to refrain from using vaginal douching within 24 hours prior to the measurement. Results from these assessments are presented in Table 9.

TABLE 9

Primary Efficacy Analysis Results of Change from Baseline (Screening) to Day 15 in Vaginal pH

| Population | Statistics | Estradiol 10 µg | Placebo | Difference Between Treatment Means | 90% CI for Difference[1] | Estradiol 10 µg vs. Placebo P-value[2] |
|---|---|---|---|---|---|---|
| Intent-to-Treat | N | 24 | 24 | — | — | — |
| | Least-Squares Mean | −0.974 | −0.339 | −0.635 | (−0.900, −0.368) | 0.0002 |
| | Mean ± SD | −0.917 ± 0.686 | −0.396 ± 0.659 | — | — | — |
| | Median | −1.00 | −0.500 | — | — | — |
| | Min, Max | −2.00, 0.500 | −1.50, 0.500 | — | — | — |

[1]Confidence interval for the estradiol 10 µg-Placebo from ANCOVA with treatment as a fixed effect and baseline as a covariate.
[2]P-value for treatment comparison from ANCOVA with treatment as a fixed effect and baseline as a covariate.

Most Bothersome Symptoms Data

Subjects were asked to specify the symptom that she identified as the "most bothersome symptom." During the screening period all of the subjects were provided with a questionnaire to self-assess the symptoms of VVA: (1) vaginal dryness; (2) vaginal or vulvar irritation, burning, or itching; (3) dysuria; (4) dyspareunia; (5) vaginal bleeding associated with sexual activity. Each symptom, with the exception of vaginal bleeding associated with sexual activity, was measured on a scale of 0 to 3, where 0=none, 1=mild, 2=moderate, and 3=severe. Vaginal bleeding associated with sexual activity was measured in a binary scale: N=no bleeding; Y=bleeding. The subject's responses were recorded. All randomized subjects were also provided a questionnaire to self-assess the symptoms of VVA at Visit 1—Randomization/Baseline (day 1) and at Visit 3—End of the treatment (day 15). Subjects recorded their self-assessments daily in a diary and answers were collected on days 8 and 15 (end of treatment). Pre-dose evaluation results obtained at Visit 1 were considered as baseline data for the statistical analyses. Data from these assessments are presented in Tables 10 and 11.

TABLE 10

Baseline Characteristics for Vaginal Atrophy Symptoms (ITT Population)

| WA Symptom | Statistics | Estradiol 10 µg | Placebo | Estradiol 10 µg vs. Placebo P-value[1] |
|---|---|---|---|---|
| Vaginal dryness | N of Subjects | 24 | 24 | — |
| | Mean | 2.292 | 2.375 | 0.68231 |
| Vaginal or vulvar irritation/burning/itching | N of Subjects | 24 | 24 | — |
| | Mean | 0.875 | 1.333 | 0.08721 |
| Pain, burning or stinging when urinating | N of Subjects | 24 | 24 | — |
| | Mean | 0.583 | 0.625 | 0.87681 |
| Vaginal pain associated with sexual activity | N of Subjects[2] | 12 | 12 | — |
| | Mean | 2.083 | 2.333 | 0.54281 |
| Vaginal bleeding associated with sexual activity | N of Subjects[2] | 12 | 12 | — |
| | Percent[3] | 25.00 | 33.33 | 0.31463 |

[1]P-value for treatment comparison from ANOVA/ANCOVA with treatment as a fixed effect and Baseline as a covariate when appropriate.
[2]N = number of subjects sexually active at baseline.
[3]Percent of subjects with bleeding, evaluated using Fisher's Exact Test.

TABLE 11

Additional Efficacy Analysis Results of Change from Baseline (Randomization) to Day 15 in Severity of Vaginal Atrophy Symptoms

| Symptom | Statistical Method[1] | Least-Squares Mean Estradiol 10 µg | Placebo | Difference Between Treatment Means | 90% CI for Difference[2] | Estradiol 10 µg vs. Placebo P-value |
|---|---|---|---|---|---|---|
| Vaginal dryness | ANCOVA | 0.980 | 0.729 | 0.251 | −0.706, 0.204 | 0.3597 |
| Vaginal or vulvar Irritation/burning/itching | ANCOVA | 0.694 | 0.514 | 0.180 | −0.549, 0.189 | 0.4159 |
| Pain/Burning/Stinging (Urination) | ANCOVA | 0.391 | 0.359 | 0.032 | −0.263, 0.200 | 0.8185 |
| Vaginal pain associated with sexual activity | ANOVA | 0.800 | 0.500 | 0.300 | −1.033, 0.433 | 0.4872 |

[1]ANOVA model contained a fixed effect for treatment. ANCOVA added baseline as a covariate to the model.
[2]Confidence interval for the difference between estradiol 10 µg and Placebo treatment least-squares means.

Changes to the most bothersome symptom from the baseline was scored according to the evaluation of VVA symptoms generally set forth above. Tables 13 and 14 show a comparison between the pharmaceutical composition 1 and placebo generally for most bothersome symptom and vaginal atrophy symptom. It is noteworthy to point out that these measurement demonstrated a trend of improvement, though not statistically significant, at day 15.

TABLE 13

Primary Efficacy Analysis Results of Change from Baseline
(Randomization) to Day 15 in Severity of the Most Bothersome VVA

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-Squares Mean | −1.043 | −1.042 | −0.002 | (−0.497, 0.493) | 0.9951 |
| | Mean ± SD | −1.043 ± 0.928 | −1.042 ± 1.08 | — | — | — |
| | Median | −1.00 | −1.00 | — | — | — |
| | Min, Max | −3.00, 0.00 | −3.00, 0.00 | — | — | — |

[1]Confidence interval for the estradiol 10 μg-Placebo from ANOVA with treatment as a fixed effect.
[2]P-value for treatment comparison from ANOVA with treatment as a fixed effect.

TABLE 14

Additional Efficacy Analysis Results of Change from Baseline (Randomization) to
Day 15 in Severity of Vaginal Atrophy Symptoms

| Symptom | Statistical Method[1] | Least-Squares Mean | | Difference Between Treatment Means | 90% CI for Difference[2] | TX-12-004-HR vs. Placebo P-value |
| | | TX-12-004-HR | Placebo | | | |
|---|---|---|---|---|---|---|
| Dryness | ANCOVA | −0.980 | −0.729 | −0.251 | (−0.706, 0.204) | 0.3597 |
| Irritation | ANCOVA | −0.694 | −0.514 | −0.180 | (−0.549, 0.189) | 0.4159 |
| Pain (Sex) | ANOVA | −0.800 | −0.500 | −0.300 | (−1.033, 0.433) | 0.4872 |
| Pain/Burning/Stinging (Urination) | ANCOVA | −0.391 | −0.359 | −0.032 | (−0.263, 0.200) | 0.8185 |

[1]ANOVA model contained a fixed effect for treatment. ANCOVA added baseline as a covariate to the model.
[2]Confidence interval for the difference between TX-12-004-HR and Placebo treatment least-squares means.

With respect to the most bothersome symptoms data presented in Tables 13 and 14, the period over which the data was measured is generally considered insufficient to make meaningful conclusions. However, the trends observed as part of this study suggest that the data will show improvement of the most bothersome symptoms when data for a longer time period is collected.

The absence or presence of any vaginal bleeding associated with sexual activity was also measured as one of the most bothersome symptoms. The data for vaginal bleeding associated with sexual activity is reported in Table 15.

TABLE 15

Primary Efficacy Analysis Results of Change from
Baseline (Randomization) to Day 15
in Vaginal Bleeding Associated with Sexual Activity

| | | Baseline (Randomization) and Day 15 Summary of Vaginal Bleeding | | | |
|---|---|---|---|---|---|
| Treatment | N* | Bleeding/ No Bleeding (Success)[2] | Bleeding/ Bleeding (Failure) | No Bleeding/ Bleeding (Failure) | No Bleeding/ No Bleeding (NC) |
| Estradiol 10 μg | 10 | 2 (100%) | 0 | 0 | 8 |
| Placebo | 10 | 1 (20%) | 3 | 1 | 5 |
| P-Value for Estradiol 10 μg vs. Placebo[1] | | 0.1429 | — | — | — |

*N = Total number of patients within each treatment group who were sexually active at both Baseline and Day 15 and provided a response at both visits.
NC = No Change - not considered in the statistical comparison.
[1]P-value for treatment comparison from Fisher's Exact Test.
[2]Percent is based on the number of subjects classified as either a Success or a Failure (N = 2 for estradiol 10 μg; N = 5 for Placebo Estradiol Level/Pharmacokinetics Data In this study, the systemic exposure to estradiol following once daily intravaginal administration of estradiol 10 μg for 14 days was investigated. Descriptive statistics of the plasma estradiol concentrations taken at each sampling time and the observed $C_{max}$ and $T_{max}$ values were recorded in Tables 16 and 17. No statistically significant difference in the systemic concentration of estradiol 10 μg versus the placebo group was observed, which suggests the estradiol is not carried into the blood stream where it will have a systemic effect. Rather, it remains in localized tissues; the effect of estradiol is therefore believed be local to the location of administration (i.e., the vagina). The lower limits of detection of the assays used to measure the pharmacokinetic data may have affected the measured the accuracy of the PK values presented. Additional PK studies were performed with more accurate assays in Examples 8 and 9.

For the purpose of monitoring the estradiol level during the study blood samples were collected at 0.0, 1.0, 3.0, and 6.0 hours relative to dosing on day 1; prior to dosing on day 8; and prior to dosing on day 15. Efforts were made to collect blood samples at their scheduled times. Sample collection and handling procedures for measurement of estradiol blood level was performed according to procedure approved by the sponsor and principal investigator. All baseline and post-treatment plasma estradiol concentrations were determined using a validated bioanalytical (UPLC-MS/MS) methods. These data are shown in Tables 16 and 17.

TABLE 16

Descriptive Statistics of Estradiol Concentrations (pg/mL) at Each Sampling Time

| Treatment | Sampling Time | | | | | |
|---|---|---|---|---|---|---|
| | 0 Hour | 1 Hour | 3 Hours | 6 Hours | Pre-dose Day 8 | Pre-dose Day 15 |
| Estradiol 10 µg | | | | | | |
| N | 24 | 24 | 24 | 24 | 24 | 22 |
| Mean ± SD | 20.1 ± 5.74 | 28.7 ± 5.89 | 25.7 ± 5.71 | 23.4 ± 7.91 | 21.4 ± 9.28 | 23.4 ± 8.72 |
| Median | 20.2 | 28.9 | 24.7 | 22.3 | 20.7 | 20.7 |
| Min, Max | 2.63, 38.3 | 18.8, 43.9 | 19.3, 47.5 | 3.31, 52.3 | 2.09, 52.2 | 17.9, 54.7 |
| Placebo | | | | | | |
| N | 26 | 26 | 26 | 26 | 25 | 24 |
| Mean ± SD | 20.5 ± 4.29 | 21.0 ± 6.14 | 19.0 ± 5.92 | 26.9 ± 17.36 | 29.9 ± 22.51 | 28.1 ± 16.80 |
| Median | 20.8 | 20.8 | 20.9 | 21.7 | 21.6 | 21.1 |
| Min, Max | 4.03, 29.1 | 3.19, 41.2 | 3.15, 26.9 | 15.1, 90.0 | 15.0, 116.2 | 14.7, 81.3 |

TABLE 17

Descriptive Statistics of Estradiol $C_{max}$ and $T_{max}$ on Day 1

| | Estradiol 10 µg | | Placebo | |
|---|---|---|---|---|
| | $C_{max}$ | $T_{max}$ | $C_{max}$ | $T_{max}$ |
| N | 24 | 24 | 26 | 26 |
| Mean ± SD | 30.7 ± 7.47 | 2.12 ± 1.73 | 27.5 ± 17.26 | 4.00 ± 2.68 |
| Geometric Mean | 29.9 | — | 24.7 | — |
| Median | 29.8 | 1.00 | 22.1 | 6.00 |
| Min, Max | 19.7, 52.3 | 1.00, 6.00 | 15.1, 90.0 | 0.00, 6.00 |
| CV % | 24.3% | 81.3% | 62.9% | 67.1% |

Assessment of Vaginal Mucosa Data

The investigators rated the vaginal mucosal appearance at day 1 (pre-dose) and day 15. Vaginal color, vaginal epithelial integrity, vaginal epithelial surface thickness, and vaginal secretions were evaluated according to the following degrees of severity: none, mild, moderate, or severe using scales 0 to 3, where 0=none, 1=mild, 2=moderate, and 3=severe. Results from these investigators rated assessments are presented in Tables 18, 19, 20, and 21.

TABLE 18

Primary Efficacy Analysis Results of Change from Baseline (Randomization) to Day 15 in Investigator's Assessment of the Vaginal Mucosa (Assessment of Vaginal Color)

| Population | Statistics | Estradiol 10 µg | Placebo | Difference Between Treatment Means | 90% CI for Difference[1] | Estradiol 10 µg vs. Placebo P-value[2] |
|---|---|---|---|---|---|---|
| Intent-to-Treat | N | 24 | 24 | — | — | — |
| | Least-squares Mean | −0.199 | −0.009 | −0.191 | (−0.434, 0.052) | 0.1945 |
| | Mean ± SD | −0.333 ± 0.565 | 0.125 ± 0.741 | | | |

TABLE 18-continued

Primary Efficacy Analysis Results of Change from Baseline (Randomization) to Day 15 in Investigator's Assessment of the Vaginal Mucosa (Assessment of Vaginal Color)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| | Median | 0.00 | 0.00 | — | — | — |
| | Min, Max | −2.00, 0.00 | −1.00, 2.00 | — | — | — |

[1]Confidence interval for the estradiol 10 μg-Placebo from ANCOVA with treatment as a fixed effect and baseline as a covariate.
[2]P-value for treatment comparison from ANCOVA with treatment as a fixed effect and baseline as a covariate.

TABLE 19

Primary Efficacy Analysis Results of Change from Baseline (Randomization) to Day 15 in Investigator's Assessment of the Vaginal Mucosa (Assessment of Vaginal Epithelial Integrity)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-squares Mean | −0.342 | 0.176 | −0.518 | (−0.726, −0.311) | 0.0001 |
| | Mean ± SD | −0.417 ± 0.584 | 0.250 ± 0.442 | | | |
| | Median | 0.00 | 0.00 | — | — | — |
| | Min, Max | −1.00, 1.00 | 0.00, 1.00 | — | — | — |

[1]Confidence interval for the estradiol 10 μg-Placebo from ANCOVA with treatment as a fixed effect and baseline as a covariate.
[2]P-value for treatment comparison from ANCOVA with treatment as a fixed effect and baseline as a covariate.

TABLE 20

Primary Efficacy Analysis Results of Change from Baseline (Randomization) to Day 15 in Investigator's Assessment of the Vaginal Mucosa (Assessment of Vaginal Epithelial Surface Thickness)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-squares Mean | −0.034 | −0.133 | 0.099 | (−0.024, 0.221) | 0.1820 |
| | Mean ± SD | −0.125 ± 0.338 | −0.042 ± 0.550 | | | |
| | Median | 0.00 | 0.00 | — | — | — |
| | Min, Max | −1.00, 0.00 | −1.00, 1.00 | — | — | — |

[1]Confidence interval for the estradiol 10 μg-Placebo from ANCOVA with treatment as a fixed effect and baseline as a covariate.
[2]P-value for treatment comparison from ANCOVA with treatment as a fixed effect and baseline as a covariate.

TABLE 21

Primary Efficacy Analysis Results of Change from Baseline (Randomization) to Day 15 in Investigator's Assessment of the Vaginal Mucosa (Assessment of Vaginal Secretions)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-squares Mean | −0.643 | −0.274 | −0.369 | (−0.661, 0.076) | 0.0401 |

TABLE 21-continued

Primary Efficacy Analysis Results of Change from Baseline (Randomization) to Day 15 in Investigator's Assessment of the Vaginal Mucosa (Assessment of Vaginal Secretions)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
|  | Mean ± SD | −0.792 ± 0.779 | −0.125 ± 0.741 | — | — | — |
|  | Median | −1.00 | 0.00 | — | — | — |
|  | Min, Max | −2.00, 1.00 | −2.00, 2.00 | — | — | — |

[1]Confidence interval for the estradiol 10 μg-Placebo from ANCOVA with treatment as a fixed effect and baseline as a covariate.
[2]P-value for treatment comparison from ANCOVA with treatment as a fixed effect and baseline as a covariate.

Delivery Vehicle Disintegration Data

Assessment of capsule disintegration in the vagina (presence or absence) at Day 1 (6 hours after dosing) and Day 15. Results of this assessment is presented in Table 22.

TABLE 22

Capsule Disintegration State in the Vagina on Day 1 and Day 15

|  | Estradiol 10 μg | | Placebo | |
|---|---|---|---|---|
|  | Day 1 | Day 15 | Day 1 | Day 15 |
| No evidence of capsule present | 23 (95.8%) | 24 (100.0%) | 26 (100.0%) | 24 (92.3%) |
| Evidence of capsule present | 0 (0.0%) | 0 (0.0%) | 0 (0.0%) | 0 (0.0%) |
| Assessment not done | 1 (4.2%) | 0 (0.0%) | 0 (0.0%) | 2 (7.7%) |

Serum hormone level data was collected to measure the serum concentrations of estradiol. These data were used for screening inclusion and were determined using standard clinical chemistry methods.

Appropriateness of Measurements

The selection of the efficacy measurements used in this study was based on FDA's recommendations for studies of estrogen and estrogen/progestin drug products for the treatment of moderate to severe vasomotor symptoms associated with the menopause and moderate to severe symptoms of vulvar and vaginal atrophy associated with the menopause (*Food and Drug Administration, Guidance for Industry, Estrogen and Estrogen/Progestin Drug Products to Treat Vasomotor Symptoms and Vulvar and Vaginal Atrophy Symptoms Recommendations for Clinical Evaluation.* January 2003, hereby incorporated by reference).

Standard clinical, laboratory, and statistical procedures were utilized in the trial. All clinical laboratory procedures were generally accepted and met quality standards.

Statistical Methods:

Efficacy:

Analysis of variance (ANOVA) was used to evaluate the change from baseline differences between the subjects receiving estradiol 10 μg and placebo capsules for all efficacy endpoints, except for vaginal bleeding, to estimate the effect size and variability of the effect. In some cases, for example, for some vaginal atrophy symptoms, the change from baseline (post dose response) was correlated with the baseline value (p<0.05), so baseline was included as a covariate to adjust for this correlation (Analysis of Covariance, ANCOVA). The 90% confidence intervals on the differences between estradiol 10 μg and placebo endpoint means were determined to evaluate the effect size. The change from baseline in vaginal bleeding associated with sexual activity was evaluated in terms of the proportion of subjects who had treatment success or failure. Any subject reporting bleeding at baseline who did not report bleeding at Day 15 was considered to have been successfully treated. Any subject reporting bleeding at day 15 was considered a treatment failure, regardless of whether they reported baseline bleeding or not. Subjects reporting no bleeding at both baseline and day 15 were classified as no-change and were excluded from the statistical evaluation. The difference in the proportion of subjects with success between the two treatment groups was statistically evaluated using Fisher's Exact Test. Results of this difference in proportion are presented in Table 10.

Measurements of Treatment Compliance

Subjects were required to complete a diary in order to record treatment compliance. Diaries were reviewed for treatment compliance at day 8 and day 15 visits. A total of 45 subjects (21 subjects in the estradiol 10 μg group and 24 subjects in the placebo group) were 100% compliant with the treatment regimen.

Due to the investigative nature of the study, no adjustments were made for multiplicity of endpoints.

Safety:

The frequency and severity of all adverse events were summarized descriptively by treatment group.

Results: All forty eight (48) subjects who completed the study were included in the primary efficacy analyses. The results of efficacy analyses are presented throughout Tables 5, 6, and 7.

Conclusions

Efficacy

The two-week treatment with pharmaceutical composition 10 μg led to a statistically significant greater mean decrease in percent of parabasal cells than did placebo treatment (54% vs. 5%, p<0.0001), as illustrated in Table 6. At the same time, a significantly greater mean increase in the percent of superficial cells was observed with the pharmaceutical composition (35%) than with the placebo capsules (9%), with the difference being highly statistically significant (p=0.0002), as illustrated in Table 7. The difference in pH reduction between the pharmaceutical composition (0.97 units) compared to that for the placebo (0.34 units) was only slightly greater than 0.5 units, but the difference was detected as statistically significant (p=0.0002), as illustrated in Table 9.

While the decrease in severity of the most bothersome symptom was essentially the same (~1 unit) for both pharmaceutical composition and placebo, the reductions in the severity of the individual symptoms of vaginal dryness, irritation and pain during sexual activity were all marginally better for the active treatment than for the placebo treatment. None of the differences between the two treatments, all of which were ≤0.3 units, were detected as statistically significant. There was no difference between the two treatments in regard to reduction of pain/burning/stinging during urination (~0.4 unit reduction). The length of the study was not long enough to show a separation between the most bothersome symptoms in the pharmaceutical composition and placebo. However, the trends of most bothersome symptoms suggest that with a suitable period of time, significantly significant differences between the two treatments would be observed.

The two-week treatment with estradiol 10 µg capsules showed no statistically detectable difference in regard to reduction of severity from baseline according to the investigator's assessment of vaginal color or vaginal epithelial surface thickness. Pharmaceutical composition capsules did demonstrate a statistically significant greater reduction than did placebo in severity of atrophic effects on vaginal epithelial integrity (−0.34 vs. 0.18, p=0.0001) and vaginal secretions (−0.64 vs. −0.27, p=0.0401).

Descriptive statistical analyses (mean, median, geometric mean, standard deviation, CV, minimum and maximum, $C_{max}$, and $T_{max}$) were conducted on the estradiol concentrations at each sampling time, the peak concentration on day 1 and the time of peak concentration. Results from this assessment are presented in Tables 16 and 17.

A pharmaceutical composition comprising estradiol 10 µg outperformed placebo treatment in regard to improvement in the Maturation Index, reduction in vaginal pH, reduction in the atrophic effects on epithelial integrity and vaginal secretions. The lack of statistical significance between the two treatments in regard to reduction of severity for the most bothersome symptom, and the individual vaginal atrophy symptoms of dryness, irritation, pain associated with sexual activity, and pain/burning/stinging during urination, is not unexpected given the small number of subjects in the study and the short duration of therapy. Too few subjects in the study had vaginal bleeding associated with sexual activity to permit any meaningful evaluation of this vaginal atrophy symptom.

Of the 48 subjects enrolled in the study, 45 subjects were 100% compliant with the treatment regimen. Of the remaining three subjects, one removed herself from the study due to personal reasons and the other two subjects each missed one dose due to an adverse event.

Safety

Although the Day 1 mean plasma estradiol peak concentration for the pharmaceutical composition was somewhat higher than that for the Placebo (ratio of geometric means=1.21:Test Product (estradiol 10 µg) 21%>Placebo), no statistically significant difference was determined. However, the assay methods were questionable, resulting in questionable PK data. Additional PK studies were performed in Examples 8 and 9.

There were no serious adverse events in the study.

Overall, the pharmaceutical composition comprising estradiol 10 µg was well tolerated when administered intravaginally in once daily regimen for 14 days.

Example 8: PK Study (25 µg Formulation)

A PK study was undertaken to compare the 25 µg formulation disclosed herein (Pharmaceutical Composition 3) to the RLD. The results of the PK study for estradiol are summarized in Table 23. The p values for these data demonstrate statistical significance, as shown in Table 24.

TABLE 23

Statistical Summary of the Comparative Bioavailability Data for Unscaled Average BE studies of Estradiol, Least Square Geometric Means of Estradiol, Ratio of Means and 90% Confidence Intervals, Fasting/Fed Bioequivalence Study (Study No.: ESTR-1K-500-12); Dose 25 µg estradiol

| Parameter | Test | N | RLD | N | Ratio (%) | 90% C.I. |
|---|---|---|---|---|---|---|
| $C_{max}$ (pg/mL) | 23.0839 | 36 | 42.7024 | 36 | 54.06 | 44.18-66.14 |
| $AUC_{0-24}$ (pg · hr/mL) | 89.2093 | 36 | 292.0606 | 36 | 30.54 | 23.72-39.34 |

TABLE 24

P-values for Table 23

| | P-Value | |
|---|---|---|
| Effect | $C_{max}$ | $AUC_{0-24}$ |
| Treatment | <.0001 | <.0001 |
| Sequence | 0.4478 | 0.5124 |
| Period | 0.4104 | 0.7221 |

As illustrated in Table 23, baseline adjusted PK data illustrates that the formulations disclosed herein unexpectedly show a 54% decrease in $C_{max}$ and a 31% decrease in the AUC relative to the RLD. This result is desirable because the estradiol is intended only for local absorption. These data suggest a decrease in the circulating levels of estradiol relative to the RLD. Moreover, it is noteworthy to point out that the $C_{max}$ and AUC levels of estradiol relative to placebo are not statistically differentiable, which suggests that the formulations disclosed herein have a negligible systemic effect. As shown in Table 24, there was no significant difference between the test and reference products due to sequence and period effects. However, there was a significant difference due to treatment effect for both $C_{max}$ and AUC.

Pharmacokinetics for circulating total estrone, a metabolite of estradiol, is show in Table 25. These data show that the total circulating estrone for the formulations disclosed herein resulted in a 55% decrease in the $C_{max}$ for circulating estrone, and a 70% decrease in the AUC for circulating estrone.

TABLE 25

Statistical Summary of the Comparative Bioavailability Data for Unscaled Average BE studies of Estrone, Least Square Geometric Means, Ratio of Means and 90% Confidence Intervals, Fasting/Fed Bioequivalence Study (Study No.: ESTR-1K-500-12); Dose 25 µg estradiol

| Parameter | Test | N | RLD | N | Ratio (%) | 90% C.I. |
|---|---|---|---|---|---|---|
| $C_{max}$ (pg/mL) | 10.7928 | 36 | 23.5794 | 36 | 45.77 | 32.95 to 63.59 |
| $AUC_{0-24}$ (pg · hr/mL) | 51.2491 | 36 | 165.4664 | 36 | 30.97 | 19.8-48.45 |

TABLE 26

P-values for Table 25

| Effect | P-Value $C_{max}$ | $AUC_{0-24}$ |
|---|---|---|
| Treatment | 0.0002 | <.0001 |
| Sequence | 0.1524 | 0.0464 |
| Period | 0.0719 | 0.0118 |

There was a significant difference between test and reference products due to treatment effect whereas there was no significant difference due to sequence and period effects for $C_{max}$. For AUC, there was a significant difference between test and reference products due to treatment, sequence, and period effects.

PK for circulating total estrone sulfate is shown in Table 27. These data show that the total circulating estrone sulfate for the pharmaceutical compositions disclosed herein resulted in a 33% decrease in the $C_{max}$ and a 42% decrease in the AUC for circulating estrone sulfate.

TABLE 27

Statistical Summary of the Comparative Bioavailability Data for Unscaled Average BE studies of Estrone Sulfate, Least Square Geometric Means of Estrone Sulfate, Ratio of Means and 90% Confidence Intervals, Fasting/Fed Bioequivalence Study (Study No.: ESTR-1K-500-12), Dose 25 μg estradiol

| Parameter | Test | N | RLD | N | Ratio (%) | 90% C.I. |
|---|---|---|---|---|---|---|
| $C_{max}$ (pg/mL) | 490.0449 | 36 | 730.5605 | 36 | 67.08 | 53.84-83.57 |
| $AUC_{0-24}$ (pg · hr/mL) | 4232.9914 | 36 | 7323.0827 | 36 | 57.80 | 43.23-77.29 |

TABLE 28

P-values for Table 27

| Effect | P-Value $C_{max}$ | $AUC_{0-24}$ |
|---|---|---|
| Treatment | 0.0042 | 0.0031 |
| Sequence | 0.5035 | 0.9091 |
| Period | 0.1879 | 0.8804 |

There was a significant difference between test and reference products due to treatment effect whereas there was no significant difference due sequence and period effects for both $C_{max}$ and AUC.

Example 9: PK Study (10 μg Formulation)

A PK study was undertaken to compare the 10 μg formulation disclosed herein (Pharmaceutical Composition 2) to the RLD. The results of the PK study for estradiol are summarized in Table 29-40, and FIGS. 9-14.

A PK study was undertaken to compare pharmaceutical compositions disclosed herein having 10 μg of estradiol to the RLD. The results of the PK study for estradiol are summarized in Tables 29-34, which demonstrate that the pharmaceutical compositions disclosed herein more effectively prevented systemic absorption of the estradiol. Table 35 shows that the pharmaceutical compositions disclosed herein had a 28% improvement over the RLD for systemic blood concentration $C_{max}$ and 72% AUC improvement over the RLD.

TABLE 29

Summary of Pharmacokinetic Parameters of Test product (T) of Estradiol-Baseline adjusted (N = 34)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 15.7176 ± 7.9179 | 50.3761 | 13.9000 | 6.5000 | 49.6000 |
| $AUC_{0-24}$ (pg · hr/mL) | 53.0100 ± 19.5629 | 36.9041 | 49.9750 | 24.3000 | 95.1500 |
| $t_{max}$ (hr) | 1.98 ± 1.29 | 65.34 | 2.00 | 1.00 | 8.05 |

TABLE 30

Summary of Pharmacokinetic Parameters of Reference product (R) of Estradiol-Baseline adjusted (N = 34)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 24.1882 ± 11.9218 | 49.2877 | 24.1500 | 1.0000 | 55.3000 |
| $AUC_{0-24}$ (pg · hr/mL) | 163.8586 ± 72.0913 | 43.9960 | 158.0375 | 2.0000 | 304.8500 |
| $t_{max}$ (hr) | 10.53 ± 5.58 | 52.94 | 8.06 | 2.00 | 24.00 |

TABLE 31

Geometric Mean of Test Product (T) and Reference product (R) of Estradiol-Baseline adjusted (N = 34)

| Pharmacokinetic Parameter | Geometric Mean Test Product (T) | Reference Product (R) |
|---|---|---|
| $C_{max}$ (pg/mL) | 14.3774 | 20.3837 |
| $AUC_{0-24}$ (pg · hr/mL) | 49.6231 | 132.9218 |
| $t_{max}$ (hr) | 1.75 | 9.28 |

TABLE 32

Statistical Results of Test product (T) versus Reference product (R) for Estradiol-Baseline adjusted (N = 34)

| Pharmacokinetic Parameter | Geometric Least Square Mean Test Product (T) | Reference Product (R) | Intra Subject CV % | T/R Ratio % | 90% Confidence Interval |
|---|---|---|---|---|---|
| $C_{max}$ (pg/mL) | 14.4490 | 20.1980 | 60.68 | 71.54* | 56.82-90.08 |
| $AUC_{0-24}$ (pg · hr/mL) | 49.7310 | 131.0400 | 70.64 | 37.95* | 29.21-49.31 |

*Comparison was detected as statistically significant by ANOVA (α = 0.05).

The PK data for total estrone likewise demonstrated reduced systemic exposure when compared to the RLD. Table 33 shows the pharmaceutical compositions disclosed herein reduced systemic exposure by 25% for $C_{max}$ and 49% for AUC.

TABLE 33

Summary of Pharmacokinetic Parameters of Test product (T) of Estrone-Baseline adjusted (N = 33)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 6.8485 ± 6.5824 | 96.1149 | 5.4000 | 1.3000 | 36.3000 |
| $AUC_{0-24}$ (pg · hr/mL) | 34.7051 ± 27.9541 | 80.5476 | 30.8500 | 3.3500 | 116.7500 |
| $t_{max}$ (hr) | 9.12 ± 8.83 | 96.80 | 4.00 | 1.00 | 24.00 |

TABLE 34

Summary of Pharmacokinetic Parameters of Reference product (R) of Estrone-Baseline adjusted (N = 33)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 8.8333 ± 7.1469 | 80.9086 | 6.7000 | 2.7000 | 30.3000 |
| $AUC_{0-24}$ (pg · hr/mL) | 63.0042 ± 46.5484 | 73.8814 | 51.2800 | 8.8000 | 214.0000 |
| $t_{max}$ (hr) | 11.16 ± 7.24 | 64.95 | 10.00 | 4.00 | 24.00 |

TABLE 35

Geometric Mean of Test Product (T) and Reference product (R) of Estrone-Baseline adjusted (N = 33)

| Pharmacokinetic Parameter | Geometric Mean | |
|---|---|---|
| | Test Product (T) | Reference Product (R) |
| $C_{max}$ (pg/mL) | 5.1507 | 6.9773 |
| $AUC_{0-24}$ (pg · hr/mL) | 24.2426 | 48.2377 |
| $t_{max}$ (hr) | 5.87 | 9.07 |

TABLE 36

Statistical Results of Test product (T) versus Reference product (R) for Estrone-Baseline adjusted (N = 33)

| Pharmacokinetic Parameter | Geometric Least Square Mean | | Intra Subject CV % | T/R Ratio % | 90% Confidence Interval |
|---|---|---|---|---|---|
| | Test Product (T) | Reference Product (R) | | | |
| $C_{max}$ (pg/mL) | 5.1620 | 6.9280 | 47.59 | 74.50* | 61.69-89.97 |
| $AUC_{0-24}$ (pg · hr/mL) | 24.1960 | 47.9020 | 73.66 | 50.51* | 38.37-66.50 |

*Comparison was detected as statistically significant by ANOVA (α = 0.05).

The PK data for estrone sulfate likewise demonstrated reduced systemic exposure when compared to the RLD. Table 37 shows the pharmaceutical compositions disclosed herein reduced systemic exposure by 25% for $C_{max}$ and 42% for AUC.

TABLE 37

Summary of Pharmacokinetic Parameters of Test product (T) of Estrone Sulfate-Baseline adjusted (N = 24)

| Pharmacokinetic Parameter | Arithmetic Mean ± Standard Deviation | Coefficient of Variation | Median | Minimum | Maximum |
|---|---|---|---|---|---|
| $C_{max}$ (ng/mL) | 13.9042 ± 7.0402 | 50.6339 | 11.1500 | 1.3000 | 39.0000 |
| $AUC_{0-24}$ (ng · hr/mL) | 97.9953 ± 80.8861 | 82.5408 | 76.2750 | 5.1025 | 338.0000 |
| $t_{max}$ (hr) | 6.33 ± 4.56 | 71.93 | 4.00 | 4.00 | 24.00 |

TABLE 38

Summary of Pharmacokinetic Parameters of Reference product (R) of Estrone Sulfate-Baseline adjusted (N = 24)

| Pharmacokinetic Parameter | Arithmetic Mean ± Standard Deviation | Coefficient of Variation | Median | Minimum | Maximum |
|---|---|---|---|---|---|
| $C_{max}$ (ng/mL) | 19.2542 ± 11.3633 | 59.0173 | 15.2000 | 7.0000 | 53.7000 |
| $AUC_{0-24}$ (ng · hr/mL) | 177.6208 ± 166.2408 | 93.5931 | 124.0000 | 20.0000 | 683.0500 |
| $t_{max}$ (hr) | 10.33 ± 5.58 | 54.05 | 10.00 | 2.00 | 24.00 |

TABLE 39

Geometric Mean of Test Product (T) and Reference product (R) of Estrone Sulfate-Baseline adjusted (N = 24)

| Pharmacokinetic Parameter | Geometric Mean | |
|---|---|---|
| | Test Product (T) | Reference Product (R) |
| $C_{max}$ (ng/mL) | 12.1579 | 16.8587 |
| $AUC_{0-24}$ (ng · hr/mL) | 66.5996 | 121.5597 |
| $t_{max}$ (hr) | 5.49 | 8.83 |

TABLE 40

Statistical Results of Test product (T) versus Reference product (R) for Estrone Sulfate-Baseline adjusted (N = 24)

| Pharmacokinetic Parameter | Geometric Least Square Mean | | Intra Subject CV % | T/R Ratio % | 90% Confidence Interval |
|---|---|---|---|---|---|
| | Test Product (T) | Reference Product (R) | | | |
| $C_{max}$ (ng/mL) | 12.3350 | 16.5470 | 48.02 | 74.55* | 59.43-93.51 |
| $AUC_{0-24}$ (ng · hr/mL) | 68.5260 | 118.4170 | 73.87 | 57.87* | 41.68-80.35 |

*Comparison was detected as statistically significant by ANOVA (α = 0.05).

Example 10: Randomized, Double-Blind, Placebo-Controlled Multicenter Study of Estradiol Vaginal Softgel Capsules for Treatment of VVA Investigational Plan The study was a randomized, double-blind, placebo-controlled multicenter study design. Postmenopausal subjects who meet the study entry criteria will be randomized in a 1:1:1:1 ratio to receive Estradiol Vaginal Softgel Capsule 4 µg, Estradiol Vaginal Softgel Capsule 10 µg, Estradiol Vaginal Softgel Capsule 25 µg, or matching placebo. Subjects will be asked to self-assess the symptoms of vulvar or vaginal atrophy including vaginal pain associated with sexual activity, vaginal dryness, vulvar or vaginal itching or irritation by completing the VVA symptom self-assessment questionnaire and identification of her MBS at screening visit 1A to determine eligibility for the study. The VVA symptom Self-Assessment Questionnaire, vaginal cytology, vaginal pH, and vaginal mucosa will be assessed at screening visit 1B. These assessments will determine continued eligibility and will be used as the baseline assessments for the study. Randomized subjects will then complete the Questionnaire during visits 3, 4, 5, and 6.

The primary efficacy endpoints for the study included: (A) change from baseline to week 12 in the percentage of vaginal superficial cells (by vaginal cytologic smear) compared to placebo; (B) change from baseline to week 12 in the percentage of vaginal parabasal cells (by vaginal cytologic smear) compared to placebo; (C) change from baseline at week 12 in vaginal pH as compared to placebo; and (D) change from baseline to week 12 on the severity of the MBS of dyspareunia (vaginal pain associated with sexual activity) associated with VVA as compared to placebo.

The secondary efficacy endpoints for the study included: (E) change from baseline to weeks 2, 6, and 8 in the percentage of vaginal superficial cells (by vaginal cytologic smear) compared to placebo; (F) change from baseline to weeks 2, 6, and 8 in the percentage of vaginal parabasal cells (by vaginal cytologic smear) compared to placebo; (G) change from baseline to weeks 2, 6, and 8 in vaginal pH as compared to placebo; (H) change from baseline to weeks 2, 6, and 8 on the severity of the MBS of dyspareunia (vaginal pain associated with sexual activity) associated with VVA as compared to placebo; (I) change from baseline to weeks 2, 6, 8, and 12 on the severity of vaginal dryness and vulvar or vaginal itching or irritation associated with VVA as compared to placebo; (J) change in visual evaluation of the vaginal mucosa from baseline to weeks 2, 6, 8, and 12 compared to placebo; (K) assessment of standard PK parameters as defined in the SAP for serum estradiol, estrone, and estrone conjugates at Screening Visit 1A, days 1, 14, and 84 of treatment in a subset of subjects (PK substudy) utilizing baseline corrected and uncorrected values [as outlined in the Statistical Analysis Plan (SAP)]; and (L) change from baseline in the Female Sexual Function Index (FSFI) at week 12 compared to placebo.

The safety endpoints for the study included: (1) Adverse events; (2) Vital signs; (3) Physical examination findings; (4) Gynecological examination findings; (5) Clinical laboratory tests; (6) Pap smears; and (7) Endometrial biopsy.

Approximately 100 sites in the United States and Canada screened approximately 1500 subjects to randomize 747 subjects in this study (modified intent to treatment population, or all subjects who have taken at least one dose of the pharmaceutical compositions disclosed herein), with a target of 175 subjects randomized to each treatment group (175 in each active treatment group and 175 in the placebo group to complete 560 subjects). Actual subjects enrolled are 186 subjects in the 4 µg formulation group, 188 subjects in the 10 µg formulation group, 186 subjects in the 25 µg formulation group, and 187 subjects in the placebo group, for a total of 747 subjects in the study. Within each treatment group, 15 subjects also participated in a PK substudy.

Subjects were assigned to one of four treatment groups: (1) 4 µg formulation; (2) 10 µg formulation; (3) 25 µg formulation; and (4) placebo.

Most subjects participated in the study for 20-22 weeks. This included a 6 to 8 week screening period (6 weeks for subjects without an intact uterus and 8 weeks for subjects with an intact uterus), 12 weeks on the investigational product, and a follow-up period of approximately 15 days after the last dose of investigational product. Some subjects' involvement lasted up to 30 weeks when an 8-week washout period was necessary. Subjects who withdrew from the study were not replaced regardless of the reason for withdrawal.

Figure 9:
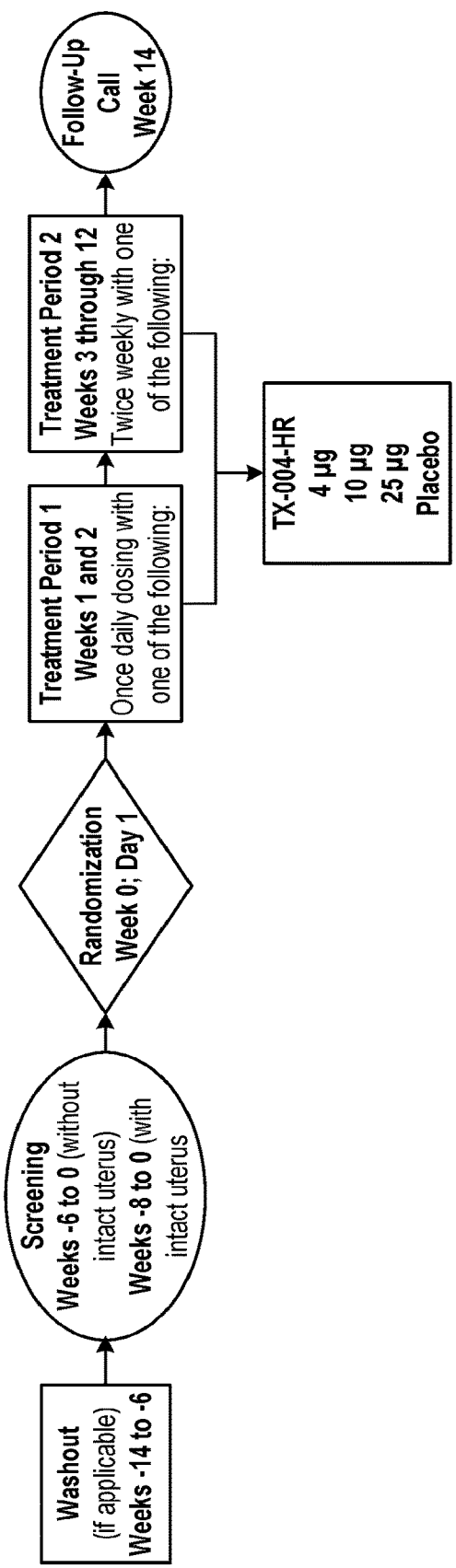
FIG. 9 is a study schematic diagram.
Figure 10:
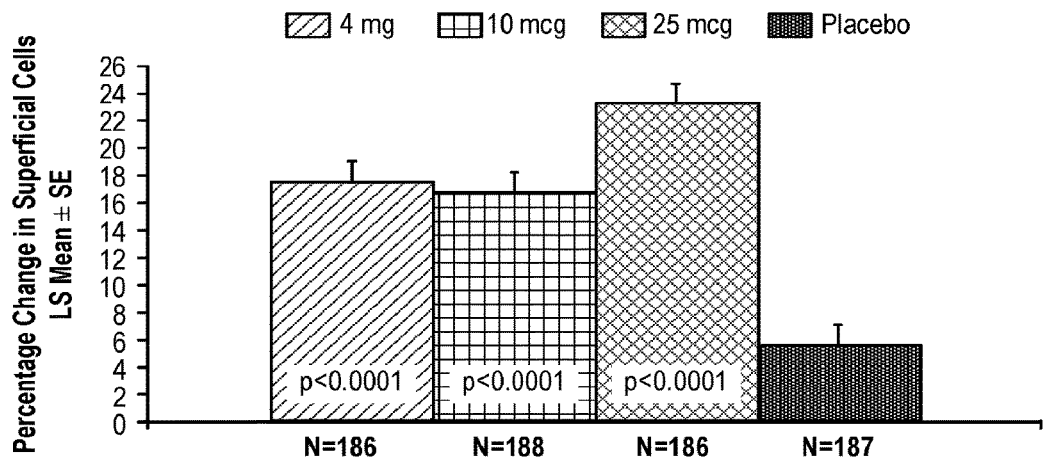
FIG. 10 shows the percentage change in superficial cells at 12 weeks compared to placebo.
Figure 11:
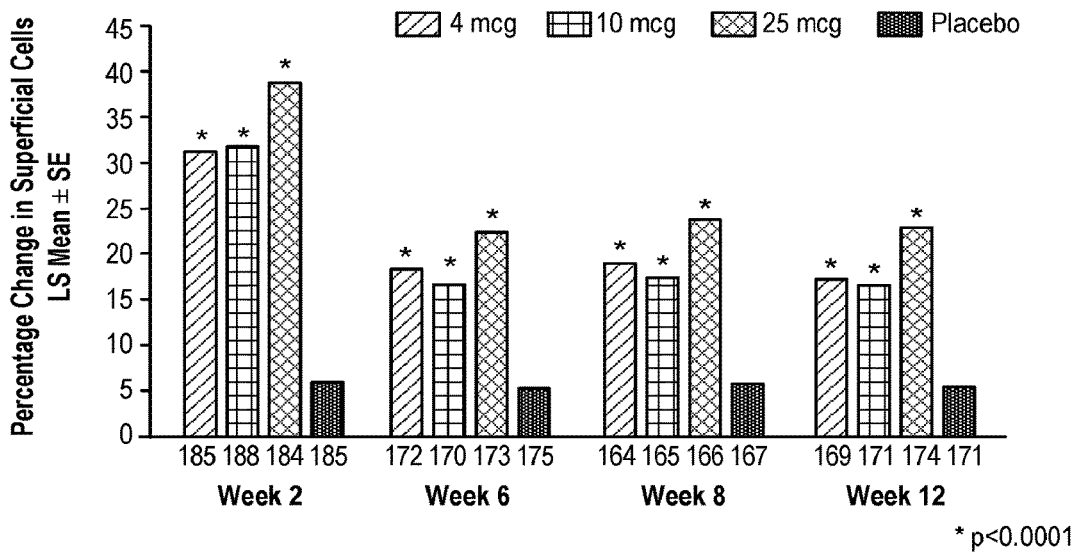
FIG. 11 shows the percentage change in superficial cells at week 2, week 6, week 8, and week 12 compared to placebo.
Figure 12:
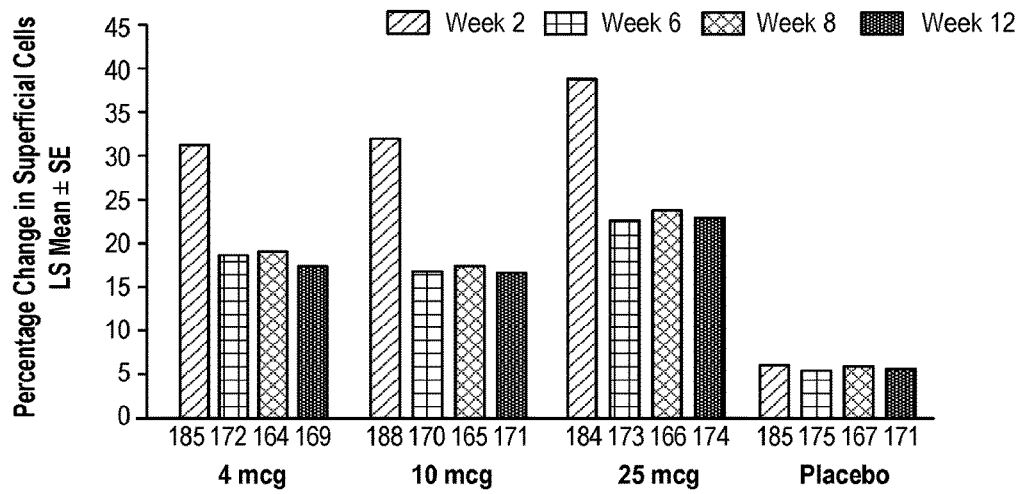
FIG. 12 shows percentage change in superficial cells per dose for each of week 2, week 6, week 8, and week 12 compared to placebo.
Figure 13:
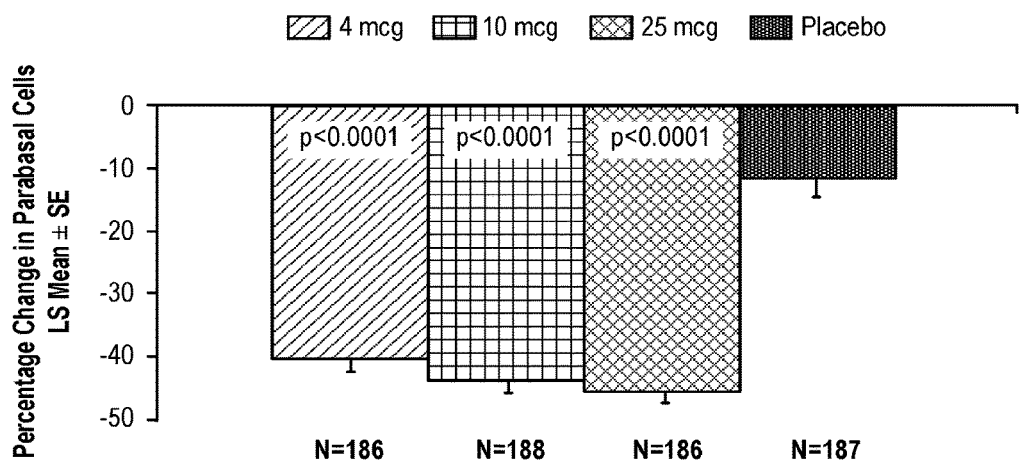
FIG. 13 shows the percentage change in parabasal cells at 12 weeks compared to placebo.
Figure 14:
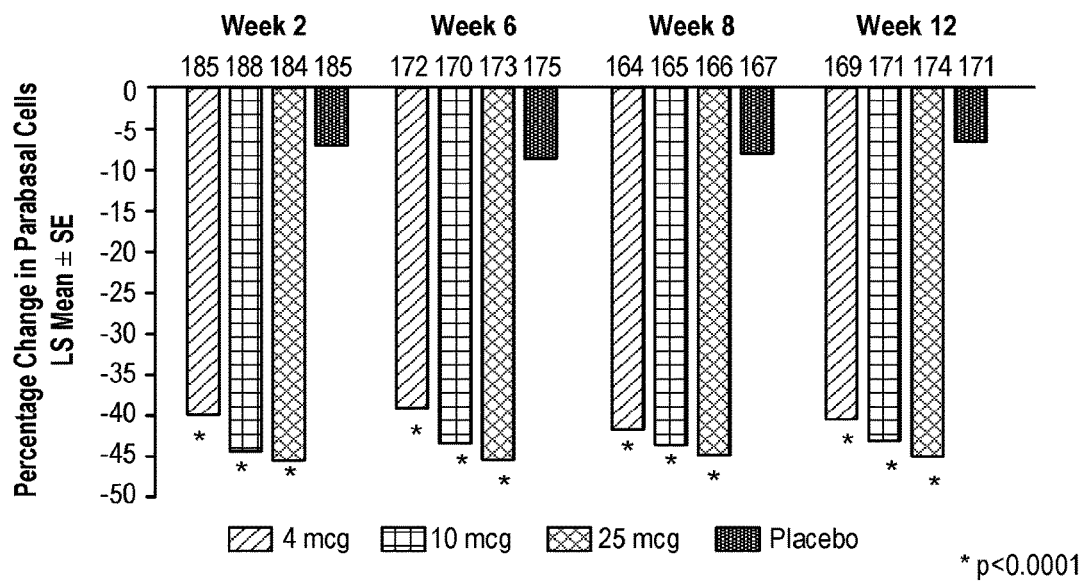
FIG. 14 shows the percentage change in parabasal cells at week 2, week 6, week 8, and week 12 compared to placebo.

The study schematic diagram shown in FIG. 9. There were two treatment periods; once daily intravaginal administration of one of the listed investigational products for 2 weeks, followed by a twice weekly intravaginal administration for 10 weeks.

The subject inclusion criteria included: (1) postmenopausal female subjects between the ages of 40 and 75 years (at the time of randomization) with at least: 12 months of spontaneous amenorrhea (women <55 years of age with history of hysterectomy without bilateral oophorectomy prior to natural menopause must have follicle stimulating hormone (FSH) levels >40 mIU/mL); or 6 months of spontaneous amenorrhea with follicle stimulating hormone (FSH) levels >40 mIU/mL; or At least 6 weeks postsurgical bilateral oophorectomy.

The subject inclusion criteria also included: (2) ≤5% superficial cells on vaginal cytological smear; (3) Vaginal pH >5.0; (4) Moderate to severe symptom of vaginal pain associated with sexual activity considered the most bothersome vaginal symptom by the subject at screening visit 1A; (5) Moderate to severe symptom of vaginal pain associated with sexual activity at screening visit 1B; (6) Onset of moderate to severe dyspareunia in the postmenopausal years; (7) Subjects were sexually active (i.e., had sexual activity with vaginal penetration within approximately 1 month of screening visit 1A); and (8) Subjects anticipated having sexual activity (with vaginal penetration) during the conduct of the trial For subjects with an intact uterus, the subject inclusion criteria also included: (9) subjects had an acceptable result from an evaluable screening endometrial biopsy. The endometrial biopsy reports by the two central pathologists at screening specified one of the following: proliferative endometrium; weakly proliferative endometrium; disordered proliferative pattern; secretory endometrium; endometrial tissue other (i.e., benign, inactive, or atrophic fragments of endometrial epithelium, glands, stroma, etc.); endometrial tissue insufficient for diagnosis; no endometrium identified; no tissue identified; endometrial hyperplasia; endometrial malignancy; or other findings (endometrial polyp not present, benign endometrial polyp, or other endometrial polyp). Identification of sufficient tissue to evaluate the biopsy by at least one pathologist was required.

For subjects with a Body Mass Index (BMI) less than or equal to 38 kg/m$^2$, the subject inclusion criteria also included: (10) BMI values were rounded to the nearest integer (ex. 32.4 rounds down to 32, while 26.5 rounds up to 27).

In general, the inclusion criteria also included: (11) in the opinion of the investigator, the subject was believed likely to comply with the protocol and complete the study.

The exclusion criteria included: (1) use of oral estrogen-, progestin-, androgen-, or SERM-containing drug products within 8 weeks before screening visit 1A (entry of washout was permitted); use of transdermal hormone products within 4 weeks before screening visit 1A (entry of washout was permitted); use of vaginal hormone products (rings, creams, gels) within 4 weeks before screening visit 1A (entry of washout was permitted); use of intrauterine progestins within 8 weeks before screening visit 1A (entry of washout was permitted); use of progestin implants/injectables or estrogen pellets/injectables within 6 months before screening visit 1A (entry of washout was not permitted); or use of vaginal lubricants or moisturizers within 7 days before the screening visit 1B vaginal pH assessment.

The exclusion criteria also included: (2) a history or active presence of clinically important medical disease that might confound the study or be detrimental to the subject, including, for example: hypersensitivity to estrogens; endometrial hyperplasia; undiagnosed vaginal bleeding; a history of a chronic liver or kidney dysfunction/disorder (e.g., Hepatitis C or chronic renal failure); thrombophlebitis, thrombosis, or thromboembolic disorders; cerebrovascular accident, stroke, or transient ischemic attack; myocardial infarction or ischemic heart disease; malignancy or treatment for malignancy, within the previous 5 years, with the exception of basal cell carcinoma of the skin or squamous cell carcinoma of the skin (a history of estrogen dependent neoplasia, breast cancer, melanoma, or any gynecologic cancer, at any time, excluded the subject); and endocrine disease (except for controlled hypothyroidism or controlled non-insulin dependent diabetes mellitus).

The exclusion criteria also included: (3) recent history of known alcohol or drug abuse; (4) history of sexual abuse or spousal abuse that was likely to interfere with the subject's assessment of vaginal pain with sexual activity; (5) current history of heavy smoking (more than 15 cigarettes per day) or use of e-cigarettes; (6) use of an intrauterine device within 12 weeks before screening visit 1A; (7) use of an investigational drug within 60 days before screening visit 1A; (8) any clinically important abnormalities on screening physical exam, assessments, electrocardiogram (ECG), or laboratory tests; (9) known pregnancy or a positive urine pregnancy test; and (10) current use of marijuana.

In this study, if a subject discontinued or was withdrawn, the subject was not replaced. At the time of consent, each subject was given a unique subject number that identified their clinical site and sequential number. In addition to the assigned subject number, subject initials were used for identification. The clinical trial was performed in compliance with standard operating procedures as well as regulations set forth by FDA, ICH E6 (R1) guidelines, and other relevant regulatory authorities. Compliance was achieved through clinical trial-specific audits of clinical sites and database review.

Statistical Methods

Efficacy. The primary objective of the trial was to assess the efficacy of estradiol vaginal softgel capsules (4 µg, 10 µg, and 25 µg) when compared to placebo on vaginal superficial cells, vaginal parabasal cells, vaginal pH, and on the symptom of moderate to severe dyspareunia (vaginal pain associated with sexual activity) as the MBS at week 12. To account for the multiple comparisons of testing placebo to each of the three doses of estradiol (4 µg, 10 µg, and 25 µg) and the multiple testing of the four co-primary endpoints, a closed procedure was performed (see, Edwards D, Madsen J. "Constructing multiple procedures for partially ordered hypothesis sets." *Stat Med* 2007: 26-5116-24, incorporated by reference herein).

Determination of Sample Size.

The sample size needed per dose vs. placebo for each test of hypothesis in the modified intent-to-treat (MITT) population to achieve a given power was calculated using reference data from other studies (see, Bachman, G., et al. "Efficacy and safety of low-dose regimens of conjugated estrogens cream administered vaginally." *Menopause,* 2009. 16(4): p. 719-27; Simon, J., et al. "Effective Treatment of Vaginal Atrophy With an Ultra-Low-Dose Estradiol Vaginal Tablet." *Obstetrics & Gynecology,* 2008. 112(5): p. 1053-60; FDA Medical Officer's Review of Vagifem [NDA 20-908, Mar. 25, 1999, Table 6, p 12.], each incorporated by reference herein). Table 41 below provides the effect sizes, power, and sample size determinations for each of the primary endpoints. In general, subjects in the study met all inclusion/exclusion criteria and had moderate to severe dyspareunia as their most bothersome symptom of VVA. Based on the power analysis and the design considerations, approximately 175 subjects per treatment arm were enrolled.

TABLE 41

Power Analysis and Sample Size Determinations
Four Primary Endpoints in a Closed Procedure
Mean Change from Baseline to Week
12 Compared to Placebo (MMRM)
Power (One-way ANOVA, Alpha = 0.005, one-tailed)

| Primary Endpoint | Effect Size (%)* | Power Based Upon N = 140 per group per MITT |
|---|---|---|
| % Parabasal Cells | 150.3% | >0.999 |
| % Superficial Cells | 115.3% | >0.999 |
| Vaginal pH | 77.4% | >0.999 |
| Severity of Dyspareunia** | 30.0%, 41.2%, 70.5% | 0.50, 0.80, >0.999 |

*Range from 30% (Vagifem 10 µg; see, Simon 2008, supra), 41.2% (Vagifem 25 µg; see, FDA 1999, supra),70.5% (Premarin cream 2/week; see, Bachman 2009, supra)
**Effect Size is calculated for all primary endpoints as 100% times difference (treated minus placebo) in mean changes at week 12 from baseline.

All subjects who were randomly assigned and had at least 1 dose of investigational product formed the intent-to-treat (ITT) population. The Modified intent-to-treat (MITT) population was defined as all ITT subjects with a baseline and at least one follow-up value for each of the primary endpoints, each subject having taken at least one dose of investigational product, and was the primary efficacy population. The efficacy-evaluable (EE) population was defined as all MITT subjects who completed the clinical trial, were at least 80% compliant with investigational product, had measurements for all primary efficacy endpoints, and were deemed to be protocol compliant, with no significant protocol violations. The safety population included all ITT subjects.

The primary efficacy analyses were conducted on the MITT subjects with supportive efficacy analyses conducted on the EE population. For analysis purposes, subjects were required to complete all visits, up to and including Visit 6 (week 12), to be considered as having completed the study.

Analysis of Efficacy Endpoints.

For all numerically continuous efficacy endpoints, which included the four primary endpoints (mean change from baseline to week 12), active treatment group means were compared to placebo using an ANCOVA adjusting for the baseline level.

Primary and secondary efficacy endpoints were measured at baseline and at 2, 6, 8, and 12 weeks. The analysis examined change from baseline. Therefore, ANCOVAs were based on a repeated measures mixed effects model (MMRM) where the random effect was subject and the two fixed effects were treatment group and visit (2, 6, 8, and 12 weeks). Baseline measures and age were used as covariates. ANCOVAs were therefore not calculated independently for each study collection period. The analyses started with the full model but, interaction terms for visit (week 2, 6, 8, and 12) with treatment only remained where statistically significant ($p<0.05$).

The following three pair-wise comparisons were performed using the appropriate ANCOVA contrast for week 12 (primary) and weeks 2, 6, and 8 (secondary) changes from baseline: (1) active treatment, high dose group vs placebo; (2) active treatment, middle dose group vs placebo; and (3) active treatment, low dose group vs placebo.

Safety Outcome Measures.

Adverse events, vital signs, physical examination findings, gynecological examination findings, clinical laboratory tests, pap smears, and endometrial biopsy were the safety parameters. Adverse events and SAEs were summarized for each treatment group and overall for all active treatment groups with the proportion of subjects reporting each event. Actual values and change from baseline in vital signs, and all laboratory test parameters were summarized for each treatment group and overall for all active treatment groups with descriptive statistics at each assessment obtained.

Endometrial Biopsy Assessment.

Three independent pathologists with expertise in gynecologic pathology, blinded to treatment and to each other's readings, determined the diagnosis for endometrial biopsy slides during the conduct of the study. All visit 6, early termination, and on-treatment unscheduled endometrial biopsies were centrally read by three of the pathologists. Each pathologist's report was classified into one of the following three categories: category 1: not hyperplasia/not malignancy—includes proliferative endometrium, weakly proliferative endometrium, disordered proliferative pattern, secretory endometrium, endometrial tissue other (i.e., benign, inactive or atrophic fragments of endometrial epithelium, glands, stroma, etc.), endometrial tissue insufficient for diagnosis, no endometrium identified, no tissue identified, other; category 2: hyperplasia—includes simple hyperplasia with or without atypia and complex hyperplasia with or without atypia; category 3: malignancy—endometrial malignancy.

The final diagnosis was based on agreement of two of the three reads. Consensus was reached when two of the three pathologist readers agreed on any of the above categories. For example, any 2 subcategories of "not hyperplasia/not malignancy" were classified as "Category 1: not hyperplasia/not malignancy." If all three readings were disparate (i.e., each fell into a different category—category 1, 2, or 3), the final diagnosis was based on the most severe of the three readings.

The analysis population for endometrium hyperplasia was the endometrial hyperplasia (EH) population. An EH subject at week 12 was one who was randomly assigned and took at least 1 dose of investigational product, with no exclusionary protocol violation (as detailed at the Statistical Analysis Plan), and had a pretreatment endometrial biopsy and a biopsy on therapy.

Treatment of Subjects

The study used a double-blind design. Investigational product was supplied as 3 doses of Estradiol Vaginal Softgel Capsules (4 µg, 10 µg, and 25 µs) and matching placebo capsules. All subjects manually inserted one capsule into the vaginal cavity daily for 14 days (2 weeks) followed by twice weekly for 10 weeks according to one of the following treatment arms:

TABLE 42

Treatment Arms and Administration

| Regimen | Capsules | Capsules |
|---|---|---|
| Treatment 1 | 1 capsule daily of 4 µg vaginal softgel for 2 weeks | 1 capsule twice weekly of 4 µg vaginal softgel for 10 weeks |
| Treatment 2 | 1 capsule daily of 10 µg vaginal softgel for 2 weeks | 1 capsule twice weekly of 10 µg vaginal softgel for 10 weeks |
| Treatment 3 | 1 capsule daily of 25 µg vaginal softgel for 2 weeks | 1 capsule twice weekly of 25 µg vaginal softgel for 10 weeks |
| Treatment 4 | 1 capsule daily of placebo vaginal softgel for 2 weeks | 1 capsule twice weekly of placebo vaginal softgel for 10 weeks |

Investigational product was dispensed to all eligible subjects at visit 2. Each subject was provided a total of 30 soft gel capsules of investigational product in a labeled bottle, allowing for extra capsules for accidental loss or damage. A second bottle was dispensed at Visit 5. Each subject was trained by the clinical site to self-administer intravaginally one capsule daily at approximately the same hour for 2 weeks (14 days). The drug administration instructions included: "Remove vaginal capsule from the bottle; find a position most comfortable for you; insert the capsule with the smaller end up into vaginal canal for about 2 inches." Starting on Day 15, each subject administered 1 capsule twice weekly for the remaining 10 weeks. Twice weekly dosing was approximately 3-4 days apart, and generally did not exceed more than twice in a seven day period. For example, if the Day 15 dose was inserted on Sunday, the next dose was inserted on Wednesday or Thursday. At randomization visit 2 (day 1), subjects received their first dose of investigational product at the clinical facility under the supervision of the study personnel.

The investigational estradiol vaginal softgel drug products used in the study are pear-shaped, opaque, light pink softgel capsules. The capsules contain the solubilized estradiol pharmaceutical compositions disclosed herein as Pharmaceutical Compositions 4-7. When the softgel capsules come in contact with the vaginal mucosa, the soft gelatin capsule releases the pharmaceutical composition, into the vagina. In embodiments, the soft gelatin capsule completely dissolves.

The placebo used in the study contained the excipients in the investigational estradiol vaginal softgel capsule without the estradiol (see, e.g., Pharmaceutical Composition 7). The packaging of the investigational products and placebo were identical to maintain adequate blinding of investigators. Neither the subject nor the investigator was able to identify the treatment from the packaging or label of the investigational products.

A subject was required to use at least 80% of the investigational product to be considered compliant with investigational medication administration. Capsule count and diary cards were be used to determine subject compliance at each study visit. Subjects were randomly assigned in a 1:1:1:1 ratio to receive Estradiol Vaginal Softgel Capsule 4 µg (Pharmaceutical Composition 4), Estradiol Vaginal Softgel Capsule 10 µg (Pharmaceutical Composition 5), Estradiol Vaginal Softgel Capsule 25 µg (Pharmaceutical Composition 6), or placebo (Pharmaceutical Composition 7).

Concomitant medications/treatments were used to treat chronic or intercurrent medical conditions at the discretion of the investigator. The following medications were prohibited for the duration of the study: investigational drugs other than the investigational Estradiol Vaginal Softgel Capsule; estrogen-, progestin-, androgen (i.e., DHEA) or SERM-containing medications other than the investigational product; medications, remedies, and supplements known to treat vulvar/vaginal atrophy; vaginal lubricants and moisturizers (e.g., Replens) be discontinued 7 days prior to Visit 1B vaginal pH assessment; and all medications excluded before the study.

Efficacy Assessments

Vaginal cytological smears were collected from the lateral vaginal walls according to standard procedures and sent to a central laboratory to evaluate vaginal cytology. The percentage of superficial, parabasal, and intermediate cells was determined. All on-therapy/early termination vaginal cytology results were blinded to the Sponsor, Investigators, and subjects.

Vaginal pH was determined at screening Visit 1B and visits 3, 4, 5, and 6/end of treatment. Subjects were not allowed to use vaginal lubricants or moisturizers within 7 days of the screening vaginal pH assessment or at any time afterwards during the study. The subjects were advised not to have sexual intercourse and to refrain from using vaginal douching within 24 hours prior to the measurement for all scheduled vaginal pH assessments. After insertion of an unlubricated speculum, a pH indicator strip was applied to the lateral vaginal wall until it became wet, taking care to avoid cervical mucus, blood or semen that are known to affect vaginal pH. The color of the strip was compared immediately with a colorimetric scale and the measurement was recorded.

During the gynecological examinations, the investigator performed a visual evaluation of vaginal mucosa using a four-point scale (0=none, 1=mild, 2=moderate, and 3=severe) to assess parameters of vaginal secretions, vaginal epithelial integrity, vaginal epithelial surface thickness, and vaginal color according to the table below.

| Assessment Criteria | Severity | | | |
| --- | --- | --- | --- | --- |
| | No atrophy | Mild | Moderate | Severe |
| Vaginal secretions | normal clear secretions noted on vaginal walls | superficial coating of secretions, difficulty with speculum insertion | scant not covering the entire vaginal vault, may need lubrication with speculum insertion to prevent pain | none, inflamed, ulceration noted, need lubrication with speculum insertion to prevent pain |
| Vaginal epithelial integrity | normal | vaginal surface bleeds with scraping | vaginal surface bleeds with light contact | vaginal surface has petechiae before contact and bleeds with light contact |
| Vaginal epithelial surface thickness | rogation and elasticity of vault | poor rogation with some elasticity noted of vaginal vault | smooth, some elasticity of vaginal vault | smooth, no elasticity, constriction of the upper one third of vagina or loss of vaginal tone (cystocele and rectocele) |
| Vaginal color | pink | lighter in color | pale in color | transparent, either no color or inflamed |

The VVA symptom self-assessment questionnaire, shown below, is an instrument for subjects to self-assess their symptoms of vulvar or vaginal atrophy, including vaginal pain associated with sexual activity, vaginal dryness, vulvar or vaginal itching, or irritation. At screening visit 1A subjects were asked to complete the questionnaire and identify their most bothersome symptoms, and the results of the survey were used to determine initial eligibility for the study. At visit 1A, subjects were also asked to indicate which moderate or severe symptoms bothered them most. The questionnaire was administered again at screening visit 1B and used to determine continued eligibility for the study.

| VVA SYMPTOMS SELF-ASSESSMENT | | |
| --- | --- | --- |
| Please Rate your Vulvar and/or Vaginal | Severity Score (Please select only ONE) | |
| Symptoms | 0 = None  1 = Mild  2 = Moderate  3 = Severe | |
| 1 | Pain associated with sexual activity (with vaginal penetration). | |
| 2 | Vaginal dryness. | |
| 3 | Vulvar and/or vaginal itching or irritation. | |

Randomized subjects were asked to complete the VVA Symptom Self-Assessment Questionnaire at visits 3, 4, 5, and 6. Subjects were asked to indicate if no sexual activity with vaginal penetration was experience since the previous visit. Screening visit 1B evaluation results were considered as Baseline data for the statistical analyses.

The Female Sexual Function Index (FSFI) is a brief, multidimensional scale for assessing sexual function in women (see, Rosen, 2000, supra 26: p. 191-208, incorporated by reference herein). The scale consists of 19 items that assess sexual function over the past 4 weeks and yield domain scores in six areas: sexual desire, arousal, lubrication, orgasm, satisfaction, and pain. Further validation of the instrument was conducted to extend the validation to include dyspareunia/vaginismus (pain), and multiple sexual dysfunctions (see, Weigel, M., et al. "The Female Sexual Function Index (FSFI): Cross-Validation and Development of Clinical Cutoff Scores." *Journal of Sex & Marital*

*Therapy*, 2005. 31: p. 1-20, incorporated by reference herein). The FSFI was conducted at Visits 2 and 6. Subjects participating in the PK substudy were not assessed using FSFI.

Safety Assessments

A complete medical history, including demographic data (age and race/ethnicity) gynecological, surgical, and psychiatric history and use of tobacco and alcohol was recorded at the washout/screening visit 1A prior to any washout period; this history included a review of all past and current diseases and their respective durations as well as any history of amenorrhea.

A complete physical examination was conducted at screening visit 1A and visit 6/end of treatment. The physical examination included, at a minimum, examination of the subject's general appearance, HEENT (head, eyes, ears, nose, and throat), heart, lungs, musculoskeletal system, gastrointestinal (GI) system, neurological system, lymph nodes, abdomen, and extremities. The subject's height was measured at washout/screening visit 1A only and body weight (while the subject is lightly clothed) was be measured at washout/screening visit 1A and end of treatment. BMI was calculated at washout/screening visit 1A. Vital signs (body temperature, heart rate [HR], respiration rate [RR], and sitting blood pressure [BP]) were measured at all visits after the subject had been sitting for ≥10 minutes. If the initial BP reading was above 140 mmHg systolic or 90 mmHg diastolic, the option for a single repeat assessment performed 15 minutes later was provided. A standard 12-lead ECG was obtained at screening visit 1A and visit 6 or early termination.

Subjects were required to have a pelvic examination and Pap smear performed during the screening visit 1B and visit 6 or early termination. The Pap smear was required for all subjects with or without an intact uterus and cervix. For subjects without an intact cervix the Pap smear was obtained by sampling the apex of the vaginal cuff. All subjects were required to have a Pap smear done during screening, regardless of any recent prior assessment. Subjects who discontinued the study after 2 weeks of investigational product were required to have an end of treatment Pap smear. Subjects had a breast examination performed during screening visit 1A and at visit 6 or early termination.

Endometrial biopsies were performed by a board-certified gynecologist at screening and at visit 6/end of treatment. Unscheduled endometrial biopsies were performed during the study, when indicated for medical reasons. The screening biopsy was performed at screening visit 1B, after the subject's initial screening visit assessments indicated that the subject was otherwise an eligible candidate for the study.

At screening, endometrial biopsies were read centrally by two pathologists. A candidate subject was excluded from the study if at least one pathologist assessed the endometrial biopsy as endometrial hyperplasia, endometrial cancer, proliferative endometrium, weakly proliferative endometrium, or disordered proliferative pattern, or if at least one pathologist identified an endometrial polyp with hyperplasia, glandular atypia of any degree (e.g., atypical nuclei), or cancer. Additionally, identification of sufficient tissue to evaluate the biopsy by at least one pathologist was required for study eligibility. The option for one repetition of the screening endometrial biopsy was made available when an initial endometrial biopsy was performed and both of the primary pathologists reported endometrial tissue insufficient for diagnosis, no endometrium was identified, or no tissue was identified, and if the subject had met all other protocol-specified eligibility criteria to date. The visit 6 (or early termination) endometrial biopsies and on treatment unscheduled biopsies were assessed by three pathologists.

During the study, at early termination, and at the end of the study, any subject with a diagnosis of endometrial hyperplasia was withdrawn and treated with 10 mg of Medroxyprogesterone acetate (MPA) for 6 months unless deemed otherwise by the PI. For unscheduled biopsies, the histological diagnosis of endometrial polyp did not force withdrawal unless atypical nuclei were present.

A urine pregnancy test was conducted at screening visit 1A unless the subject had a history of tubal ligation, bilateral oophorectomy, or was ≥55 years of age and had experienced cessation of menses for at least 1 year.

Blood samples for blood chemistry, hematology, coagulation tests, and hormone levels and urine samples for urine analysis were collected and sent to a central laboratory. Blood Chemistry (sodium, potassium, chloride, total cholesterol, blood urea nitrogen (BUN), iron, albumin, total protein, aspartate aminotransferase (AST), alanine aminotransferase (ALT), alkaline phosphatase, creatinine, calcium, phosphorous, uric acid, total bilirubin, glucose and triglycerides (must be fasting minimum of 8 hours). A fasting glucose of >125 mg/dL will require a HgA1C) was monitored. Hematology (complete blood count (CBC) including white blood cell count and differential, red blood cell count, hemoglobin, hematocrit, and platelet count) was monitored. Hormone Levels (follicle-stimulating hormone (FSH) (not required for subjects with ≥12 months of spontaneous amenorrhea or bilateral oophorectomy), estradiol, estrone, and estrone conjugates and SHBG for subjects in the PK substudy) were monitored. Urine Analysis (appearance, specific gravity, protein, and pH) was conducted.

Pharmacokinetic Assessment

Seventy-two subjects were also enrolled in a pharmacokinetic (PK) substudy. In those subjects participating in the PK substudy, time 0 h serum blood samples were obtained at screening visit 1A, day 1, and day 14 prior to dosing for baseline. The baseline was characterized by the average of the two pre-treatment samples. Serum blood samples were then obtained on day 1 and day 14 at five post dose time points (2 h, 4 h, 6 h, 10 h, and 24 h). On study days 1 (visit 2) and 14 (visit 3) a baseline pretreatment blood sample (Time 0 h) was collected from each subject prior to insertion of the investigational product. After insertion of the product, blood samples were drawn at 2, 4, 6, 10, and 24 hours following insertion. The last PK sample (approximately day 84) was obtained 4 days following the last insertion of investigational product.

Blood samples were analyzed to characterize area under the curve (AUC), time of maximum concentration ($t_{max}$), minimum concentration ($C_{min}$), and maximum concentration ($C_{max}$). Blood samples were also analyzed to measure the levels of estradiol, estrone, and estrone conjugates. No fasting requirements were applied. Sex hormone binding globulin (SHBG) levels were obtained at pre-treatment baseline (day 1, visit 2), and day 14 at the 0 h and on the day 84 final hormone blood draw.

A symptoms/complaints and medications diary was dispensed at all visits and subjects were instructed on completion. The subjects used the diary to record symptoms/complaints (including stop and start dates and treatment received) and prior medications/treatments (including indication, stop, and start dates). A copy of the diary was made at each visit and re-dispensed to the subject. A dosing diary was dispensed at visit 2 and at visit 3 and subjects were be instructed on completion. Subjects recorded investigational product usage and sexual activity. The dosing diary dispensed at visit 3 was re-dispensed at visits 4 and 5. A copy of the diary was made at each visit prior to re-dispensing to the subject.

Study Visits

Study visits were typically conducted so as to include the activities outlined in Table 43.

Screening Period Visits (Visits 1A and 1B).

Subjects not requiring washout begin screening procedures at visit 1A as described above for the washout period. With the exception of vital signs, procedures performed at washout will not be repeated at screening visit 1A. In general, screening visits 1A and 1B were completed within

TABLE 43

Schedule of Assessments—Main Study

| Activity | Washout Week −14 to −6 | Visit 1A Screening Week −6 to 0 | Visit 1B Screening Week −4 to 0 | Visit 2: Randomization/ Baseline Week 0 Day 1 | Visit 3: Interim Week 2 Day 14 (±3 d) | Visit 4: Interim Week 6 Day 42 (±3 d) | Visit 5: Interim Week 8 Day 56 (±3 d) | Visit 6: End of Treatment or Early Term Week 12 Day 84 (±3 d) | Telephone Interview Week 14 approximately 15 days after last dose of IP |
|---|---|---|---|---|---|---|---|---|---|
| Informed consent | | X | X | | | | | | |
| Demographics/Medical and Gynecological history and prior medications | | X | X | | | | | | |
| Weight | | X | X | | | | | X | |
| Height and BMI calculation | | X | X | | | | | | |
| Vital signs | X | X | X | X | X | X | X | X | |
| MBS | | | X | | | | | | |
| Subject VVA Self-Assessment Questionnaire | | X | X | | X | X | X | X | |
| Physical examination including breast exam | | X | | | | | | X | |
| Laboratory safety tests (Hematology, Serum Chemistry, FSHP, Urinalysis) | | X | | | | | | X | |
| 12-Lead ECG | | X | | | | | | X | |
| Pelvic exam | | | X | | | | | X | |
| Vaginal pH | | | X | | X | X | X | X | |
| Papanicolaou (Pap) smear | | | X | | | | | X | |
| Investigator assessment of vaginal mucosa | | | X | | X | X | X | X | |
| Vaginal cytological smear | | | X | | X | X | X | X | |
| Mammogram | | X | | | | | | | |
| Endometrial biopsy | | | X | | | | | X | |
| Diary Dispense | X | X | X | X | X | X | X | | |
| Diary Collection | | X | X | X | X | X | X | X | |
| FSFI | | | | X | | | | X | |
| Satisfaction Survey | | | | | | | | X | |
| Urine pregnancy test | | X | | | | | | | |
| Randomization | | | | X | | | | | |
| Dispense Investigational Product bottle | | | | X | | | X | | |
| Re-dispense Investigational Product bottle | | | | | X | X | | | |
| Treatment administration instruction | | | | X | X | X | X | | |
| Collect unused investigational product and used bottles; assess compliance | | | | | X | X | X | X | |
| Adverse event monitoring | | X | X | X | X | X | X | X | X |
| Concomitant medications | | X | X | X | X | X | X | X | X |

Washout Period Visit (if Applicable; Weeks −14 to −6).

The purpose of this visit was to discuss the study with a potential subject and obtain informed consent that is signed and dated before any procedures, including washout are performed. Subjects who agreed to discontinue current treatment began washout after the consent form was signed. A symptoms/complaints and medication diary was dispensed at this visit and the subject was instructed in how to complete the diary. Once the washout period was completed, the subject will return to the site for visit 1A.

The activities and assessments conducted during the visit included: informed consent; demographics; medical/gynecological history; collection of prior and concomitant medication information; height, body weight measurement and BMI calculation; collection of vital signs (body temperature, HR, RR, and BP); dispensation of symptoms/complaints diary and instruction in how to complete the diary 6 weeks (42 days) for subjects without a uterus or within 8 weeks (56 days) for subjects with a uterus. All screening assessments were completed prior to randomization. The investigators reviewed the results from all screening procedures and determined if the subjects were eligible for enrollment into the study.

Visit 1A (Approximately Week −6 to 0).

Visit 1A was conducted after the wash-out period (if applicable) or after the subject provided informed consent. The subject was advised to fast for 8 hours prior to the visit for blood draws.

Procedures and evaluations conducted at the visit included: informed consent; demographics; medical/gynecological history; collection of the symptoms/complaints and medications diary from washout (if applicable) and review with the subject; recording of prior medication information; recording and assessment of adverse events (AEs) starting from the signing of informed consent; height, body weight measurement and BMI calculation; collection of vital signs (body temperature, HR, RR, and BP); physical examination; breast examination (including a mammogram conducted up to nine months prior to Visit 2); urine pregnancy test as required; blood and urine sample collection for blood chemistry (minimum fast of 8 hrs), hematology, and urinalysis; serum FSH as required; 12-Lead ECG.

At visit 1A, the VVA symptom self-assessment questionnaire was conducted and most bothersome symptoms were identified, with the subject self-identifying moderate or severe pain with sexual activity as her MBS to continue screening. The symptoms/complaints and medications diary was dispensed, and subjects were instructed in how to complete the diary. Subjects were instructed to refrain from use of vaginal lubricants for 7 days and sexual intercourse/vaginal douching for 24 hours prior to the vaginal pH assessment to be done at visit 1B.

Visit 1B (Approximately Week −4 to Week 0).

Visit 1B was conducted after the subject's initial screening visit and after the other screening results indicated that the subject was otherwise an eligible candidate for the study (preferably around the middle of the screening period).

Procedures and evaluations conducted at the visit included: VVA symptom self-assessment questionnaire, the subject having indicated moderate to severe pain with sexual activity with vaginal penetration in order to continue screening; collection of vital signs (body temperature, HR, RR, and BP); pelvic examination; investigator assessment of vaginal mucosa as described above; assessment of vaginal pH (sexual intercourse or vaginal douching within 24 hrs prior to the assessment being prohibited, and a subject's vaginal pH being >5.0 to continue screening); Pap smear; vaginal cytological smear (one repetition being permitted during screening if no results were obtained from the first smear); endometrial biopsy performed as described above; review of the symptoms/complaints and medications diary with the subject.

Visit 2 (Week 0; Randomization/Baseline).

Subjects who met entry criteria were randomized to investigational product at this visit. Procedures and evaluations conducted at the visit included: self-administration of FSFI by subjects not participating in the PK substudy; review of the symptoms/complaints and medications diary with the subject; review of evaluations performed at screening visits and verification of present of all inclusion criteria and the absence of all exclusion criteria; collection of vital signs (body temperature, HR, RR, and BP); randomization, with subjects meeting all entry criteria being randomized and allocated a bottle number; dispensation of investigational product and instruction in how to insert the capsule vaginally, with subjects receiving their first dose of investigational product under supervision; dispensation of dosing diary and instruction on completion of the treatment diary, including recording investigational product usage and sexual activity.

Visit 3 (Week 2, Day 14±3 Days).

Procedures and evaluations conducted at the visit included: completion of the VVA symptom self-assessment questionnaire; review of the symptoms/complaints and medications diaries with the subject; collection of vital signs (body temperature, HR, RR, and BP); Assessment of vaginal mucosa; assessment of vaginal pH (with sexual intercourse or vaginal douching within 24 hrs prior to the assessment being prohibited); vaginal cytological smear; collection of unused investigational product and bottle for assessment of compliance/accountability; re-dispensation of investigational product and re-instruction in how to insert the capsule vaginally if necessary; review of the completed dosing diary with the subject.

Visit 4 (Week 6, Day 42±3 Days).

Procedures and evaluations conducted at the visit included: completion of the VVA symptom self-assessment questionnaire; review of the symptoms/complaints and medications diary with the subject; collection of vital signs (body temperature, HR, RR, and BP); assessment of vaginal mucosa as described above; vaginal cytological smear; assessment of vaginal pH (with sexual intercourse or vaginal douching within 24 hrs prior to the assessment being prohibited); collection of unused investigational product for assessment of compliance/accountability; re-dispensation of investigational product and re-instruction in how to insert the capsule vaginally if necessary; review of the completed dosing diary with the subject.

Visit 5 (Week 8, Day 56±3 Days).

Procedures and evaluations conducted at the visit included: completion of the VVA symptom self-assessment questionnaire; review of the symptoms/complaints and medications diary with the subject; collection of vital signs (body temperature, HR, RR, and BP); assessment of vaginal mucosa as described above; vaginal cytological smear; assessment of vaginal pH (with sexual intercourse or vaginal douching within 24 hrs prior to the assessment being prohibited); collection of unused investigational product for assessment of compliance/accountability; re-dispensation of investigational product and re-instruction in how to insert the capsule vaginally if necessary; review of the completed dosing diary with the subject.

Visit 6 (Week 12, Day 84±3 Days or Early Termination).

This visit was performed if a subject withdraws from the study before visit 6. Procedures performed at this visit included: completion of the VVA symptom self-assessment questionnaire; review of the subject the dosing diary, symptoms/complaints, and medications diaries with the subject; collection of blood and urine sample collection for blood chemistry (minimum fast of 8 hrs), hematology, and urinalysis; collection of vital signs (body temperature, HR, RR, and BP) and weight; performance of 12-lead-ECG; collection of unused investigational product and container for assessment of compliance/accountability; physical examination; breast exam; assessment of vaginal mucosa as described above; assessment of vaginal pH (with sexual intercourse or vaginal douching within 24 hrs prior to the assessment being prohibited); vaginal cytological smear; Pap smear; endometrial biopsy; self-administration of FSFI by subjects not participating in the PK substudy; self-administration of survey titled "Acceptability of product administration Survey" by subjects.

Follow-Up Interview (Approximately 15 Days after the Last Dose of Investigational Product).

Each subject who received investigational product received a follow-up phone call, regardless of the duration of therapy, approximately 15 days following the last dose of investigational product. The follow-up generally took place after receipt of all safety assessments (e.g., endometrial biopsy and mammography results). The follow-up included: review of ongoing adverse events and any new adverse events that occurred during the 15 days following the last dose of investigational product; review of ongoing concomitant medications and any new concomitant medications that occurred during the 15 days following the last dose of investigational product; and discussion of all end of study safety assessments and determination if further follow up or clinic visit is required.

PK Substudy Visit Procedures and Schedule

Screening Visit 1A.

In addition to the procedures listed described above, activities in the PK substudy also included: provision of informed consent by subject and agreement to participate in the PK substudy; collection of a serum blood sample during the visit for baseline assessment of estradiol, estrone, and estrone conjugates.

Visit 2 (Week 0, Day 1).

In addition to the procedures listed described above, activities in the PK substudy also included collection of serum blood sample obtained prior to the administration of investigational product (timepoint 0 h) for baseline assessment of estradiol, estrone, estrone conjugates, and SHBG. The investigational product was self-administered by the subject after the pre-treatment blood sample has been taken. After investigational product administration, serum blood samples were obtained at 2 h, 4 h, 6 h, 10 h, and 24 h timepoints for estradiol, estrone, and estrone conjugates (serum samples were generally taken within +/−5 minutes at 2 h and 4 h, within +/−15 minutes at 6 h, and within +/−1 h at 10 h and 24 h). The subject was released from the site after the 10 hour sample and instructed to return to the site the next morning for the 24 hour blood draw. The subject was instructed not to self-administer the day 2 dose until instructed by the site personnel to dose at the clinical site. The subject was released from the clinical site following the 24 hour blood sample and administration of the day 2 dose.

Visit 3 (Week 2, Day 14).

The visit must occurred on day 14 with no visit window allowed. In addition to the procedures listed above, the PK substudy included collection of a serum blood sample prior to the administration of day 14 dose (timepoint 0 h) for SHBG and PK assessments. The subject self-administered the day 14 dose at the clinical site, and serum blood samples were obtained at 2 h, 4 h, 6 h, 10 h, and 24 h timepoints for estradiol, estrone, and estrone conjugates. The subject was released from the site after the 10 hour sample and instructed to return to the site the next morning for the 24 hour blood draw. The subject was instructed not to self-administer the day 15 dose until instructed by the site personnel to dose at the clinical site. The subject was released from the clinical site following the 24 hour blood sample and administration of the day 15 dose. The subject was be instructed to administer the next dose of study drug on day 18 or day 19 and continue dosing on a bi-weekly basis at the same time of day for each dose.

Visit 6 (Week 12, Day 84±3 Days, or at Early Termination).

The visit took place 4 days after last IP dose or early termination. A serum sample for estradiol, estrone, and estrone conjugates and SHBG was drawn in addition to the procedures described above.

PK sub-study visits were typically conducted so as to include the activities outlined in Table 44.

TABLE 44

Schedule of Assessments for PK Sub-study

| Activity | Washout Week −14 to −6 | Visit 1A Screening Week −6 to 0 | Visit 1B Screening Week −4 to 0 | Visit 2: Randomization/ Baseline Week 0 Day 1 | Visit 3: Interim Week 2 Day 14 (no window) | Visit 4: Interim Week 6 Day 42 (±3 d) | Visit 5: Interim Week 8 Day 56 (±3 d) | Visit 6: End of treatment or Early Term Week 12 Day 84 (±3 d) (4 days after last IP dose) | Telephone Interview Week 14 approximately 15 days after last dose of IP |
|---|---|---|---|---|---|---|---|---|---|
| PK sub-study Informed consent | | X | X | | | | | | |
| Demographics/Medical and Gynecological history and prior medications | | X | X | | | | | | |
| Weight | | X | X | | | | | X | |
| Height and BMI calculation | | X | X | | | | | | |
| Vital signs | | X | X | X | X | X | X | X | |
| MBS | | X | | | | | | | |
| Subject VVA Self-Assessment Questionnaire | | X | X | | X | X | X | X | |
| Physical examination including breast exam | | X | | | | | | X | |
| Laboratory safety tests (Hematology, Serum Chemistry, FSHP, Urinalysis) | | X | | | | | | X | |
| PK Serum Blood Samples (Estradiol, Estrone, Estrone Conjugates) | | X | | X | X | | | X | |
| Serum blood samples for SHBG | | | | X | X | | | X | |
| 12-Lead ECG | | X | | | | | | X | |
| Pelvic exam | | | X | | | | | X | |
| Vaginal pH | | | X | | X | X | X | X | |
| Papanicolaou (Pap) smear | | | X | | | | | X | |
| Investigator assessment of vaginal mucosa | | | X | | X | X | X | X | |
| Vaginal cytological smear | | | X | | X | X | X | X | |
| Mammogram | | X | | | | | | | |
| Endometrial biopsy | | | X | | | | | X | |
| Diary Dispense | X | X | X | X | X | X | X | | |
| Diary Collection | | X | X | X | X | X | X | X | |

TABLE 44-continued

Schedule of Assessments for PK Sub-study

| Activity | Washout Week −14 to −6 | Visit 1A Screening Week −6 to 0 | Visit 1B Screening Week −4 to 0 | Visit 2: Randomization/ Baseline Week 0 Day 1 | Visit 3: Interim Week 2 Day 14 (no window) | Visit 4: Interim Week 6 Day 42 (±3 d) | Visit 5: Interim Week 8 Day 56 (±3 d) | Visit 6: End of treatment or Early Term Week 12 Day 84 (±3 d) (4 days after last IP dose) | Telephone Interview Week 14 approximately 15 days after last dose of IP |
|---|---|---|---|---|---|---|---|---|---|
| Satisfaction Survey | | | | | | | | X | |
| Urine pregnancy test | X | | | | | | | | |
| Randomization | | | | X | | | | | |
| Dispense new Investigational Product (IP) bottle | | | | X | | | X | | |
| Re-dispense Investigational Product (IP) bottle | | | | | X | X | | | |
| IP administration instruction | | | | X | X | X | X | | |
| Collect unused IP and used bottles; assess compliance | | | | | X | X | X | X | |
| Adverse event monitoring | | X | X | X | X | X | X | X | X |
| Concomitant medications | | X | X | X | X | X | X | X | X |

An Adverse Event (AE) in the study was defined as the development of an undesirable medical condition or the deterioration of a pre-existing medical condition following or during exposure to a pharmaceutical product, whether or not considered casually related to the product. An AE could occur from overdose of investigational product. In this study, an AE can include an undesirable medical condition occurring at any time, including baseline or washout periods, even if no study treatment has been administered.

Relationship to Investigational Product

The investigators determined the relationship to the investigational product for each AE (Not Related, Possibly Related, or Probably Related). The degree of "relatedness" of the adverse event to the investigational product was described as follows: not related—no temporal association and other etiologies are likely the cause; possible—temporal association, but other etiologies are likely the cause. However, involvement of the investigational product cannot be excluded; probable—temporal association, other etiologies are possible but unlikely. The event may respond if the investigational product is discontinued.

Example 11: Efficacy Results of Randomized, Double-Blind, Placebo-Controlled Multicenter Study Each of the three doses showed statistical significance compared with placebo for the primary endpoints. Each of the three doses showed statistical significance compared with placebo for the secondary endpoints. Table 45 shows the statistical significance of the experimental data for each of the four co-primary endpoints. Each of the dosages met each of the four co-primary endpoints at a statistically significant level. The 25 mcg dose of TX-004HR demonstrated highly statistically significant results at the p≤0.0001 level compared to placebo across all four co-primary endpoints. The 10 mcg dose of TX-004HR demonstrated highly statistically significant results at the p≤0.0001 level compared to placebo across all four co-primary endpoints. The 4 mcg dose of TX-004HR also demonstrated highly statistically significant results at the p≤0.0001 level compared to placebo for the endpoints of superficial vaginal cells, parabasal vaginal cells, and vaginal pH; the change from baseline compared to placebo in the severity of dyspareunia was at the p=0.0255 level.

TABLE 45

Statistical Significance of Results for Co-Primary Endpoints (Based on Mean Change from Baseline to Week 12 Compared to Placebo)

| | 25 mcg | 10 mcg | 4 mcg |
|---|---|---|---|
| Superficial Cells | P < 0.0001 | P < 0.0001 | P < 0.0001 |
| Parabasal Cells | P < 0.0001 | P < 0.0001 | P < 0.0001 |
| Vaginal pH | P < 0.0001 | P < 0.0001 | P < 0.0001 |
| Severity of Dyspareunia | P = 0.0001 | P = 0.0001 | P = 0.0255 |

Statistical improvement over placebo was also observed for all three doses at the first assessment at week two and sustained through week 12. The pharmacokinetic data for all three doses demonstrated low systemic absorption, supporting the previous Phase 1 trial data. TX-004HR was well tolerated, and there were no clinically significant differences compared to placebo-treated women with respect to adverse events. There were no drug-related serious adverse events reported.

As shown in the data below, in the MITT population (n=747) at week 12, all TX-004HR doses compared with placebo significantly decreased the percentage of parabasal cells and vaginal pH, significantly increased the percentage of superficial cells, and significantly reduced the severity of dyspareunia (all p≤0.00001 except dyspareunia at 4 μg p=0.0149).

At weeks 2, 6, and 8, the percentage of parabasal cells and vaginal pH significantly decreased p<0.00001); the percentage of superficial cells significantly increased (p<0.00001); and the severity of dyspareunia significantly improved from baseline with all TX-004HR doses vs placebo (4 μg p<0.03; 10 μg and 25 μg p<0.02).

Moderate-to-severe vaginal dryness was reported by 93% at baseline and significantly improved (p<0.02) for all doses at weeks 2, 6, 8, and 12 (except 4 μg at week 2). Vulvar and/or vaginal itching or irritation significantly improved (p<0.05) for 10 μg at weeks 8 and 12, and for 25 μg at week 12.

TX-004HR was well tolerated, had high acceptability, and no treatment-related serious AEs were reported in the safety population (n=764). There were no clinically significant differences in any AEs or treatment-related SAEs between TX-004HR and placebo. Very low to negligible systemic levels of estradiol were observed.

All TX-004HR doses were safe and effective and resulted in very low to negligible systemic absorption of E2 in women with VVA and moderate-to-severe dyspareunia. Onset of effect was seen as early as 2 weeks and was maintained throughout the study and acceptability was very high. This novel product provides a promising new treatment option for women experiencing menopausal VVA.

Cytology

Figure 15:
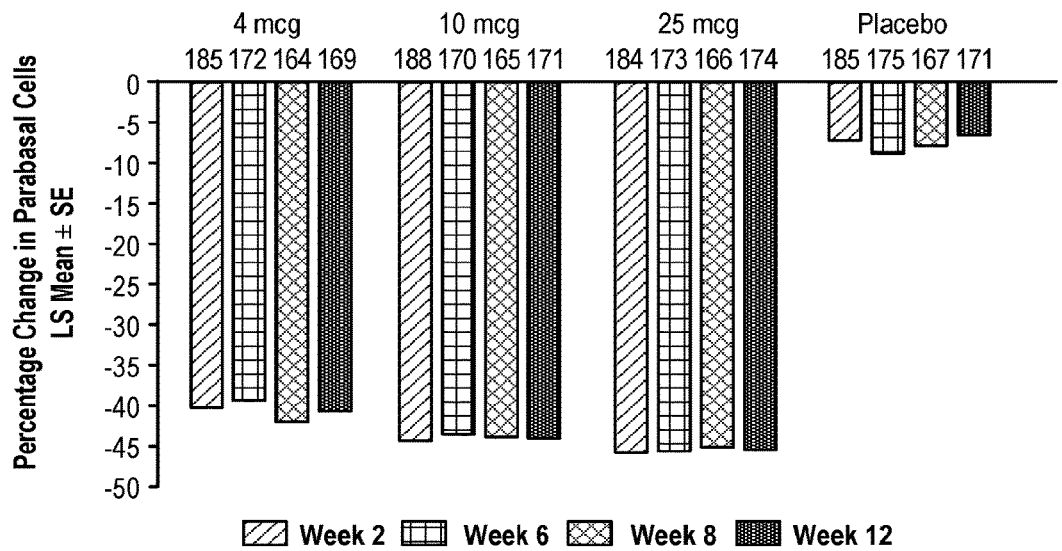
FIG. 15 shows the percentage change in parabasal cells per dose for each of week 2, week 6, week 8, and week 12 compared to placebo

Vaginal cytology data was collected as vaginal smears from the lateral vaginal walls according to procedures presented above to evaluate vaginal cytology at screening and Visit 6—End of treatment (day 84). The change in the Maturation Index was assessed as a change in cell composition measured at Visit 1—Baseline (day 1) compared to the cell composition measured at Visit 3—End of treatment (day 84). The change in percentage of superficial, parabasal, and intermediate cells obtained from the vaginal mucosal epithelium from a vaginal smear was recorded. Results from these assessments for superficial cells are presented in Table 46 and Table 47, as well as FIG. 10, FIG. 11, and FIG. 12. Results from these assessments for parabasal cells are presented in Table 48 and Table 49, as well as FIG. 13, FIG. 14, and FIG. 15.

Superficial Cells

TABLE 46

Superficial Cells P-values by Treatment Week

|  | 4 µg | 10 µg | 25 µg |
| --- | --- | --- | --- |
| Week 2 | <0.0001 | <0.0001 | <0.0001 |
| Week 6 | <0.0001 | <0.0001 | <0.0001 |
| Week 8 | <0.0001 | <0.0001 | <0.0001 |
| Week 12 | <0.0001 | <0.0001 | <0.0001 |

TABLE 47

Superficial Cells Change in Severity from Baseline by Treatment Week (change in percent of total vaginal cells)

|  | 4 µg | 10 µg | 25 µg | Placebo |
| --- | --- | --- | --- | --- |
| Week 2 | 31.35(1.496) | 31.93(1.488) | 38.85(1.5) | 6.05(1.498) |
| Week 6 | 18.41(1.536) | 16.88(1.543) | 22.65(1.532) | 5.43(1.525) |
| Week 8 | 19.04(1.561) | 17.41(1.558) | 23.88(1.554) | 5.98(1.551) |
| Week 12 | 17.5(1.542) | 16.72(1.54) | 23.2(1.529) | 5.63(1.537) |

The study showed the formulations disclosed herein across all doses increased the percentage of superficial cells across all dosages in a statistically significant way.

Parabasal Cells

TABLE 48

Parabasal Cells P-values by Treatment Week

|  | 4 µg | 10 µg | 25 µg |
| --- | --- | --- | --- |
| Week 2 | <0.0001 | <0.0001 | <0.0001 |
| Week 6 | <0.0001 | <0.0001 | <0.0001 |
| Week 8 | <0.0001 | <0.0001 | <0.0001 |
| Week 12 | <0.0001 | <0.0001 | <0.0001 |

TABLE 49

Parabasal Cells Change in Severity from Baseline by Treatment Week (change in percent of total vaginal cells)

|  | 4 µg | 10 µg | 25 µg | Placebo |
| --- | --- | --- | --- | --- |
| Week 2 | −40.23(1.719) | −44.42(1.708) | −45.6(1.723) | −7(1.72) |
| Week 6 | −39.36(1.75) | −43.55(1.752) | −45.61(1.746) | −9.23(1.741) |
| Week 8 | −41.87(1.768) | −43.78(1.764) | −45.08(1.762) | −7.86(1.76) |
| Week 12 | −40.63(1.755) | −44.07(1.751) | −45.55(1.745) | −6.73(1.75) |

The increase of superficial cells and decrease of parabasal cells showed statistical significance over placebo at week 2 and for every week thereafter, including at week 12. Administration of the pharmaceutical formulation resulted in rapid onset of action, as early as two weeks after the initial administration. Rapid onset of action may be coupled with the rapid absorption demonstrated in the pharmacokinetic data presented below.

pH

Figure 16:
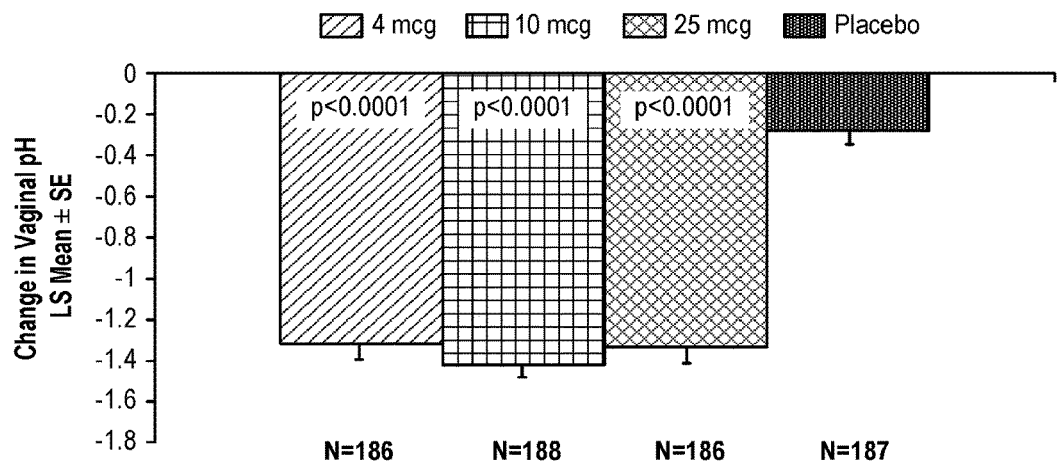
FIG. 16 shows the percentage change in pH at 12 weeks compared to placebo.
Figure 17:
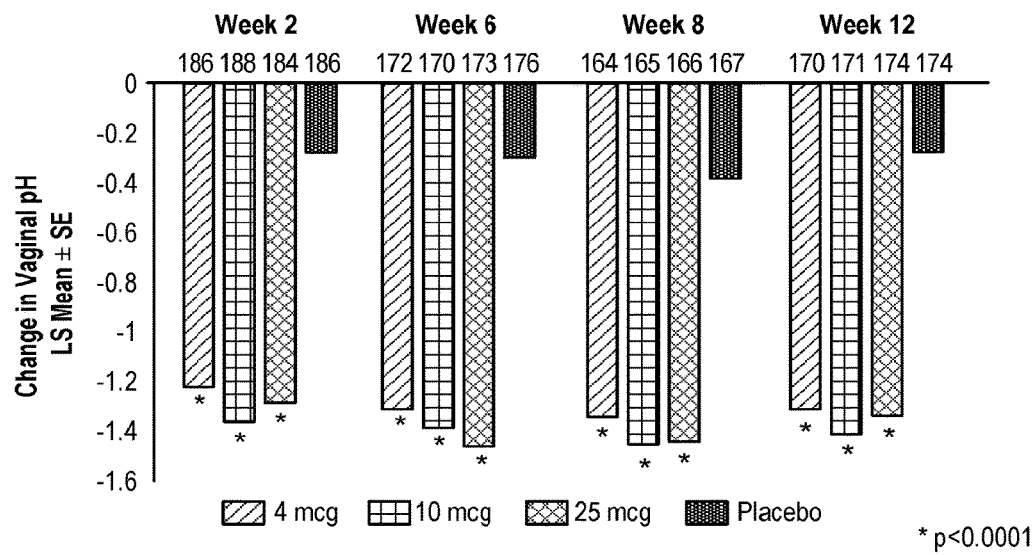
FIG. 17 shows the percentage change in pH at week 2, week 6, week 8, and week 12 compared to placebo.
Figure 18:
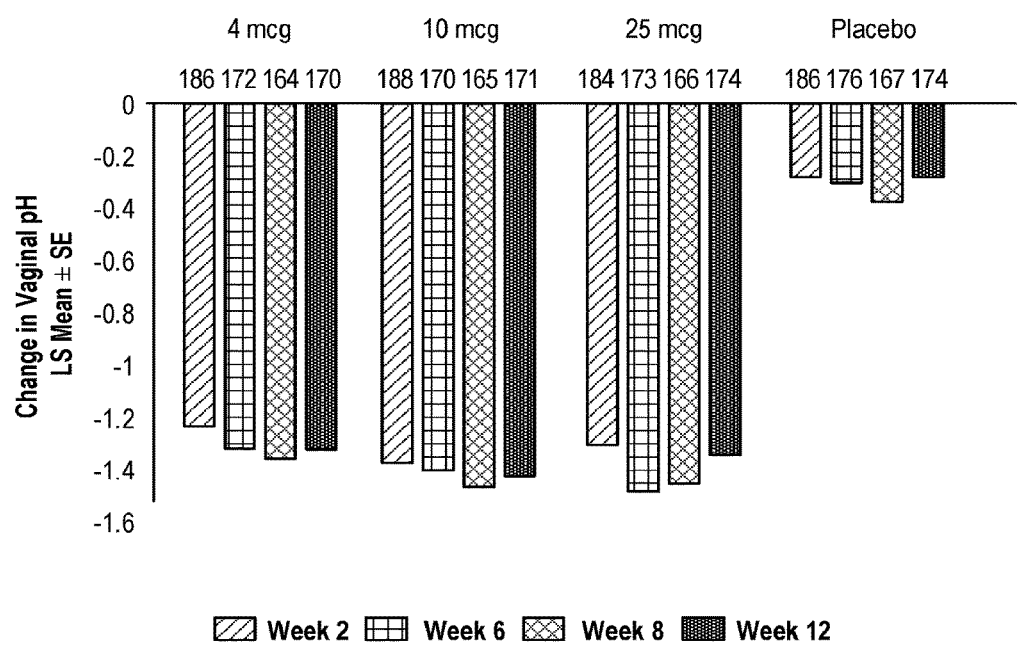
FIG. 18 shows the percentage change in pH per dose for each of week 2, week 6, week 8, and week 12 compared to placebo.
Figure 19A:
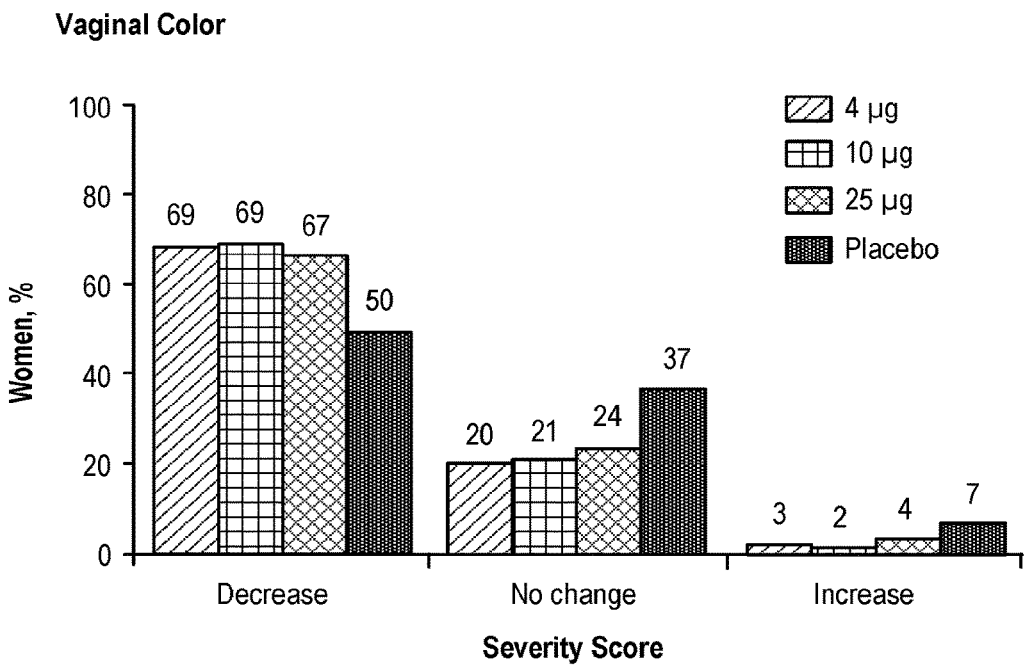
FIG. 19A shows the change in visual assessments from baseline to week 12 in vaginal color in a modified itent to treat (MITT) population.
Figure 19B:
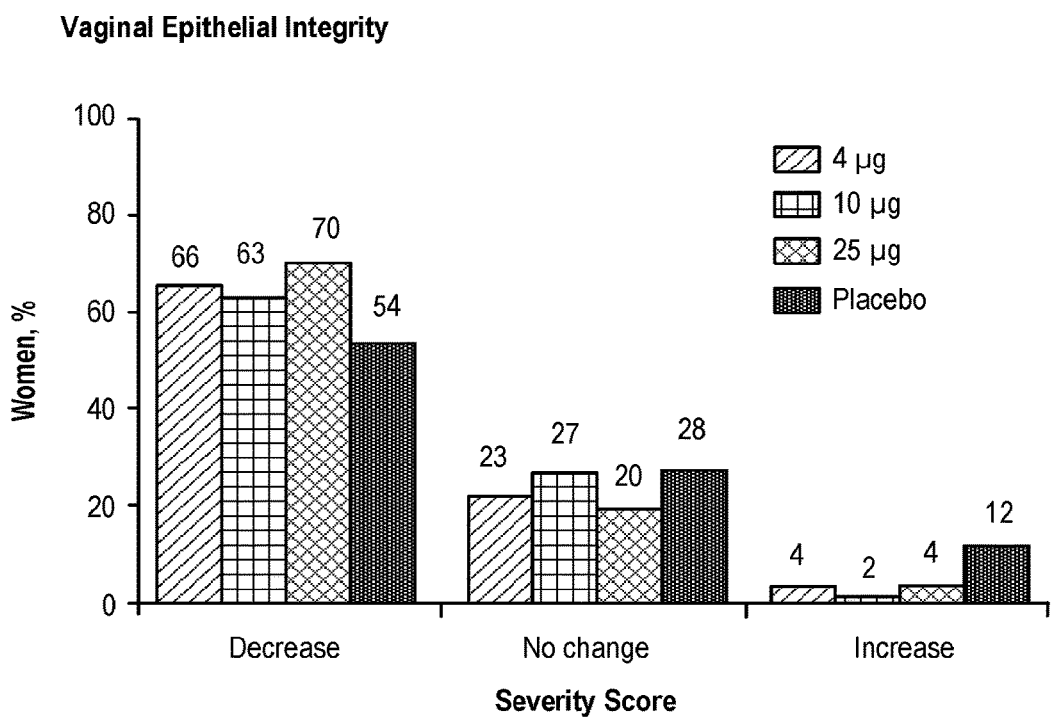
FIG. 19B shows the change in visual assessments from baseline to week 12 in vaginal epithelial integrity in a modified itent to treat (MITT) population.
Figure 19C:
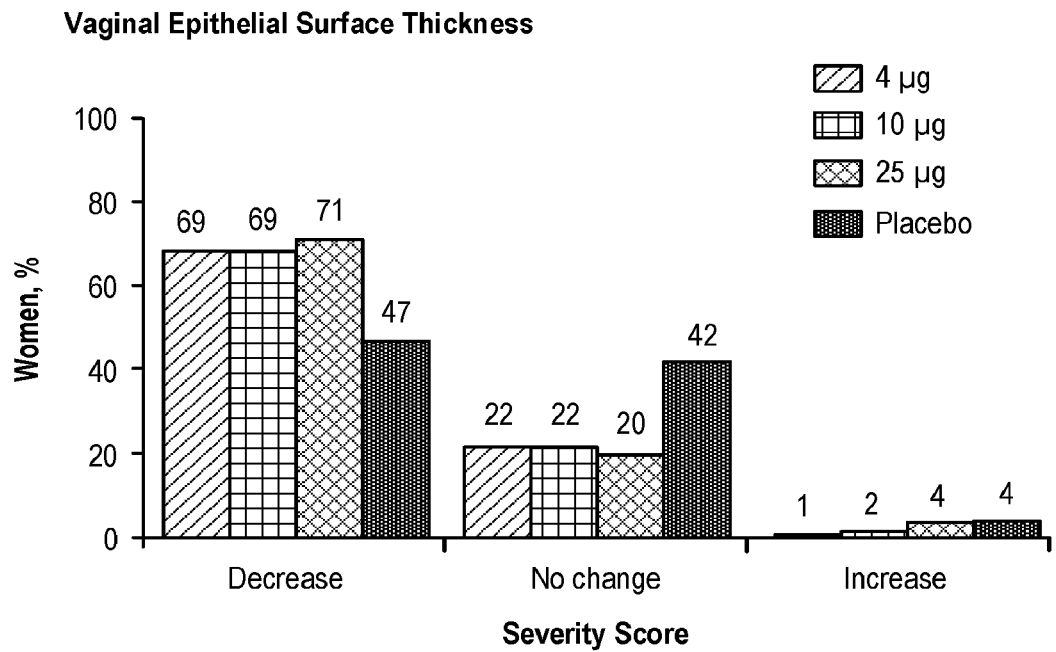
FIG. 19C shows the change in visual assessments from baseline to week 12 in vaginal epithelial thickness a modified itent to treat (MITT) population.
Figure 19D:
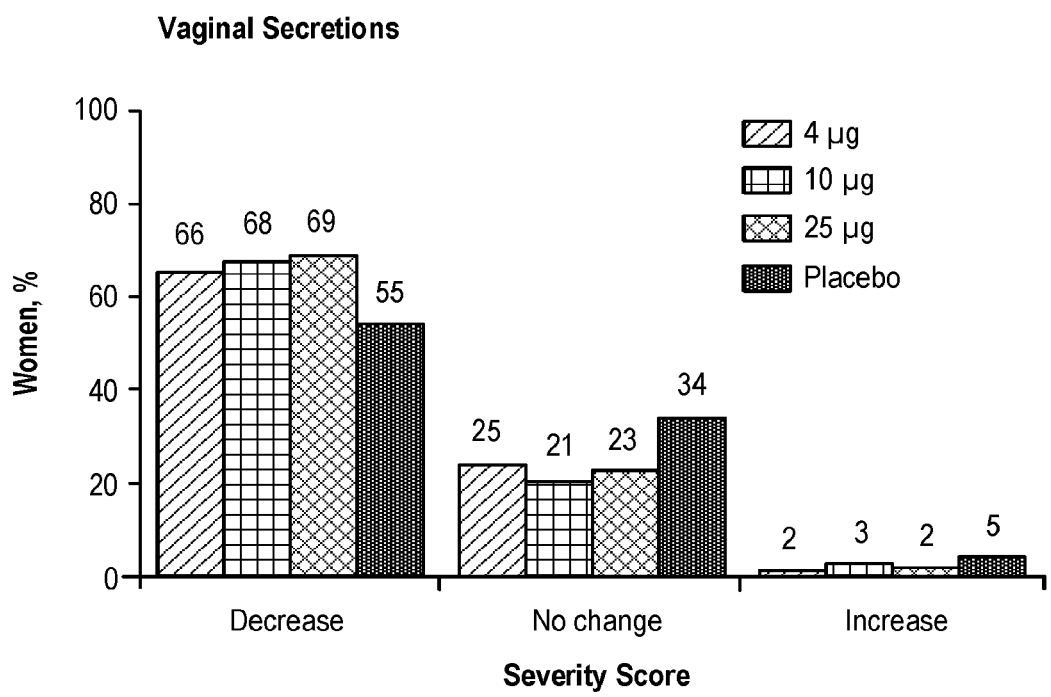
FIG. 19D shows the change in visual assessments from baseline to week 12 in vaginal secretions in a modified itent to treat (MITT) population.

Vaginal pH was measured at Screening and Visit 6—End of treatment (day 84). The pH measurement was obtained as disclosed herein. Results from these assessments are presented in Table 50 and Table 51, and FIG. 16, FIG. 17, and FIG. 18.

TABLE 50 pH P-values by Treatment Week

|  | 4 µg | 10 µg | 25 µg |
| --- | --- | --- | --- |
| Week 2 | <0.0001 | <0.0001 | <0.0001 |
| Week 6 | <0.0001 | <0.0001 | <0.0001 |
| Week 8 | <0.0001 | <0.0001 | <0.0001 |
| Week 12 | <0.0001 | <0.0001 | <0.0001 |

TABLE 51 pH Change in Severity from Baseline by Treatment Week (change in pH)

|  | 4 µg | 10 µg | 25 µg | Placebo |
| --- | --- | --- | --- | --- |
| Week 2 | −1.23(0.064) | −1.37(0.064) | −1.3(0.065) | −0.28(0.064) |
| Week 6 | −1.32(0.066) | −1.4(0.066) | −1.48(0.066) | −0.3(0.065) |
| Week 8 | −1.35(0.067) | −1.46(0.067) | −1.45(0.066) | −0.38(0.066) |
| Week 12 | −1.32(0.066) | −1.42(0.066) | −1.34(0.066) | −0.28(0.066) |

The decrease in vaginal pH was observed at statistically significant levels at week 2 and through the end of the study. Surprisingly, the pH decreased in all three pharmaceutical formulations tested and at all three dosages of over a full pH unit for all three doses.

Most Bothersome Symptoms

Dyspareunia

Subjects were asked to specify the symptom that she identified as the "most bothersome symptom." During the screening period all of the subjects were provided with a questionnaire to self-assess the symptoms of VVA: (1) dyspareunia; (2) vaginal dryness; and (3) vaginal or vulvar irritation, burning, or itching. Each symptom was measured on a scale of 0 to 3, where 0=none, 1=mild, 2=moderate, and 3=severe. Each subject was given a questionnaire at each visit and the responses were recorded. All randomized subjects were also provided a questionnaire to self-assess the symptoms of VVA at Visit 1 and on each subsequent visit through Visit 6—End of the treatment (day 84). Subjects recorded their self-assessments daily in a diary and answers were collected on visits 8 and 15 (end of treatment). Pre-dose evaluation results obtained at Visit 1 were considered as baseline data for the statistical analyses. Data from these assessments for dyspareunia are presented in Table 52 and Table 53. Data from these assessments for dryness are presented in Table 54 and Table 55.

TABLE 52

Dyspareunia P-values by Treatment Week

| | 4 µg | 10 µg | 25 µg |
|---|---|---|---|
| Week 2 | 0.026 | 0.0019 | 0.0105 |
| Week 6 | 0.0069 | 0.0009 | <0.0001 |
| Week 8 | 0.0003 | <0.0001 | <0.0001 |
| Week 12 | 0.0149 | <0.0001 | <0.0001 |

TABLE 53

Dyspareunia Change in Severity from Baseline by Treatment Week (0 to 3 severity scale)

| | 4 µg | 10 µg | 25 µg | Placebo |
|---|---|---|---|---|
| Week 2 | −0.99(0.072) | −1.08(0.072) | −1.02(0.073) | −0.76(0.072) |
| Week 6 | −1.3(0.072) | −1.37(0.072) | −1.48(0.072) | −1.03(0.07) |
| Week 8 | −1.52(0.073) | −1.64(0.074) | −1.62(0.075) | −1.15(0.072) |
| Week 12 | −1.52(0.071) | −1.69(0.071) | −1.69(0.071) | −1.28(0.07) |

Each of the 4 µg, 10 µg, and 25 µg formulations tests demonstrated an early onset of action at week 2 for the most bothersome symptom of dyspareunia, evidenced by the statistically significant results (measured by p-value) in Table 52. After two weeks, each dose demonstrated separation from placebo in improvement in the most bothersome symptom of dyspareunia.

Coupled with the PK data presented below, these results show that the formulations disclosed herein provide a bolus of estradiol within two hours of administration, which resulted in a decrease in the severity of dyspareunia as early as two weeks later. Estradiol is rapidly absorbed at around two hours, which is significantly faster than the formulations of the prior art that sought an extended release profile. The rapid absorption of estradiol is believed to be a result of administration with a liquid formulation.

Surprisingly, the 4 µg formulation showed clinical effectiveness at two weeks along with the 25 µg and 10 µg dosage levels. These data demonstrate that 4 µg is an effective dose, and can be effective as early as two weeks after administration for the most bothersome symptom of dyspareunia.

Dryness

TABLE 54

Dryness P-values by Treatment Week

| | 4 µg | 10 µg | 25 µg |
|---|---|---|---|
| Week 2 | 0.1269 | 0.0019 | 0.0082 |
| Week 6 | 0.0094 | 0.0001 | 0.0005 |
| Week 8 | 0.0128 | <0.0001 | 0.0008 |
| Week 12 | 0.0014 | <0.0001 | <0.0001 |

TABLE 55

Dryness Change in Severity from Baseline by Treatment Week (0 to 3 severity scale)

| | 4 µg | 10 µg | 25 µg | Placebo |
|---|---|---|---|---|
| Week 2 | −0.86(0.066) | −1.01(0.065) | −0.96(0.066) | −0.72(0.066) |
| Week 6 | −1.14(0.067) | −1.27(0.068) | −1.23(0.067) | −0.9(0.067) |
| Week 8 | −1.25(0.069) | −1.44(0.068) | −1.34(0.068) | −1.01(0.068) |
| Week 12 | −1.27(0.068) | −1.47(0.067) | −1.47(0.067) | −0.97(0.067) |

Each of the 4 µg, 10 µg, and 25 µg formulations tests demonstrated an early onset of action at week 2 for the most bothersome symptom of dryness, evidenced by the statistically significant results (measured by p-value) in Table 54. After two weeks, each dose demonstrated separation from placebo in improvement in the most bothersome symptom of dryness.

Irritation/Itching

TABLE 56

Irritation/Itching P-values by Treatment Week

| | 4 µg | 10 µg | 25 µg |
|---|---|---|---|
| Week 2 | 0.9616 | 0.2439 | 0.6518 |
| Week 6 | 0.7829 | 0.2328 | 0.4118 |
| Week 8 | 0.0639 | 0.0356 | 0.0914 |
| Week 12 | 0.0503 | 0.0055 | 0.0263 |

TABLE 57

Irritation/Itching Change in Severity from Baseline by Treatment Week (0 to 3 severity scale)

| | 4 µg | 10 µg | 25 µg | Placebo |
|---|---|---|---|---|
| Week 2 | −0.47(0.054) | −0.56(0.053) | −0.51(0.054) | −0.47(0.054) |
| Week 6 | −0.57(0.055) | −0.64(0.055) | −0.61(0.055) | −0.55(0.055) |
| Week 8 | −0.74(0.056) | −0.76(0.056) | −0.73(0.056) | −0.59(0.056) |
| Week 12 | −0.75(0.055) | −0.81(0.055) | −0.77(0.055) | −0.6(0.055) |

Vulvar and/or vaginal itching or irritation significantly improved ($p<0.05$) for 10 µg at weeks 8 and 12, and for 25 µg at week 12. Moreover, the trend for 4 µg was an improvement in itching week over week to nearly being statistically significant at week 12.

Coupled with the PK data presented below, these results show that the formulations disclosed herein provide a bolus of estradiol within two hours of administration, which resulted in a decrease in the severity of dryness as early as two weeks later. Estradiol is rapidly absorbed at around two hours, which is significantly faster than the formulations of the prior art that sought an extended release profile. The rapid absorption of estradiol is believed to be a result of administration with a liquid formulation.

Surprisingly, the 4 µg formulation showed clinical effectiveness at two weeks along with the 25 µg and 10 µg dosage levels. These data demonstrate that 4 µg is an effective dose, and can be effective as early as two weeks after administration for the most bothersome symptom of dryness.

As described above, each dose was compared with placebo for change from baseline to week 12 in the percentages of vaginal superficial cells and parabasal cells, vaginal pH, and severity of dyspareunia (co-primary endpoints). The proportion of responders (defined as women with ≥2 of the following at week 12: vaginal superficial cells >5%, vaginal pH <5.0, ≥1 category improvement from baseline dyspareunia score) was compared in TX-004HR groups vs placebo. Pre-specified subgroup analyses of co-primary endpoints were analyzed by age (≤56 years, 57-61 years, and ≥62 years), BMI (≤24 kg/m², 25-28 kg/m², and ≥29 kg/m²), uterine status, parity, and vaginal births. Pharmacokinetic (PK) parameters were compared with placebo in a sub-analysis of the main study.

The proportion of responders was significantly higher for all TX-004HR dose groups vs placebo (p<0.0001 for all). All TX-004HR doses vs placebo significantly improved percentage of superficial and parabasal cells, vaginal pH, and severity of dyspareunia at 12 weeks. Subgroup analyses showed generally similar results for percentage of superficial and parabasal cells and vaginal pH irrespective of age, BMI, uterine status, parity, and vaginal births. Severity of dyspareunia was significantly reduced at 12 weeks with all TX-004HR doses vs placebo in most subgroups (Table 57A).

The PK sub-analysis (n=72), described in more detail below, found AUC and $C_{avg}$ parameters for E2 and estrone (E1) with 4 µg and 10 µg TX-004HR to be similar to placebo. Increases occurred in E2 AUC and $C_{avg}$ with 25 µg vs placebo but remained within the normal postmenopausal range. E2 levels at day 84 were similar between the TX-004HR groups and placebo, indicating no systemic drug accumulation.

All doses of TX-004HR were associated with robust efficacy and demonstrated a statistically significant difference vs placebo for increasing superficial cells, decreasing parabasal cells and vaginal pH, and reducing the severity of dyspareunia. Age, BMI, uterine status, parity and vaginal births generally did not affect TX-004HR efficacy. These results occurred with negligible systemic absorption of TX-004HR estradiol doses of 4 µg, 10 µg, and 25 µg.

TABLE 57A

Change from baseline to week 12 in the severity of dyspareunia (LS mean change ± SE).

| Key clinical factors | | Placebo (n = 187) | | TX-004HR 4 µg (n = 186) | | TX-004HR 10 µg (n = 188) | | TX-004HR 25 µg (n = 186) | |
| --- | --- | --- | --- | --- | --- | --- | --- | --- | --- |
| Age, years | ≤56 | n = 52 | −1.25 ± 0.119 | n = 50 | −1.58 ± 0.122 | n = 61 | −1.77 ± 0.112† | n = 65 | −1.86 ± 0.108‡ |
| | 57-61 | n = 53 | −1.39 ± 0.118 | n = 50 | −1.42 ± 0.121 | n = 49 | −1.63 ± 0.121 | n = 47 | −1.79 ± 0.125* |
| | ≥62 | n = 58 | −1.19 ± 0.122 | n = 51 | −1.52 ± 0.126 | n = 44 | −1.66 ± 0.138† | n = 47 | −1.38 ± 0.135 |
| BMI, kg/m² | ≤24 | n = 56 | −1.14 ± 0.115 | n = 58 | −1.48 ± 0.113* | n = 56 | −1.6 ± 0.117† | n = 51 | −1.72 ± 0.123‡ |
| | 25 to 28 | n = 57 | −1.48 ± 0.118 | n = 45 | −1.51 ± 0.131 | n = 52 | −1.78 ± 0.124 | n = 58 | −1.77 ± 0.117 |
| | ≥29 | n = 50 | −1.21 ± 0.125 | n = 48 | −1.56 ± 0.125 | n = 46 | −1.71 ± 0.129† | n = 50 | −1.57 ± 0.124* |
| Uterine status | Intact | n = 101 | −1.35 ± 0.086 | n = 82 | −1.66 ± 0.095* | n = 84 | −1.74 ± 0.095† | n = 85 | −1.81 ± 0.094‡ |
| | Non-intact | n = 62 | −1.15 ± 0.115 | n = 69 | −1.35 ± 0.108 | n = 70 | −1.63 ± 0.108† | n = 74 | −1.55 ± 0.107* |
| Pregnancy status | Pregnancy = 0 | n = 16 | −1.18 ± 0.220 | n = 17 | −1.28 ± 0.217 | n = 19 | −1.26 ± 0.209 | n = 13 | −1.64 ± 0.257 |
| | Pregnancy ≥1 | n = 147 | −1.28 ± 0.073 | n = 134 | −1.55 ± 0.075* | n = 135 | −1.74 ± 0.076§ | n = 146 | −1.70 ± 0.073‡ |
| Vaginal births | Vaginal birth = 0 | n = 26 | −1.19 ± 0.171 | n = 22 | −1.74 ± 0.189* | n = 29 | −1.68 ± 0.161* | n = 31 | −1.76 ± 0.160* |
| | Vaginal birth ≥1 | n = 121 | −1.30 ± 0.080 | n = 112 | −1.51 ± 0.082 | n = 106 | −1.77 ± 0.085‡ | n = 115 | −1.69 ± 0.082‡ |

*p < 0.05;
†p < 0.01;
‡p < 0.001;
§p < 0.0001 vs placebo.

Visual evaluation of the vaginal epithelium, a secondary endpoint of the trial, was performed during gynecological examinations at baseline and weeks 2, 6, 8, and 12. A four-point score (0=none, 1=mild, 2=moderate, 3=severe) was used to assess changes in vaginal color, vaginal epithelial integrity, vaginal epithelial surface thickness, and vaginal secretions. Change from baseline to each time point was compared with placebo using the mixed effect model repeat measurement (MMRM) analysis.

At baseline, women had mean scores of 1.8 for vaginal color, 1.5 for epithelial integrity, 1.9 for epithelial surface thickness, and 1.7 for secretions. These scores were consistent with VVA reflecting pallor, diminished vaginal wall integrity and thickness, and secretions. Significant improvements from baseline at weeks 2, 6, 8 and 12 (Table 57B; FIG. 19A-FIG. 19D) were observed for all 3 doses of TX-004HR compared with placebo in vaginal color (white to pink), epithelial integrity, epithelial surface thickness and secretions (p<0.001 for all). After 12 weeks, women in the active TX-004HR treatment groups had mean scores less than 1 in all four characterized categories. Vaginal visual examination of women in the 3 TX-004HR groups had greater reported improvements from baseline in all vaginal parameters examined than placebo subjects and at all time points. These improved vaginal visual scores reflect other observed measures of efficacy of TX-004HR (4 µg, 10 µg, and 25 µg) at treating moderate-to-severe VVA in postmenopausal women, with negligible to very low systemic E2 absorption.

TABLE 57B

Change from baseline at week 12 in vaginal parameters

| Vaginal Parameters, mean (SD) | | TX-004HR 4 µg (n = 171) | TX-004HR 10 µg (n = 173) | TX-004HR 25 µg (n = 175) | Placebo (n = 175) |
|---|---|---|---|---|---|
| Vaginal epithelial color | Baseline | 1.8(0.61) | 1.7(0.59) | 1.8(0.60) | 1.7(0.64) |
| | 12 weeks | 0.8(0.67) | 0.7(0.64) | 0.8(0.68) | 1.2(0.80) |
| | Change | −1.0(0.82) | −1.1(0.80) | −1.0(0.88) | −0.6(0.83) |
| | LS Mean (SE) | −0.97(0.05)* | −1.06(0.05)* | −0.96(0.05)* | −0.60(0.05) |
| Vaginal epithelial integrity | Baseline | 1.6(0.84) | 1.4(0.83) | 1.5(0.77) | 1.5(0.84) |
| | 12 weeks | 0.5(0.69) | 0.4(0.57) | 0.5(0.66) | 0.9(0.91) |
| | Change | −1.0(0.93) | −1.0(0.89) | −1.0(0.91) | −0.6(0.98) |
| | LS Mean (SE) | −0.97(0.05)* | −1.07(0.05)* | −1.01(0.05)* | −0.60(0.05) |
| Vaginal epithelial surface thickness | Baseline | 1.9(0.67) | 1.8(0.63) | 1.9(0.59) | 1.9(0.65) |
| | 12 weeks | 0.9(0.66) | 0.8(0.63) | 0.9(0.69) | 1.3(0.85) |
| | Change | −1.0(0.76) | −1.0(0.79) | −0.9(0.80) | −0.6(0.82) |
| | LS Mean (SE) | −0.98(0.05)* | −1.03(0.05)* | −0.94(0.05)* | −0.61(0.05) |
| Vaginal secretions | Baseline | 1.8(0.68) | 1.7(0.66) | 1.7(0.63) | 1.8(0.63) |
| | 12 weeks | 0.8(0.69) | 0.6(0.67) | 0.7(0.71) | 1.1(0.84) |
| | Change | −1.0(0.82) | −1.0(0.86) | −1.0(0.85) | −0.7(0.79) |
| | LS Mean (SE) | −1.01(0.05)* | −1.06(0.05)* | −1.04(0.05)* | −0.64(0.05) |

Data is mean (SD) unless otherwise noted;
*MMRM $p < 0.0001$ vs placebo.

Figure 20A:
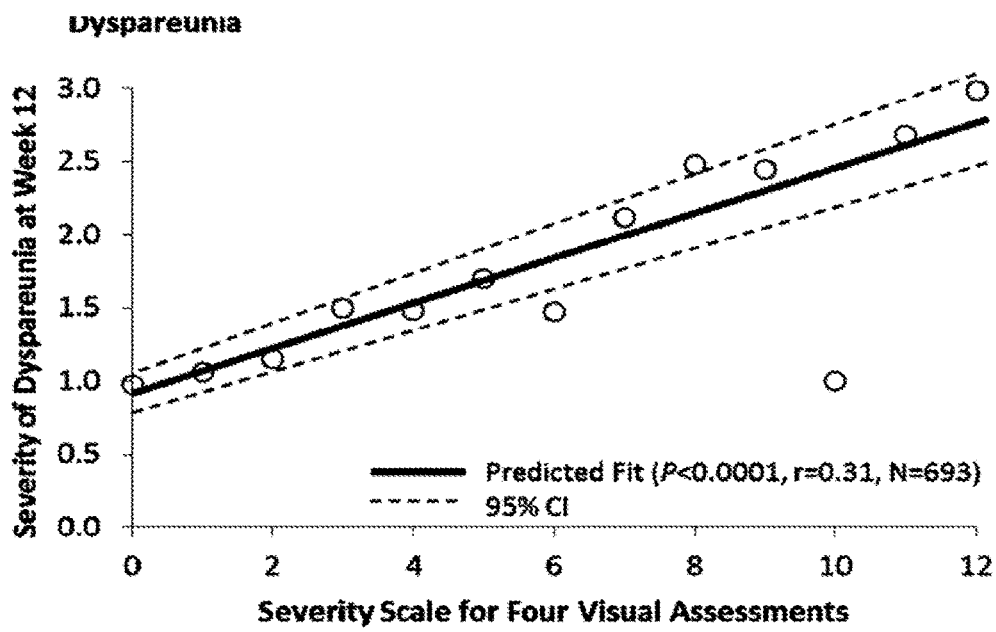
FIG. 20A shows the correlation between the total sum of four visual assessments and dyspareunia at week 12 in an intent to treat (ITT) population.
Figure 20B:
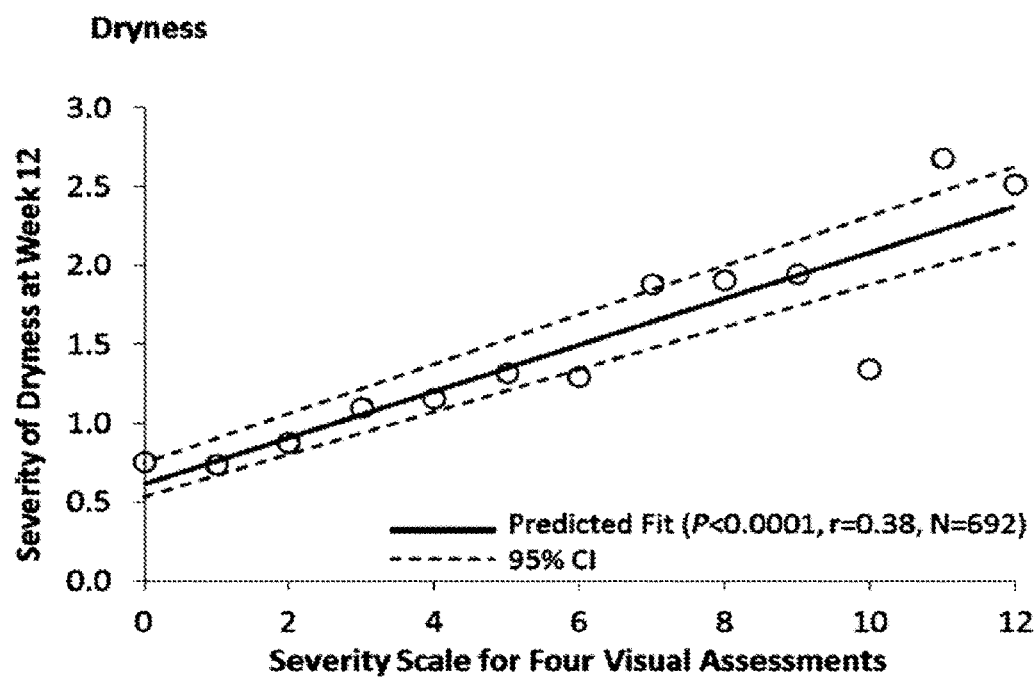
FIG. 20B shows the correlation between the total sum of four visual assessments and vaginal dryness at week 12 in an intent to treat (ITT) population.

A direct correlation was observed between the total sum of the individual visual examination score and severity of dyspareunia (r=0.31; P<0.0001) as well as the severity of vaginal dryness (r=0.38; P<0.0001) at 12 weeks when all subjects were analyzed independent of treatment. See, FIG. 20A and FIG. 20B. Interestingly, women treated with placebo also showed some improvements in their scores at week 2, but while women treated with TX-004HR showed continued improvements through 12 weeks of treatment, such continued improvements were not observed to the same extent with the placebo. Three possible explanations for the improvements observed with the placebo include the potential lubricating effect of the excipient Miglyol, a fractionated coconut oil contained in all softgel capsules, improved appearance based on vaginal lubrication caused by increased sexual activity and/or bias on the part of the physicians performing the examinations as they may anticipate improvement. Nevertheless, TX-004HR still significantly improved evaluated signs and symptoms of VVA better than placebo.

Since visual inspection of the vagina with the 4-point assessment tool positively correlated with dyspareunia and vaginal dryness in this study, this tool may help healthcare professionals diagnose VVA and assess its treatment, and provide a vehicle for health care professionals to initiation discussion with their patients about a sensitive topic. Several large-scale studies have shown that it is difficult for patients to discuss vulvovaginal health openly with their health care professionals because they are either embarrassed, uninformed about VVA and its treatments, or believe that the topic is not appropriate for discussion. Therefore, of the 50% of postmenopausal women who have symptoms of VVA, far fewer seek treatment. Visual examination of the vagina may help practitioners identify women at risk of dyspareunia and vaginal dryness, and allow them to proactively engage women in conversations about VVA symptoms such as dyspareunia and dryness and discuss available treatment options.

Example 12: Pharmacokinetics Results in Randomized, Double-Blind, Placebo-Controlled Multicenter Study While some approved local estrogens effectively treat VVA, systemic estradiol may increase with local administration. TX-004HR is a new low-dose vaginal softgel capsule containing solubilized natural estradiol designed to provide excellent efficacy with negligible systemic absorption. Up to three times lower systemic estrogen levels were previously reported with TX-004HR vs an approved low-dose vaginal estradiol tablet. The present studies show that VVA efficacy can be achieved with negligible systemic absorption as measured by PK in postmenopausal women with moderate-to-severe dyspareunia.

The terms "minimal systemic effect," "low systemic absorption," and "negligible systemic absorption," as used herein, mean that the disclosed formulations and methods result in low to minimal absorption of estradiol in women, especially women with VVA and/or dyspareunia. In fact, it has surprisingly been found that the disclosed formulations and methods result in negligible to very low systemic absorption of estradiol, which remains in the postmenopausal range. The finding is borne out by the examples provided herein that demonstrate that the $C_{max}$ and AUC levels of estradiol relative to placebo were not statistically differentiable, which indicates that the formulations disclosed herein have a negligible systemic effect. As such, the disclosed formulations and methods advantageously provide local benefits in patients with VVA and/or dyspareunia (i.e., the disclosed formulations are extremely effective in increasing the superficial cells, decreasing parabasal cells, and decreasing pH) without increasing systemic levels.

A PK substudy was part of a large, multicenter, double-blind, randomized, placebo-controlled phase 3 trial evaluating the efficacy and safety of TX-004HR (4 µg, 10 µg, and 25 µg) compared with placebo for treating postmenopausal moderate-to-severe dyspareunia. Women received TX-004HR or placebo once daily for 2 weeks then twice weekly for 10 wks.

Figure 21:
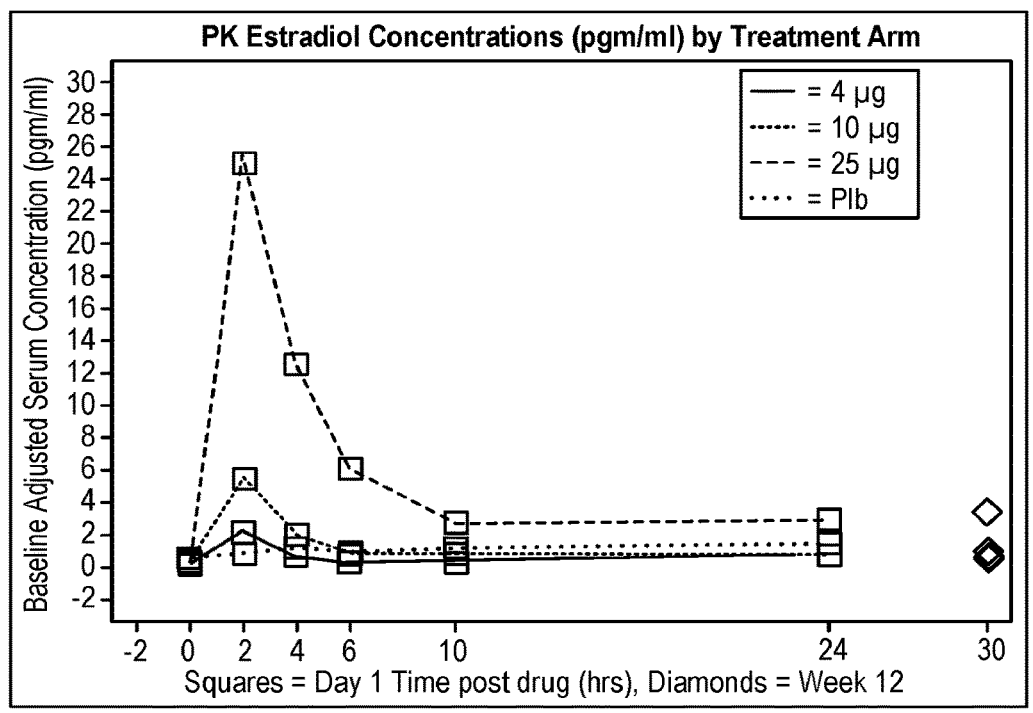
FIG. 21 shows baseline adjusted estradiol serum concentration (pg/mL) assessed on Day 1 (squares) and Week 12 (diamonds) for four treatment artms.
Figure 22:
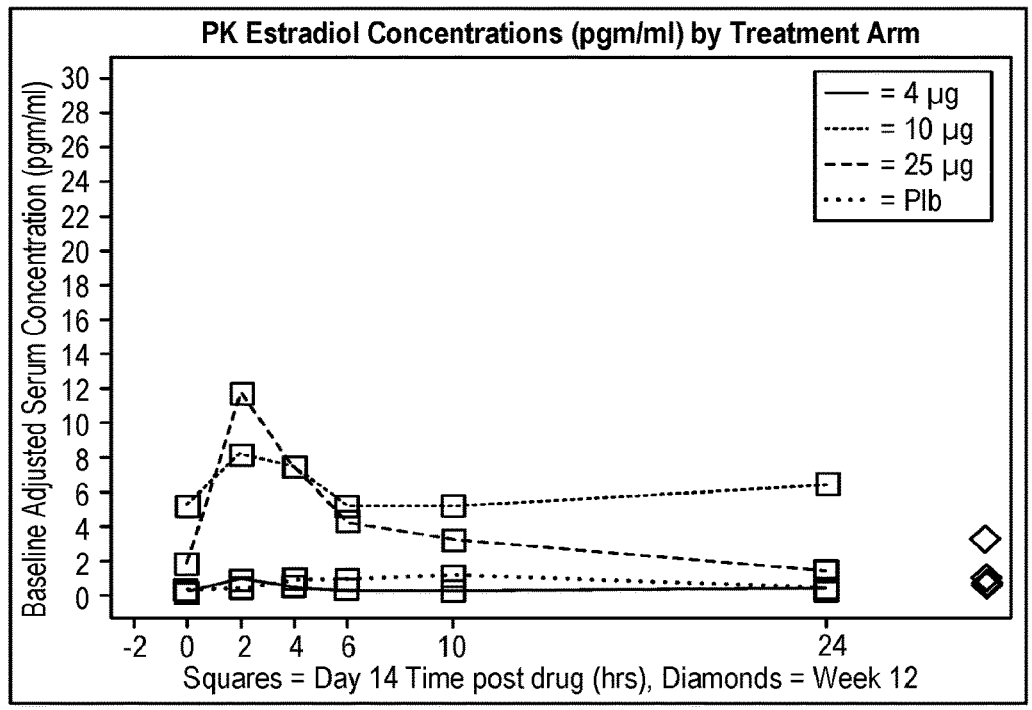
FIG. 22 shows baseline adjusted estradiol serum concentration (pg/mL) assessed on Day 14 (squares) and Week 12 (diamonds) for four treatment artms.

In this study, the systemic exposure to estradiol following once daily intravaginal administration of estradiol 25 µg, 10 µg, 4 µg, and placebo were investigated on days 1, 14, and 84 as described herein. Descriptive statistics of the plasma estradiol concentrations taken at each sampling time and the observed $C_{max}$ values were recorded, as shown in the tables below and FIG. 21 and FIG. 22, for estradiol, estrone, and estrone conjugates for all three doses. Serum estradiol, estrone, estrone conjugates, and sex hormone binding globulin were measured.

For PK, serum was sampled pre-dose and at 2, 4, 6, 10, and 24 h post-dose on days 1 and 14 for estradiol, estrone (E1), and estrone conjugates (E1Cs). Baseline-adjusted results are shown here; unadjusted data will be presented. Efficacy endpoints were change from baseline to week 12 for vaginal superficial cells (%), vaginal parabasal cells (%), vaginal pH, and severity of dyspareunia. Secondary endpoints were severity of dryness and itching/irritation. Blood chemistry was tested at week 12.

The substudy randomized 72 women (mean age 59 y) at 11 centers. Mean area under the concentration-time curve (AUC) and average concentration ($C_{avg}$) for estradiol were not significantly different vs placebo with 4 μg and 10 μg TX-004HR, but were significantly higher with 25 μg at day 1 (AUC 130 vs 13.8 h*pg/mL and Cavg 5.4 vs 0.4 pg/mL) and day 14 (AUC 84.6 vs 7.1 h*pg/mL and Cavg 3.5 vs −0.2 pg/mL).

Mean estradiol peak concentration ($C_{max}$) was not significantly different with 4 μg (day 1: 2.6 pg/mL; day 14: 1.3 pg/mL) vs placebo (day 1: 2.1 pg/mL; day 14: 1.0 pg/mL), and although significant, was negligible with 10 μg (day 1: 6.0 pg/mL; day 14: 3.0 pg/mL) and very low for 25 μg (day 1: 26.2 pg/mL; day 14: 12.0 pg/mL).

E1 and E1Cs AUC, $C_{avg}$, $C_{max}$, $C_{min}$ did not differ vs placebo, except for E1Cs on day 1 when AUC was significantly higher with 25 μg (2454 vs 83.0 h*pg/mL), $C_{max}$ with 10 μg and 25 μg (90.2 and 198.6 pg/mL, respectively vs 27.1 pg/mL), and $C_{avg}$ with 10 μg (8.0 vs −33.7 pg/mL).

In the overall study TX004-HR showed robust efficacy for symptoms of dyspareunia, vaginal dryness and irritation at 12 weeks with all 3 doses compared with placebo.

Vaginal TX-004HR resulted in negligible to very low systemic absorption of estradiol, which remained in the postmenopausal range. TX-004HR improved the signs and symptoms of VVA. This study supports local benefits of estradiol without increasing systemic exposure.

The pharmacokinetic data for estradiol demonstrates the rapid absorption of the formulations disclosed herein for all three doses. Surprisingly, while the pharmacokinetic data was extremely low for all three doses, each dose was extremely effective in increasing the superficial cells, decreasing parabasal cells, and decreasing pH.

The pharmaceutical compositions disclosed herein provide an improved safety profile over other options for treating VVA. The combination of low systemic estradiol, while retaining efficacy was a surprising result for all three doses.

Estradiol Concentration

TABLE 58

Pharmacokinetics Estradiol Baseline (pg/mL)

| | 4 μg | 10 μg | 25 μg | Placebo |
|---|---|---|---|---|
| Baseline | 4.7(4.41) | 5(3.52) | 3.6(1.86) | 4.6(2.56) |

TABLE 59

Pharmacokinetics Estradiol Day 1 (pg/mL)

| | 4 μg | 10 μg | 25 μg | Placebo |
|---|---|---|---|---|
| Predose | 3.1(1.56) | 4.9(3.47) | 3.6(1.81) | 4.1(2.45) |
| 2 hour | 6.1(2.3) | 10.4(4.89) | 28.7(17.91) | 4.8(3.33) |
| 4 hour | 4.3(1.68) | 6.7(3.59) | 16.1(14.75) | 5(3.59) |
| 6 hour | 3.7(1.96) | 5.7(3.16) | 9.7(6.86) | 4.8(3.53) |

TABLE 59-continued

Pharmacokinetics Estradiol Day 1 (pg/mL)

| | 4 μg | 10 μg | 25 μg | Placebo |
|---|---|---|---|---|
| 10 hour | 3.7(1.47) | 5.5(2.92) | 6.2(2.37) | 5.2(3.61) |
| 24 hour | 4.2(2.02) | 5.4(4.44) | 6.2(8.43) | 5.1(4.42) |

TABLE 60

Pharmacokinetics Estradiol Day 14 (pg/mL)

| | 4 μg | 10 μg | 25 μg | Placebo |
|---|---|---|---|---|
| Predose | 3.5(1.63) | 3.8(2.56) | 5.2(2.89) | 4.2(3.07) |
| 2 hour | 4.3(2.01) | 6.3(2.29) | 15.3(7.72) | 4.2(2.44) |
| 4 hour | 4(1.7) | 5.9(2.55) | 11(4.86) | 4.7(3.2) |
| 6 hour | 3.9(1.92) | 5.1(2.32) | 7.9(3.35) | 4.7(2.97) |
| 10 hour | 3.8(2.12) | 5(3) | 6.8(3.76) | 5.1(3.53) |
| 24 hour | 3.6(1.89) | 3.7(2.05) | 4.9(4.35) | 3.9(2.43) |

TABLE 61

Pharmacokinetics Estradiol End of Study (pg/mL)

| | 4 μg | 10 μg | 25 μg | Placebo |
|---|---|---|---|---|
| Post Dosing | 4.3(2.69) | 4.8(2.57) | 6.7(11.51) | 4.4(2.6) |

Estradiol Area Under the Curve (0-24 Hours)

TABLE 62

Estradiol Area Under the Curve (0-24 hours) (h*pg/mL)

| | 4 μg | 10 μg | 25 μg | Placebo |
|---|---|---|---|---|
| Day 1 | 91.7(37.86) | 138.2(75.22) | 217.4(99.02) | 116.6(77.3) |
| Day 14 | 87.2(42.77) | 110.1(54.57) | 171.6(80.13) | 104.2(66.39) |

TABLE 63

Estradiol Area Under the Curve (0-24 hours) (Baseline Adjusted) (h*pg/mL)

| | 4 μg | 10 μg | 25 μg | Placebo |
|---|---|---|---|---|
| Day 1 | 12(13.89) | 21.9(19.16) | 130.4(111.95) | 13.8(28.86) |
| Day 14 | 7.2(12.08) | 13.7(18.77) | 84.6(62.7) | 7.1(20.28) |

TABLE 64

Estradiol Area Under the Curve (0-24 hours) P-values Pairwise Test vs. 4 μg

| | 10 μg | 25 μg |
|---|---|---|
| Day 1 | 0.0242 | <0.0001 |
| Day 14 | 0.1777 | 0.0005 |

TABLE 65

Estradiol Area Under the Curve (0-24 hours) P-values Pairwise Test vs. Placebo

| | 4 μg | 10 μg | 25 μg |
|---|---|---|---|
| Day 1 | 0.2292 | 0.4028 | 0.0021 |
| Day 14 | 0.3829 | 0.7724 | 0.0108 |

TABLE 66

Estradiol Area Under the Curve (0-24 hours) P-values Pairwise Test vs. 4 µg (Baseline Adjusted)

|  | 10 µg | 25 µg |
|---|---|---|
| Day 1 | 0.082 | 0.0001 |
| Day 14 | 0.2373 | <0.0001 |

TABLE 67

Estradiol Area Under the Curve (0-24 hours) P-values Pairwise Test vs. Placebo (Baseline Adjusted)

|  | 4 µg | 10 µg | 25 µg |
|---|---|---|---|
| Day 1 | 0.8134 | 0.3238 | 0.0002 |
| Day 14 | 0.979 | 0.3235 | <0.0001 |

TABLE 68

Estradiol Area Under the Curve (0-24 hours) Ratio (Day 14) of Day 14 to Day 1

|  | 4 µg | 10 µg | 25 µg | Placebo |
|---|---|---|---|---|
| AUC Ratio of Day 14 to Day 1 | 0.971(0.2358) | 0.876(0.1937) | 0.955(0.6633) | 0.949(0.225) |
| Pairwise test vs 4 µg | — | 0.2022 | 0.9246 | — |
| Pairwise test vs Placebo | 0.7859 | 0.3101 | 0.9748 | — |

Estradiol $C_{max}$

TABLE 69

$C_{max}$ (pg/mL)

|  | 4 µg | 10 µg | 25 µg | Placebo |
|---|---|---|---|---|
| Day 1 | 6.5(2.13) | 10.9(5) | 29.8(17.51) | 6.6(4.85) |
| Day 14 | 4.8(2.31) | 7.3(2.36) | 15.7(7.61) | 5.5(3.43) |

TABLE 70

$C_{max}$ (Baseline Adjusted) (pg/mL)

|  | 4 µg | 10 µg | 25 µg | Placebo |
|---|---|---|---|---|
| Day 1 | 2.6(2.17) | 6(4.44) | 26.2(18.19) | 2.1(3.48) |
| Day 14 | 1.3(1.08) | 3(1.73) | 12(7.32) | 1(1.81) |

TABLE 71

$C_{max}$ P-values Pairwise Test vs. 4 µg

|  | 10 µg | 25 µg |
|---|---|---|
| Day 1 | 0.0013 | <0.0001 |
| Day 14 | 0.0033 | <0.0001 |

TABLE 72

$C_{max}$ P-values Pairwise Test vs. Placebo

|  | 4 µg | 10 µg | 25 µg |
|---|---|---|---|
| Day 1 | 0.9586 | 0.0116 | <0.0001 |
| Day 14 | 0.5174 | 0.0702 | <0.0001 |

TABLE 73

$C_{max}$ P-values Pairwise Test vs. 4 µg (Baseline Adjusted)

|  | 10 µg | 25 µg |
|---|---|---|
| Day 1 | 0.0055 | <0.0001 |
| Day 14 | 0.002 | <0.0001 |

TABLE 74

$C_{max}$ P-values Pairwise Test vs. Placebo (Baseline Adjusted)

|  | 4 µg | 10 µg | 25 µg |
|---|---|---|---|
| Day 1 | 0.6074 | 0.0059 | <0.0001 |
| Day 14 | 0.5088 | 0.0022 | <0.0001 |

TABLE 75

$C_{max}$ Ratio (Day 14) of Day 14 to Day 1

|  | 4 µg | 10 µg | 25 µg | Placebo |
|---|---|---|---|---|
| $C_{max}$ Ratio of Day 14 to Day 1 | 0.77(0.2633) | 0.804(0.3245) | 0.929(1.5011) | 0.933(0.2406) |
| Pairwise test vs | — | 0.7399 | 0.6702 | — |
| Pairwise test vs Placebo | 0.0702 | 0.1946 | 0.9931 | — |

Estradiol $C_{avg}$

TABLE 76

$C_{avg}$ (pg/mL)

|  | 4 µg | 10 µg | 25 µg | Placebo |
|---|---|---|---|---|
| Day 1 | 3.9(1.46) | 5.8(3.13) | 9.1(4.13) | 4.9(3.22) |
| Day 14 | 3.6(1.78) | 4.6(2.27) | 7.1(3.34) | 4.3(2.77) |

TABLE 77

$C_{avg}$ (Baseline Adjusted) (pg/mL)

|  | 4 µg | 10 µg | 25 µg | Placebo |
|---|---|---|---|---|
| Day 1 | 0(1.93) | 0.8(0.95) | 5.4(4.66) | 0.4(1.35) |
| Day 14 | 0.1(0.68) | 0.2(1.22) | 3.5(2.61) | −0.2(1.28) |

TABLE 78

$C_{avg}$ P-values Pairwise Test vs. 4 µg

|  | 10 µg | 25 µg |
|---|---|---|
| Day 1 | 0.0294 | <0.0001 |
| Day 14 | 0.1777 | 0.0005 |

TABLE 79

| $C_{avg}$ P-values Pairwise Test vs. Placebo | | | |
|---|---|---|---|
| | 4 μg | 10 μg | 25 μg |
| Day 1 | 0.267 | 0.4028 | 0.0021 |
| Day 14 | 0.3829 | 0.7724 | 0.0108 |

TABLE 80

| $C_{avg}$ P-values Pairwise Test vs. 4 μg (Baseline Adjusted) | | |
|---|---|---|
| | 10 μg | 25 μg |
| Day 1 | 0.1076 | 0.0001 |
| Day 14 | 0.7759 | <0.0001 |

TABLE 81

| $C_{avg}$ P-values Pairwise Test vs. Placebo (Baseline Adjusted) | | | |
|---|---|---|---|
| | 4 μg | 10 μg | 25 μg |
| Day 1 | 0.5126 | 0.2564 | 0.0001 |
| Day 14 | 0.4098 | 0.3629 | <0.0001 |

TABLE 82

| $C_{avg}$ Ratio (Day 14) of Day 14 to Day 1 | | | | |
|---|---|---|---|---|
| | 4 μg | 10 μg | 25 μg | Placebo |
| $C_{avg}$ Ratio of Day 14 to Day 1 | 0.77(0.2633) | 0.804(0.3245) | 0.929(1.5011) | 0.933(0.2406) |
| Pairwise test vs | — | 0.7399 | 0.6702 | — |
| Pairwise test vs Placebo | 0.0702 | 0.1946 | 0.9931 | — |

Estradiol $T_{max}$

TABLE 83

| $T_{max}$ (h) | | | | |
|---|---|---|---|---|
| | 4 μg | 10 μg | 25 μg | Placebo |
| Day 1 | 7(9.36) | 6.1(8.04) | 4.6(7.09) | 8.6(6.74) |
| Day 14 | 9.3(8.86) | 4(2.57) | 2.7(1.94) | 7.2(3) |

TABLE 84

| $T_{max}$ P-values Pairwise Test vs. 4 μg | | |
|---|---|---|
| | 10 μg | 25 μg |
| Day 1 | 0.7566 | 0.3834 |
| Day 14 | 0.0206 | 0.004 |

TABLE 85

| $T_{max}$ P-values Pairwise Test vs. Placebo | | | |
|---|---|---|---|
| | 4 μg | 10 μg | 25 μg |
| Day 1 | 0.5705 | 0.3255 | 0.0943 |
| Day 14 | 0.3576 | 0.0019 | <0.0001 |

Estrone Concentration

TABLE 86

| Pharmacokinetics Estrone Baseline (pg/mL) | | | | |
|---|---|---|---|---|
| | 4 μg | 10 μg | 25 μg | Placebo |
| Baseline | 15.9(6.02) | 19.7(9.18) | 16.3(7.71) | 20.4(9.67) |

TABLE 87

| Pharmacokinetics Estrone Day 1 (pg/mL) | | | | |
|---|---|---|---|---|
| | 4 μg | 10 μg | 25 μg | Placebo |
| Predose | 14.7(4.44) | 21(8.51) | 17.2(8.5) | 18.3(8.54) |
| 2 hour | 13.3(4.52) | 20(8.53) | 18.9(6.7) | 18.9(11.25) |
| 4 hour | 13(4.68) | 19.3(7.4) | 19.4(7.06) | 19.9(13.87) |
| 6 hour | 13.9(6.04) | 19.6(8.89) | 19.1(8.1) | 19(11.69) |
| 10 hour | 13.4(4.94) | 19.7(8.53) | 18.8(7.18) | 19.3(11.65) |
| 24 hour | 14.3(5.92) | 21.2(9.89) | 16.6(6.06) | 22.9(17.18) |

TABLE 88

| Pharmacokinetics Estrone Day 14 (pg/mL) | | | | |
|---|---|---|---|---|
| | 4 μg | 10 μg | 25 μg | Placebo |
| Predose | 15.8(5.15) | 21.7(14.25) | 18.6(8.49) | 18.7(9.38) |
| 2 hour | 13.6(5.3) | 19.7(10.2) | 19.8(9.08) | 17.3(7.99) |
| 4 hour | 14(5.25) | 21(13.46) | 19.9(7.26) | 20.4(11.41) |
| 6 hour | 14(5.11) | 20.7(10.4) | 19.3(6.47) | 16.1(7.54) |
| 10 hour | 14.2(5.51) | 20.1(11.93) | 19.3(8.24) | 19(8.17) |
| 24 hour | 14.5(4.69) | 20.1(9.34) | 16.7(6.09) | 18.9(8.24) |

TABLE 89

| Pharmacokinetics Estrone End of Study (pg/mL) | | | | |
|---|---|---|---|---|
| | 4 μg | 10 μg | 25 μg | Placebo |
| Post Dosing | 4.328(2.7619) | 4.643(2.5807) | 6.652(11.508) | 4.363(2.5982) |

Estrone Area Under the Curve (0-24 Hours)

TABLE 90

| Estrone Area Under the Curve (0-24 hours) (h*pg/mL) | | | | |
|---|---|---|---|---|
| | 4 μg | 10 μg | 25 μg | Placebo |
| Day 1 | 290.2(123.67) | 462.7(195.64) | 419.1(147.85) | 467.9(278.78) |
| Day 14 | 326.6(114.09) | 464.1(243.92) | 428.7(161.75) | 426.8(180.67) |

TABLE 91

| Estrone Area Under the Curve (0-24 hours) (Baseline Adjusted) (h*pg/mL) | | | | |
|---|---|---|---|---|
| | 4 μg | 10 μg | 25 μg | Placebo |
| Day 1 | 7.2(20.91) | 10.9(24.55) | 44.3(54.27) | 43.5(97.41) |
| Day 14 | 15(41.53) | 43.2(84.87) | 55.6(78.06) | 17.4(45.27) |

TABLE 92

Estrone Area Under the Curve (0-24 hours)
P-values Pairwise Test vs. 4 μg

|  | 10 μg | 25 μg |
|---|---|---|
| Day 1 | 0.003 | 0.0076 |
| Day 14 | 0.042 | 0.0393 |

TABLE 93

Estrone Area Under the Curve (0-24 hours)
P-values Pairwise Test vs. Placebo

|  | 4 μg | 10 μg | 25 μg |
|---|---|---|---|
| Day 1 | 0.0193 | 0.9487 | 0.519 |
| Day 14 | 0.0621 | 0.6117 | 0.9738 |

TABLE 94

Estrone Area Under the Curve (0-24 hours) P-values
Pairwise Test vs. 4 μg (Baseline Adjusted)

|  | 10 μg | 25 μg |
|---|---|---|
| Day 1 | 0.6195 | 0.0104 |
| Day 14 | 0.2251 | 0.0658 |

TABLE 95

Estrone Area Under the Curve (0-24 hours) P-values
Pairwise Test vs. Placebo (Baseline Adjusted)

|  | 4 μg | 10 μg | 25 μg |
|---|---|---|---|
| Day 1 | 0.1311 | 0.167 | 0.9761 |
| Day 14 | 0.8721 | 0.2746 | 0.0886 |

TABLE 96

Estrone Area Under the Curve (0-24 hours) Ratio (Day 14) of Day 14 to Day 1

|  | 4 μg | 10 μg | 25 μg | Placebo |
|---|---|---|---|---|
| AUC Ratio of Day 14 to Day 1 | 1.234(0.5824) | 1.023(0.2675) | 1.039(0.1941) | 1.006(0.2316) |
| Pairwise test vs | — | 0.1722 | 0.1866 | — |
| Pairwise test vs Placebo | 0.1432 | 0.848 | 0.6544 | — |

Estrone $C_{max}$

TABLE 97

$C_{max}$ (pg/mL)

|  | 4 μg | 10 μg | 25 μg | Placebo |
|---|---|---|---|---|
| Day 1 | 15.7(6.07) | 23.5(9.87) | 21.9(7.73) | 25.7(18.43) |
| Day 14 | 16(5.5) | 23.9(13.45) | 22.4(8.95) | 22.8(10.89) |

TABLE 98

$C_{max}$ (Baseline Adjusted) (pg/mL)

|  | 4 μg | 10 μg | 25 μg | Placebo |
|---|---|---|---|---|
| Day 1 | 0.4(3.05) | 3.2(2.99) | 5.1(4.78) | 6.3(12.81) |
| Day 14 | 0.6(3.49) | 3.7(8.79) | 5.6(4.81) | 3.4(5.69) |

TABLE 99

$C_{max}$ P-values Pairwise Test vs. 4 μg

|  | 10 μg | 25 μg |
|---|---|---|
| Day 1 | 0.007 | 0.0126 |
| Day 14 | 0.0301 | 0.0163 |

TABLE 100

$C_{max}$ P-values Pairwise Test vs. Placebo

|  | 4 μg | 10 μg | 25 μg |
|---|---|---|---|
| Day 1 | 0.0373 | 0.6567 | 0.4223 |
| Day 14 | 0.0275 | 0.7878 | 0.8979 |

TABLE 101

$C_{max}$ P-values Pairwise Test vs. 4 μg (Baseline Adjusted)

|  | 10 μg | 25 μg |
|---|---|---|
| Day 1 | 0.0087 | 0.0013 |
| Day 14 | 0.1975 | 0.0014 |

TABLE 102

$C_{max}$ P-values Pairwise Test vs. Placebo (Baseline Adjusted)

|  | 4 μg | 10 μg | 25 μg |
|---|---|---|---|
| Day 1 | 0.0659 | 0.3046 | 0.71 |
| Day 14 | 0.0938 | 0.933 | 0.2249 |

TABLE 103

| $C_{max}$ Ratio (Day 14) of Day 1 | | | | |
|---|---|---|---|---|
| | 4 µg | 10 µg | 25 µg | Placebo |
| $C_{max}$ Ratio of Day 14 to Day 1 | 1.029(0.2346) | 1.042(0.3436) | 1.041(0.2179) | 1.039(0.2916) |
| Pairwise test vs | — | 0.9035 | 0.8835 | — |
| Pairwise test vs Placebo | 0.9188 | 0.9788 | 0.982 | — |

Estrone $C_{avg}$

TABLE 104

| $C_{avg}$ (pg/mL) | | | | |
|---|---|---|---|---|
| | 4 µg | 10 µg | 25 µg | Placebo |
| Day 1 | 13(4.72) | 19.3(8.15) | 17.5(6.16) | 19.5(11.62) |
| Day 14 | 13.6(4.75) | 19.3(10.16) | 17.9(6.74) | 17.8(7.53) |

TABLE 105

| $C_{avg}$ (Baseline Adjusted) (pg/mL) | | | | |
|---|---|---|---|---|
| | 4 µg | 10 µg | 25 µg | Placebo |
| Day 1 | −2.3(2.26) | −1.1(2.66) | 0.7(3.73) | 0.1(5.03) |
| Day 14 | −1.7(3.25) | −0.9(5.91) | 1.1(4.81) | −1.6(3.8) |

TABLE 106

| $C_{avg}$ P-values Pairwise Test vs. 4 µg | | |
|---|---|---|
| | 10 µg | 25 µg |
| Day 1 | 0.0075 | 0.0207 |
| Day 14 | 0.042 | 0.0393 |

TABLE 107

| $C_{avg}$ P-values Pairwise Test vs. Placebo | | | |
|---|---|---|---|
| | 4 µg | 10 µg | 25 µg |
| Day 1 | 0.0363 | 0.9487 | 0.519 |
| Day 14 | 0.0621 | 0.6117 | 0.9738 |

TABLE 108

| $C_{avg}$ P-values Pairwise Test vs. 4 µg (Baseline Adjusted) | | |
|---|---|---|
| | 10 µg | 25 µg |
| Day 1 | 0.1345 | 0.0057 |
| Day 14 | 0.6351 | 0.0495 |

TABLE 109

| $C_{avg}$ P-values Pairwise Test vs. Placebo (Baseline Adjusted) | | | |
|---|---|---|---|
| | 4 µg | 10 µg | 25 µg |
| Day 1 | 0.0712 | 0.3751 | 0.691 |
| Day 14 | 0.912 | 0.7058 | 0.0742 |

TABLE 110

| $C_{avg}$ Ratio (Day 14) of Day 14 to Day 1 | | | | |
|---|---|---|---|---|
| | 4 µg | 10 µg | 25 µg | Placebo |
| $C_{avg}$ Ratio of Day 14 to Day 1 | 1.029(0.2346) | 1.042(0.3436) | 1.041(0.2179) | 1.039(0.2916) |
| Pairwise test vs | — | 0.9035 | 0.8835 | — |
| Pairwise test vs Placebo | 0.9188 | 0.9788 | 0.982 | — |

Estrone $T_{max}$

TABLE 111

| $T_{max}$ (h) | | | | |
|---|---|---|---|---|
| | 4 µg | 10 µg | 25 µg | Placebo |
| Day 1 | 14.1(9.37) | 11.9(9.76) | 9.1(7.43) | 12.1(9.39) |
| Day 14 | 10.9(9.03) | 10.4(8.93) | 6.3(6.9) | 12.2(9.24) |

TABLE 112

| $T_{max}$ P-values Pairwise Test vs. 4 µg | | |
|---|---|---|
| | 10 µg | 25 µg |
| Day 1 | 0.4862 | 0.0849 |
| Day 14 | 0.8711 | 0.0982 |

TABLE 113

| $T_{max}$ P-values Pairwise Test vs. Placebo | | | |
|---|---|---|---|
| | 4 µg | 10 µg | 25 µg |
| Day 1 | 0.5341 | 0.9449 | 0.2997 |
| Day 14 | 0.6824 | 0.5639 | 0.0391 |

Estrone Conjugates

TABLE 114

| Pharmacokinetics Estrone Conjugates Baseline (pg/mL) | | | | |
|---|---|---|---|---|
| | 4 µg | 10 µg | 25 µg | Placebo |
| Baseline | 250.3(162.91) | 259.7(208.51) | 374.4(586.45) | 280.7(171.26) |

TABLE 115

Pharmacokinetics Estrone Conjugates Day 1 (pg/mL)

|  | 4 µg | 10 µg | 25 µg | Placebo |
|---|---|---|---|---|
| Predose | 225.1(215.01) | 218.6(147.84) | 312.4(410.38) | 271.2(153.33) |
| 2 hour | 206.8(163.2) | 273.1(176.59) | 396.6(408.16) | 223.4(162.11) |
| 4 hour | 241.7(176.87) | 267.2(161.79) | 413.3(343.25) | 241.8(139.77) |
| 6 hour | 240.6(181.14) | 266(184.92) | 477.8(472.66) | 265(154.01) |
| 10 hour | 223(150.42) | 243.5(173.71) | 436.4(461) | 258(133.21) |
| 24 hour | 229.4(186.79) | 268.4(221.29) | 306.4(322.91) | 268.8(153.22) |

TABLE 116

Pharmacokinetics Estrone Conjugates Day 14 (pg/mL)

|  | 4 µg | 10 µg | 25 µg | Placebo |
|---|---|---|---|---|
| Predose | 212.7(140.19) | 319.1(326.71) | 411.1(624.14) | 256.1(133.07) |
| 2 hour | 212.4(145.02) | 420.4(560.53) | 434.3(491.31) | 285.6(158.61) |
| 4 hour | 240.2(155.7) | 429.3(506.01) | 505.1(618.47) | 273.1(148.76) |
| 6 hour | 225.8(164.76) | 359.2(346.26) | 483.8(515.95) | 267.7(181.53) |
| 10 hour | 238.3(152.45) | 417.6(517.51) | 492.5(598.16) | 306.9(178.68) |
| 24 hour | 206.4(154.26) | 349(345.91) | 309.6(380.88) | 240.1(115.84) |

TABLE 117

Pharmacokinetics Estrone Conjugates End of Study (pg/mL)

|  | 4 µg | 10 µg | 25 µg | Placebo |
|---|---|---|---|---|
| Post Dosing | 237.4(151.19) | 221.7(188.05) | 499.7(1089.67) | 250(148.72) |

Estrone Conjugates Area Under the Curve (0-24 Hours)

TABLE 118

Estrone Conjugates Area Under the Curve (0-24 hours) (h*pg/mL)

|  | 4 µg | 10 µg | 25 µg | Placebo |
|---|---|---|---|---|
| Day 1 | 5077.5(3798.39) | 5931.9(4209.95) | 9126(9186.37) | 5637.9(3151.49) |
| Day 14 | 5172.9(3382.89) | 8978(9811.23) | 9930.2(11711.99) | 6275.2(3397.54) |

TABLE 119

Estrone Conjugates Area Under the Curve (0-24 hours) (Baseline Adjusted) (h*pg/mL)

|  | 4 µg | 10 µg | 25 µg | Placebo |
|---|---|---|---|---|
| Day 1 | 375.5(843.98) | 422.4(473.83) | 2454.3(2600.25) | 83(229.06) |
| Day 14 | 660.5(1230.69) | 3767.2(7671.38) | 3059(4792.46) | 665.4(1552.19) |

TABLE 120

Estrone Conjugates Area Under the Curve (0-24 hours) P-values Pairwise Test vs. 4 µg

|  | 10 µg | 25 µg |
|---|---|---|
| Day 1 | 0.5219 | 0.0931 |
| Day 14 | 0.1392 | 0.1166 |

TABLE 121

Estrone Conjugates Area Under the Curve (0-24 hours) P-values Pairwise Test vs. Placebo

|  | 4 µg | 10 µg | 25 µg |
|---|---|---|---|
| Day 1 | 0.639 | 0.8157 | 0.1472 |
| Day 14 | 0.3503 | 0.2898 | 0.2246 |

TABLE 122

Estrone Conjugates Area Under the Curve (0-24 hours) P-values Pairwise Test vs. 4 µg (Baseline Adjusted)

|  | 10 µg | 25 µg |
|---|---|---|
| Day 1 | 0.8349 | 0.0028 |
| Day 14 | 0.1087 | 0.0537 |

TABLE 123

Estrone Conjugates Area Under the Curve (0-24 hours) P-values Pairwise Test vs. Placebo (Baseline Adjusted)

|  | 4 µg | 10 µg | 25 µg |
|---|---|---|---|
| Day 1 | 0.1894 | 0.0134 | 0.001 |
| Day 14 | 0.992 | 0.1225 | 0.0654 |

TABLE 124

Estrone Conjugates Area Under the Curve (0-24 hours) Ratio (Day 14) of Day 14 to Day 1

|  | 4 µg | 10 µg | 25 µg | Placebo |
|---|---|---|---|---|
| AUC Ratio of Day 14 to Day 1 | 1.115(0.4539) | 1.444(1.0121) | 1.107(0.3545) | 1.125(0.4522) |
| Pairwise test vs | — | 0.2279 | 0.9587 | — |
| Pairwise test vs Placebo | 0.9459 | 0.2427 | 0.8975 | — |

Estrone Conjugates $C_{max}$

TABLE 125

| $C_{max}$ (pg/mL) | | | | |
|---|---|---|---|---|
| | 4 µg | 10 µg | 25 µg | Placebo |
| Day 1 | 273.1(196.36) | 329.4(226.58) | 542.1(475.49) | 309.8(146.07) |
| Day 14 | 289(183.79) | 511.7(568.75) | 579.5(610.1) | 343.6(182.2) |

TABLE 126

| $C_{max}$ (Baseline Adjusted) (pg/mL) | | | | |
|---|---|---|---|---|
| | 4 µg | 10 µg | 25 µg | Placebo |
| Day 1 | 35.4(89.09) | 90.2(65.2) | 198.6(301.53) | 27.1(49.69) |
| Day 14 | 48.2(132.61) | 277.8(493.64) | 236.1(372.42) | 67(121.81) |

TABLE 127

| $C_{max}$ P-values Pairwise Test vs. 4 µg | | |
|---|---|---|
| | 10 µg | 25 µg |
| Day 1 | 0.4261 | 0.0333 |
| Day 14 | 0.1332 | 0.0685 |

TABLE 128

| $C_{max}$ P-values Pairwise Test vs. Placebo | | | |
|---|---|---|---|
| | 4 µg | 10 µg | 25 µg |
| Day 1 | 0.5369 | 0.7629 | 0.0625 |
| Day 14 | 0.3902 | 0.2533 | 0.1356 |

TABLE 129

| $C_{max}$ P-values Pairwise Test vs. 4 µg (Baseline Adjusted) | | |
|---|---|---|
| | 10 µg | 25 µg |
| Day 1 | 0.039 | 0.0345 |
| Day 14 | 0.0726 | 0.0579 |

TABLE 130

| $C_{max}$ P-values Pairwise Test vs. Placebo (Baseline Adjusted) | | | |
|---|---|---|---|
| | 4 µg | 10 µg | 25 µg |
| Day 1 | 0.7444 | 0.0033 | 0.0318 |
| Day 14 | 0.6735 | 0.1065 | 0.0928 |

TABLE 131

| $C_{max}$ Ratio (Day 14) of Day 14 to Day 1 | | | | |
|---|---|---|---|---|
| | 4 µg | 10 µg | 25 µg | Placebo |
| $C_{max}$ Ratio of Day 14 to Day 1 | 1.13(0.4068) | 1.524(1.1682) | 1.144(0.4569) | 1.11(0.5404) |

TABLE 131-continued

| $C_{max}$ Ratio (Day 14) of Day 14 to Day 1 | | | | |
|---|---|---|---|---|
| | 4 µg | 10 µg | 25 µg | Placebo |
| Pairwise test vs | — | 0.1969 | 0.9226 | — |
| Pairwise test vs Placebo | 0.9043 | 0.1919 | 0.8406 | — |

Estrone Conjugates $C_{avg}$

TABLE 132

| $C_{avg}$ (pg/mL) | | | | |
|---|---|---|---|---|
| | 4 µg | 10 µg | 25 µg | Placebo |
| Day 1 | 215.9(154.77) | 247.2(175.41) | 380.3(382.77) | 244.6(128.1) |
| Day 14 | 215.5(140.95) | 374.1(408.8) | 413.8(488) | 261.5(141.56) |

TABLE 133

| $C_{avg}$ (Baseline Adjusted) (pg/mL) | | | | |
|---|---|---|---|---|
| | 4 µg | 10 µg | 25 µg | Placebo |
| Day 1 | −21.8(88.41) | 8(34.21) | 36.8(291.72) | −33.7(46.95) |
| Day 14 | −25.3(120.69) | 140.2(330.6) | 70.3(300.36) | −7.9(89.89) |

TABLE 134

| $C_{avg}$ P-values Pairwise Test vs. 4 µg | | |
|---|---|---|
| | 10 µg | 25 µg |
| Day 1 | 0.5701 | 0.1004 |
| Day 14 | 0.1392 | 0.1166 |

TABLE 135

| $C_{avg}$ P-values Pairwise Test vs. Placebo | | | |
|---|---|---|---|
| | 4 µg | 10 µg | 25 µg |
| Day 1 | 0.5562 | 0.9602 | 0.1741 |
| Day 14 | 0.3503 | 0.2898 | 0.2246 |

TABLE 136

| $C_{avg}$ P-values Pairwise Test vs. 4 µg (Baseline Adjusted) | | |
|---|---|---|
| | 10 µg | 25 µg |
| Day 1 | 0.1804 | 0.4201 |
| Day 14 | 0.0606 | 0.2305 |

TABLE 137

$C_{avg}$ P-values Pairwise Test vs. Placebo (Baseline Adjusted)

|  | 4 μg | 10 μg | 25 μg |
|---|---|---|---|
| Day 1 | 0.6353 | 0.0047 | 0.3473 |
| Day 14 | 0.6439 | 0.0928 | 0.3244 |

TABLE 138

$C_{avg}$ Ratio (Day 14) of Day 14 to Day 1

|  | 4 μg | 10 μg | 25 μg | Placebo |
|---|---|---|---|---|
| $C_{avg}$ Ratio of Day 14 to Day 1 | 1.13(0.4068) | 1.524(1.1682) | 1.144(0.4569) | 1.11(0.5404) |
| Pairwise test vs | — | 0.1969 | 0.9226 | — |
| Pairwise test vs Placebo | 0.9043 | 0.1919 | 0.8406 | — |

Estrone Conjugates $T_{max}$

TABLE 139

$T_{max}$ (h)

|  | 4 μg | 10 μg | 25 μg | Placebo |
|---|---|---|---|---|
| Day 1 | 10.9(8.66) | 9.2(9.25) | 5.4(2.64) | 13.1(9.7) |
| Day 14 | 8.4(7.79) | 9(8.6) | 5.9(2.87) | 8.1(6.76) |

TABLE 140

$T_{max}$ P-values Pairwise Test vs. 4 μg

|  | 10 μg | 25 μg |
|---|---|---|
| Day 1 | 0.5609 | 0.0154 |
| Day 14 | 0.8173 | 0.2178 |

TABLE 141

Tmax P-values Pairwise Test vs. Placebo

|  | 4 μg | 10 μg | 25 μg |
|---|---|---|---|
| Day 1 | 0.4893 | 0.2253 | 0.003 |
| Day 14 | 0.9256 | 0.739 | 0.2087 |

In the phase 3 trial, all doses of TX-004HR compared with placebo (MITT n=747) significantly improved the 4 co-primary endpoints at week 2 through week 12, as well as the secondary endpoints of vaginal dryness by week 6 and vulvar and/or vaginal itching or irritation by week 12 (except 4 μg, p=0.0503), and was well-tolerated with no treatment-related serious AEs reported. The phase 3 PK study (n=72) showed no difference in systemic E2 levels for 4 μg and 10 μg TX-004HR vs placebo, as measured by AUC and $C_{avg}$. E2 AUC and $C_{avg}$ with 25 μg TX-004HR was higher than placebo, but average concentrations remained within the normal postmenopausal range (Table 142). E2 levels at day 84 were similar to placebo indicating no systemic drug accumulation. SHBG concentrations did not change with treatment. The two phase 2 studies (n=36 for each) of TX-004HR 10 μg and 25 μg resulted in statistically significantly lower E2 absorption than an approved E2 tablet at identical doses, with 25 μg TX-004HR demonstrating AUC less than ⅓ that of the approved product (Table 143).

TABLE 142

Phase 3 study PK parameters for E2 (unadjusted mean ± SD).

|  |  | $AUC_{0-24}$ (pg*hr/mL) | | | $C_{avg}$ (pg/mL) | | |
|---|---|---|---|---|---|---|---|
| Day | Dose (μg) | TX-004HR | Placebo | p-value | TX-004HR | Placebo | p-value |
| 1 | 4 | 91.7 ± 37.9 | 116.6 ± 77.3 | NS | 3.92 ± 1.46 | 4.86 ± 3.22 | NS |
|  | 10 | 138.2 ± 75.2 | 116.6 ± 77.3 | NS | 5.76 ± 3.13 | 4.86 ± 3.22 | NS |
|  | 25 | 217.4 ± 99.0 | 116.6 ± 77.3 | 0.0021 | 9.06 ± 4.13 | 4.86 ± 3.22 | 0.0021 |
| 14 | 4 | 87.2 ± 42.8 | 104.2 ± 66.4 | NS | 3.63 ± 1.78 | 4.34 ± 2.77 | NS |
|  | 10 | 110.1 ± 54.6 | 104.2 ± 66.4 | NS | 4.59 ± 2.27 | 4.34 ± 2.77 | NS |
|  | 25 | 171.6 ± 80.1 | 104.2 ± 66.4 | 0.0108 | 7.15 ± 3.34 | 4.34 ± 2.77 | 0.0108 |

TABLE 143

Phase 2 studies PK parameters for E2 (baseline adjusted geometric mean).

|  | $AUC_{0-24}$ (pg*hr/mL) | | | $C_{max}$ (pg/mL) | | |
|---|---|---|---|---|---|---|
| Dose (μg) | TX-004HR | Vaginal Tablet | p-value | TX-004HR | Vaginal Tablet | p-value |
| 10 | 49.62 | 132.92 | <0.0001 | 14.38 | 20.38 | 0.0194 |
| 25 | 89.21 | 292.06 | <0.0001 | 23.08 | 42.70 | <0.0001 |

With robust efficacy demonstrated as early as 2 weeks and up to 12 weeks at all 3 doses, TX-004HR 4 µg and 10 µg showed negligible systemic E2 absorption, while 25 µg resulted in very low systemic absorption of E2 in the phase 3 trial. TX-004HR 10 µg and 25 showed lower systemic E2 exposure than equivalent doses of an approved E2 tablet. The absence of clinically meaningful increases in E2 concentrations paired with data consistent with a lack of systemic effects (e.g., no increase in SHBG) shows that TX-004 HR delivers excellent efficacy with negligible to very low systemic exposure.

Figure 23:
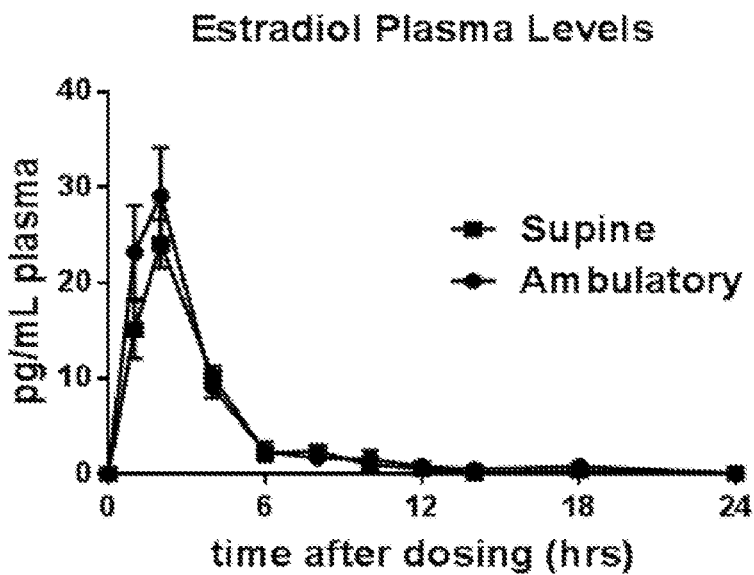
FIG. 23 shows estradiol plasma levels measured in subjects following a supine period after administration of the estradiol formulation, compared with plasma levels measured in subjects following an ambulatory period after administration of the estradiol formulation.

The impact of normal daily activities for 4 hours post dose was evaluated, in comparison with the impact of remaining in the supine position for 4 hours post dose on the pharmacokinetic (PK) profile of TX-004HR 25 mcg. In two studies, at the same site, the same sixteen healthy postmenopausal female subjects were fasted for at least 10 hours prior to dosing through 4 hours following dosing. Subjects received a 25 mcg dose of TX-004HR administered intravaginally by trained female study personnel. Following their first dose, the subjects were required to remain in a supine position for 4 hours following dosing. Following the second dose, after 5 minutes resting time, the subjects were instructed to be ambulatory in the clinic and refrain from reclining for the 4 hours following dosing. Blood samples were collected at pre-defined intervals up to 24 hours after dosing. Plasma samples were analyzed for estradiol using LC-MS/MS. See, e.g., FIG. 23. PK parameters were calculated on an individual and group mean basis with baseline correction.

The mean $C_{max}$ and $AUC_{0-24}$ of estradiol was not significantly different with ambulation than with supination. On an individual subject basis, the majority showed similar $C_{max}$ and $AUC_{0-24}$ levels with ambulation as with supination. There were no signs of posture having an effect on absorption rate as evidenced by the similarity in group average and individual subject $T_{max}$. In addition, there was no difference between the group mean profiles when compared on an individual time point basis, further demonstrating that posture had no effect on absorption. The systemic exposure of estradiol in TX-004HR 25 mcg was generally low and occurred regardless of whether the subjects were ambulatory or supine for 4 hours after dosing. An important advantage of the formulation is that a woman can be ambulatory almost immediately after the formulation is administered, as opposed to other known formulations that require a subject to remain in a supine position after administration. Generally, other known formulations direct administration before bed at night because of the requirement to be supine, which requirement is unnecessary in the pharmaceutical compositions disclosed herein because the pharmaceutical compositions disclosed herein adhere to the vaginal tissue, the capsule dissolves rapidly, and the formulation is released into the vagina and rapidly absorbed by the vaginal tissue. Because activity level does not adversely affect the systemic absorption of estradiol, the formulation of the invention gives the patient more flexibility with her dosing regimen.

Example 13: Safety Results in Randomized, Double-Blind, Placebo-Controlled Multicenter Study Safety endpoints in the study included vital signs, clinical laboratory tests (blood chemistry, hematology, hormone levels, urine analysis), ECG, physical and gynecological examination findings, pap smears, endometrial biopsies, and adverse events (AEs). AEs included undesirable medical conditions occurring at any time during all study phases including the washout period, whether or not a study treatment had been administered. An AE was considered treatment emergent if it occurred after study drug administration, or if it was pre-existing and worsened during 120 days post-dose follow up. Participants were given a diary with instructions to record product use, sexual activity, symptoms/complaints, and other medications. AEs, concomitant medications, and vital signs were recorded and assessed at each study visit from screening to week 12.

TX-004HR had a favorable safety profile and was well tolerated. No clinically significant differences in AEs were observed between treatment and placebo groups (Table 144). Headache was the most commonly reported TEAE, followed by vaginal discharge, nasopharyngitis, and vulvovaginal pruritus (Table 144). Headache was the only treatment-related TEAE that was numerically more frequent in women receiving TX-004HR than those receiving placebo (3.7% for 4-µg dose vs 3.1% for placebo). Vaginal discharge was reported by numerically fewer women in any of the TX-004HR groups than by women in the placebo group. Most TEAEs were mild to moderate in severity. Few participants (1.8%) discontinued the study due to AEs.

TABLE 144

Number (%) of treatment emergent adverse events (TEAE) reported for ≥3% in any treatment arm of the safety population.

| Preferred Term | TX-004HR 4 µg (n = 191) | TX-004HR 10 µg (n = 191) | TX-004HR 25 µg (n = 190) | Placebo (n = 192) |
|---|---|---|---|---|
| Any subject with reported TEAE | 97 (50.8) | 94 (49.2) | 93 (48.9) | 111 (57.8) |
| Headache | 12 (6.3) | 14 (7.3) | 6 (3.2) | 15 (7.8) |
| Vaginal discharge | 5 (2.6) | 6 (3.1) | 4 (2.1) | 13 (6.8) |
| Nasopharyngitis | 5 (2.6) | 6 (3.1) | 7 (3.7) | 10 (5.2) |
| Vulvovaginal pruritus | 4 (2.1) | 3 (1.6) | 7 (3.7) | 10 (5.2) |
| Back pain | 9 (4.7) | 1 (0.5) | 4 (2.1) | 8 (4.2) |
| Urinary tract infection | 5 (2.6) | 5 (2.6) | 8 (4.2) | 4 (2.1) |
| Upper respiratory tract infection | 5 (2.6) | 6 (3.1) | 3 (1.6) | 5 (2.6) |
| Oropharyngeal pain | 1 (0.5) | 0 (0) | 6 (3.2) | 1 (0.5) |

Nine serious TEAEs were reported in 8 subjects; however, none were considered related to treatment. Complete heart block, appendicitis, endophthalmitis, and chronic obstructive pulmonary disease were each reported by a different participant in the 25 µg group. Sinus node dysfunction and ankle fracture were both reported for one women, and arthralgia and malignant melanoma were each reported for one women in the 10 µg group. None of the women in the 4 µg group had reports of serious TEAEs. One woman in the placebo group was reported to have a cervical myelopathy. No deaths occurred during the study.

No diagnoses of endometrial hyperplasia or malignancy from endometrial biopsies were observed at week 12. Total cholesterol numerically decreased from baseline to week 12 by a mean of 0.024 mmol/L to 0.07 mmol/L in the treatment groups, and by 0.008 mmol/L in the placebo group. No clinically meaningful increases in triglycerides were observed in any active treatment groups compared with placebo. Sex hormone binding globulin (SHBG) concentrations (measured in a subset of 72 women) did not increase with treatment relative to placebo or baseline at week 12. No clinically significant changes in any laboratory parameters were found.

The phase 3 clinical trial demonstrated that TX-004HR at 4 µg, 10 µg, and 25 µg doses is safe and effective for treating vaginal changes and self-reported symptoms of VVA in postmenopausal women. Statistically significant and clinically meaningful improvements in all of the 4 pre-specified co-primary endpoints (increase in the percentage of vaginal superficial cells, decrease in the percentage of vaginal parabasal cells and vaginal pH, and decrease in severity of the MBS of dyspareunia) occurred as early as 2 weeks with all 3 doses of TX-004HR as compared with placebo, and were sustained throughout the 12-week trial. Additionally, improvements were found for the secondary endpoints of vaginal dryness and vulvar or vaginal irritation and itching. These improvements were achieved without increasing systemic estrogen concentrations (4 µg and 10 µg) or with negligible (25 µg) systemic estrogen exposure, as found in pharmacokinetic studies. TX-004HR was also well-tolerated with no clinically significant differences found between treatment and placebo groups in any AEs or treatment-related AEs, and no treatment-related serious AEs.

The results demonstrate early onset of action in the clinical signs of VVA with statistically significantly improved changes compared with placebo. The efficacy results here were somewhat numerically higher than data from a 12-week, randomized, controlled trial that compared a 10-µg vaginal estradiol tablet with placebo, which showed significant improvements in the percentages of superficial and parabasal cells, and in pH compared with placebo (see, Simon et al. *Obstet Gynecol.* 2008; 112:1053-1060). At 12 weeks, improvements were smaller with the 10-µg estradiol tablet (change of 13% in superficial cells, −37% in parabasal cells, and −1.3 in vaginal pH) than what was observed in this study with the 10-µg TX-004HR dose (change of 17% in superficial cells, −44% in parabasal cells, and −1.4 in vaginal pH). While improvements in some objective (cell and pH) endpoints were seen with the estradiol tablet within 2 weeks of treatment, the patient-reported improvements in a composite score of subjective symptoms were not observed until 8 weeks of therapy, which can be perceived as a disadvantage for many users. That clinical trial did not assess individual symptoms. A second randomized, controlled trial of 10-µg and 25-µg estradiol tablets similarly did not find significant improvements over placebo in the composite score of vaginal symptoms with either dose until 7 weeks of treatment (week 2, NS). Likewise, the SERM, ospemifene, was evaluated in a clinical trial for the treatment of dyspareunia, and statistically significant improvements were not observed until week 12. See, Bachmann et al. *Obstet Gynecol.* 2008; 111:67-76; Portman et al. *Menopause.* 2013; 20:623-630.

Importantly, the results reported here showed significant improvement in dyspareunia within 2 weeks with all 3 doses of TX-004HR, with reductions in severity scores from 1.5 to 1.7 points at week 12, which were comparable or superior to reductions of 1.2 to 1.6 points reported for other currently approved dyspareunia treatments. See, VAGIFEM® (estradiol vaginal tablets) Prescribing Information. Bagsvaerd, Denmark: Novo Nordisk Pharmaceuticals Inc.; 2012; PREMARIN® (conjugated estrogens tablets, USP) Prescribing Information. Philadelphia, Pa.: Wyeth Pharmaceuticals Inc.; 2010; OSPHENA® (ospemifene) tablets, for oral use. Prescribing Information. Shionogi, Inc. 2013.

Additionally, vaginal dryness improved from week 2 with 10 µg and 25 µg TX-004HR. None of the currently available products reported as early an onset of action for the symptom of vaginal dryness associated with VVA as did TX-004HR. Furthermore, TX-004HR 10 µg and 25 µg showed significant improvement in vaginal irritation and/or itching at week 12, while none of the currently available products on the market are reported to improve these symptoms. See, Portman et al. *Maturitas.* 2014; 78:91-98; Eriksen et al. *Eur J Obstet Gynecol Reprod Biol.* 1992; 44:137-144.

Based on a large survey of postmenopausal women in the United States, only a small proportion (7%) of women are thought to receive prescription vaginal estrogen therapy alone for their VVA, probably due to lack of information about available treatments, avoidance of discussion of the topic with health care practitioners, or dissatisfaction with currently available products (see, e.g., Kingsberg et al. *J Sex Med.* 2013; 10:1790-1799). Eliminating the need for an applicator or individually measuring doses is intended to give women a more positive user experience and thus potentially better compliance, resulting in overall better efficacy of treatment.

The results with TX-004HR in this study exemplify one of the advantages of local vaginal estrogen therapies: rapid symptom resolution without increasing systemic estrogen concentrations. The mean area under the concentration-time curve (AUC) and average concentration ($C_{avg}$) for estradiol were not significantly different from placebo with 4 µg and 10 µg TX-004HR. Although statistically higher AUC for estradiol was observed with the 25 µg dose, estradiol levels remained within the postmenopausal range with no evidence of accumulation by day 84. Although there was negligible systemic absorption, rapid efficacy was observed within 2 weeks of dosing with all doses of TX-004HR.

TX-004HR was well-tolerated. The 4 most commonly reported TEAEs, including vaginal discharge and vulvovaginal pruritus, were experienced by fewer women in any TX-004HR group than in the placebo group, and were mostly mild to moderate in severity. By comparison, in a 12-week study of the efficacy of ospemifene, vaginal discharge was reported more than 6-times more frequently in the ospemifene group than in the placebo group (see, Portman et al. *Menopause.* 2013; 20:623-630). Genital pruritus was also reported 4-times more frequently in women treated with Vagifem 10-µg tablets than with placebo in a 12-month randomized study (see, Vagifem® (estradiol vaginal tablets) Prescribing Information. Bagsvaerd, Denmark: Novo Nordisk Pharmaceuticals Inc.; 2012). Importantly, endometrial findings after TX-004HR were benign as no hyperplasia or malignancies were reported in biopsies at 12 weeks. Onset of effect was seen as early as 2 weeks and was maintained throughout the study. TX-004HR was well tolerated as reported here and systemic estrogen exposure was negligible to very low as demonstrated by the pharmacokinetic study.

Example 14: Results of Female Sexual Function Index in Randomized, Double-Blind, Placebo-Controlled Multicenter Study The trial was a randomized, double-blind, placebo controlled, multicenter, phase 3 study. Treatments were self-administered vaginally, once daily, for 2 weeks and then twice weekly, for 10 weeks. Female sexual dysfunction (FSD) was evaluated using the multidimensional Female Sexual Function Index (FSFI) at baseline and at week 12. The FSFI is a brief, validated, self-reporting questionnaire consisting of 19 questions designed to assess the areas of arousal, desire, orgasm, lubrication, and pain. The Index defines sexual dysfunction by a total FSFI score (the sum of the individual domain scores) of ≤26.55 out of a possible maximum score of 36.

Postmenopausal women (40-75 years; BMI ≤38 kg/m2) were included if they had ≤5% superficial cells on vaginal cytological smear; vaginal pH >5.0; self-identified most bothersome symptom (MBS) of moderate-to severe dyspareunia; and anticipated sexual activity (with vaginal penetration) during the trial period. Vulvar and vaginal atrophy (VVA) treatments, including vaginal lubricants and moisturizers, were discontinued within 7 days prior to screening. Use of oral estrogen-, progestin-, androgen-, or SERM-containing drug products were prohibited within 8 weeks of study start. Changes from baseline in total and individual domain FSFI scores for each dose were compared with placebo using ANCOVA with baseline as a covariate.

764 postmenopausal women were randomized to 4 µg (n=191), 10 µg (n=191), or 25 µg (n=190) vaginal estradiol softgel capsules or placebo (n=192). The majority of the women were white (87%) with a mean age of 59 years and a mean BMI of 26.7 kg/m² (Table 145). The FSFI questionnaire was completed by those who were not in the PK sub-study (n=692; 90.6%). The average baseline total FSFI score of 14.8 for all women indicated FSD in the subjects.

TABLE 145

Summary of subjects enrolled in study

| | Composition 4<br>4 µg<br>(n = 186) | Composition 5<br>10 µg<br>(n = 188) | Composition 6<br>25 µg<br>(n = 186) | Composition 7<br>(n = 187) |
|---|---|---|---|---|
| Age, years | | | | |
| Mean ± SD | 59.8 ± 6.0 | 58.6 ± 6.3 | 58.8 ± 6.2 | 59.4 ± 6.0 |
| Race, n (%) | | | | |
| White | 162 (87.1) | 165 (87.8) | 161 (86.6) | 160 (85.6) |
| Black or African American | 20 (10.8) | 21 (11.2) | 24 (12.9) | 21 (11.2) |
| Asian | 3 (1.6) | 2 (1.1) | 1 (0.5) | 1 (0.5) |
| BMI, kg/m² | | | | |
| Mean ± SD | 26.6 ± 4.9 | 26.8 ± 4.7 | 26.9 ± 4.8 | 26.6 ± 4.6 |
| Baseline total FSFI Score | | | | |
| Mean ± SD | 14.8 ± 6.13 | 15.8 ± 6.24 | 14.2 ± 6.21 | 14.4 ± 6.61 |
| Baseline FSFI Pain Score | | | | |
| Mean ± SD | 1.6 ± 1.11 | 1.8 ± 1.22 | 1.7 ± 1.17 | 1.7 ± 1.20 |

The Female Sexual Function Index (FSFI) total summary score is a numerically continuous measure that was descriptively summarized at Visits 2 and 6 and the change in the total summary score (Visit 6 minus Visit 2) was also descriptively summarized. The domain sub-scores and the changes in the domain sub-scores were also descriptively summarized. Summaries were by treatment arm, and all active treatment arms combined.

In addition, the change in mean from baseline of each active treatment group from the placebo group for each numerically continuous endpoint was evaluated. The least square (LS) mean changes and the 95% CI for the difference in LS Mean changes between treated and placebo are provided. The FSFI Questionnaire consists of 19 questions divided among 6 domains, and has a minimum total score of 2.0 and a maximum score of 36.0 points. The FSFI questionnaire was administered to the randomized population except for those subjects in the PK sub-study. At Baseline, the overall mean Total Score was 14.8 (14.8 for the 4 µg group; 15.8 for the 10 µg group; 14.2 for the 25 µg group; and 14.4 for the placebo group). The LS mean change in the FSFI Total Score and domain scores from Baseline to Week 12 are summarized in Table 146.

Change from Baseline to Week 12 in FSFI total score and domains compared to placebo was assessed.

Figure 24:
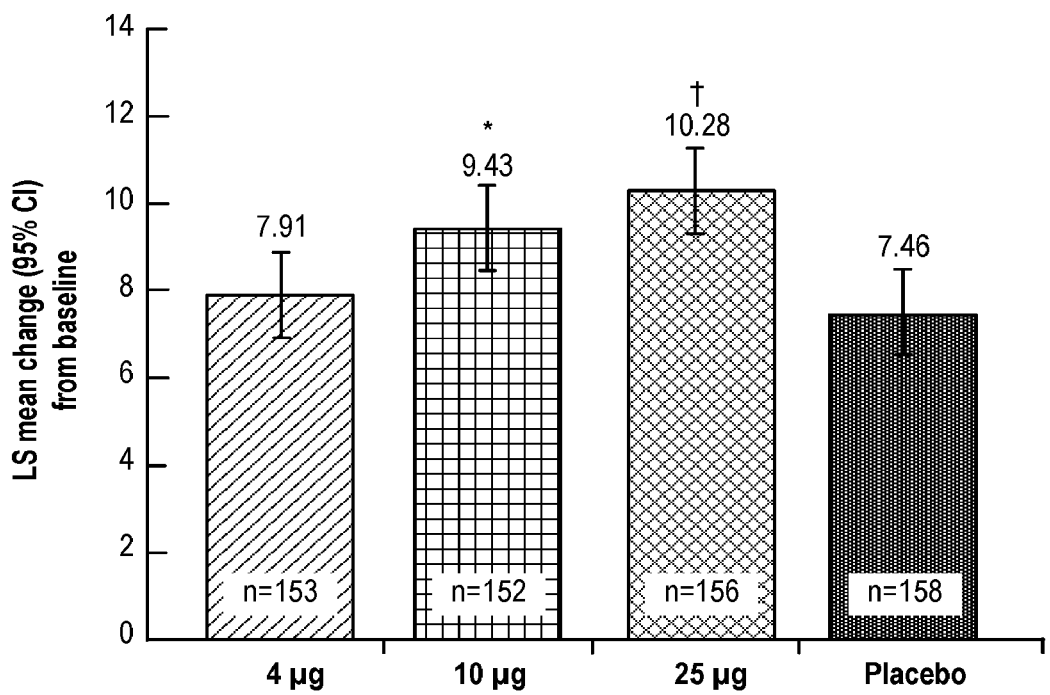
FIG. 24 shows mean change from baseline in Total FSFI score at Week 12.

After 12 weeks, total FSFI scores numerically improved from baseline in all groups, including placebo. Total FSFI score significantly increased with the 10 µg group (P<0.05) and the 25 µg group (P=0.0019) versus placebo (FIG. 24).

Figure 25A:
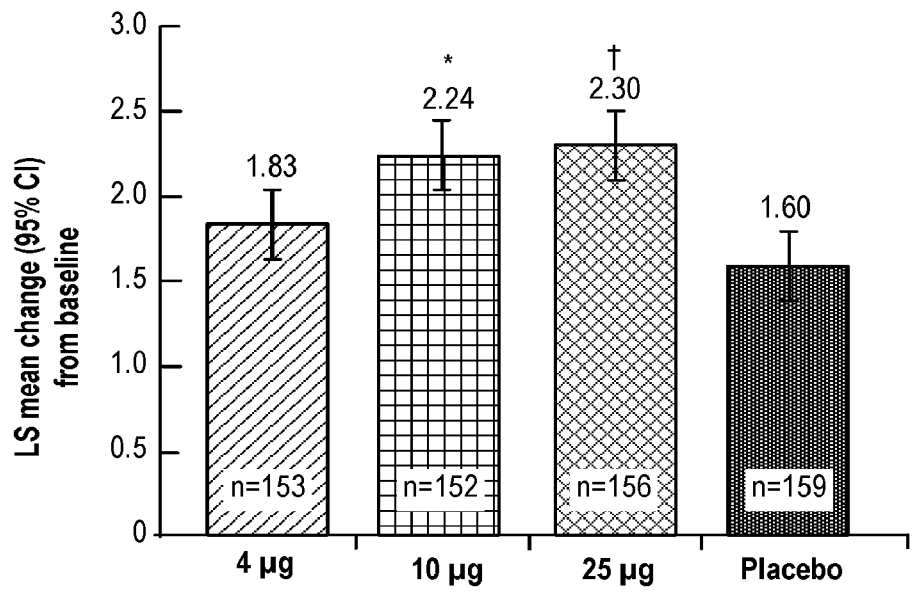
FIG. 25A shows the mean change from baseline to week 12 in the individual FSFI lubrication score.
Figure 25B:
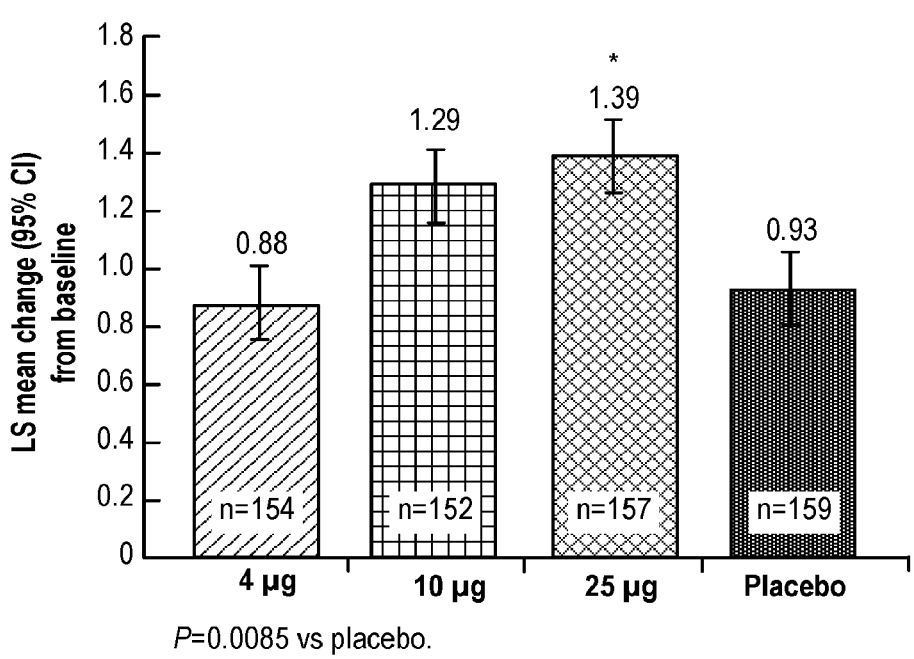
FIG. 25B shows the mean change from baseline to week 12 in the individual FSFI arousal score.
Figure 25C:
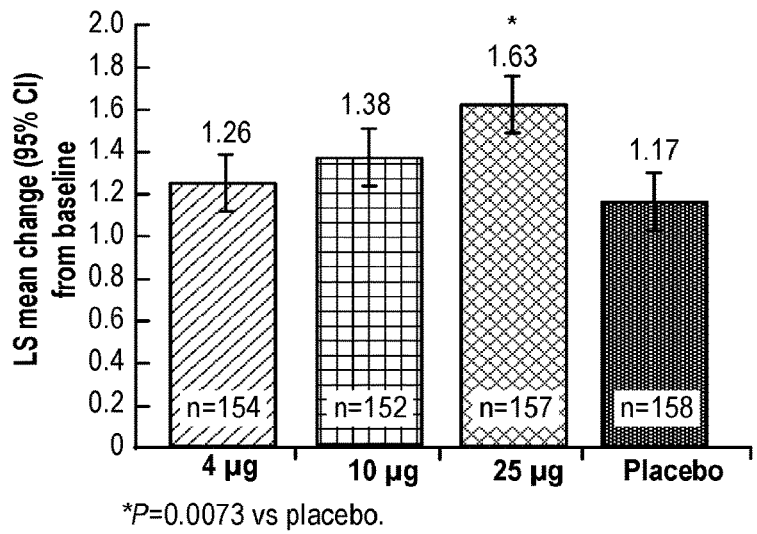
FIG. 25C shows the mean change from baseline to week 12 in the individual FSFI satisfaction score.
Figure 25D:
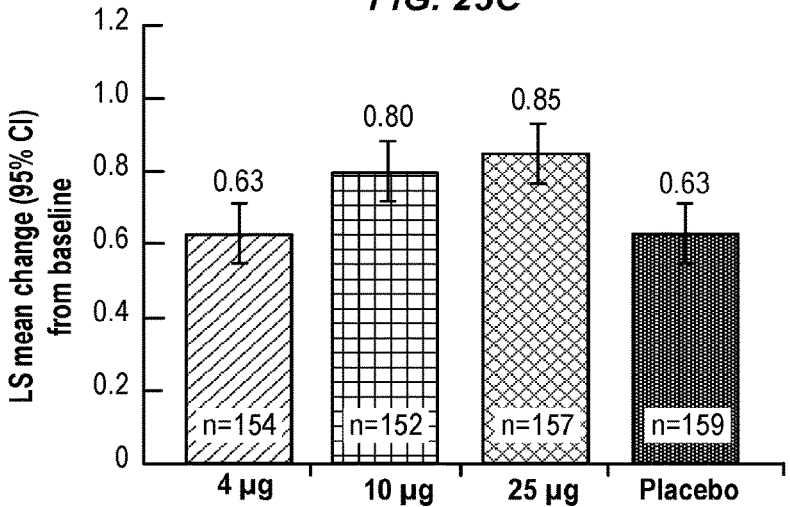
FIG. 25D shows the mean change from baseline to week 12 in the individual FSFI desire score.
Figure 25E:
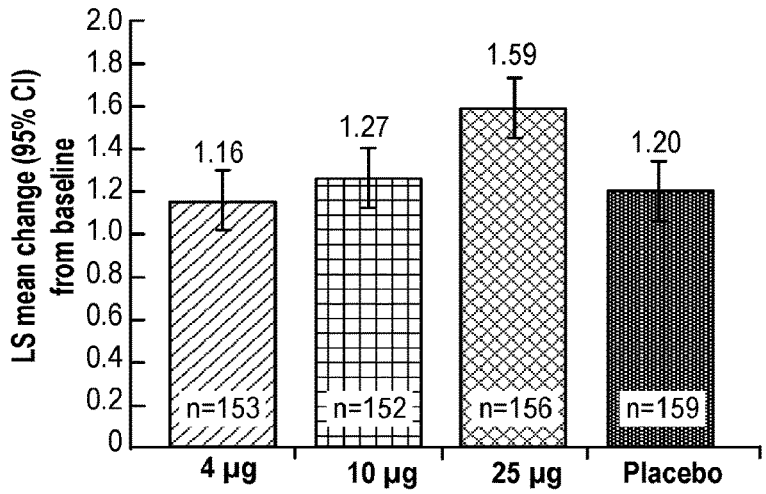
FIG. 25E shows the mean change from baseline to week 12 in the individual FSFI orgasm score.

FSFI lubrication and pain domain scores improved numerically in all groups including placebo from baseline to 12 weeks; improvements for the 10 µg group and the 25 µg group were statistically significantly greater than with placebo (FIG. 25A). The 25 µg composition significantly improved FSFI arousal (P=0.0085) and satisfaction (P=0.0073) domain scores at 12 weeks (FIG. 25B, FIG. 25C). All three doses were comparable to placebo in their effect on the FSFI domains of desire and orgasm (FIG. 25D, FIG. 25E). The 4 µg composition and placebo provided similar levels of improvement. The compositions improved FSFI in a dose-dependent manner, with the 25 µg dose having the greatest improvement. All three doses were efficacious, and the numeric improvement in subjective symptoms was highest for subjects in the 10 and 25 µg groups. The observed placebo response could be attributed to the coconut oil (Miglyol) in the formulation for the placebo and the estradiol compositions, which may also contribute to the observed benefits.

TABLE 146

Female Sexual Function Index Total and Domain Scores:

| Category | Score | 4 µg | | 10 µg | | 25 µg | | Placebo | |
|---|---|---|---|---|---|---|---|---|---|
| | | Mean | SD | Mean | SD | Mean | SD | Mean | SD |
| Total | Baseline | 14.8 | 6.13 | 15.8 | 6.24 | 14.2 | 6.21 | 14.4 | 6.61 |
| | Week 12 | 22.6 | 8.4 | 24.8 | 7.59 | 24.8 | 7.59 | 22 | 8.54 |
| | Change | 7.98 | 7.551 | 8.85 | 7.361 | 10.49 | 8.176 | 7.74 | 8.41 |
| | LS Mean | 7.909 | 0.9075 | 9.431 | 0.0492 | 10.283 | 0.0019 | 7.458 | — |
| Arousal | Baseline | 2.8 | 1.44 | 2.9 | 1.43 | 2.7 | 1.5 | 2.7 | 1.41 |
| | Week 12 | 3.6 | 1.61 | 4.1 | 1.47 | 4.1 | 1.39 | 3.6 | 1.52 |
| | Change | 0.88 | 1.615 | 1.16 | 1.632 | 1.43 | 1.646 | 1.02 | 1.607 |
| | LS Mean | 0.876 | 0.9777 | 1.288 | 0.0581 | 1.393 | 0.008 | 0.927 | — |
| Desire | Baseline | 2.6 | 1.01 | 2.7 | 1.13 | 2.6 | 1.09 | 2.7 | 1.07 |
| | Week 12 | 3.3 | 1.11 | 3.5 | 1.13 | 3.5 | 1.06 | 3.3 | 1.21 |
| | Change | 0.64 | 1.065 | 0.78 | 1.113 | 0.87 | 1.105 | 0.62 | 1.102 |
| | LS Mean | 0.626 | 1 | 0.801 | 0.2753 | 0.849 | 0.1139 | 0.628 | — |

TABLE 146-continued

Female Sexual Function Index Total and Domain Scores:

| Category | Score | 4 µg | | 10 µg | | 25 µg | | Placebo | |
|---|---|---|---|---|---|---|---|---|---|
| | | Mean | SD | Mean | SD | Mean | SD | Mean | SD |
| Lubrication | Baseline | 2.1 | 1.25 | 2.3 | 1.25 | 2 | 1.19 | 2 | 1.29 |
| | Week 12 | 3.9 | 1.84 | 4.4 | 1.56 | 4.3 | 1.65 | 3.6 | 1.77 |
| | Change | 1.84 | 1.782 | 2.12 | 1.612 | 2.36 | 1.744 | 1.64 | 1.871 |
| | LS Mean | 1.835 | 0.4023 | 2.243 | 0.0012 | 2.3 | 0.0003 | 1.591 | — |
| Orgasm | Baseline | 2.7 | 1.74 | 2.9 | 1.74 | 2.4 | 1.68 | 2.4 | 1.73 |
| | Week 12 | 3.8 | 1.89 | 4.1 | 1.75 | 4.1 | 1.66 | 3.7 | 1.97 |
| | Change | 1.12 | 1.93 | 1.09 | 1.821 | 1.68 | 1.857 | 1.31 | 1.86 |
| | LS Mean | 1.162 | 0.9978 | 1.273 | 0.9424 | 1.59 | 0.0763 | 1.189 | — |
| Satisfaction | Baseline | 2.9 | 1.37 | 3.2 | 1.43 | 2.9 | 1.37 | 2.9 | 1.49 |
| | Week 12 | 4.2 | 1.54 | 4.4 | 1.37 | 4.6 | 1.35 | 4.1 | 1.55 |
| | Change | 1.31 | 1.512 | 1.24 | 1.534 | 1.64 | 1.613 | 1.23 | 1.661 |
| | LS Mean | 1.256 | 0.8798 | 1.382 | 0.3484 | 1.628 | 0.0063 | 1.165 | — |

While the pharmaceutical compositions and methods have been described in terms of what are presently considered to be practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar embodiments. This disclosure includes any and all embodiments of the following claims.

What is claimed is:

1. A method of treating vulvovaginal atrophy (VVA), comprising vaginally administering to a subject in need thereof a liquid pharmaceutical composition comprising estradiol at a dosage of 4 mcg, wherein the composition has a viscosity in the range of about 50 cP to about 1000 cP at 25° C., and increasing the dosage of estradiol if the subject does not exhibit an improvement in a clinical response for VVA.

2. The method of claim 1, wherein the composition comprising estradiol is administered once daily for two weeks, then twice weekly thereafter.

3. The method of claim 1, wherein the estradiol is solubilized.

4. The method of claim 1, wherein a dosage form comprising the composition is manually inserted about two inches into the vagina.

5. The method of claim 1, wherein the composition comprising estradiol is encapsulated in a soft gelatin capsule.

6. The method of claim 1, wherein the subject's clinical response is measured as an improvement in one or more clinical parameters selected from the group consisting of: an increase in the percentage of vaginal superficial cells, a decrease in the percentage of vaginal parabasal cells, a decrease in vaginal pH, a decrease in the severity of moderate to severe dyspareunia, a decrease in vaginal dryness, a decrease in vulvar or vaginal itching or irritation, an increase of vaginal mucosa, an assessment of standard pK parameters, a change in the Female Sexual Function Index (FSFI), a visual vaginal assessment, and the subject's self-reported response.

7. The method of claim 1, wherein the subject's clinical response is measured by a decrease in the severity of moderate to severe dyspareunia.

8. The method of claim 1, wherein the subject's clinical response is measured by a visual vaginal assessment or by the subject's self-reported response.

9. The method of claim 1, comprising increasing the dosage of estradiol to 10 mcg if the subject does not exhibit an improvement in the clinical response.

10. The method of claim 1, comprising increasing the dosage of estradiol to 25 mcg if the subject does not exhibit an improvement in the clinical response.

11. The method of claim 1, comprising decreasing the dosage of estradiol if an improvement in the clinical response is achieved.

12. A method of treating vulvovaginal atrophy (VVA), comprising vaginally administering to a subject in need thereof a liquid pharmaceutical composition comprising estradiol once daily for two weeks, then twice weekly thereafter, wherein the composition comprises estradiol at a dosage of 4 mcg and wherein the composition has a viscosity in the range of about 50 cP to about 1000 cP at 25° C.

13. The method of claim 12, wherein the estradiol is solubilized.

14. The method of claim 12, wherein a dosage form comprising the composition is manually inserted about two inches into the vagina.

15. The method of claim 12, wherein the composition comprising estradiol is encapsulated in a soft gelatin capsule.

16. A method of treating moderate to severe dyspareunia, comprising vaginally administering to a subject in need thereof a liquid pharmaceutical composition comprising estradiol at a dosage of 4 mcg, wherein the composition has a viscosity in the range of about 50 cP to about 1000 cP at 25° C., and increasing the dosage of estradiol if the subject does not exhibit an improvement in the moderate to severe dyspareunia.

17. The method of claim 16, wherein the composition comprising estradiol is administered once daily for two weeks, then twice weekly thereafter.

18. The method of claim 16, wherein the estradiol is solubilized.

19. The method of claim 16, wherein the composition comprising estradiol is encapsulated in a soft gelatin capsule.

20. The method of claim 16, comprising increasing the dosage of estradiol to 10 mcg if the subject does not exhibit an improvement in the moderate to severe dyspareunia.

21. The method of claim 16, comprising increasing the dosage of estradiol to 25 mcg if the subject does not exhibit an improvement in the moderate to severe dyspareunia.

* * * * *